(12) United States Patent
Williams et al.

(10) Patent No.: US 9,186,677 B2
(45) Date of Patent: Nov. 17, 2015

(54) INTEGRATED APPARATUS FOR PERFORMING NUCLEIC ACID EXTRACTION AND DIAGNOSTIC TESTING ON MULTIPLE BIOLOGICAL SAMPLES

(75) Inventors: Jeff Williams, Chelsea, MI (US); Kerry Wilson, Elkhart, IN (US); Kalyan Handique, Ypsilanti, MI (US)

(73) Assignee: HANDYLAB, INC., Franklin Lakes, NJ (US)

( * ) Notice: Subject to any disclaimer, the term of this patent is extended or adjusted under 35 U.S.C. 154(b) by 209 days.

(21) Appl. No.: 12/218,498

(22) Filed: Jul. 14, 2008

(65) Prior Publication Data

US 2009/0221059 A1    Sep. 3, 2009

Related U.S. Application Data

(63) Continuation-in-part of application No. 11/985,577, filed on Nov. 14, 2007.

(60) Provisional application No. 60/959,437, filed on Jul. 13, 2007.

(51) Int. Cl.
*G01N 35/02* (2006.01)
*B01L 99/00* (2010.01)
(Continued)

(52) U.S. Cl.
CPC ............ *B01L 7/52* (2013.01); *B01L 3/5027* (2013.01); *B01L 9/527* (2013.01); *F16K 99/0001* (2013.01);
(Continued)

(58) Field of Classification Search
CPC ......... B01L 7/53; B01L 3/5027; B01L 9/527; B01L 2200/027; B01L 2200/10; B01L 2200/147; B01L 2200/148; B01L 2200/16; B01L 2300/021; B01L 2300/045; B01L 2300/0681; B01L 2300/0816; B01L 2300/0867; B01L 2300/087; B01L 2300/0887; B01L 2300/1822; B01L 2300/1827; B01L 2300/1861; B01L 2400/0442; B01L 2400/0481; B01L 2400/0487; B01L 2400/0611; B01L 2400/0677; B01L 2400/0683; F16K 99/0001; F16K 99/003; F16K 99/0032; F16K 99/0044; F16K 99/0061; F16K 2099/0084; G01N 35/026; G01N 2035/00881; G01N 2035/0425; G01N 2035/0436
USPC ............... 422/63, 65, 560, 561, 562, 564
See application file for complete search history.

(56) References Cited

U.S. PATENT DOCUMENTS 1,434,314 A   10/1922   Raich
1,616,419 A    2/1927   Wilson
(Continued)

FOREIGN PATENT DOCUMENTS

CA        2294819     1/1999
CN      103540518     1/2014
(Continued)

OTHER PUBLICATIONS

Brahmasandra et al., On-chip DNA detection in microfabricated separation systems, SPIE Conference on Microfluidic Devices and Systems, 1998, vol. 3515, pp. 242-251, Santa Clara, CA.
(Continued)

*Primary Examiner* — Paul Hyun
*Assistant Examiner* — Robert Eom
(74) *Attorney, Agent, or Firm* — Knobbe Martens Olson & Bear LLP

(57) ABSTRACT

The technology described herein generally relates to systems for extracting polynucleotides from multiple samples, particularly from biological samples, and additionally to systems that subsequently amplify and detect the extracted polynucleotides. The technology more particularly relates to microfluidic systems that carry out PCR on multiple samples of nucleotides of interest within microfluidic channels, and detect those nucleotides.

35 Claims, 121 Drawing Sheets

(51) Int. Cl.
 *B01L 7/00* (2006.01)
 *B01L 3/00* (2006.01)
 *B01L 9/00* (2006.01)
 *F16K 99/00* (2006.01)
 *G01N 35/00* (2006.01)
 *G01N 35/04* (2006.01)

(52) U.S. Cl.
 CPC .......... *F16K 99/003* (2013.01); *F16K 99/0032* (2013.01); *F16K 99/0044* (2013.01); *F16K 99/0061* (2013.01); *B01L 2200/027* (2013.01); *B01L 2200/10* (2013.01); *B01L 2200/147* (2013.01); *B01L 2200/148* (2013.01); *B01L 2200/16* (2013.01); *B01L 2300/021* (2013.01); *B01L 2300/045* (2013.01); *B01L 2300/0681* (2013.01); *B01L 2300/087* (2013.01); *B01L 2300/0816* (2013.01); *B01L 2300/0867* (2013.01); *B01L 2300/0887* (2013.01); *B01L 2300/1822* (2013.01); *B01L 2300/1827* (2013.01); *B01L 2300/1861* (2013.01); *B01L 2400/0442* (2013.01); *B01L 2400/0481* (2013.01); *B01L 2400/0487* (2013.01); *B01L 2400/0611* (2013.01); *B01L 2400/0677* (2013.01); *B01L 2400/0683* (2013.01); *F16K 2099/0084* (2013.01); *G01N 35/026* (2013.01); *G01N 2035/00881* (2013.01); *G01N 2035/0425* (2013.01); *G01N 2035/0436* (2013.01)

(56) References Cited

U.S. PATENT DOCUMENTS

| | | | |
|---|---|---|---|
| 1,733,401 A | 8/1930 | Lovekin |
| D189,404 S | 12/1960 | Nicolle |
| 3,528,449 A | 9/1970 | Witte et al. |
| 3,813,316 A | 5/1974 | Chakrabarty et al. |
| 3,985,649 A | 10/1976 | Eddelman |
| 4,018,089 A | 4/1977 | Dzula et al. |
| 4,018,652 A | 4/1977 | Lanham et al. |
| 4,038,192 A | 7/1977 | Serur |
| 4,055,395 A | 10/1977 | Honkawa et al. |
| D249,706 S | 9/1978 | Adamski |
| 4,139,005 A | 2/1979 | Dickey |
| D252,157 S | 6/1979 | Kronish et al. |
| D252,341 S | 7/1979 | Thomas |
| D254,687 S | 4/1980 | Fadler et al. |
| 4,212,744 A | 7/1980 | Oota |
| D261,033 S | 9/1981 | Armbruster |
| D261,173 S | 10/1981 | Armbruster |
| 4,301,412 A | 11/1981 | Hill et al. |
| 4,439,526 A | 3/1984 | Columbus |
| 4,457,329 A | 7/1984 | Werley et al. |
| 4,466,740 A | 8/1984 | Kano et al. |
| 4,504,582 A | 3/1985 | Swann |
| 4,522,786 A | 6/1985 | Ebersole |
| D279,817 S | 7/1985 | Chen et al. |
| D282,208 S | 1/1986 | Lowry |
| 4,599,315 A | 7/1986 | Terasaki et al. |
| 4,612,873 A | 9/1986 | Eberle |
| 4,612,959 A | 9/1986 | Costello |
| D288,478 S | 2/1987 | Carlson et al. |
| 4,647,432 A | 3/1987 | Wakatake |
| 4,654,127 A | 3/1987 | Baker et al. |
| 4,673,657 A | 6/1987 | Christian |
| 4,678,752 A | 7/1987 | Thorne et al. |
| 4,683,195 A | 7/1987 | Mullis et al. |
| 4,683,202 A | 7/1987 | Mullis |
| D292,735 S | 11/1987 | Lovborg |
| 4,720,374 A | 1/1988 | Ramachandran |
| 4,724,207 A | 2/1988 | Hou et al. |
| 4,798,693 A | 1/1989 | Mase et al. |
| 4,800,022 A | 1/1989 | Leonard |
| 4,841,786 A | 6/1989 | Schulz |
| D302,294 S | 7/1989 | Hillman |
| 4,871,779 A | 10/1989 | Killat et al. |
| 4,895,650 A | 1/1990 | Wang |
| 4,919,892 A | 4/1990 | Plumb |
| 4,921,809 A | 5/1990 | Shiff et al. |
| 4,935,342 A | 6/1990 | Seligson et al. |
| 4,946,562 A | 8/1990 | Guruswamy |
| 4,949,742 A | 8/1990 | Rando et al. |
| D310,413 S | 9/1990 | Bigler et al. |
| 4,963,498 A | 10/1990 | Hillman |
| 4,967,950 A | 11/1990 | Legg et al. |
| D312,692 S | 12/1990 | Bradley |
| 4,978,502 A | 12/1990 | Dole et al. |
| 4,978,622 A | 12/1990 | Mishell et al. |
| 4,989,626 A | 2/1991 | Takagi et al. |
| 5,001,417 A | 3/1991 | Pumphrey et al. |
| 5,004,583 A | 4/1991 | Guruswamy et al. |
| 5,048,554 A | 9/1991 | Kremer |
| 5,053,199 A | 10/1991 | Keiser et al. |
| 5,060,823 A | 10/1991 | Perlman |
| 5,061,336 A | 10/1991 | Soane |
| 5,064,618 A | 11/1991 | Baker et al. |
| 5,071,531 A | 12/1991 | Soane |
| 5,091,328 A | 2/1992 | Miller |
| D324,426 S | 3/1992 | Fan et al. |
| 5,096,669 A | 3/1992 | Lauks et al. |
| D325,638 S | 4/1992 | Sloat et al. |
| 5,126,002 A | 6/1992 | Iwata et al. |
| 5,126,022 A | 6/1992 | Soane et al. |
| D328,135 S | 7/1992 | Fan et al. |
| D328,794 S | 8/1992 | Frenkel et al. |
| 5,135,627 A | 8/1992 | Soane |
| 5,135,872 A | 8/1992 | Pouletty et al. |
| 5,147,606 A | 9/1992 | Charlton et al. |
| 5,169,512 A | 12/1992 | Wiedenmann et al. |
| D333,522 S | 2/1993 | Gianino |
| 5,186,339 A | 2/1993 | Heissler |
| 5,192,507 A | 3/1993 | Taylor et al. |
| 5,208,163 A | 5/1993 | Charlton et al. |
| 5,217,694 A | 6/1993 | Gibler et al. |
| 5,223,226 A | 6/1993 | Wittmer et al. |
| D338,275 S | 8/1993 | Fischer et al. |
| 5,250,263 A | 10/1993 | Manz |
| 5,252,743 A | 10/1993 | Barrett et al. |
| 5,256,376 A | 10/1993 | Callan et al. |
| 5,275,787 A | 1/1994 | Yuguchi et al. |
| 5,282,950 A | 2/1994 | Dietze et al. |
| 5,296,375 A | 3/1994 | Kricka et al. |
| 5,304,477 A | 4/1994 | Nagoh et al. |
| 5,304,487 A | 4/1994 | Wilding et al. |
| D347,478 S | 5/1994 | Pinkney |
| 5,311,896 A | 5/1994 | Kaartinen et al. |
| 5,311,996 A | 5/1994 | Duffy et al. |
| 5,316,727 A | 5/1994 | Suzuki et al. |
| 5,327,038 A | 7/1994 | Culp |
| 5,339,486 A | 8/1994 | Persic, Jr. |
| D351,475 S | 10/1994 | Gerber |
| D351,913 S | 10/1994 | Hieb et al. |
| 5,364,591 A | 11/1994 | Green et al. |
| 5,372,946 A | 12/1994 | Cusak et al. |
| 5,374,395 A | 12/1994 | Robinson |
| 5,389,339 A | 2/1995 | Petschek et al. |
| D356,232 S | 3/1995 | Armstrong et al. |
| 5,397,709 A | 3/1995 | Berndt |
| 5,401,465 A | 3/1995 | Smethers et al. |
| 5,411,708 A | 5/1995 | Moscetta et al. |
| 5,414,245 A | 5/1995 | Hackleman |
| 5,416,000 A | 5/1995 | Allen et al. |
| 5,422,271 A | 6/1995 | Chen et al. |
| 5,422,284 A | 6/1995 | Lau |
| 5,427,946 A | 6/1995 | Kricka et al. |
| 5,443,791 A | 8/1995 | Cathcart et al. |
| 5,474,796 A | 12/1995 | Brennan |
| D366,116 S | 1/1996 | Biskupski |
| 5,486,335 A | 1/1996 | Wilding et al. |
| 5,494,639 A | 2/1996 | Grzegorzewski |
| 5,498,392 A | 3/1996 | Wilding et al. |
| 5,503,803 A | 4/1996 | Brown |
| 5,516,410 A | 5/1996 | Schneider et al. |

(56) References Cited

U.S. PATENT DOCUMENTS

| | | |
|---|---|---|
| 5,519,635 A | 5/1996 | Miyake et al. |
| 5,529,677 A | 6/1996 | Schneider et al. |
| 5,559,432 A | 9/1996 | Logue |
| 5,565,171 A | 10/1996 | Dovichi et al. |
| 5,569,364 A | 10/1996 | Hooper et al. |
| 5,578,270 A | 11/1996 | Reichler et al. |
| 5,578,818 A | 11/1996 | Kain et al. |
| 5,579,928 A | 12/1996 | Anukwuem |
| 5,580,523 A | 12/1996 | Bard |
| 5,582,884 A | 12/1996 | Ball et al. |
| 5,585,069 A | 12/1996 | Zanzucchi et al. |
| 5,585,089 A | 12/1996 | Queen et al. |
| 5,585,242 A | 12/1996 | Bouma et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,595,708 A | 1/1997 | Berndt |
| 5,599,432 A | 2/1997 | Manz et al. |
| 5,599,503 A | 2/1997 | Manz et al. |
| 5,599,667 A | 2/1997 | Arnold, Jr. et al. |
| 5,601,727 A | 2/1997 | Bormann et al. |
| 5,603,351 A | 2/1997 | Cherukuri et al. |
| 5,605,662 A | 2/1997 | Heller et al. |
| D378,782 S | 4/1997 | LaBarbera et al. |
| 5,628,890 A | 5/1997 | Carter et al. |
| 5,630,920 A | 5/1997 | Friese et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,643,738 A | 7/1997 | Zanzucchi et al. |
| 5,646,039 A | 7/1997 | Northrup et al. |
| 5,646,049 A | 7/1997 | Tayi |
| 5,647,994 A | 7/1997 | Tuunanen et al. |
| 5,651,839 A | 7/1997 | Rauf |
| 5,652,141 A | 7/1997 | Henco et al. |
| 5,652,149 A | 7/1997 | Mileaf et al. |
| D382,346 S | 8/1997 | Buhler et al. |
| D382,647 S | 8/1997 | Staples et al. |
| 5,667,976 A | 9/1997 | Van Ness et al. |
| 5,671,303 A | 9/1997 | Shieh et al. |
| 5,674,394 A | 10/1997 | Whitmore |
| 5,674,742 A | 10/1997 | Northrup et al. |
| 5,681,484 A | 10/1997 | Zanzucchi et al. |
| 5,681,529 A | 10/1997 | Taguchi et al. |
| 5,683,657 A | 11/1997 | Mian |
| 5,699,157 A | 12/1997 | Parce |
| 5,700,637 A | 12/1997 | Southern |
| 5,705,813 A | 1/1998 | Apffel et al. |
| 5,726,026 A | 3/1998 | Wilding et al. |
| 5,726,404 A | 3/1998 | Brody |
| 5,726,944 A | 3/1998 | Taft et al. |
| 5,731,212 A | 3/1998 | Gavin et al. |
| 5,744,366 A | 4/1998 | Kricka et al. |
| 5,747,666 A | 5/1998 | Willis |
| 5,750,015 A | 5/1998 | Soane et al. |
| 5,755,942 A | 5/1998 | Zanzucchi et al. |
| 5,763,262 A | 6/1998 | Wong et al. |
| 5,770,029 A | 6/1998 | Nelson et al. |
| 5,770,388 A | 6/1998 | Vorpahl |
| 5,772,966 A | 6/1998 | Maracas et al. |
| 5,779,868 A | 7/1998 | Parce et al. |
| 5,787,032 A | 7/1998 | Heller et al. |
| 5,788,814 A | 8/1998 | Sun et al. |
| 5,800,600 A | 9/1998 | Lima-Marques et al. |
| 5,800,690 A | 9/1998 | Chow et al. |
| 5,804,436 A | 9/1998 | Okun et al. |
| D399,959 S | 10/1998 | Prokop et al. |
| 5,827,481 A | 10/1998 | Bente et al. |
| 5,842,106 A | 11/1998 | Thaler et al. |
| 5,842,787 A | 12/1998 | Kopf-Sill et al. |
| 5,846,396 A | 12/1998 | Zanzucchi et al. |
| 5,846,493 A | 12/1998 | Bankier et al. |
| 5,849,208 A | 12/1998 | Hayes et al. |
| 5,849,486 A | 12/1998 | Heller et al. |
| 5,849,489 A | 12/1998 | Heller |
| 5,849,598 A | 12/1998 | Wilson et al. |
| 5,852,495 A | 12/1998 | Parce |
| 5,856,174 A | 1/1999 | Lipshutz et al. |
| 5,858,187 A | 1/1999 | Ramsey et al. |
| 5,858,188 A | 1/1999 | Soane et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |
| 5,869,244 A | 2/1999 | Martin et al. |
| 5,872,010 A | 2/1999 | Karger et al. |
| 5,872,481 A | 2/1999 | Sevic et al. |
| 5,872,623 A | 2/1999 | Stabile et al. |
| 5,874,046 A | 2/1999 | Megerle |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,432 A | 3/1999 | Hooper et al. |
| 5,885,470 A | 3/1999 | Parce et al. |
| 5,895,762 A | 4/1999 | Greenfield et al. |
| 5,900,130 A | 5/1999 | Benregnu et al. |
| 5,912,124 A | 6/1999 | Kumar |
| 5,912,134 A | 6/1999 | Shartle |
| 5,916,522 A | 6/1999 | Boyd et al. |
| 5,916,776 A | 6/1999 | Kumar |
| 5,919,646 A | 7/1999 | Okun et al. |
| 5,919,711 A | 7/1999 | Boyd et al. |
| 5,922,591 A | 7/1999 | Anderson et al. |
| 5,927,547 A | 7/1999 | Papen et al. |
| 5,928,880 A | 7/1999 | Wilding et al. |
| 5,929,208 A | 7/1999 | Heller et al. |
| D413,391 S | 8/1999 | Lapeus et al. |
| 5,932,799 A | 8/1999 | Moles |
| 5,935,401 A | 8/1999 | Amigo |
| 5,939,291 A | 8/1999 | Loewy et al. |
| 5,942,443 A | 8/1999 | Parce et al. |
| D413,677 S | 9/1999 | Dumitrescu et al. |
| 5,948,227 A | 9/1999 | Dubrow |
| 5,955,028 A | 9/1999 | Chow |
| 5,955,029 A | 9/1999 | Wilding et al. |
| 5,957,579 A | 9/1999 | Kopf-Sill et al. |
| 5,958,203 A | 9/1999 | Parce et al. |
| 5,958,694 A | 9/1999 | Nikiforov |
| 5,959,221 A | 9/1999 | Boyd et al. |
| 5,959,291 A | 9/1999 | Jensen |
| 5,964,995 A | 10/1999 | Nikiforov et al. |
| 5,964,997 A | 10/1999 | McBride |
| 5,965,001 A | 10/1999 | Chow et al. |
| 5,965,410 A | 10/1999 | Chow et al. |
| 5,965,886 A | 10/1999 | Sauer et al. |
| 5,968,745 A | 10/1999 | Thorp et al. |
| 5,972,187 A | 10/1999 | Parce et al. |
| 5,973,138 A | 10/1999 | Collis |
| D417,009 S | 11/1999 | Boyd |
| 5,976,336 A | 11/1999 | Dubrow et al. |
| 5,980,704 A | 11/1999 | Cherukuri et al. |
| 5,980,719 A | 11/1999 | Cherukuri et al. |
| 5,981,735 A | 11/1999 | Thatcher et al. |
| 5,989,402 A | 11/1999 | Chow et al. |
| 5,992,820 A | 11/1999 | Fare et al. |
| 5,993,611 A | 11/1999 | Moroney, III et al. |
| 5,993,750 A | 11/1999 | Ghosh et al. |
| 5,997,708 A | 12/1999 | Craig |
| 6,001,229 A | 12/1999 | Ramsey |
| 6,001,231 A | 12/1999 | Kopf-Sill |
| 6,001,307 A | 12/1999 | Naka et al. |
| 6,004,515 A | 12/1999 | Parce et al. |
| 6,007,690 A | 12/1999 | Nelson et al. |
| 6,010,607 A | 1/2000 | Ramsey |
| 6,010,608 A | 1/2000 | Ramsey |
| 6,010,627 A | 1/2000 | Hood, III |
| 6,012,902 A | 1/2000 | Parce |
| D420,747 S | 2/2000 | Dumitrescu et al. |
| D421,130 S | 2/2000 | Cohen et al. |

(56) References Cited

U.S. PATENT DOCUMENTS

| | | | |
|---|---|---|---|
| 6,024,920 A | 2/2000 | Cunanan |
| D421,653 S | 3/2000 | Purcell |
| 6,033,546 A | 3/2000 | Ramsey |
| 6,043,080 A | 3/2000 | Lipshutz et al. |
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,062,261 A | 5/2000 | Jacobson et al. |
| 6,063,341 A | 5/2000 | Fassbind et al. |
| 6,063,589 A | 5/2000 | Kellogg et al. |
| 6,068,752 A | 5/2000 | Dubrow et al. |
| 6,071,478 A | 6/2000 | Chow |
| 6,074,725 A | 6/2000 | Kennedy |
| 6,074,827 A | 6/2000 | Nelson et al. |
| D428,497 S | 7/2000 | Lapeus et al. |
| 6,086,740 A | 7/2000 | Kennedy |
| 6,096,509 A | 8/2000 | Okun et al. |
| 6,100,541 A | 8/2000 | Nagle et al. |
| 6,102,897 A | 8/2000 | Lang |
| 6,103,537 A | 8/2000 | Ullman et al. |
| 6,106,685 A | 8/2000 | McBride et al. |
| 6,110,343 A | 8/2000 | Ramsey et al. |
| 6,123,205 A | 9/2000 | Dumitrescu et al. |
| 6,123,798 A | 9/2000 | Gandhi et al. |
| 6,130,098 A | 10/2000 | Handique et al. |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,149,787 A | 11/2000 | Chow et al. |
| 6,156,199 A | 12/2000 | Zuk, Jr. |
| 6,158,269 A | 12/2000 | Dorenkott et al. |
| 6,167,910 B1 | 1/2001 | Chow |
| 6,168,948 B1 | 1/2001 | Anderson et al. |
| 6,171,850 B1 | 1/2001 | Nagle et al. |
| 6,174,675 B1 | 1/2001 | Chow et al. |
| 6,180,950 B1 | 1/2001 | Olsen |
| D438,311 S | 2/2001 | Yamanishi et al. |
| 6,190,619 B1 | 2/2001 | Kilcoin et al. |
| D438,632 S | 3/2001 | Miller |
| D438,633 S | 3/2001 | Miller |
| D439,673 S | 3/2001 | Brophy et al. |
| 6,197,595 B1 | 3/2001 | Anderson et al. |
| 6,211,989 B1 | 4/2001 | Wulf et al. |
| 6,213,151 B1 | 4/2001 | Jacobson et al. |
| 6,221,600 B1 | 4/2001 | MacLeod et al. |
| 6,228,635 B1 | 5/2001 | Armstrong et al. |
| 6,232,072 B1 | 5/2001 | Fisher |
| 6,235,175 B1 | 5/2001 | Dubrow et al. |
| 6,235,313 B1 | 5/2001 | Mathiowitz et al. |
| 6,235,471 B1 | 5/2001 | Knapp et al. |
| 6,236,456 B1 | 5/2001 | Giebeler et al. |
| 6,236,581 B1 | 5/2001 | Lines et al. |
| 6,238,626 B1 | 5/2001 | Higuchi et al. |
| 6,251,343 B1 | 6/2001 | Dubrow et al. |
| 6,254,826 B1 * | 7/2001 | Acosta et al. ................... 422/65 |
| 6,259,635 B1 | 7/2001 | Torelli et al. |
| 6,261,431 B1 | 7/2001 | Mathies et al. |
| 6,267,858 B1 | 7/2001 | Parce et al. |
| D446,306 S | 8/2001 | Ochi et al. |
| 6,271,021 B1 | 8/2001 | Burns et al. |
| 6,274,089 B1 | 8/2001 | Chow et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,287,254 B1 | 9/2001 | Dodds |
| 6,287,774 B1 | 9/2001 | Nikiforov |
| 6,291,248 B1 | 9/2001 | Haj-Ahmad |
| 6,294,063 B1 | 9/2001 | Becker et al. |
| 6,302,134 B1 | 10/2001 | Kellogg et al. |
| 6,302,304 B1 | 10/2001 | Spencer |
| 6,303,343 B1 | 10/2001 | Kopf-sill |
| 6,306,273 B1 | 10/2001 | Wainright et al. |
| 6,306,590 B1 | 10/2001 | Mehta et al. |
| 6,316,774 B1 | 11/2001 | Giebeler et al. |
| 6,319,469 B1 | 11/2001 | Mian et al. |
| 6,322,683 B1 | 11/2001 | Wolk et al. |
| 6,326,083 B1 | 12/2001 | Yang et al. |
| 6,326,147 B1 | 12/2001 | Oldham et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-sill et al. |
| 6,366,924 B1 | 4/2002 | Parce |
| 6,368,561 B1 | 4/2002 | Rutishauser et al. |
| 6,368,871 B1 | 4/2002 | Christel et al. |
| 6,370,206 B1 | 4/2002 | Schenk |
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,382,254 B1 | 5/2002 | Yang et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Majer et al. |
| 6,401,552 B1 | 6/2002 | Elkins |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-sill |
| 6,425,972 B1 | 7/2002 | Mcreynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,064 B1 | 9/2002 | Vo-Dinh et al. |
| 6,453,928 B1 | 9/2002 | Kaplan et al. |
| 6,465,257 B1 | 10/2002 | Parce et al. |
| 6,468,761 B2 | 10/2002 | Yang et al. |
| 6,472,141 B2 | 10/2002 | Nikiforov |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,193 B1 * | 1/2003 | Tajima ......................... 422/100 |
| 6,511,853 B1 | 1/2003 | Kopf-sill et al. |
| D470,595 S | 2/2003 | Crisanti et al. |
| 6,515,753 B2 | 2/2003 | Maher |
| 6,517,783 B2 | 2/2003 | Horner et al. |
| 6,520,197 B2 | 2/2003 | Deshmukh et al. |
| 6,521,188 B1 | 2/2003 | Webster |
| 6,524,456 B1 | 2/2003 | Ramsey et al. |
| 6,524,790 B1 | 2/2003 | Kopf-sill et al. |
| D472,324 S | 3/2003 | Rumore et al. |
| 6,534,295 B2 | 3/2003 | Tai et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |

(56) References Cited

U.S. PATENT DOCUMENTS

| | | | |
|---|---|---|---|
| D474,280 S | 5/2003 | Niedbala et al. | |
| 6,558,916 B2 | 5/2003 | Veerapandian et al. | |
| 6,558,945 B1 | 5/2003 | Kao | |
| 6,569,607 B2 | 5/2003 | Mcreynolds | |
| 6,572,830 B1 | 6/2003 | Burdon et al. | |
| 6,575,188 B2 | 6/2003 | Parunak | |
| 6,576,459 B2 | 6/2003 | Miles et al. | |
| 6,579,453 B1 | 6/2003 | Bächler et al. | |
| 6,589,729 B2 | 7/2003 | Chan et al. | |
| 6,592,821 B1 | 7/2003 | Wada et al. | |
| 6,597,450 B1 | 7/2003 | Andrews et al. | |
| 6,602,474 B1 * | 8/2003 | Tajima | 422/102 |
| 6,613,211 B1 | 9/2003 | Mccormick et al. | |
| 6,613,512 B1 | 9/2003 | Kopf-sill et al. | |
| 6,613,580 B1 | 9/2003 | Chow et al. | |
| 6,613,581 B1 | 9/2003 | Wada et al. | |
| 6,614,030 B2 | 9/2003 | Maher et al. | |
| 6,620,625 B2 | 9/2003 | Wolk et al. | |
| 6,623,860 B2 | 9/2003 | Hu et al. | |
| 6,627,406 B1 | 9/2003 | Singh et al. | |
| D480,814 S | 10/2003 | Lafferty et al. | |
| 6,632,655 B1 | 10/2003 | Mehta et al. | |
| 6,633,785 B1 | 10/2003 | Kasahara et al. | |
| D482,796 S | 11/2003 | Oyama et al. | |
| 6,640,981 B2 | 11/2003 | Lafond et al. | |
| 6,649,358 B1 | 11/2003 | Parce et al. | |
| 6,664,104 B2 | 12/2003 | Pourahmadi et al. | |
| 6,669,831 B2 | 12/2003 | Chow et al. | |
| 6,670,153 B2 | 12/2003 | Stern | |
| D484,989 S | 1/2004 | Gebrian | |
| 6,681,616 B2 | 1/2004 | Spaid et al. | |
| 6,681,788 B2 | 1/2004 | Parce et al. | |
| 6,685,813 B2 | 2/2004 | Williams et al. | |
| 6,692,700 B2 | 2/2004 | Handique | |
| 6,695,009 B2 | 2/2004 | Chien et al. | |
| 6,706,519 B1 | 3/2004 | Kellogg et al. | |
| 6,720,148 B1 | 4/2004 | Nikiforov | |
| 6,730,206 B2 | 5/2004 | Ricco et al. | |
| 6,733,645 B1 | 5/2004 | Chow | |
| 6,734,401 B2 | 5/2004 | Bedingham et al. | |
| 6,737,026 B1 | 5/2004 | Bergh et al. | |
| 6,740,518 B1 | 5/2004 | Duong et al. | |
| D491,272 S | 6/2004 | Alden et al. | |
| D491,273 S | 6/2004 | Biegler et al. | |
| D491,276 S | 6/2004 | Langille | |
| 6,750,661 B2 | 6/2004 | Brooks et al. | |
| 6,752,966 B1 | 6/2004 | Chazan | |
| 6,756,019 B1 | 6/2004 | Dubrow et al. | |
| 6,764,859 B1 | 7/2004 | Kreuwel et al. | |
| 6,766,817 B2 | 7/2004 | da Silva | |
| 6,773,567 B1 | 8/2004 | Wolk | |
| 6,777,184 B2 | 8/2004 | Nikiforov et al. | |
| 6,783,962 B1 | 8/2004 | Olander et al. | |
| D495,805 S | 9/2004 | Lea et al. | |
| 6,787,015 B2 | 9/2004 | Lackritz et al. | |
| 6,787,016 B2 | 9/2004 | Tan et al. | |
| 6,787,111 B2 | 9/2004 | Roach et al. | |
| 6,790,328 B2 | 9/2004 | Jacobson et al. | |
| 6,790,330 B2 | 9/2004 | Gascoyne et al. | |
| 6,811,668 B1 | 11/2004 | Berndt et al. | |
| 6,818,113 B2 | 11/2004 | Williams et al. | |
| 6,819,027 B2 | 11/2004 | Saraf | |
| 6,824,663 B1 | 11/2004 | Boone | |
| D499,813 S | 12/2004 | Wu | |
| D500,142 S | 12/2004 | Crisanti et al. | |
| D500,363 S * | 12/2004 | Fanning et al. | D24/229 |
| 6,827,831 B1 | 12/2004 | Chow et al. | |
| 6,827,906 B1 | 12/2004 | Bjornson et al. | |
| 6,838,156 B1 | 1/2005 | Neyer et al. | |
| 6,838,680 B2 | 1/2005 | Maher et al. | |
| 6,852,287 B2 | 2/2005 | Ganesan | |
| 6,858,185 B1 | 2/2005 | Kopf-sill et al. | |
| 6,859,698 B2 | 2/2005 | Schmeisser | |
| 6,861,035 B2 | 3/2005 | Pham et al. | |
| 6,878,540 B2 | 4/2005 | Pourahmadi et al. | |
| 6,878,755 B2 | 4/2005 | Singh et al. | |
| 6,884,628 B2 | 4/2005 | Hubbell et al. | |
| 6,887,693 B2 | 5/2005 | McMillan et al. | |
| 6,893,879 B2 | 5/2005 | Petersen et al. | |
| 6,900,889 B2 | 5/2005 | Bjornson et al. | |
| 6,905,583 B2 | 6/2005 | Wainright et al. | |
| 6,905,612 B2 | 6/2005 | Dorian et al. | |
| 6,906,797 B1 | 6/2005 | Kao et al. | |
| 6,908,594 B1 | 6/2005 | Schaevitz et al. | |
| 6,911,183 B1 | 6/2005 | Handique et al. | |
| 6,914,137 B2 | 7/2005 | Baker | |
| 6,915,679 B2 | 7/2005 | Chien et al. | |
| 6,918,404 B2 | 7/2005 | da Silva | |
| D508,999 S | 8/2005 | Fanning et al. | |
| 6,939,451 B2 | 9/2005 | Zhao et al. | |
| 6,942,771 B1 | 9/2005 | Kayyem | |
| 6,958,392 B2 | 10/2005 | Fomovskaia et al. | |
| D512,155 S | 11/2005 | Matsumoto | |
| 6,964,747 B2 | 11/2005 | Banerjee et al. | |
| 6,977,163 B1 | 12/2005 | Mehta | |
| 6,984,516 B2 | 1/2006 | Briscoe et al. | |
| D515,707 S | 2/2006 | Sinohara et al. | |
| D516,221 S | 2/2006 | Wohlstadter et al. | |
| 7,001,853 B1 | 2/2006 | Brown et al. | |
| 7,004,184 B2 | 2/2006 | Handique et al. | |
| D517,554 S | 3/2006 | Yanagisawa et al. | |
| 7,010,391 B2 | 3/2006 | Handique et al. | |
| 7,023,007 B2 | 4/2006 | Gallagher | |
| 7,024,281 B1 | 4/2006 | Unno | |
| 7,036,667 B2 | 5/2006 | Greenstein et al. | |
| 7,037,416 B2 | 5/2006 | Parce et al. | |
| 7,038,472 B1 | 5/2006 | Chien | |
| 7,039,527 B2 | 5/2006 | Tripathi et al. | |
| 7,040,144 B2 | 5/2006 | Spaid et al. | |
| 7,049,558 B2 | 5/2006 | Baer et al. | |
| D523,153 S | 6/2006 | Akashi et al. | |
| 7,055,695 B2 | 6/2006 | Greenstein et al. | |
| 7,060,171 B1 | 6/2006 | Nikiforov et al. | |
| 7,066,586 B2 | 6/2006 | da Silva | |
| 7,069,952 B1 | 7/2006 | Mcreynolds et al. | |
| 7,099,778 B2 | 8/2006 | Chien | |
| D528,215 S | 9/2006 | Malmsater | |
| 7,101,467 B2 | 9/2006 | Spaid | |
| 7,105,304 B1 | 9/2006 | Nikiforov et al. | |
| D531,321 S | 10/2006 | Godfrey et al. | |
| 7,118,910 B2 | 10/2006 | Unger et al. | |
| 7,138,032 B2 | 11/2006 | Gandhi et al. | |
| D534,280 S | 12/2006 | Gomm et al. | |
| 7,148,043 B2 | 12/2006 | Kordunsky et al. | |
| 7,150,814 B1 | 12/2006 | Parce et al. | |
| 7,150,999 B1 | 12/2006 | Shuck | |
| D535,403 S | 1/2007 | Isozaki et al. | |
| 7,160,423 B2 | 1/2007 | Chien et al. | |
| 7,161,356 B1 | 1/2007 | Chien | |
| 7,169,277 B2 | 1/2007 | Ausserer et al. | |
| 7,169,618 B2 | 1/2007 | Skould | |
| D537,951 S | 3/2007 | Okamoto et al. | |
| D538,436 S | 3/2007 | Patadia et al. | |
| 7,192,557 B2 | 3/2007 | Wu et al. | |
| 7,195,986 B1 | 3/2007 | Bousse et al. | |
| 7,208,125 B1 | 4/2007 | Dong | |
| 7,235,406 B1 | 6/2007 | Woudenberg et al. | |
| 7,247,274 B1 | 7/2007 | Chow | |
| D548,841 S | 8/2007 | Brownell et al. | |
| D549,827 S | 8/2007 | Maeno et al. | |
| 7,252,928 B1 | 8/2007 | Hafeman et al. | |
| 7,270,786 B2 | 9/2007 | Parunak et al. | |
| D554,069 S | 10/2007 | Bolotin et al. | |
| D554,070 S | 10/2007 | Bolotin et al. | |
| 7,276,208 B2 | 10/2007 | Sevigny et al. | |
| 7,276,330 B2 | 10/2007 | Chow et al. | |
| 7,288,228 B2 | 10/2007 | Lefebvre | |
| D556,914 S | 12/2007 | Okamoto et al. | |
| 7,303,727 B1 | 12/2007 | Dubrow et al. | |
| D559,995 S | 1/2008 | Handique et al. | |
| 7,323,140 B2 | 1/2008 | Handique et al. | |
| 7,332,130 B2 | 2/2008 | Handique | |
| 7,338,760 B2 | 3/2008 | Gong et al. | |
| D566,291 S | 4/2008 | Parunak et al. | |

(56) References Cited

U.S. PATENT DOCUMENTS

| | | |
|---|---|---|
| 7,351,377 B2 | 4/2008 | Chazan et al. |
| D569,526 S | 5/2008 | Duffy et al. |
| 7,374,949 B2 | 5/2008 | Kuriger |
| 7,390,460 B2 | 6/2008 | Osawa et al. |
| 7,419,784 B2 | 9/2008 | Dubrow et al. |
| 7,422,669 B2 | 9/2008 | Jacobson et al. |
| 7,440,684 B2 | 10/2008 | Spaid et al. |
| 7,476,313 B2 | 1/2009 | Siddiqi |
| 7,494,577 B2 | 2/2009 | Williams et al. |
| 7,494,770 B2 | 2/2009 | Wilding et al. |
| 7,514,046 B2 | 4/2009 | Kechagia et al. |
| 7,518,726 B2 | 4/2009 | Rulison et al. |
| 7,521,186 B2 | 4/2009 | Burd Mehta |
| 7,527,769 B2 | 5/2009 | Bunch et al. |
| 7,553,671 B2 | 6/2009 | Sinclair et al. |
| D596,312 S | 7/2009 | Giraud et al. |
| 7,595,197 B2 | 9/2009 | Brasseur |
| 7,604,938 B2 | 10/2009 | Takahashi et al. |
| 7,635,588 B2 | 12/2009 | King et al. |
| 7,645,581 B2 | 1/2010 | Knapp et al. |
| 7,670,559 B2 | 3/2010 | Chien et al. |
| 7,674,431 B2 | 3/2010 | Ganesan |
| 7,704,735 B2 | 4/2010 | Facer et al. |
| 7,723,123 B1 | 5/2010 | Murphy et al. |
| D618,820 S | 6/2010 | Wilson et al. |
| 7,727,371 B2 | 6/2010 | Kennedy et al. |
| 7,727,477 B2 | 6/2010 | Boronkay et al. |
| D621,060 S | 8/2010 | Handique |
| 7,867,776 B2 | 1/2011 | Kennedy et al. |
| 7,892,819 B2 | 2/2011 | Wilding et al. |
| D637,737 S | 5/2011 | Wilson et al. |
| 7,998,708 B2 | 8/2011 | Handique et al. |
| 8,088,616 B2 | 1/2012 | Handique |
| 8,105,783 B2 | 1/2012 | Handique |
| 8,110,158 B2 | 2/2012 | Handique |
| 8,133,671 B2 | 3/2012 | Williams et al. |
| 8,182,763 B2 | 5/2012 | Duffy et al. |
| 8,273,308 B2 | 9/2012 | Handique et al. |
| D669,597 S | 10/2012 | Cavada et al. |
| 8,287,820 B2 | 10/2012 | Williams et al. |
| 8,323,584 B2 | 12/2012 | Ganesan |
| 8,323,900 B2 | 12/2012 | Handique et al. |
| 8,324,372 B2 | 12/2012 | Brahmasandra et al. |
| 8,415,103 B2 | 4/2013 | Handique |
| 8,420,015 B2 | 4/2013 | Ganesan et al. |
| 8,440,149 B2 | 5/2013 | Handique |
| 8,470,586 B2 | 6/2013 | Wu et al. |
| 8,473,104 B2 | 6/2013 | Handique et al. |
| D692,162 S | 10/2013 | Lentz et al. |
| 8,679,831 B2 | 3/2014 | Handique et al. |
| 8,685,341 B2 | 4/2014 | Ganesan |
| 8,703,069 B2 | 4/2014 | Handique et al. |
| 8,709,787 B2 | 4/2014 | Handique |
| 8,710,211 B2 | 4/2014 | Brahmasandra et al. |
| 8,734,733 B2 | 5/2014 | Handique |
| 8,765,076 B2 | 7/2014 | Handique et al. |
| 8,852,862 B2 | 10/2014 | Wu et al. |
| 8,883,490 B2 | 11/2014 | Handique et al. |
| 8,894,947 B2 | 11/2014 | Ganesan et al. |
| 8,895,311 B1 | 11/2014 | Handique et al. |
| 2001/0012492 A1 | 8/2001 | Acosta et al. |
| 2001/0021355 A1 | 9/2001 | Baugh et al. |
| 2001/0023848 A1 | 9/2001 | Gjerde et al. |
| 2001/0038450 A1 | 11/2001 | McCaffrey et al. |
| 2001/0046702 A1 | 11/2001 | Schembri |
| 2001/0048899 A1 | 12/2001 | Marouiss et al. |
| 2001/0055765 A1 | 12/2001 | O'Keefe et al. |
| 2002/0001848 A1 | 1/2002 | Bedingham et al. |
| 2002/0008053 A1 | 1/2002 | Hansen et al. |
| 2002/0009015 A1 | 1/2002 | Laugharn, Jr. et al. |
| 2002/0015667 A1 | 2/2002 | Chow |
| 2002/0021983 A1 | 2/2002 | Comte et al. |
| 2002/0037499 A1 | 3/2002 | Quake et al. |
| 2002/0039783 A1 | 4/2002 | McMillan et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0058332 A1 | 5/2002 | Quake et al. |
| 2002/0060156 A1 | 5/2002 | Mathies et al. |
| 2002/0068357 A1 | 6/2002 | Mathies et al. |
| 2002/0141903 A1 | 10/2002 | Parunak et al. |
| 2002/0142471 A1 | 10/2002 | Handique et al. |
| 2002/0143297 A1 | 10/2002 | Francavilla et al. |
| 2002/0143437 A1 | 10/2002 | Handique et al. |
| 2002/0155477 A1 | 10/2002 | Ito |
| 2002/0169518 A1 | 11/2002 | Luoma et al. |
| 2002/0187557 A1 | 12/2002 | Hobbs et al. |
| 2003/0019522 A1 | 1/2003 | Parunak |
| 2003/0022392 A1 | 1/2003 | Hudak |
| 2003/0049174 A1 | 3/2003 | Ganesan |
| 2003/0049833 A1 | 3/2003 | Chen et al. |
| 2003/0064507 A1 | 4/2003 | Gallagher et al. |
| 2003/0070677 A1 | 4/2003 | Handique et al. |
| 2003/0072683 A1 | 4/2003 | Stewart et al. |
| 2003/0073106 A1 | 4/2003 | Johansen et al. |
| 2003/0083686 A1 | 5/2003 | Freeman et al. |
| 2003/0087300 A1 | 5/2003 | Knapp et al. |
| 2003/0096310 A1 | 5/2003 | Hansen et al. |
| 2003/0127327 A1 | 7/2003 | Kurnik |
| 2003/0136679 A1 | 7/2003 | Bohn et al. |
| 2003/0186295 A1 | 10/2003 | Colin et al. |
| 2003/0190608 A1 | 10/2003 | Blackburn et al. |
| 2003/0199081 A1 | 10/2003 | Wilding et al. |
| 2003/0211517 A1 | 11/2003 | Carulli et al. |
| 2004/0014202 A1 | 1/2004 | King et al. |
| 2004/0014238 A1 | 1/2004 | Krug et al. |
| 2004/0018119 A1 | 1/2004 | Massaro |
| 2004/0022689 A1 | 2/2004 | Wulf et al. |
| 2004/0029258 A1 | 2/2004 | Heaney et al. |
| 2004/0029260 A1 | 2/2004 | Hansen et al. |
| 2004/0037739 A1 | 2/2004 | McNeely et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0072375 A1 | 4/2004 | Gjerde et al. |
| 2004/0086427 A1 | 5/2004 | Childers et al. |
| 2004/0086956 A1 | 5/2004 | Bachur, Jr. |
| 2004/0141887 A1 | 7/2004 | Mainquist et al. |
| 2004/0151629 A1 | 8/2004 | Pease et al. |
| 2004/0157220 A1 | 8/2004 | Kurnool et al. |
| 2004/0161788 A1 | 8/2004 | Chen et al. |
| 2004/0189311 A1 | 9/2004 | Glezer et al. |
| 2004/0200909 A1 | 10/2004 | McMillan et al. |
| 2004/0209331 A1 | 10/2004 | Ririe |
| 2004/0209354 A1 | 10/2004 | Mathies et al. |
| 2004/0219070 A1 | 11/2004 | Handique |
| 2004/0235154 A1 | 11/2004 | Oh et al. |
| 2004/0240097 A1 | 12/2004 | Evans |
| 2005/0009174 A1 | 1/2005 | Nikiforov et al. |
| 2005/0013737 A1 | 1/2005 | Chow et al. |
| 2005/0041525 A1 | 2/2005 | Pugia et al. |
| 2005/0042639 A1 | 2/2005 | Knapp et al. |
| 2005/0048540 A1 | 3/2005 | Inami et al. |
| 2005/0058574 A1 | 3/2005 | Bysouth et al. |
| 2005/0058577 A1 | 3/2005 | Micklash et al. |
| 2005/0069898 A1 | 3/2005 | Moon et al. |
| 2005/0084424 A1 | 4/2005 | Ganesan et al. |
| 2005/0106066 A1 | 5/2005 | Saltsman et al. |
| 2005/0121324 A1 | 6/2005 | Park et al. |
| 2005/0129580 A1 | 6/2005 | Swinehart et al. |
| 2005/0133370 A1 | 6/2005 | Park et al. |
| 2005/0135655 A1 | 6/2005 | Kopf-sill et al. |
| 2005/0142036 A1 | 6/2005 | Kim et al. |
| 2005/0152808 A1 | 7/2005 | Ganesan |
| 2005/0170362 A1 | 8/2005 | Wada et al. |
| 2005/0186585 A1 | 8/2005 | Juncosa et al. |
| 2005/0202470 A1 | 9/2005 | Sundberg et al. |
| 2005/0202504 A1 | 9/2005 | Anderson et al. |
| 2005/0208676 A1 | 9/2005 | Kahatt |
| 2005/0214172 A1 | 9/2005 | Burgisser |
| 2005/0220675 A1 | 10/2005 | Reed et al. |
| 2005/0227269 A1 | 10/2005 | Lloyd et al. |
| 2005/0233370 A1 | 10/2005 | Ammann et al. |
| 2005/0238545 A1 | 10/2005 | Parce et al. |

(56) References Cited

U.S. PATENT DOCUMENTS

| | | |
|---|---|---|
| 2005/0272079 A1 | 12/2005 | Burns et al. |
| 2006/0041058 A1 | 2/2006 | Yin et al. |
| 2006/0057039 A1 | 3/2006 | Morse et al. |
| 2006/0057629 A1 | 3/2006 | Kim |
| 2006/0062696 A1 | 3/2006 | Chow et al. |
| 2006/0094108 A1 | 5/2006 | Yoder et al. |
| 2006/0113190 A1 | 6/2006 | Kurnik |
| 2006/0133965 A1* | 6/2006 | Tajima et al. ............ 422/100 |
| 2006/0134790 A1 | 6/2006 | Tanaka et al. |
| 2006/0148063 A1 | 7/2006 | Fauzzi et al. |
| 2006/0165558 A1 | 7/2006 | Witty et al. |
| 2006/0165559 A1 | 7/2006 | Greenstein et al. |
| 2006/0166233 A1 | 7/2006 | Wu et al. |
| 2006/0177376 A1 | 8/2006 | Tomalia et al. |
| 2006/0177855 A1 | 8/2006 | Utermohlen et al. |
| 2006/0183216 A1 | 8/2006 | Handique |
| 2006/0201887 A1 | 9/2006 | Siddiqi |
| 2006/0207944 A1 | 9/2006 | Siddiqi |
| 2006/0210435 A1 | 9/2006 | Alavie et al. |
| 2006/0246493 A1 | 11/2006 | Jensen et al. |
| 2006/0246533 A1 | 11/2006 | Fathollahi et al. |
| 2006/0269961 A1 | 11/2006 | Fukushima et al. |
| 2007/0004028 A1 | 1/2007 | Lair et al. |
| 2007/0009386 A1 | 1/2007 | Padmanabhan et al. |
| 2007/0020699 A1 | 1/2007 | Carpenter et al. |
| 2007/0026421 A1 | 2/2007 | Sundberg et al. |
| 2007/0042441 A1 | 2/2007 | Masters et al. |
| 2007/0092901 A1 | 4/2007 | Ligler et al. |
| 2007/0098600 A1 | 5/2007 | Kayyem et al. |
| 2007/0099200 A1 | 5/2007 | Chow et al. |
| 2007/0104617 A1 | 5/2007 | Coulling et al. |
| 2007/0154895 A1 | 7/2007 | Spaid et al. |
| 2007/0177147 A1 | 8/2007 | Parce |
| 2007/0178607 A1 | 8/2007 | Prober et al. |
| 2007/0184463 A1 | 8/2007 | Molho et al. |
| 2007/0184547 A1 | 8/2007 | Handique et al. |
| 2007/0196237 A1 | 8/2007 | Neuzil et al. |
| 2007/0196238 A1 | 8/2007 | Kennedy et al. |
| 2007/0199821 A1 | 8/2007 | Chow |
| 2007/0215554 A1 | 9/2007 | Kreuwel et al. |
| 2007/0218459 A1 | 9/2007 | Miller et al. |
| 2007/0231213 A1 | 10/2007 | Prabhu et al. |
| 2007/0243626 A1 | 10/2007 | Windeyer et al. |
| 2007/0261479 A1 | 11/2007 | Spaid et al. |
| 2007/0269861 A1 | 11/2007 | Williams et al. |
| 2007/0292941 A1 | 12/2007 | Handique et al. |
| 2008/0000774 A1 | 1/2008 | Park et al. |
| 2008/0017306 A1 | 1/2008 | Liu et al. |
| 2008/0050804 A1 | 2/2008 | Handique et al. |
| 2008/0056948 A1 | 3/2008 | Dale et al. |
| 2008/0069729 A1 | 3/2008 | McNeely |
| 2008/0075634 A1 | 3/2008 | Herchenbach et al. |
| 2008/0090244 A1 | 4/2008 | Knapp et al. |
| 2008/0095673 A1 | 4/2008 | Xu |
| 2008/0118987 A1 | 5/2008 | Eastwood et al. |
| 2008/0124723 A1 | 5/2008 | Dale et al. |
| 2008/0149840 A1 | 6/2008 | Handique et al. |
| 2008/0160601 A1 | 7/2008 | Handique |
| 2008/0182301 A1 | 7/2008 | Handique et al. |
| 2008/0192254 A1 | 8/2008 | Kim et al. |
| 2008/0226502 A1 | 9/2008 | Jonsmann et al. |
| 2008/0247914 A1 | 10/2008 | Edens et al. |
| 2008/0262213 A1 | 10/2008 | Wu et al. |
| 2009/0047713 A1 | 2/2009 | Handique |
| 2009/0129978 A1 | 5/2009 | Wilson et al. |
| 2009/0130719 A1 | 5/2009 | Handique |
| 2009/0130745 A1 | 5/2009 | Williams et al. |
| 2009/0131650 A1 | 5/2009 | Brahmasandra et al. |
| 2009/0134069 A1 | 5/2009 | Handique |
| 2009/0136385 A1 | 5/2009 | Handique et al. |
| 2009/0136386 A1 | 5/2009 | Duffy et al. |
| 2009/0155123 A1 | 6/2009 | Williams et al. |
| 2009/0189089 A1 | 7/2009 | Bedingham et al. |
| 2009/0221059 A1 | 9/2009 | Williams et al. |
| 2009/0223925 A1 | 9/2009 | Morse et al. |
| 2010/0009351 A1 | 1/2010 | Brahmasandra et al. |
| 2010/0173393 A1 | 7/2010 | Handique et al. |
| 2011/0008825 A1 | 1/2011 | Ingber et al. |
| 2011/0027151 A1 | 2/2011 | Handique et al. |
| 2011/0158865 A1 | 6/2011 | Miller et al. |
| 2011/0207140 A1 | 8/2011 | Handique et al. |
| 2011/0210257 A9 | 9/2011 | Handique et al. |
| 2012/0022695 A1 | 1/2012 | Handique et al. |
| 2012/0085416 A1 | 4/2012 | Ganesan |
| 2012/0122108 A1 | 5/2012 | Handique |
| 2012/0160826 A1 | 6/2012 | Handique |
| 2012/0171759 A1 | 7/2012 | Williams et al. |
| 2012/0183454 A1 | 7/2012 | Handique |
| 2012/0258463 A1 | 10/2012 | Duffy et al. |
| 2013/0037564 A1 | 2/2013 | Williams et al. |
| 2013/0071851 A1 | 3/2013 | Handique et al. |
| 2013/0096292 A1 | 4/2013 | Brahmasandra et al. |
| 2013/0101990 A1 | 4/2013 | Handique et al. |
| 2013/0164832 A1 | 6/2013 | Ganesan et al. |
| 2013/0217013 A1 | 8/2013 | Steel et al. |
| 2013/0217102 A1 | 8/2013 | Ganesan et al. |
| 2013/0251602 A1 | 9/2013 | Handique et al. |
| 2013/0280131 A1 | 10/2013 | Handique et al. |
| 2013/0288358 A1 | 10/2013 | Handique et al. |
| 2014/0030798 A1 | 1/2014 | Wu et al. |
| 2014/0045186 A1 | 2/2014 | Gubatayao et al. |
| 2014/0206088 A1 | 7/2014 | Lentz et al. |
| 2014/0212882 A1 | 7/2014 | Handique et al. |
| 2014/0227710 A1 | 8/2014 | Handique et al. |
| 2014/0297047 A1 | 10/2014 | Ganesan et al. |
| 2014/0323357 A1 | 10/2014 | Handique et al. |
| 2014/0323711 A1 | 10/2014 | Brahmasandra et al. |
| 2014/0329301 A1 | 11/2014 | Handique et al. |
| 2014/0342352 A1 | 11/2014 | Handique et al. |
| 2014/0377850 A1 | 12/2014 | Handique et al. |

FOREIGN PATENT DOCUMENTS

| | | |
|---|---|---|
| DE | 19929734 | 12/1999 |
| DE | 19833293 C1 | 1/2000 |
| EP | 0365828 A2 | 5/1990 |
| EP | 0766256 | 4/1997 |
| EP | 1541237 A2 | 6/2005 |
| EP | 2372367 A1 | 10/2011 |
| FR | 2672301 | 8/1992 |
| FR | 2795426 | 12/2000 |
| JP | 58212921 A | 12/1983 |
| JP | S62-119460 | 5/1987 |
| JP | H01-502319 | 8/1989 |
| JP | 04-053555 U | 5/1992 |
| JP | 06-064156 U | 9/1994 |
| JP | 07-020010 | 1/1995 |
| JP | H07-290706 | 11/1995 |
| JP | H08-122336 | 5/1996 |
| JP | H08-211071 | 8/1996 |
| JP | H08-285859 | 11/1996 |
| JP | H09-325151 | 12/1997 |
| JP | H11-515106 | 12/1999 |
| JP | 2000-275255 | 10/2000 |
| JP | 2001-502319 | 2/2001 |
| JP | 2001-509437 | 7/2001 |
| JP | 3191150 B2 | 7/2001 |
| JP | 2001-515216 | 9/2001 |
| JP | A-2001-527220 | 12/2001 |
| JP | 2002-503331 | 1/2002 |
| JP | 2002-215241 | 7/2002 |
| JP | 2002-544476 | 12/2002 |
| JP | A-2003-500674 | 1/2003 |
| JP | 2003-047839 A | 2/2003 |
| JP | 2003-047840 A | 2/2003 |
| JP | 2003-516125 | 5/2003 |
| JP | 2003-185584 | 7/2003 |
| JP | 2003-299485 | 10/2003 |
| JP | 2003-329693 | 11/2003 |
| JP | 2004-506179 A | 2/2004 |
| JP | 2004-150797 A | 5/2004 |
| JP | 2004-531360 A | 10/2004 |
| JP | 2004-361421 | 12/2004 |
| JP | 2004-536291 | 12/2004 |

(56) References Cited

FOREIGN PATENT DOCUMENTS

| | | |
|---|---|---|
| JP | 2005-009870 | 1/2005 |
| JP | 2005-511264 | 4/2005 |
| JP | 2005-514718 | 5/2005 |
| JP | 2005-518825 | 6/2005 |
| JP | 2005-176613 A | 7/2005 |
| JP | 2005-192554 | 7/2005 |
| JP | A-2005-204661 | 8/2005 |
| JP | 2005-525816 | 9/2005 |
| JP | 2005-291954 A | 10/2005 |
| JP | 2005-532043 | 10/2005 |
| JP | 2005-323519 | 11/2005 |
| JP | 2006-021156 A | 1/2006 |
| JP | 2006-094866 A | 4/2006 |
| JP | 2006-167569 | 6/2006 |
| JP | 2007-074960 | 3/2007 |
| JP | 2007-097477 | 4/2007 |
| JP | 2007-510518 | 4/2007 |
| JP | 2007-514405 A | 6/2007 |
| JP | 2007-178328 | 7/2007 |
| WO | WO 88/06633 | 9/1988 |
| WO | WO 90/12350 | 10/1990 |
| WO | WO 92/05443 | 4/1992 |
| WO | WO 94/11103 | 5/1994 |
| WO | WO 96/04547 | 2/1996 |
| WO | WO 97/05492 | 2/1997 |
| WO | WO 97/21090 | 6/1997 |
| WO | WO 98/00231 | 1/1998 |
| WO | WO 98/22625 | 5/1998 |
| WO | WO 98/49548 | 11/1998 |
| WO | WO 98/53311 | 11/1998 |
| WO | WO 99/01688 | 1/1999 |
| WO | WO 99/09042 | 2/1999 |
| WO | WO 99/12016 | 3/1999 |
| WO | WO 99/33559 | 7/1999 |
| WO | WO 01/05510 | 1/2001 |
| WO | WO 01/014931 | 3/2001 |
| WO | WO 01/27614 | 4/2001 |
| WO | WO 01/28684 | 4/2001 |
| WO | WO 01/041931 | 6/2001 |
| WO | WO 01/054813 | 8/2001 |
| WO | WO 01/89681 | 11/2001 |
| WO | WO 02/072264 | 9/2002 |
| WO | WO 02/078845 | 10/2002 |
| WO | WO 03/012325 | 2/2003 |
| WO | WO 03/012406 | 2/2003 |
| WO | WO 03/048295 | 6/2003 |
| WO | WO 03/055605 | 7/2003 |
| WO | WO 03/076661 | 9/2003 |
| WO | WO 2004/007081 | 1/2004 |
| WO | WO 2004/048545 | 6/2004 |
| WO | WO 2004/055522 | 7/2004 |
| WO | WO 2004/074848 | 9/2004 |
| WO | WO 2004/094986 | 11/2004 |
| WO | WO 2005/011867 | 2/2005 |
| WO | WO 2005/030984 | 4/2005 |
| WO | WO 2005/107947 | 11/2005 |
| WO | WO 2005/108620 | 11/2005 |
| WO | WO 2005/116202 | 12/2005 |
| WO | WO 2005/118867 | 12/2005 |
| WO | WO 2006/010584 | 2/2006 |
| WO | WO 2006/032044 | 3/2006 |
| WO | WO 2006/066001 | 6/2006 |
| WO | WO 2006/079082 | 7/2006 |
| WO | WO 2006/113198 | 10/2006 |
| WO | WO2006119280 A2 * | 11/2006 |
| WO | WO 2007/044917 | 4/2007 |
| WO | WO 2007/050327 | 5/2007 |
| WO | WO 2007/064117 | 6/2007 |
| WO | WO 2007/091530 | 8/2007 |
| WO | WO 2007/112114 | 10/2007 |
| WO | WO 2008/030914 | 3/2008 |
| WO | WO 2008/060604 | 5/2008 |
| WO | WO 2009/012185 | 1/2009 |
| WO | WO 2010/118541 | 10/2010 |

OTHER PUBLICATIONS

Handique et al., 2001, Mathematical modeling of drop mixing in a split-type microchannel, J. Micromech Microeng, 11:548-554.

International Search Report and Written Opinion dated Apr. 4, 2008 for PCT/US07/07513.

International Search Report and Written Opinion for PCT/US07/024022 dated Jan. 5, 2009.

Mascini et al., "DNA electrochemical biosensors", Fresenius J. Anal. Chem., 369: 15-22, (2001).

Nakagawa et al., Fabrication of amino silane-coated microchip for DNA extraction from whole blood, J of Biotechnology, Mar. 2, 2005, vol. 116, pp. 105-111.

Plambeck et al., "Electrochemical Studies of Antitumor Antibiotics", J. Electrochem Soc.: Electrochemical Science and Technology (1984), 131(11): 2556-2563.

Wang, "Survey and Summary, from DNA Biosensors to Gene Chips", Nucleic Acids Research, 28(16):3011-3016, (2000).

Bollet, C. et al., "A simple method for the isolation of chromosomal DNA from Gram positive or acid-fast bacteria", Nucleic Acids Research, vol. 19, No. 8 (1991), p. 1955.

Breadmore, M.C. et al., "Microchip-Based Purification of DNA from Biological Samples", Anal. Chem., vol. 75 (2003), pp. 1880-1886.

Brody, et al., Diffusion-Based Extraction in a Microfabricated Device, Sensors and Actuators Elsevier, 1997, vol. A58, No. 1, pp. 13-18.

Broyles, et al., "Sample Filtration, Concentration, and Separation Integrated on Microfluidic Devices" Analytical Chemistry (American Chemical Society), vol. 75 No. 11: pp. 2761-2767.

Burns et al., "An Integrated Nanoliter DNA Analysis Device", Science 282:484-487 (1998).

Carlen et al., "Paraffin Actuated Surface Micromachined Valve," in IEEE MEMS 2000 Conference, p. 381-385, Miyazaki, Japan, Jan. 2000.

Chung, Y. et al., "Microfluidic chip for high efficiency DNA extraction", Miniaturisation for Chemistry, Biology & Bioengineering, vol. 4, No. 2 (Apr. 2004), pp. 141-147.

Handique K., et al., On-Chip Thermopneumatic Pressure for Discrete Drop Pumping, Analytical Chemistry, American Chemical Society, Apr. 15, 2001, vol. 73, No. 8, 1831-1838.

Handique, K. et al, "Microflidic flow control using selective hydrophobic patterning", SPIE, vol. 3224, pp. 185-194 (1997).

Handique, K. et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.

Handique, K. et al., "Mathematical Modeling of Drop Mixing in a Slit-Type Micochannel", J. Micromech. Microeng., 11:548-554 (2001).

Handique, K. et al., "Nanoliter Liquid Metering in Microchannels Using Hydrophobic Patterns", Anal. Chem., 72:4100-4109 (2000).

He, et al., Microfabricated Filters for Microfludic Analytical Systems, Analytical Chemistry, American Chemical Society, 1999, vol. 71, No. 7, pp. 1464-1468.

Ibrahim, et al., Real-Time Microchip PCR for Detecting Single-Base Differences in Viral and Human DNA, Analytical Chemistry, American Chemical Society, 1998, vol. 70, No. 9, pp. 2013-2017.

Khandurina, et al., Microfabricated Porous Membrane Structure for Sample Concentraction and Electrophoretic Analysis, Analytical Chemistry American Chemical Society, 1999, vol. 71, No. 9, pp. 1815-1819.

Kopp, et al., Chemical Amplification: Continuous-Flow PCR on a Chip, www.sciencemag.org, 1998, vol. 280, pp. 1046-1048.

Kutter, et al., Solid Phase Extraction on Microfludic Devices, J. Microcolumn Separations, John Wiley & Sons, Inc., 2000, vol. 12, No. 2, pp. 93-97.

Lagally, et al., Single-Molecule DNA Amplification and Analysis in an Integrated Microfluidic Device, Analytical Chemistry, American Chemical Society, 2001, vol. 73, No. 3 pp. 565-570.

Livache, T. et al., "Polypyrrole DNA chip on a Silicon Device: Example of Hepatitis C Virus Genotyping", Analytical Biochemistry, vol. 255 (1998), pp. 188-194.

(56) References Cited

OTHER PUBLICATIONS

Northrup, et al., A Miniature Analytical Instrument for Nucleic Acids Based on Micromachined Silicon Reaction Chambers, Analytical Chemistry, American Chemical Society, 1998, vol. 70, No. 5, pp. 918-922.

Oleschuk, et al., Trapping of Bead-Based Reagents within Microfluidic Systems,: On-Chip Solid-Phase Extraction and Electrochromatography, Analytical Chemistry, American Chemical Society, 2000, vol. 72, No. 3, pp. 585-590.

Orchid BioSciences, Inc., www.orchid.com, Jul. 6, 2001.

Roche, et al. "Ectodermal commitment of insulin-producing cells derived from mouse embryonic stem cells" Faseb J (2005) 19: 1341-1343.

Ross, et al., Analysis of DNA Fragments from Conventional and Microfabricated PCR Devices Using Delayed Extraction MALDI-TOF Mass Spectrometry, Analytical Chemistry, American Chemical Society, 1998, vol. 70, No. 10, pp. 2067-2073.

Shoffner, M. A. et al., Chip PCR.I. Surface Passivation of Microfabricated Silicon-Glass Chips for PCR, Nucleic Acids Research, Oxford University Press, 1996, vol. 24, No. 2, 375-379.

Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.

Waters, et al., Microchip Device for Cell Lysis, Multiplex PCR Amplification, and Electrophoretic Sizing, Analytical Chemistry, American Chemical Society, 1998, vol. 70, No. 1, pp. 158-162.

Weigl, et al., Microfluidic Diffusion-Based Separation and Detection, www.sciencemag.org, 1999, vol. 283, pp. 346-347.

Yoza, Brandon et al., DNA extraction using bacterial magnetic particles modified with hyperbranched polyamidoamine dendrimer, Mar. 20, 2003, vol. 101, No. 3, 219-228.

Yoza, et al., "Fully Automated DNA Extraction fro Blood Using Magnetic Particles Modified with a Hyperbranched Polyamidomine Dendrimer", Journal of Bioscience and Bioengineering, 95(1):21-26, 2003.

Goldmeyer et al., "Identification of Staphylococcus aureus and Determination of Methicillin Resistance Directly from Positive Blood Cultures by Isothermal Amplification and a Disposable Detection Device", J Clin Microbiol. (Apr. 2008) 46(4): 1534-1536.

Meyers, R.A., Molecular Biology and Biotechnology: A Comprehensive Desk Reference; VCH Publishers, Inc. New York, NY; (1995) pp. 418-419.

Kuo et al., "Remnant cationic dendrimers block RNA migration in electrophoresis after monophasic lysis", J Biotech. (2007) 129: 383-390.

Tanaka et al., "Modification of DNA extraction from maize using polyamidoamine-dendrimer modified magnetic particles", Proceedings of the 74th Annual Meeting of the Electrochemical Society of Japan, Mar. 29, 2007; Faculty of Engineering, Science University of Tokyo; 2 pages.

Wu et al., "Polycationic dendrimers interact with RNA molecules: polyamine dendrimers inhibit the catalytic activity of Candida ribozymes", Chem Commun. (2005) 3: 313-315.

Zhou et al., "Cooperative binding and self-assembling behavior of cationic low molecular-weight dendrons with RNA molecules", Org Biomol Chem. (2006) 4(3): 581-585.

Zhou et al., "PANAM dendrimers for efficient siRNA delivery and potent gene silencing", Chem Comm.(Camb.) (2006) 22: 2362-2364.

\* cited by examiner

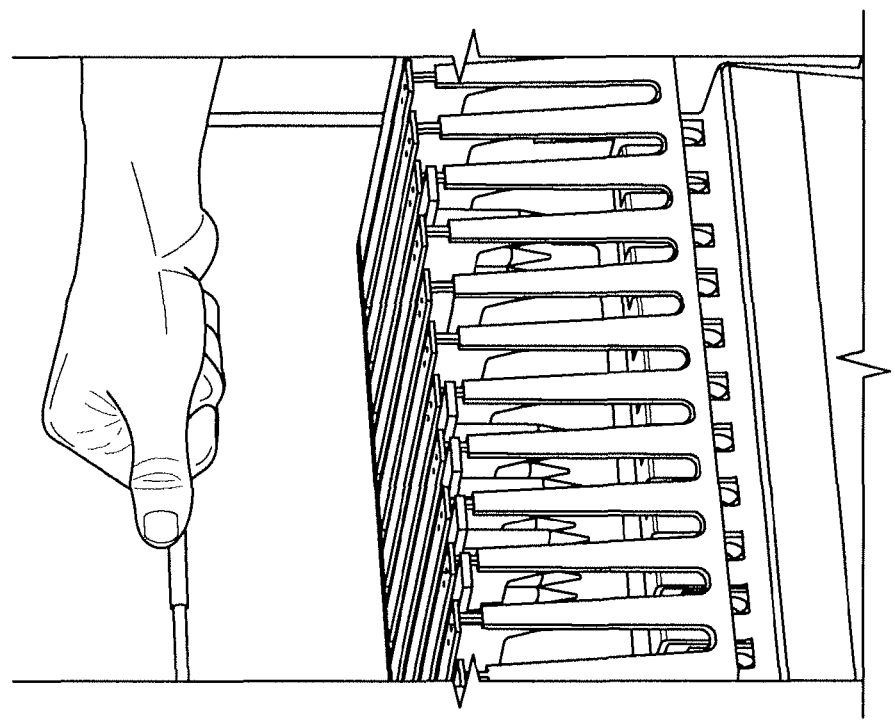
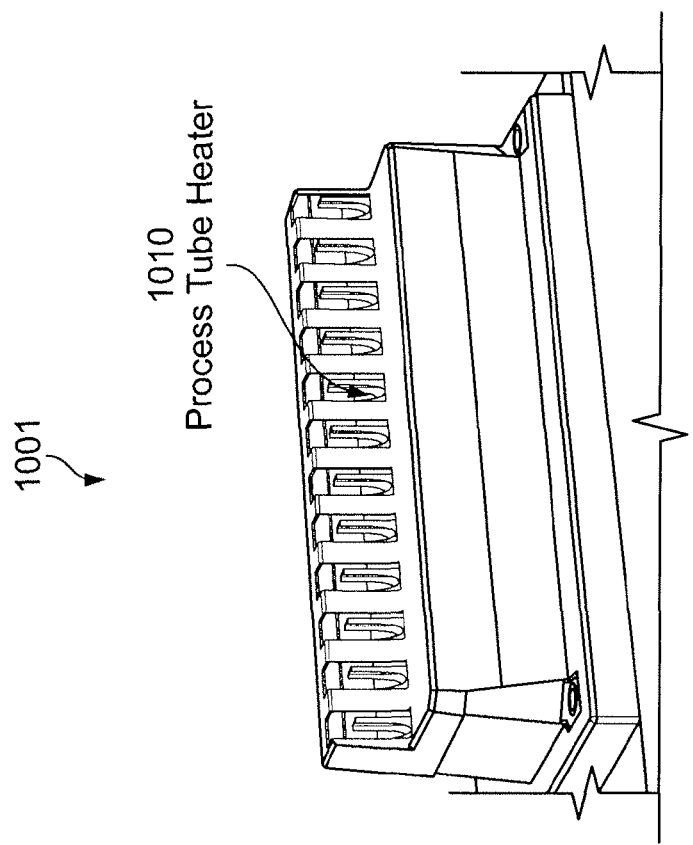
FIG. 6

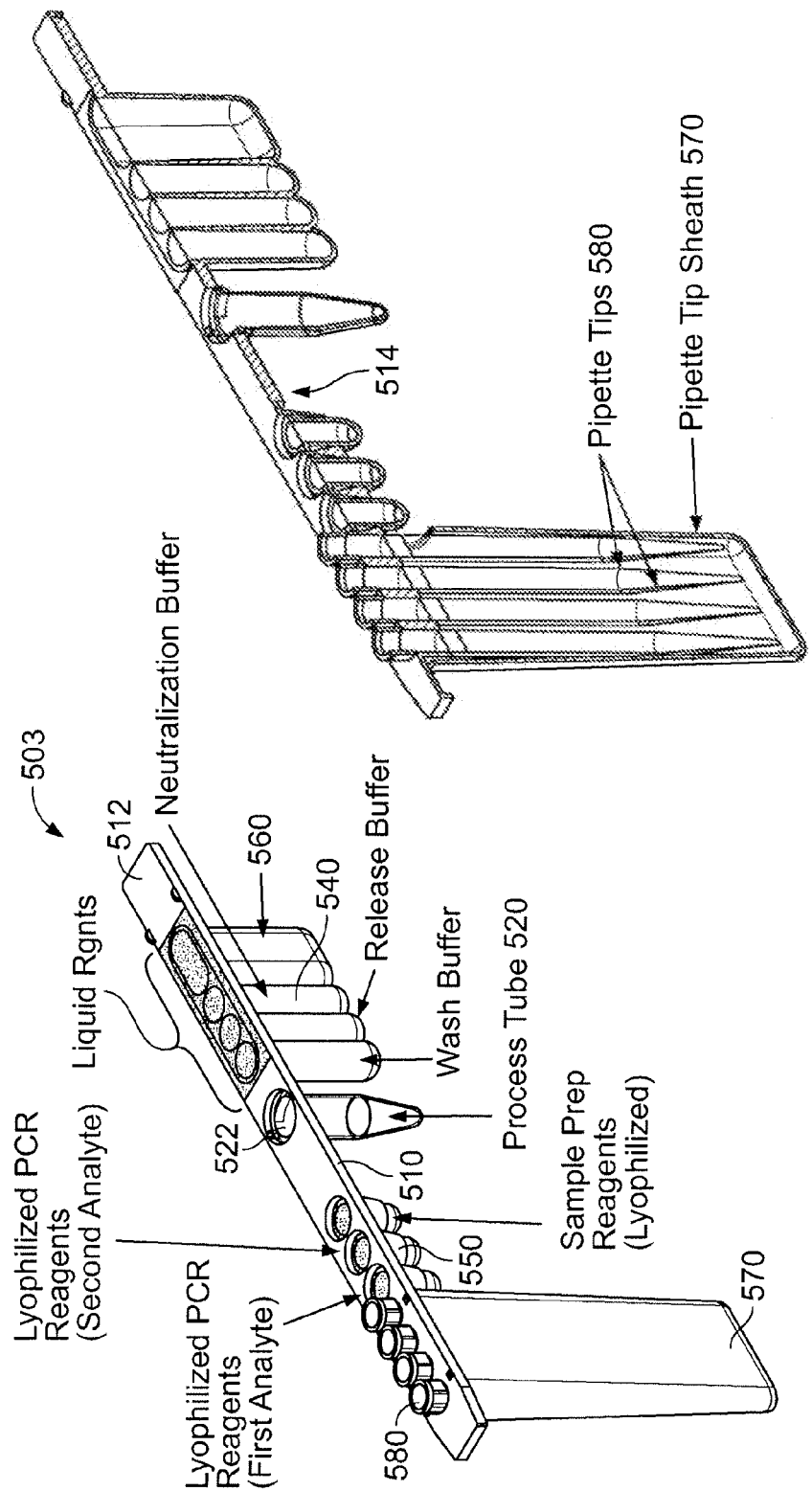

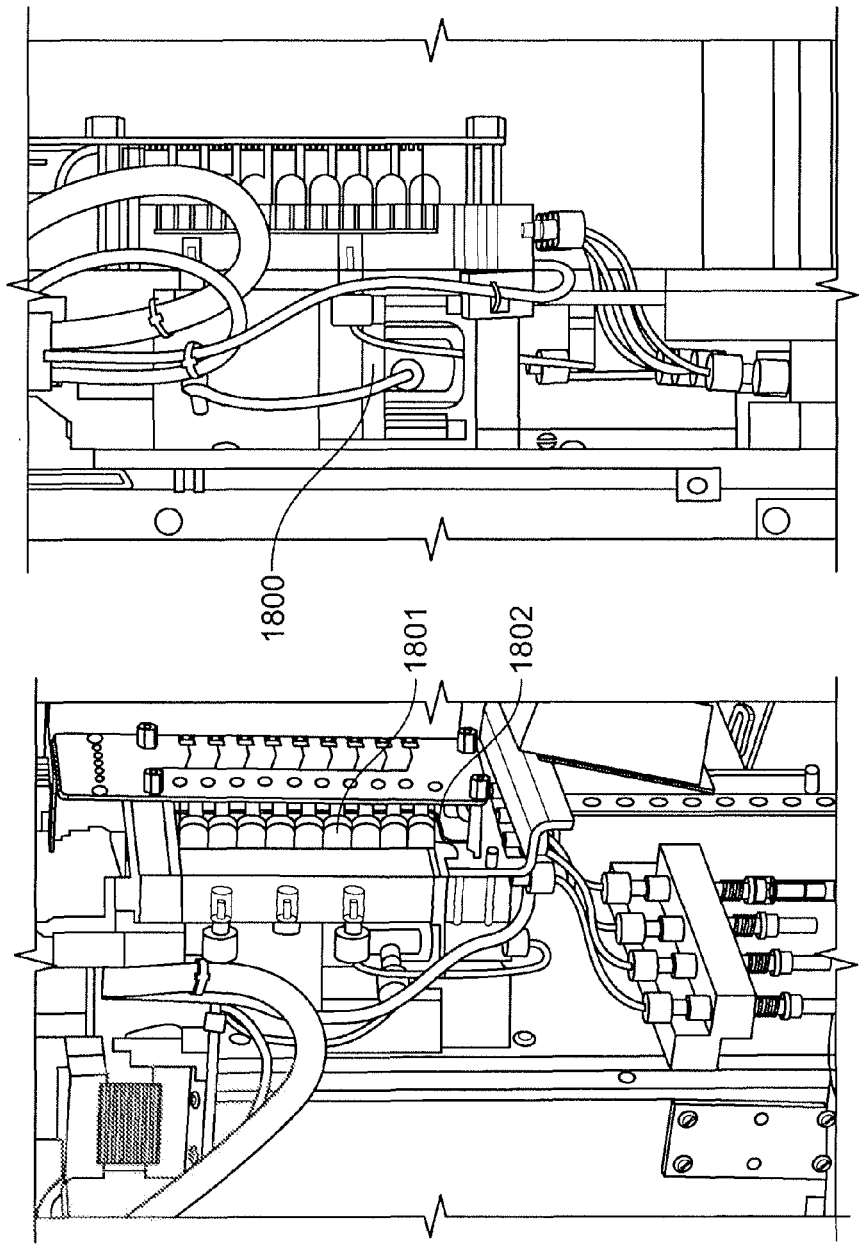

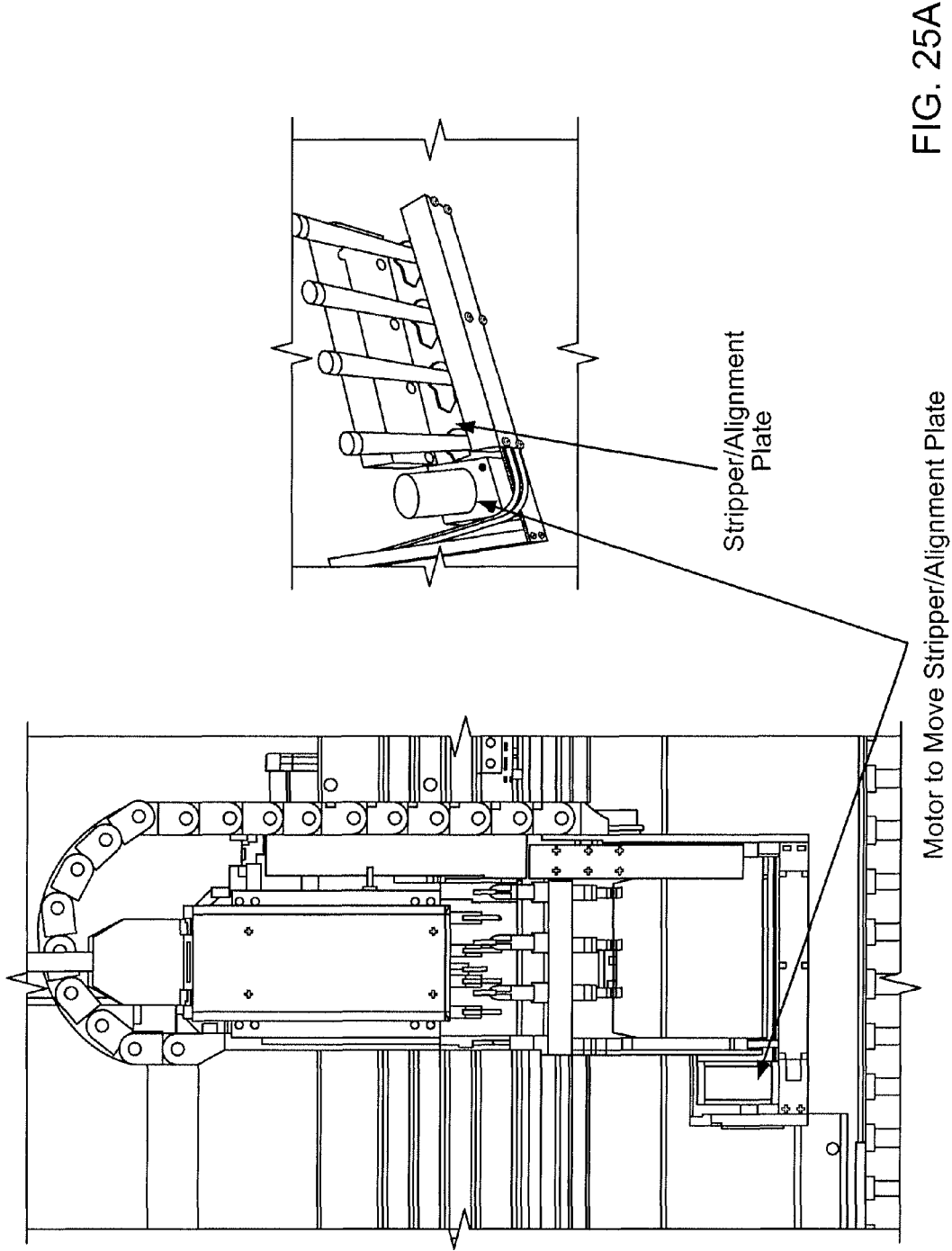

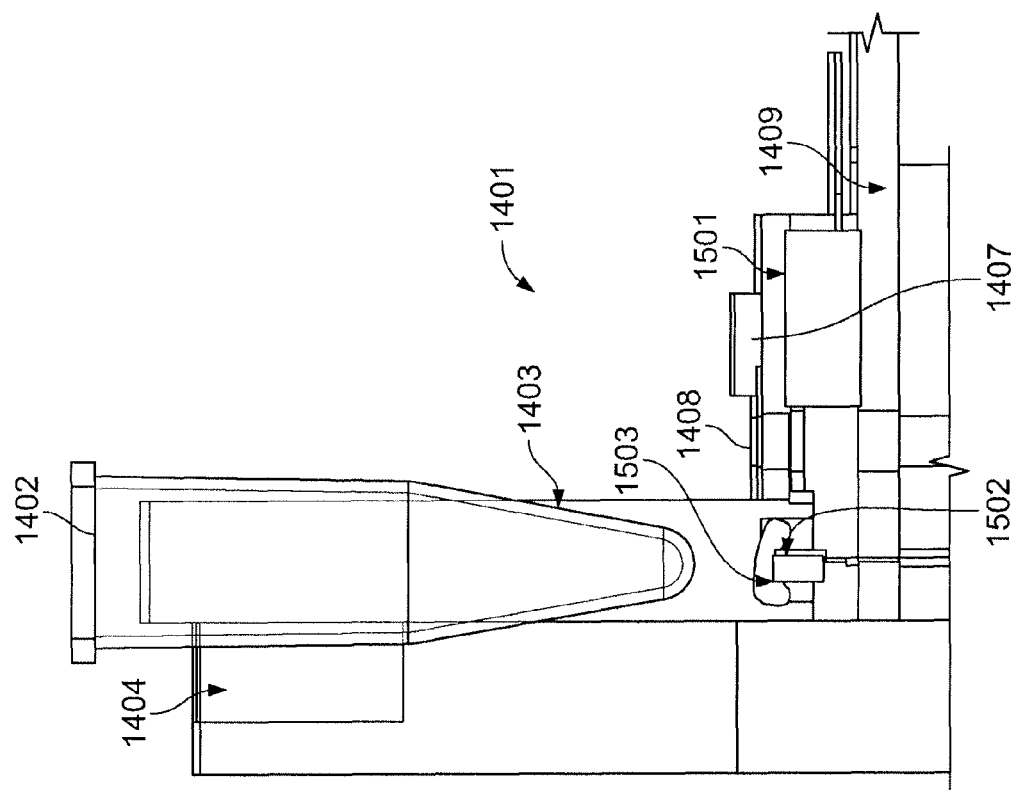
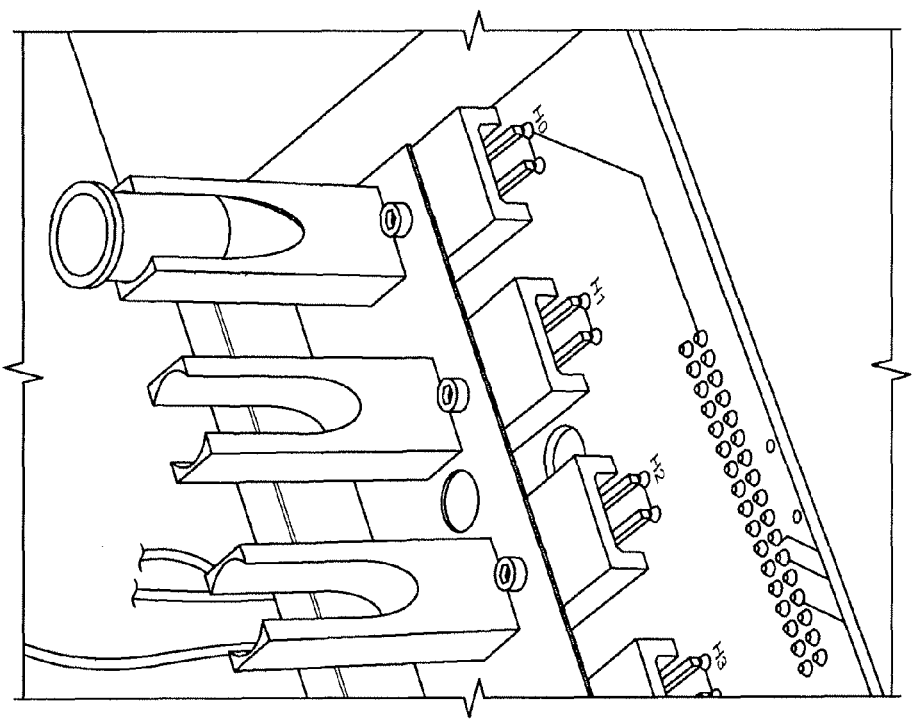
FIG. 26

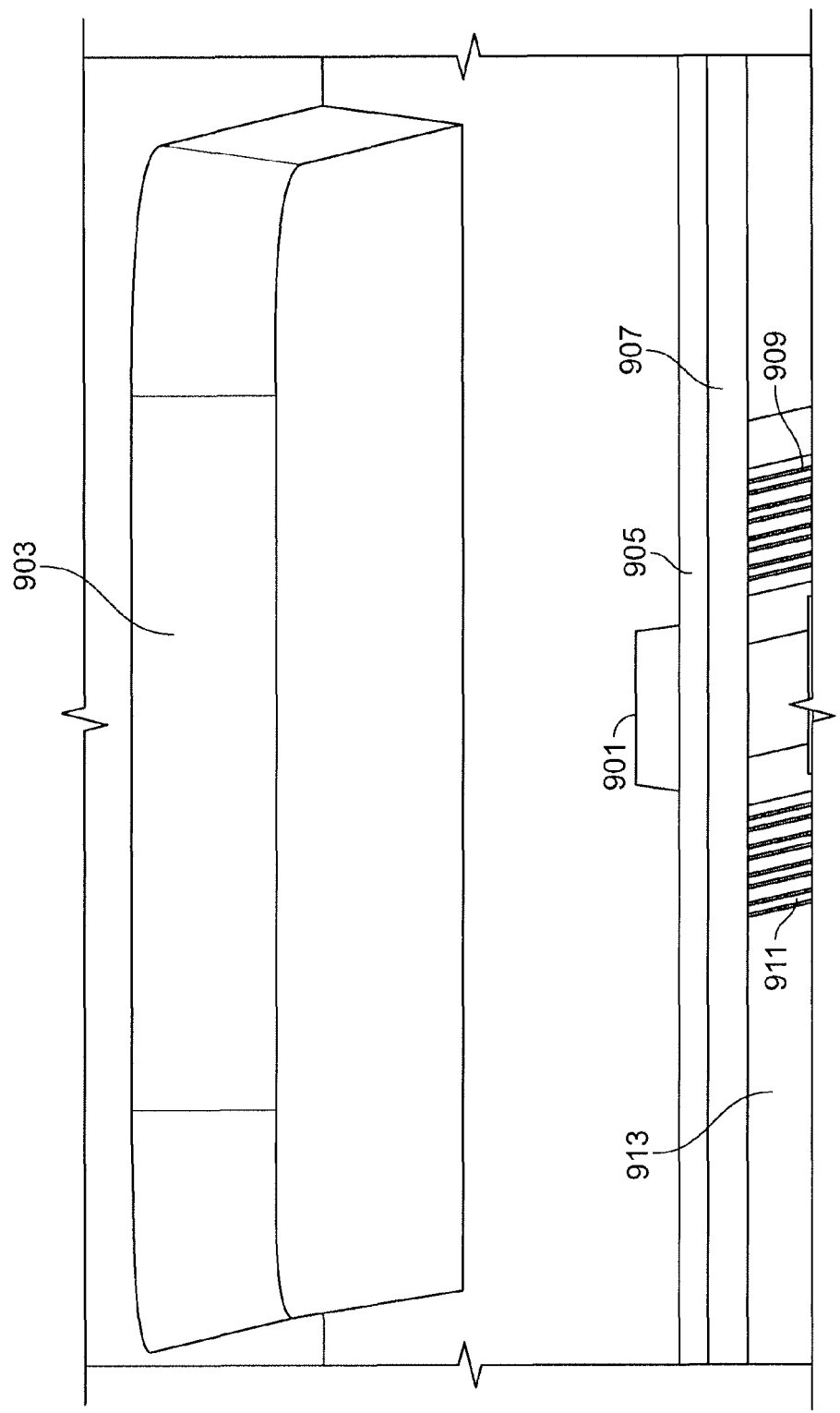

Capillary action of controlled volume of wax causes it to fill up the Wax up to the right interface without blocking the liquid flowable microchannel Fluid Distribution Head

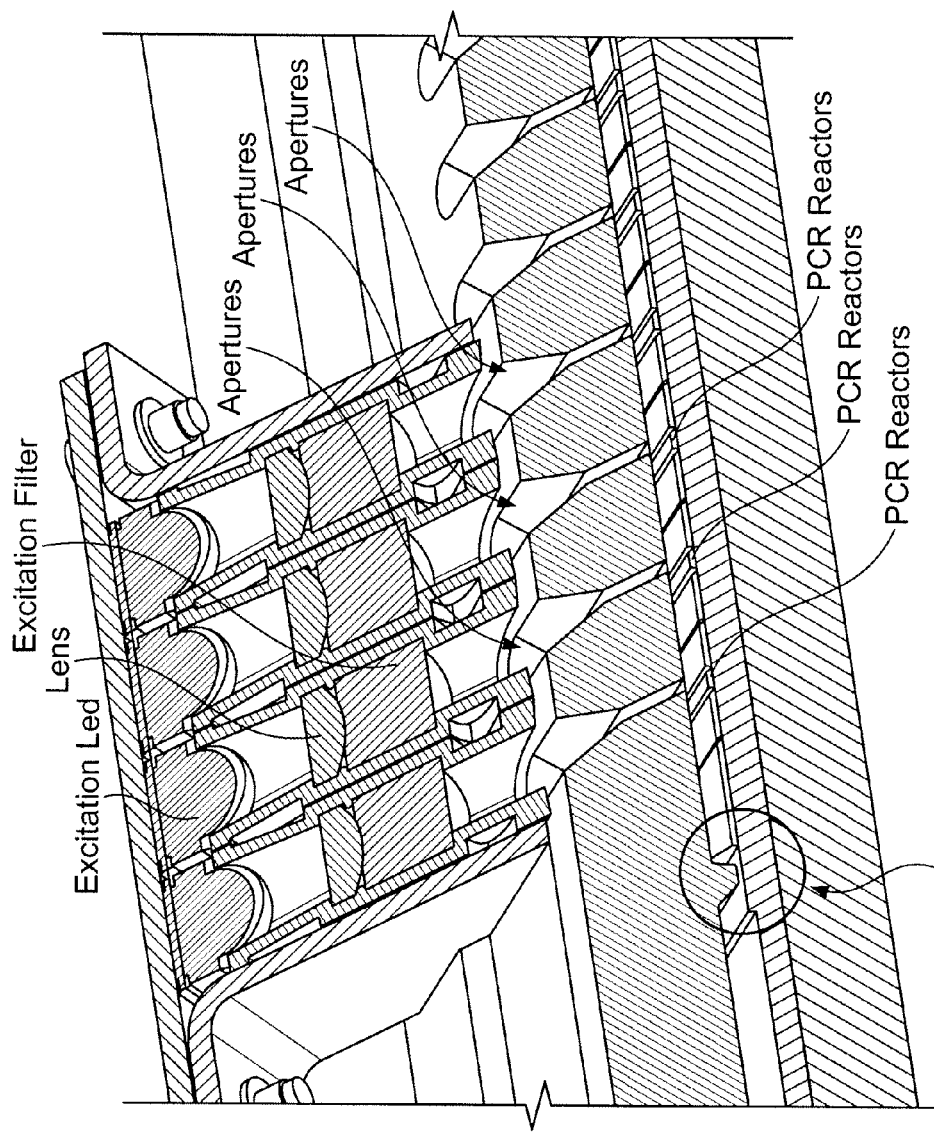

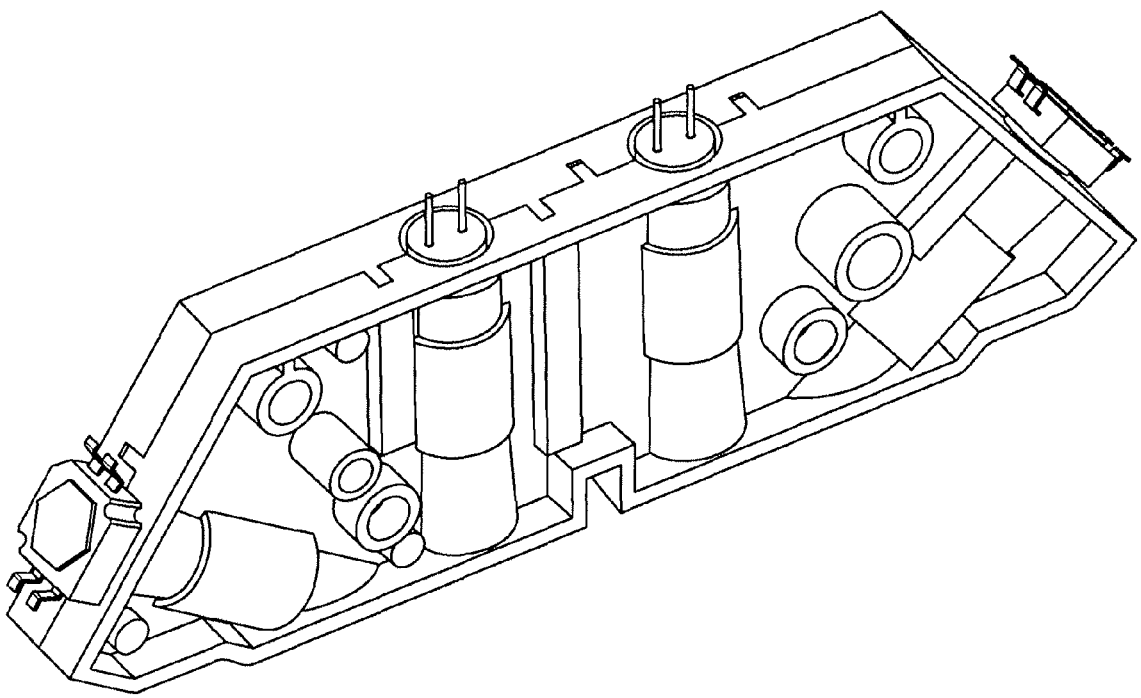
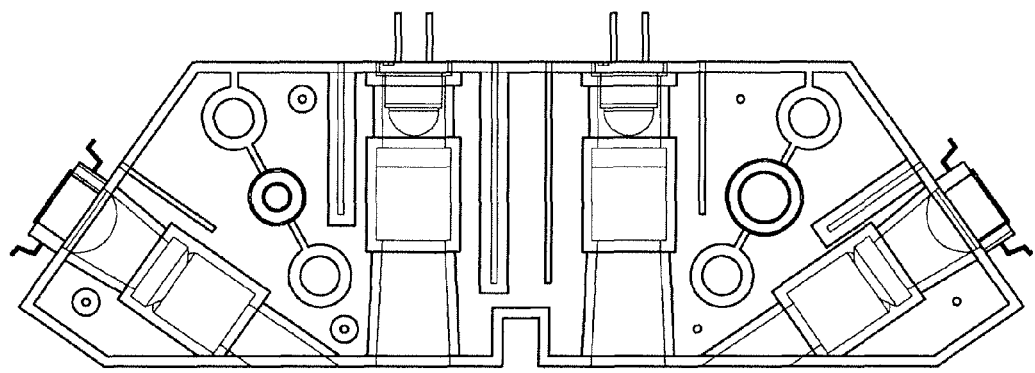
FIG. 83

FIG. 85C

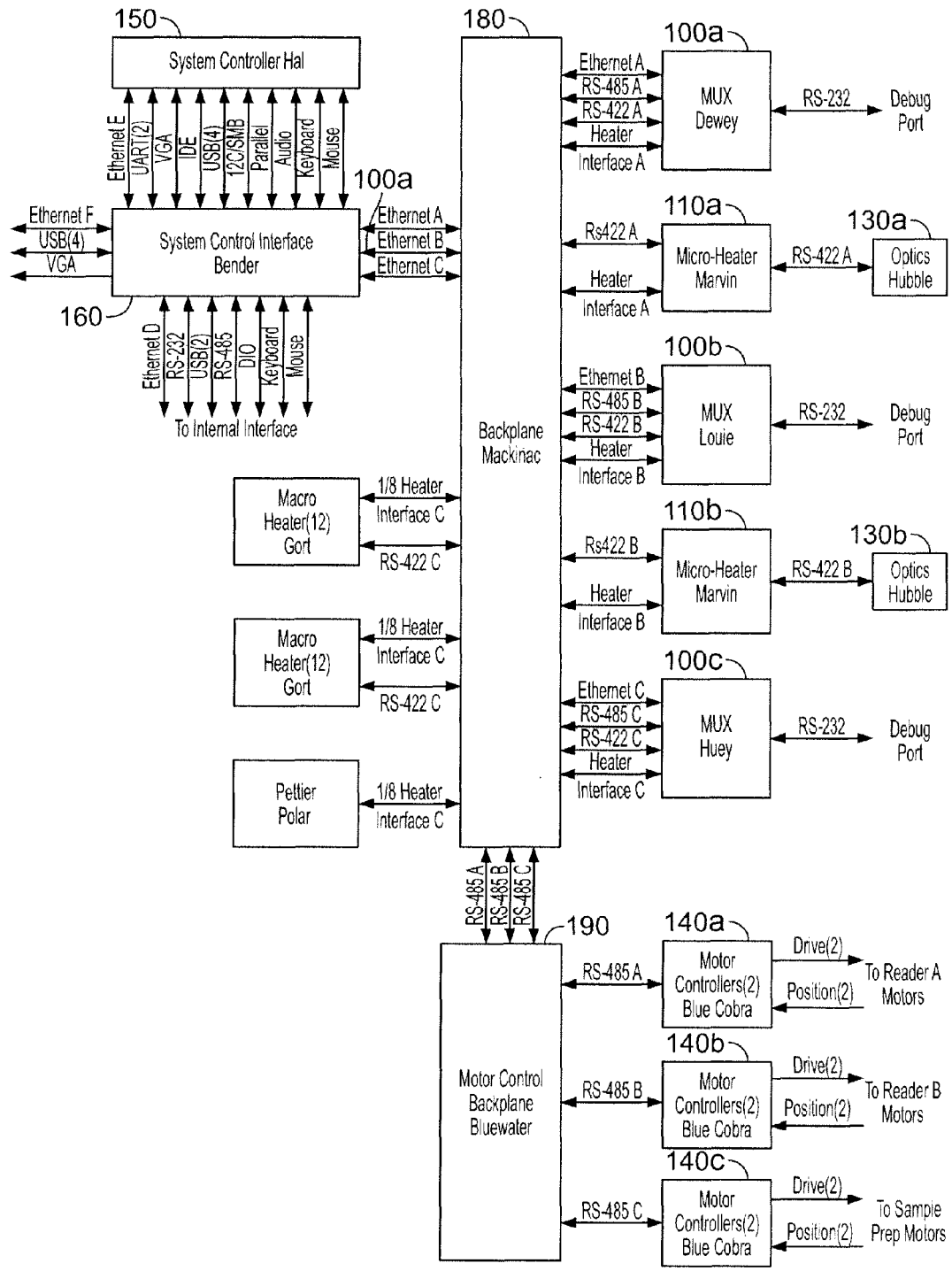
FIG. 86 Electronics Block Diagram

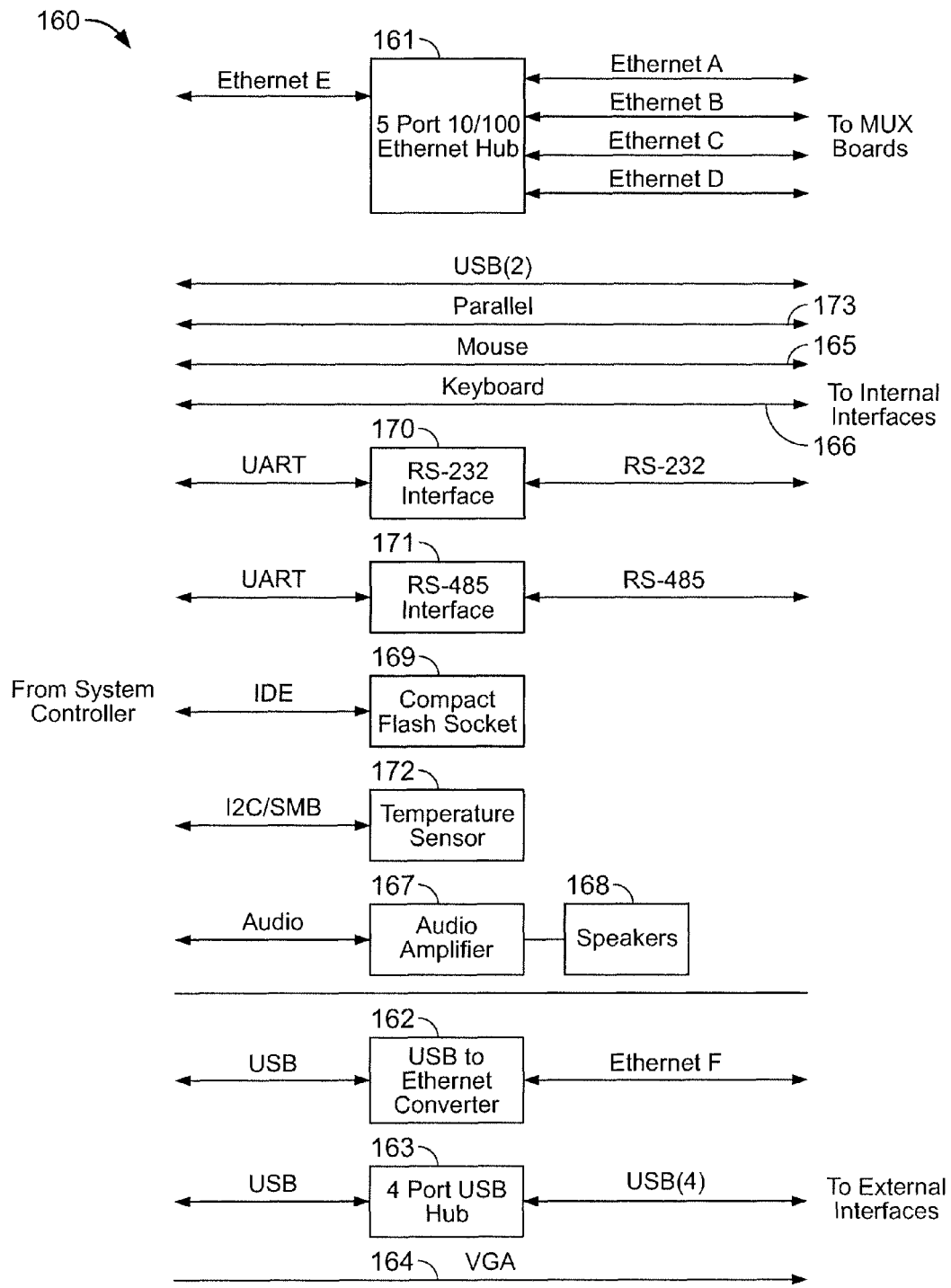
FIG. 87 Processor Base Board Block Diagram

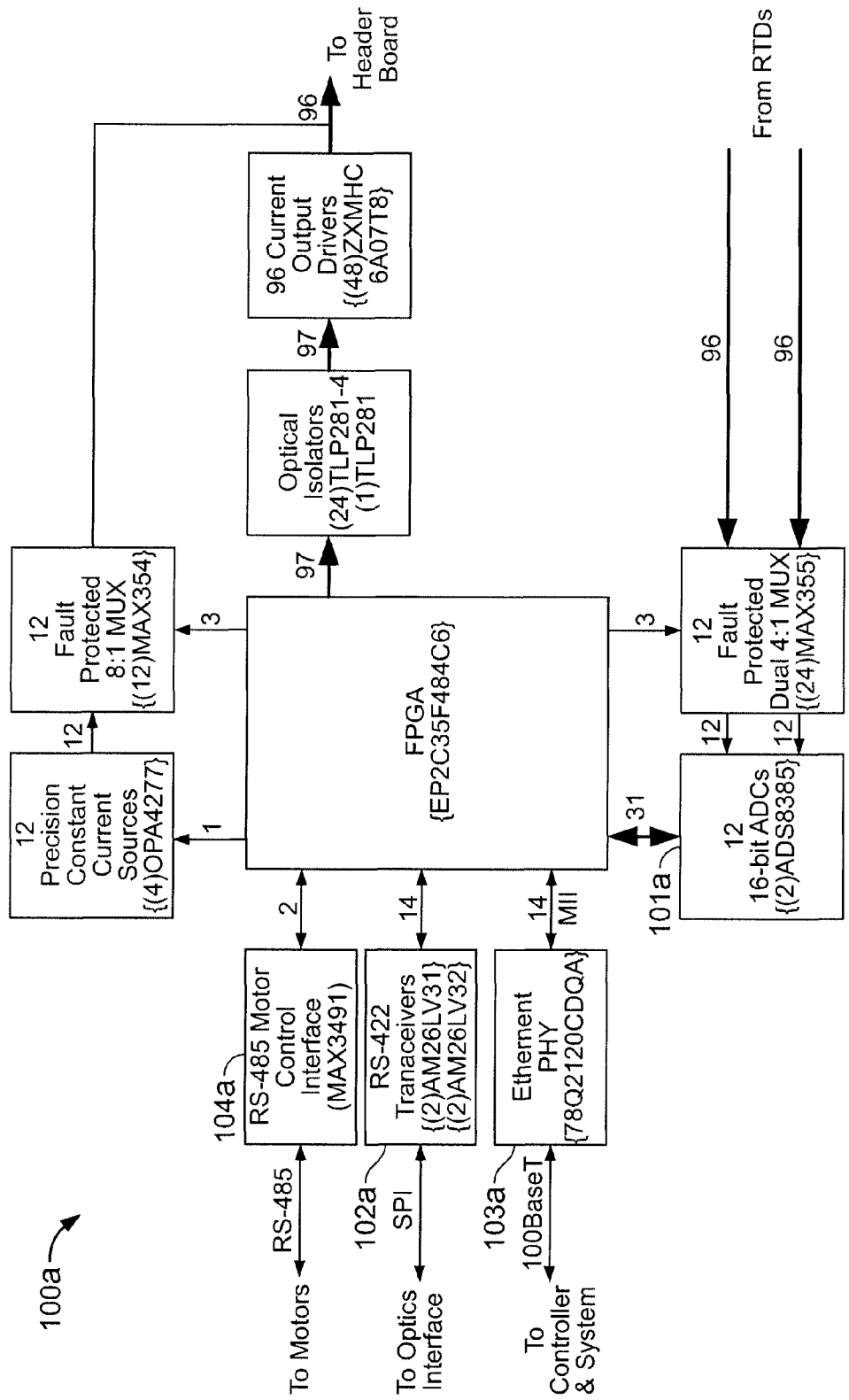
FIG. 88 MUX Board Block Diagram

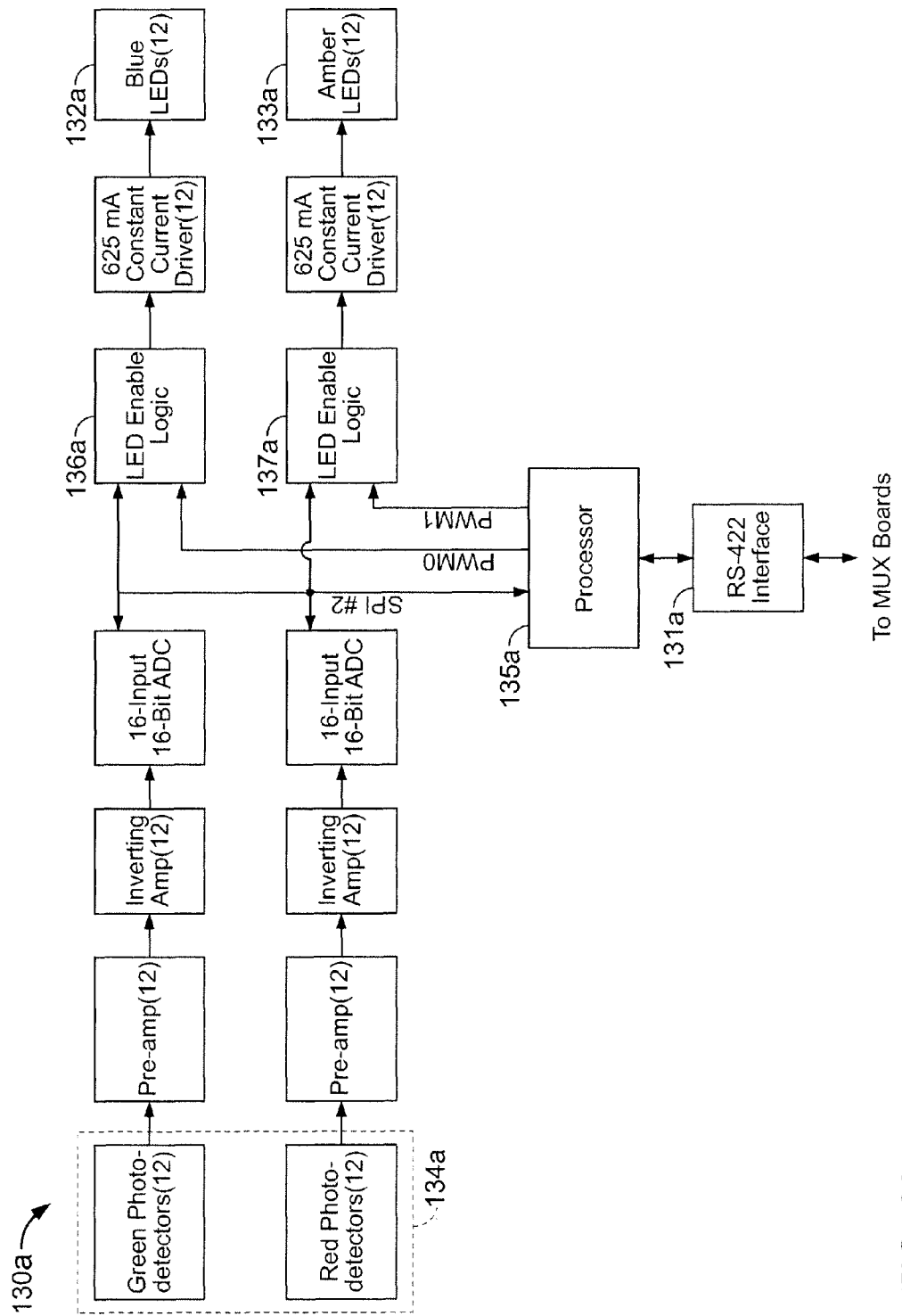
FIG. 89 MUX Board Block Diagram

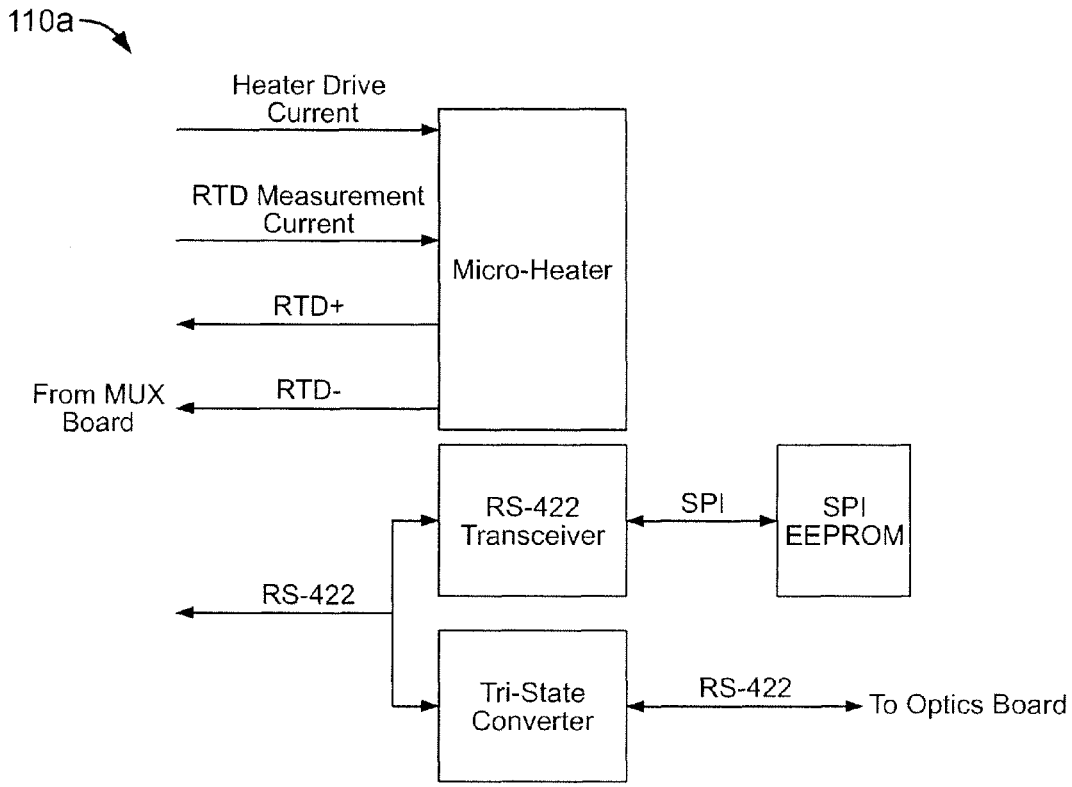
FIG. 90 Micro-Heater Board Block Diagram
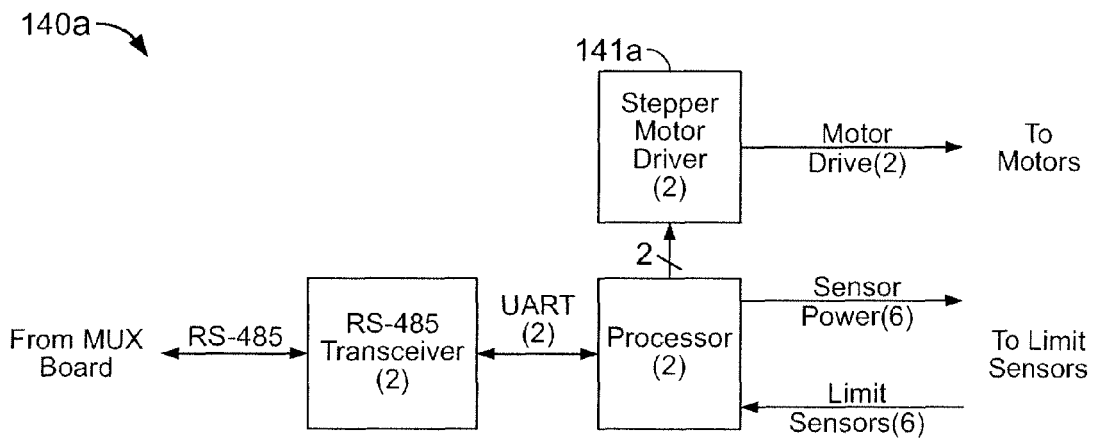
FIG. 91 Motor Control Board Block Diagram

INTEGRATED APPARATUS FOR PERFORMING NUCLEIC ACID EXTRACTION AND DIAGNOSTIC TESTING ON MULTIPLE BIOLOGICAL SAMPLES

CLAIM OF PRIORITY

This application claims the benefit of priority to U.S. provisional patent application Ser. No. 60/959,437, filed Jul. 13, 2007, and to U.S. utility application Ser. No. 11/985,577, filed Nov. 14, 2007, both of which are incorporated herein by reference in their entirety.

TECHNICAL FIELD

The technology described herein generally relates to systems for extracting polynucleotides from multiple samples, particularly from biological samples, and additionally to systems that subsequently amplify and detect the extracted polynucleotides. The technology more particularly relates to microfluidic systems that carry out PCR on multiple samples of nucleotides of interest within microfluidic channels, and detect those nucleotides.

BACKGROUND

The medical diagnostics industry is a critical element of today's healthcare infrastructure. At present, however, in vitro diagnostic analyses no matter how routine have become a bottleneck in patient care. There are several reasons for this. First, many diagnostic analyses can only be done with highly specialist equipment that is both expensive and only operable by trained clinicians. Such equipment is found in only a few locations—often just one in any given urban area. This means that most hospitals are required to send out samples for analyses to these locations, thereby incurring shipping costs and transportation delays, and possibly even sample loss or mishandling. Second, the equipment in question is typically not available 'on-demand' but instead runs in batches, thereby delaying the processing time for many samples because they must wait for a machine to fill up before they can be run.

Understanding that sample flow breaks down into several key steps, it would be desirable to consider ways to automate as many of these as possible. For example, a biological sample, once extracted from a patient, must be put in a form suitable for a processing regime that typically involves using PCR to amplify a vector (such as a nucleotide) of interest. Once amplified, the presence of a nucleotide of interest from the sample needs to be determined unambiguously. Preparing samples for PCR is currently a time-consuming and labor intensive step, though not one requiring specialist skills, and could usefully be automated. By contrast, steps such as PCR and nucleotide detection (or 'nucleic acid testing') have customarily only been within the compass of specially trained individuals having access to specialist equipment.

There is a need for a method and apparatus of carrying out sample preparation on samples in parallel, with or without PCR and detection on the prepared biological samples, and preferably with high throughput, but in a manner that can be done routinely at the point of care, or without needing the sample to be sent out to a specialized facility.

The discussion of the background herein is included to explain the context of the inventions described herein. This is not to be taken as an admission that any of the material referred to was published, known, or part of the common general knowledge as at the priority date of any of the claims.

Throughout the description and claims of the specification the word "comprise" and variations thereof, such as "comprising" and "comprises", is not intended to exclude other additives, components, integers or steps.

SUMMARY

A diagnostic apparatus, comprising: a first module configured to extract nucleic acid simultaneously from a plurality of nucleic-acid containing samples, wherein the first module comprises: one or more racks, each configured to accept a number of samples and a corresponding number of holders, wherein each holder comprises a process chamber, a waste chamber, one or more pipette tips, and one or more receptacles, wherein the one or more receptacles contain respectively sufficient quantities of one or more reagents for carrying out extraction of nucleic acid from a sample; a magnetic separator configured to move relative to the process chambers of each holder; a heater assembly configured to independently heat each of the process chambers; and a liquid dispenser configured to carry out fluid transfer operations on two or more holders simultaneously; and a second module configured to simultaneously amplify the nucleic acid extracted from the plurality of samples, wherein the second module comprises: one or more bays, each configured to receive a microfluidic cartridge, wherein the cartridge is configured to separately accept and to separately amplify the nucleic acid extracted from multiple samples; and one or more detection systems.

A diagnostic apparatus comprising: one or more racks, on each of which is mounted a number of nucleic acid containing samples and a corresponding number of holders, wherein each holder comprises a process chamber, a waste chamber, one or more pipette tips, and one or more receptacles, wherein the one or more receptacles contain, respectively, sufficient quantities of one or more reagents for carrying out extraction of nucleic acid from a sample; a magnetic separator movable from a first position to a second position adjacent to the process chamber of each of the one or more holders; a heater assembly comprising a number of heater units, each of which is in thermal contact with one of the process chambers; one or more bays, each bay having a shape complementary to a shape of a microfluidic cartridge, wherein the cartridge comprises a number of inlets each of which is in fluid communication with one of a number of channels in which nucleic acid extracted from one of the number of samples is amplified, and wherein the cartridge further comprises one or more windows that permit detection of amplified nucleic acid; a liquid dispenser having one or more dispensing heads, wherein the liquid dispenser is movable from a first position above a first holder to a second position above a second holder, and is movable from the first position above the first holder to a different position above the first holder, and is further movable from a position above one of the holders to a position above one of the number of inlets; and one or more detection systems positioned in proximity to the one or more windows.

A diagnostic instrument comprising: a liquid handling unit that extracts nucleic acid from a sample in a unitized reagent strip; a microfluidic cartridge that, in conjunction with a heater element, carries out real-time PCR on nucleic acid extracted from the sample; and a detector that provides a user with a diagnosis of whether the sample contains a nucleotide of interest.

Also described herein are methods of using the diagnostic apparatus, including a method of diagnosing a number of samples in parallel, using the apparatus.

A unitized reagent holder, comprising: a strip, to which is attached: a single process tube; one or more receptacles, each of which holding a reagent selected from the group consisting of: a sample preparation reagent, PCR reagents for a first analyte, and one or more liquid reagents; a waste tube; one or more sockets configured to hold one or more pipette tips; and a pipette tip sheath configured to surround the one or more pipette tips.

A liquid dispenser, comprising: one or more sensors; a manifold; one or more pumps in fluid communication with the manifold; one or more dispense heads in fluid communication with the manifold; a gantry that provides freedom of translational motion in three dimensions; and electrical connections that accept electrical signals from an external controller, wherein the liquid dispenser has no inlet or outlet for fluids, other than through the one or more pumps.

A separator for magnetic particles, comprising: one or more magnets aligned linearly; a motorized shaft upon which the one or more magnets can rise or fall in such a manner that the one or more magnets attains close proximity to one or more receptacles containing magnetic particles; and control circuitry to control motion of the motorized shaft.

An integrated separator and heater, comprising: a heater assembly, wherein the heater assembly comprises a plurality of independently controllable heater units, each of which is configured to accept and to heat a process chamber; one or more magnets aligned linearly; a motorized shaft upon which the one or more magnets can rise or fall in such a manner that the one or more magnets attains close proximity to one or more of the process chambers; and control circuitry to control motion of the motorized shaft and heating of the heater units.

A preparatory apparatus comprising: a first module configured to extract nucleic acid simultaneously from a number of nucleic-acid containing samples, wherein the first module comprises: one or more racks, each configured to accept the number of samples and a corresponding number of holders, wherein each holder comprises a process chamber, a waste chamber, one or more pipette tips, and one or more receptacles, wherein the one or more receptacles contain, respectively, sufficient quantities of one or more reagents for carrying out extraction of nucleic acid from a sample; a magnetic separator configured to move relative to the process chambers of each holder; a heater assembly configured to independently heat each of the process chambers; and a liquid dispenser configured to carry out fluid transfer operations on two or more holders simultaneously; and a second module configured to receive and to store the nucleic acid extracted from the number of samples.

A preparatory apparatus comprising: one or more racks, on each of which is mounted a number of nucleic acid containing samples and a corresponding number of holders, wherein each holder comprises a process chamber, a waste chamber, one or more pipette tips, and one or more receptacles, wherein the one or more receptacles contain, respectively, sufficient quantities of one or more reagents for carrying out extraction of nucleic acid from a sample; a magnetic separator movable from a first position to a second position adjacent to the process chambers of each holder; a heater assembly comprising a number of heater units, each of which is in contact with a process chamber; a liquid dispenser movable from a first position above a first holder to a second position above a second holder; and a storage compartment having a number of compartments, wherein each compartment stores the nucleic acid extracted from one of the number of samples.

A unitized reagent holder, comprising: a strip, to which is attached: a single process tube; one or more receptacles, each of which holding a reagent selected from the group consisting of: a sample preparation reagent, and one or more liquid reagents; a waste tube; one or more sockets configured to hold one or more pipette tips; and a pipette tip sheath configured to surround the one or more pipette tips.

The present technology additionally includes a process for extracting nucleic acid from multiple samples in parallel, using the apparatus as described herein.

BRIEF DESCRIPTION OF SELECTED DRAWINGS

FIG. 1A shows a schematic of a preparatory apparatus;
FIG. 1B shows a schematic of a diagnostic apparatus.
FIG. 2 shows a schematic of control circuitry.
FIGS. 3A and 3B show exterior views of an exemplary apparatus.
FIG. 4 shows an exemplary interior view of an apparatus.
FIG. 5 shows perspective views of an exemplary rack for sample holders.
FIG. 6 shows perspective views of the rack of FIG. 5 in conjunction with a heater unit.
FIG. 7 shows a perspective view of an exemplary rack for sample holders.
FIGS. 8A-8K show various views of the rack of FIG. 7.
FIG. 9 shows an area of an apparatus configured to accept a rack of FIG. 7.
FIGS. 10A and 10B show an first exemplary embodiment of a reagent holder having a pipette sheath, in perspective view (FIG. 10A) and underside view (FIG. 10B).
FIG. 11 shows an exemplary embodiment of a reagent holder not having a pipette sheath, in perspective view.
FIGS. 12A-12C show a second exemplary embodiment of a reagent holder having a pipette sheath, in perspective view (FIG. 12A) and cross-sectional view (FIG. 12B), and exploded view (FIG. 12C).
FIGS. 13A and 13B show a stellated feature on the interior of a reagent tube, in cross-sectional (FIG. 13A) and plan (FIG. 13B) view.
FIG. 14 shows a sequence of pipetting operations in conjunction with a reagent tube having a stellated feature.
FIG. 15 shows embodiments of a laminated layer.
FIG. 16 shows a sequence of pipetting operations in conjunction with a laminated layer.
FIGS. 17A-17D show an exemplary kit containing holders and reagents.
FIG. 18 shows a liquid dispense head.
FIGS. 19A-19C show a liquid dispense head.
FIG. 20 shows an exemplary distribution manifold.
FIG. 21 shows a scanning read-head attached to a liquid dispense head.
FIG. 22 shows a barcode scanner in cross-sectional view.
FIG. 23 shows a barcode reader positioned above a microfluidic cartridge.
FIG. 24 shows pipette tip sensors.
FIGS. 25A and 25B show an exemplary device for stripping pipette tip.
FIG. 26 shows a heater unit in perspective and cross-sectional view.
FIG. 27 shows an integrated heater and separator unit in cross-sectional view.
FIG. 28 shows a cartridge auto-loader.
FIG. 29 shows a cartridge stacker.
FIG. 30 shows a cartridge stacker in position to deliver a cartridge to an auto-loader.
FIG. 31 shows a cartridge loading system.
FIG. 32 shows a disposal unit for used cartridges.

FIG. 40A additionally shows the valve in an open state, and the valve in a closed state.

FIG. 48 shows a view in cross-section of a microfluidic cartridge.

FIGS. 79A, 79B show cutaway portions of the detection unit of FIG. 78.

Figure 80:
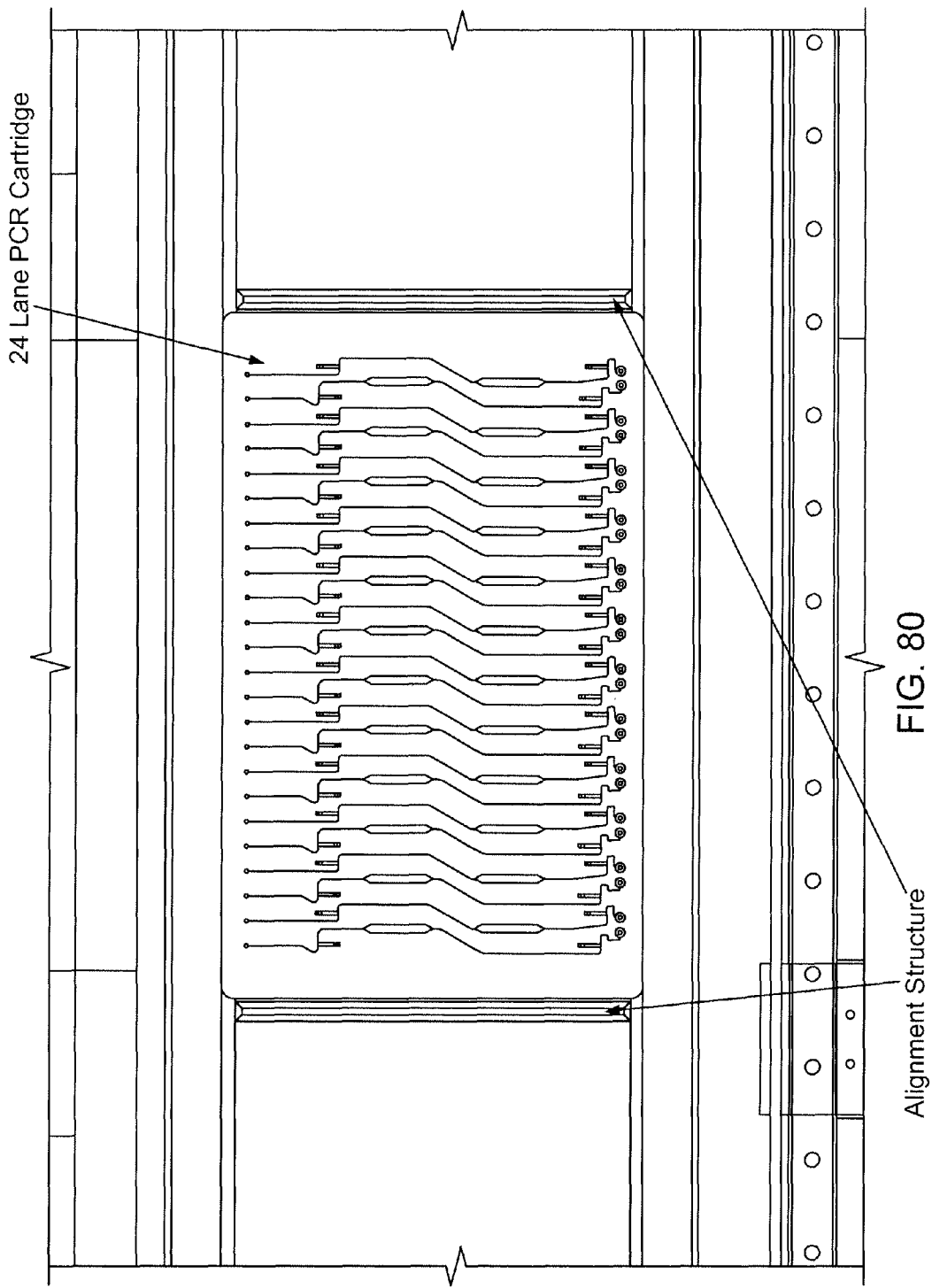
Figure 81:
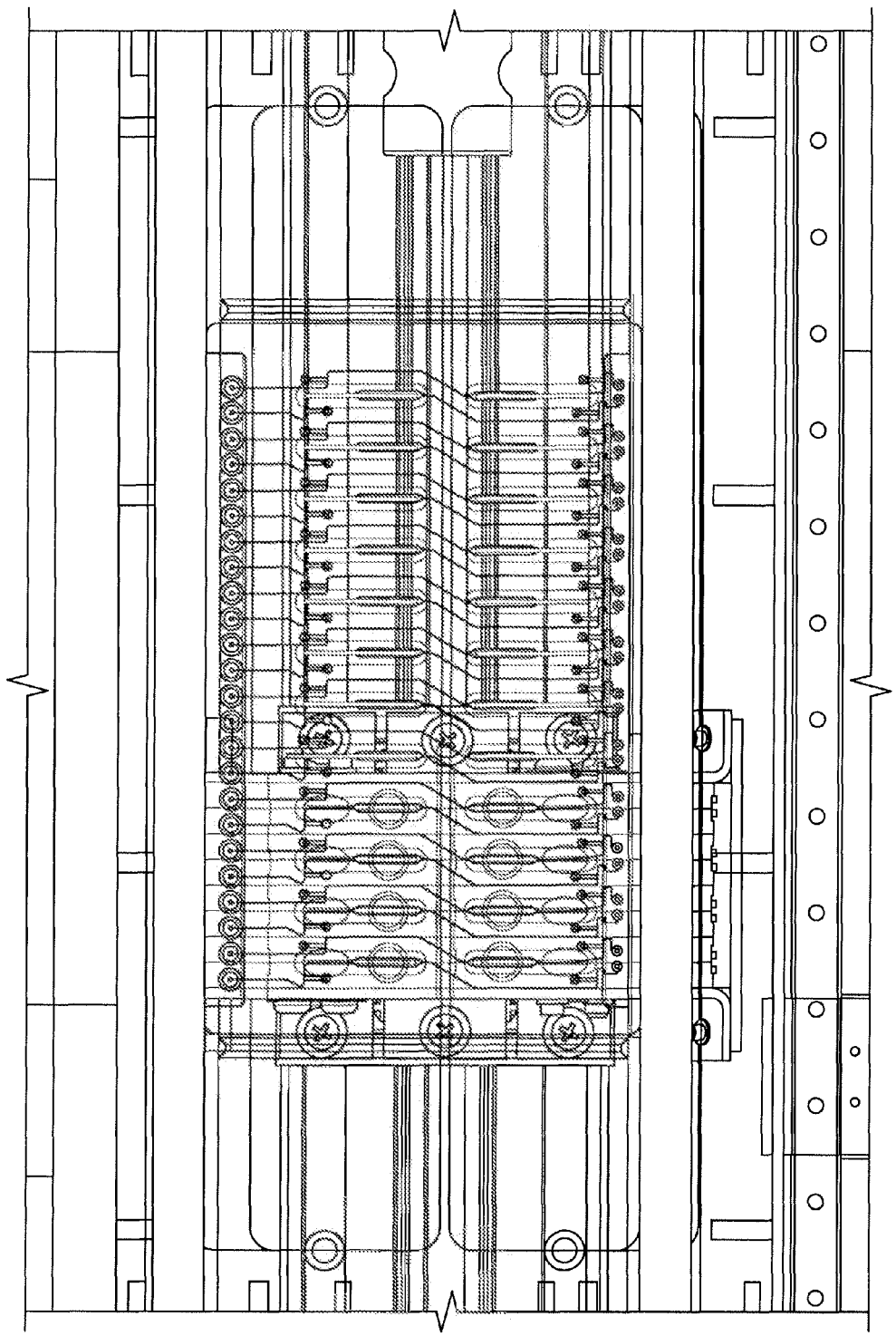

FIGS. 80, and 81 show alignment of the detection unit with a microfluidic cartridge.

Figure 82:
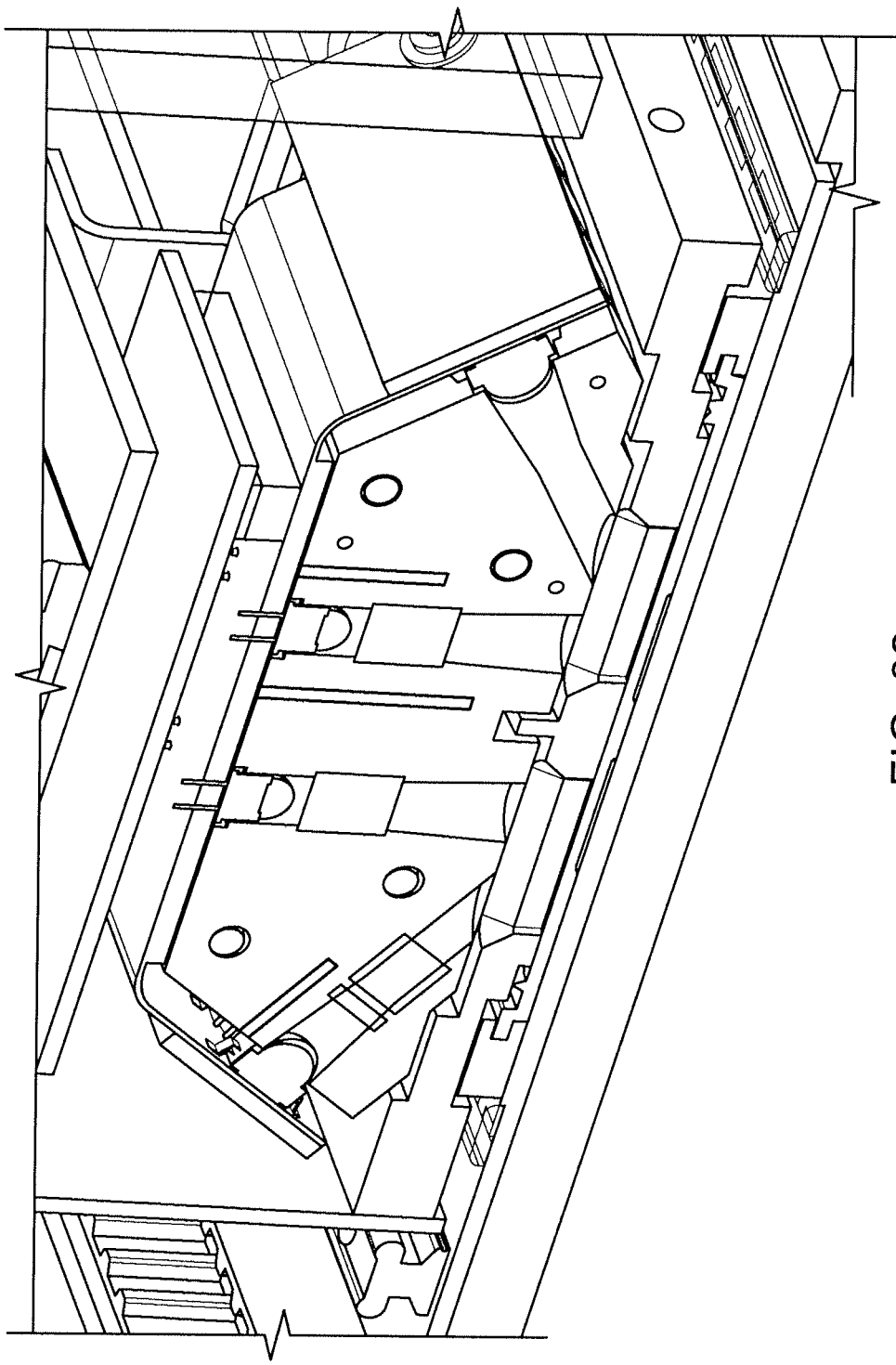

FIGS. 82 and 83 show exterior and cutaways, respectively, of an optics block.

Figure 84:
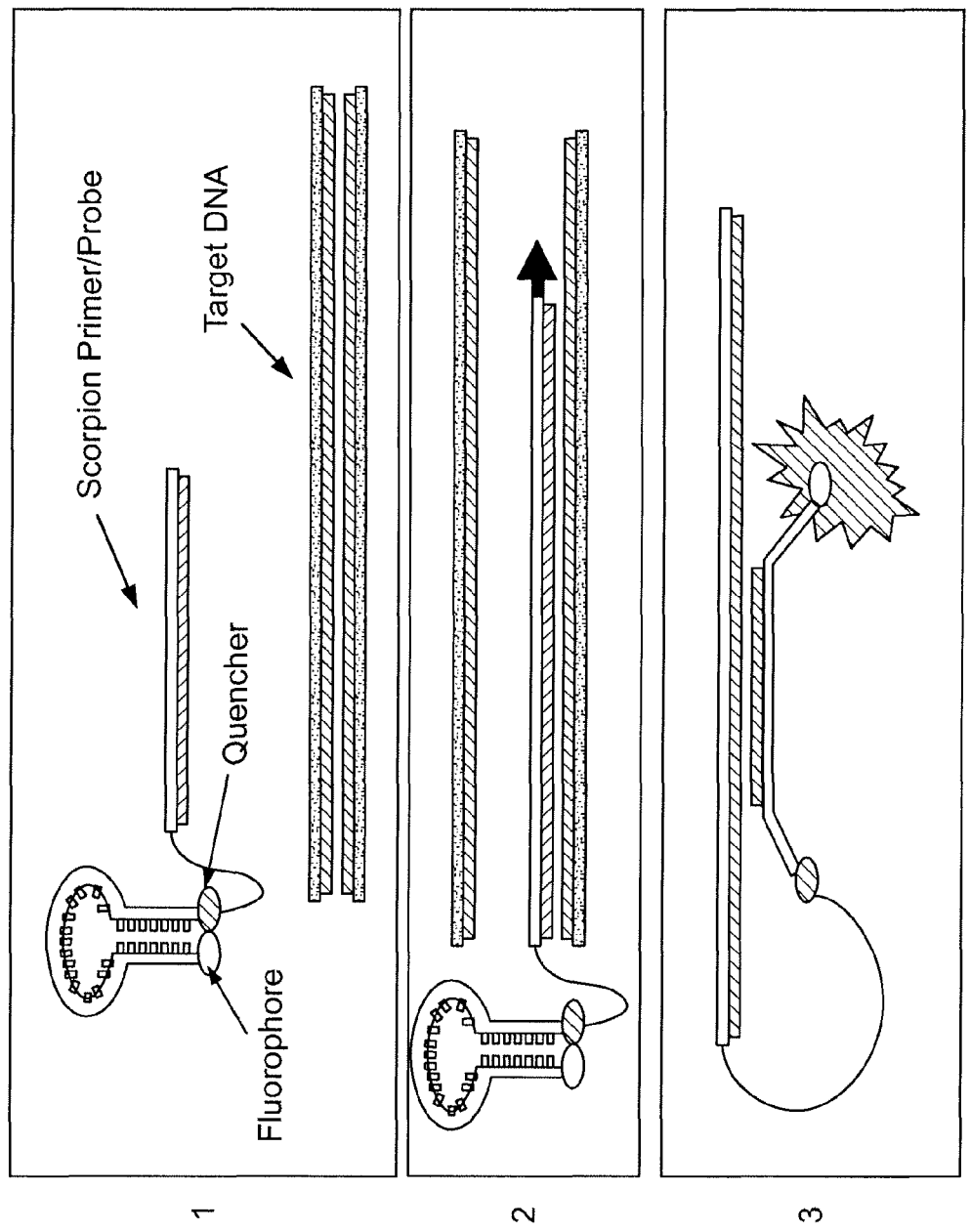

FIG. 84 shows a Scorpion reaction, schematically.

Figure 85A:
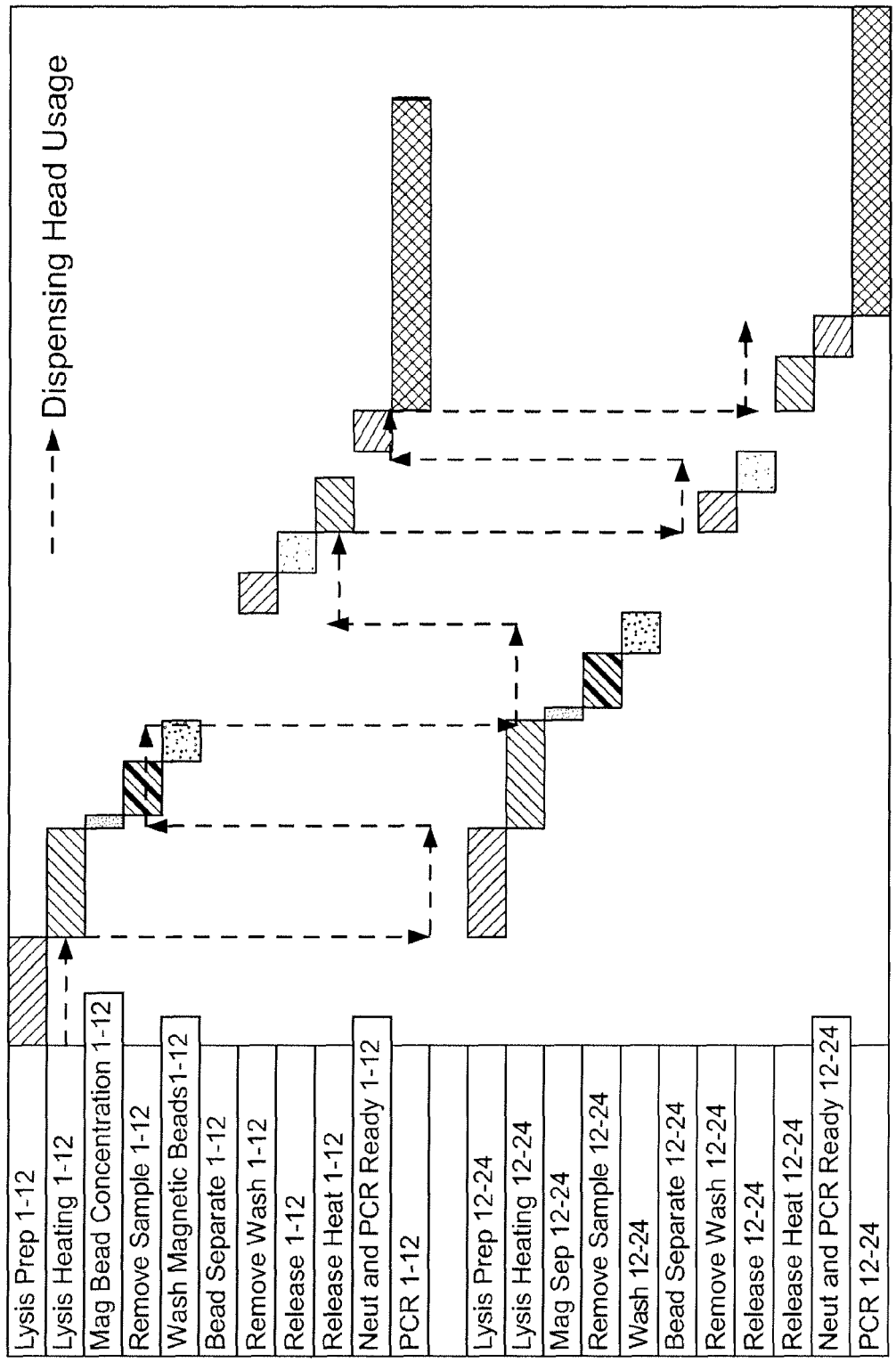
Figure 85B:
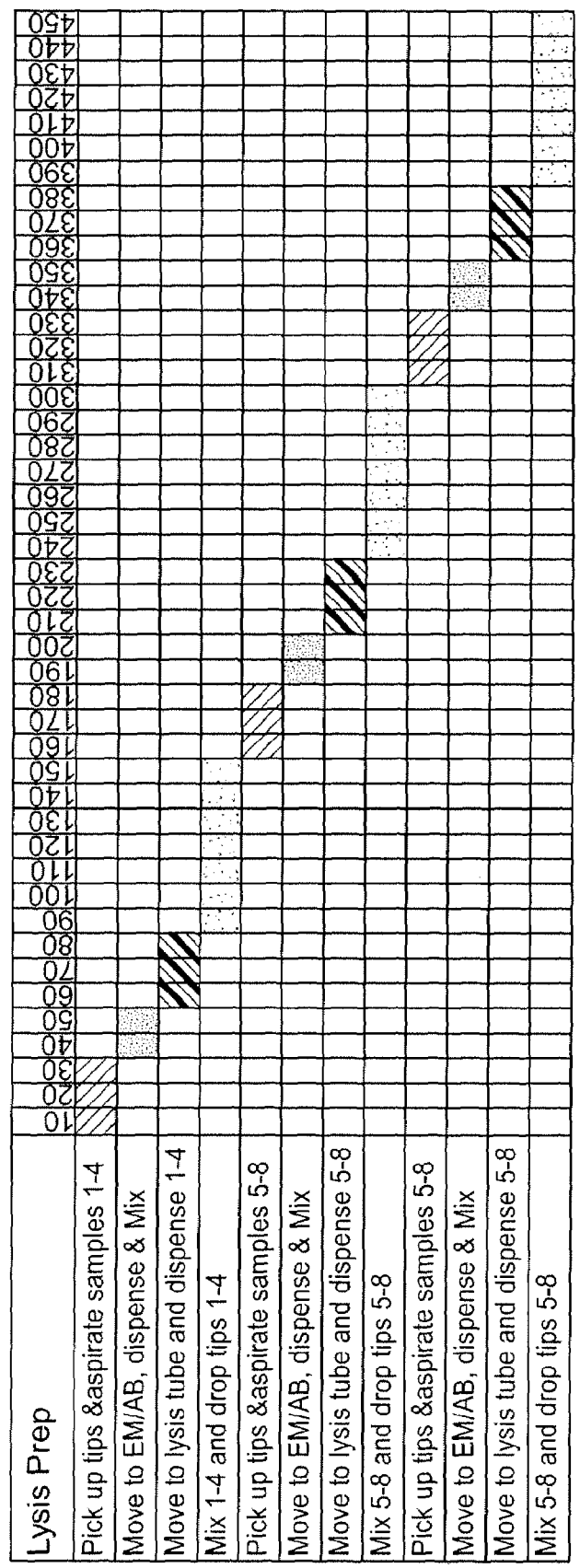
Figure 85C:
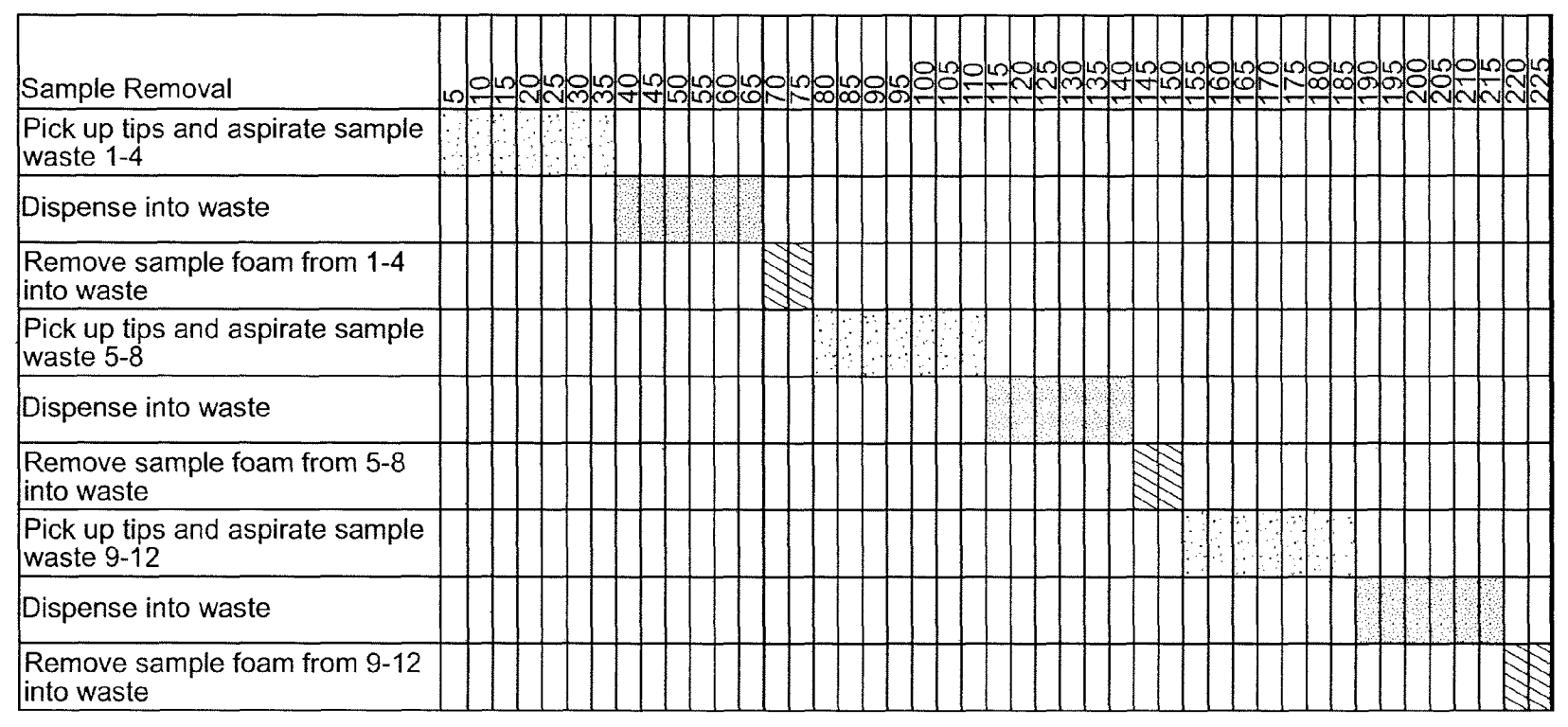

FIGS. 85A-85C show, schematically, pipette head usage during various preparatory processes.

FIGS. 86-91 show exemplary layouts of electronics control circuitry.

DETAILED DESCRIPTION

Nucleic acid testing (NAT) as used herein is a general term that encompasses both DNA (Deoxyribonucleic acid) and RNA (Ribonucleic acid) testing. Exemplary protocols that are specific to RNA and to DNA are described herein. It is to be understood that generalized descriptions where not specific to RNA or to DNA either apply to each equally or can be readily adapted to either with minor variations of the description herein as amenable to one of ordinary skill in the art. It is also to be understood that the terms nucleic acid and polynucleotide may be used interchangeably herein.

The apparatuses as described herein therefore find application to analyzing any nucleic acid containing sample for any purpose, including but not limited to genetic testing, and clinical testing for various infectious diseases in humans. Targets for which clinical assays currently exist, and that may be tested for using the apparatus and methods herein may be bacterial or viral, and include, but are not limited to: *Chlamydia Trachomatis* (CT); *Neisseria Gonorrhea* (GC); Group B *Streptococcus*; HSV; HSV Typing; CMV; Influenza A & B; MRSA; RSV; TB; *Trichomonas*; Adenovirus; *Bordatella*; BK; JC; HHV6; EBV; Enterovirus; and *M. pneumoniae*.

The apparatus herein can be configured to run on a laboratory benchtop, or similar environment, and can test approximately 45 samples per hour when run continuously throughout a normal working day. This number can be increased, according to the number of tests that can be accommodated in a single batch, as will become clear from the description herein. Results from individual raw samples are typically available in less than 1 hour.

Where used herein, the term "module" should be taken to mean an assembly of components, each of which may have separate, distinct and/or independent functions, but which are configured to operate together to produce a desired result or results. It is not required that every component within a module be directly connected or in direct communication with every other. Furthermore, connectivity amongst the various components may be achieved with the aid of a component, such as a processor, that is external to the module.

Apparatus Overview

Figure 1A:
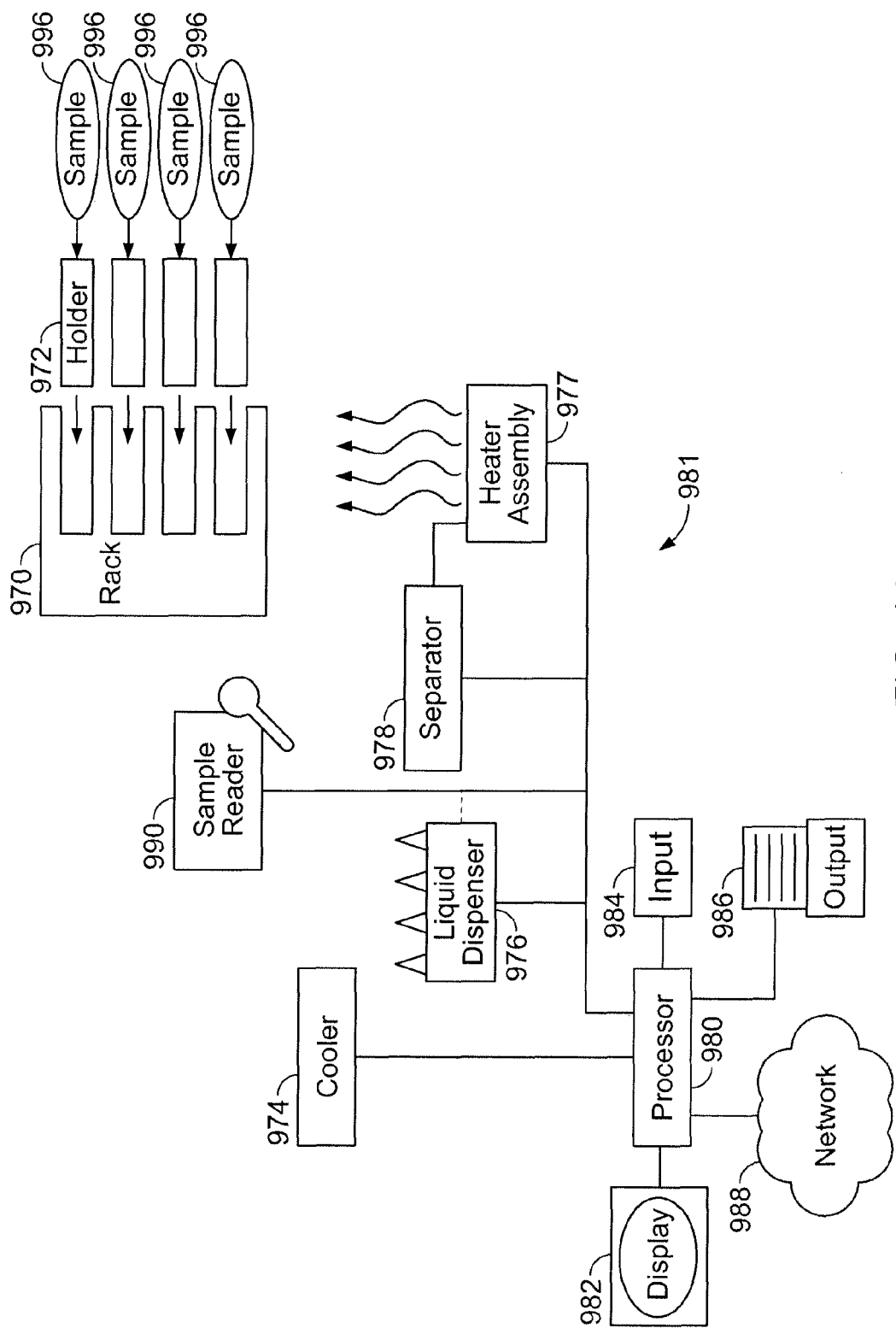
Figure 1B:
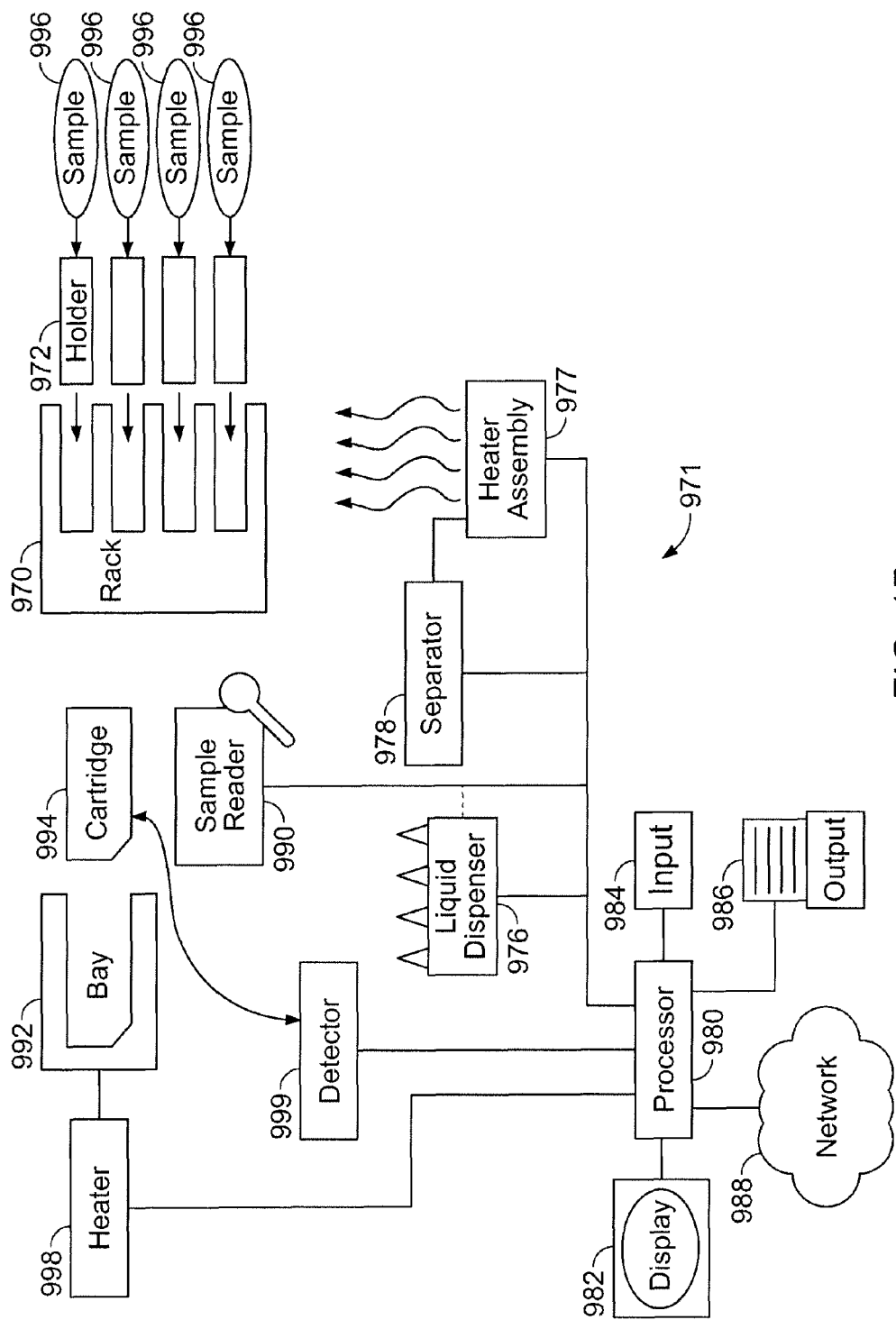

An apparatus having various components as further described herein can be configured into at least two formats, preparatory and diagnostic, as shown respectively in FIGS. 1A and 1B. A schematic overview of a preparatory apparatus 981 for carrying out sample preparation as further described herein is shown in FIG. 1A. An overview of a diagnostic apparatus 971 is shown in FIG. 1B. The geometric arrangement of the components of systems 971, 981 shown in FIGS. 1A and 1B is exemplary and not intended to be limiting.

A processor 980, such as a microprocessor, is configured to control functions of various components of the system as shown, and is thereby in communication with each such component requiring control. It is to be understood that many such control functions can optionally be carried out manually, and not under control of the processor. Furthermore, the order in which the various functions are described, in the following, is not limiting upon the order in which the processor executes instructions when the apparatus is operating. Thus, processor 980 can be configured to receive data about a sample to be analyzed, e.g., from a sample reader 990, which may be a barcode reader, an optical character reader, or an RFID scanner (radio frequency tag reader). It is also to be understood that, although a single processor 980 is shown as controlling all operations of apparatus 971 and 981, such operations may be distributed, as convenient, over more than one processor.

Processor 980 can be configured to accept user instructions from an input 984, where such instructions may include instructions to start analyzing the sample, and choices of operating conditions. Although not shown in FIGS. 1A and 1B, in various embodiments, input 984 can include one or more input devices selected from the group consisting of: a keyboard, a touch-sensitive surface, a microphone, a trackpad, a retinal scanner, a holographic projection of an input device, and a mouse. A suitable input device may further comprise a reader of formatted electronic media, such as, but not limited to, a flash memory card, memory stick, USB-stick, CD, or floppy diskette. An input device may further comprise a security feature such as a fingerprint reader, retinal scanner, magnetic strip reader, or bar-code reader, for ensuring that a user of the system is in fact authorized to do so, according to pre-loaded identifying characteristics of authorized users. An input device may additionally—and simultaneously—function as an output device for writing data in connection with sample analysis. For example, if an input device is a reader of formatted electronic media, it may also be a writer of such media. Data that may be written to such media by such a device includes, but is not limited to, environmental information, such as temperature or humidity, pertaining to an analysis, as well as a diagnostic result, and identifying data for the sample in question.

Processor 980 can be also configured to communicate with a display 982, so that, for example, information about an analysis is transmitted to the display and thereby communicated to a user of the system. Such information includes but is not limited to: the current status of the apparatus; progress of PCR thermocycling; and a warning message in case of malfunction of either system or cartridge. Additionally, processor 980 may transmit one or more questions to be displayed on display 982 that prompt a user to provide input in response thereto. Thus, in certain embodiments, input 984 and display 982 are integrated with one another.

Processor 980 can be optionally further configured to transmit results of an analysis to an output device such as a printer, a visual display, a display that utilizes a holographic projection, or a speaker, or a combination thereof.

Processor 980 can be still further optionally connected via a communication interface such as a network interface to a computer network 988. The communication interface can be one or more interfaces selected from the group consisting of: a serial connection, a parallel connection, a wireless network connection, a USB connection, and a wired network connection. Thereby, when the system is suitably addressed on the network, a remote user may access the processor and transmit instructions, input data, or retrieve data, such as may be stored in a memory (not shown) associated with the processor, or on some other computer-readable medium that is in communication with the processor. The interface may also thereby permit extraction of data to a remote location, such as a personal computer, personal digital assistant, or network storage device such as computer server or disk farm. The apparatus may further be configured to permit a user to e-mail results of an analysis directly to some other party, such as a healthcare provider, or a diagnostic facility, or a patient.

Additionally, in various embodiments, the apparatus can further comprise a data storage medium configured to receive data from one or more of the processor, an input device, and a communication interface, the data storage medium being one or more media selected from the group consisting of: a hard disk drive, an optical disk drive, a flash card, and a CD-Rom.

Processor 980 can be further configured to control various aspects of sample preparation and diagnosis, as follows in overview, and as further described in detail herein. In FIGS. 1A and 1B, the apparatus 981 (or 971) is configured to operate in conjunction with a complementary rack 970. The rack is itself configured, as further described herein, to receive a number of biological samples 996 in a form suitable for work-up and diagnostic analysis, and a number of holders 972 that are equipped with various reagents, pipette tips and receptacles. The rack is configured so that, during sample work-up, samples are processed in the respective holders, the processing including being subjected, individually, to heating and cooling via heater assembly 977. The heating functions of the heater assembly can be controlled by the processor 980. Heater assembly 977 operates in conjunction with a separator 978, such as a magnetic separator, that also can be controlled by processor 980 to move into and out of close proximity to one or more processing chambers associated with the holders 972, wherein particles such as magnetic particles are present.

Liquid dispenser 976, which similarly can be controlled by processor 980, is configured to carry out various suck and dispense operations on respective sample, fluids and reagents in the holders 972, to achieve extraction of nucleic acid from the samples. Liquid dispenser 976 can carry out such operations on multiple holders simultaneously. Sample reader 990 is configured to transmit identifying indicia about the sample, and in some instances the holder, to processor 980. In some embodiments a sample reader is attached to the liquid dispenser and can thereby read indicia about a sample above which the liquid dispenser is situated. In other embodiments the sample reader is not attached to the liquid dispenser and is independently movable, under control of the processor. Liquid dispenser 976 is also configured to take aliquots of fluid containing nucleic acid extracted from one or more samples and direct them to storage area 974, which may be a cooler. Area 974 contains, for example, a PCR tube corresponding to each sample. In other embodiments, there is not a separate Area 974, but a cooler can be configured to cool the one or more holders 972 so that extracted nucleic acid is cooled and stored in situ rather than being transferred to a separate location.

FIG. 1B shows a schematic embodiment of a diagnostic apparatus 971, having elements in common with apparatus 981 FIG. 1A but, in place of a storage area 974, having a receiving bay 992 in which a cartridge 994 is received. The receiving bay is in communication with a heater 998 that itself can be controlled by processor 980 in such a way that specific regions of the cartridge are heated at specific times during analysis. Liquid dispenser 976 is thus configured to take aliquots of fluid containing nucleic acid extracted from one or more samples and direct them to respective inlets in cartridge 994. Cartridge 994 is configured to amplify, such as by carrying out PCR, on the respective nucleic acids. The processor is also configured to control a detector 999 that receives an indication of a diagnosis from the cartridge 994. The diagnosis can be transmitted to the output device 986 and/or the display 982, as described hereinabove.

A suitable processor 980 can be designed and manufactured according to, respectively, design principles and semiconductor processing methods known in the art.

Embodiments of the apparatuses shown in outline in FIGS. 1A and 1B, as with other exemplary embodiments described herein, is advantageous because they do not require locations within the apparatus suitably configured for storage of reagents. Neither do embodiments of the system, or other exemplary embodiments herein, require inlet or outlet ports that are configured to receive reagents from, e.g., externally stored containers such as bottles, canisters, or reservoirs. Therefore, the apparatuses in FIGS. 1A and 1B are self-contained and operate in conjunction with holders 972, wherein the holders are pre-packaged with reagents, such as in locations within it dedicated to reagent storage.

The apparatuses of FIGS. 1A and 1B may be configured to carry out operation in a single location, such as a laboratory setting, or may be portable so that they can accompany, e.g., a physician, or other healthcare professional, who may visit patients at different locations. The apparatuses are typically provided with a power-cord so that they can accept AC power from a mains supply or generator. An optional transformer (not shown) built into each apparatus, or situated externally between a power socket and the system, transforms AC input power into a DC output for use by the apparatus. The apparatus may also be configured to operate by using one or more batteries and therefore is also typically equipped with a battery recharging system, and various warning devices that alert a user if battery power is becoming too low to reliably initiate or complete a diagnostic analysis.

The apparatuses of FIGS. 1A and 1B may further be configured, in other embodiments, for multiplexed sample analysis and/or analysis of multiple batches of samples, where, e.g., a single rack holds a single batch of samples. In one such configuration, instances of a system, as outlined in FIG. 1B, accept and to process multiple microfluidic cartridges 994. Each component shown in FIGS. 1A and 1B may therefore be present as many times as there are batches of samples, though the various components may be configured in a common housing.

In still another configuration, a system is configured to accept and to process multiple cartridges, but one or more components in FIGS. 1A and 1B is common to multiple cartridges. For example, a single apparatus may be configured with multiple cartridge receiving bays, but a common processor, detector, and user interface suitably configured to permit concurrent, consecutive, or simultaneous, control of the various cartridges. It is further possible that such an embodiment, also utilizes a single sample reader, and a single output device.

In still another configuration, a system as shown in FIG. 1B is configured to accept a single cartridge, wherein the single cartridge is configured to process more than 1, for example, 2, 3, 4, 5, or 6, samples in parallel, and independently of one another. Exemplary technology for creating cartridges that can handle multiple samples is described elsewhere, e.g., in U.S. application Ser. No. 60/859,284, incorporated herein by reference.

It is further consistent with the present technology that a cartridge can be tagged, e.g., with a molecular bar-code indicative of the sample, to facilitate sample tracking, and to minimize risk of sample mix-up. Methods for such tagging are described elsewhere, e.g., in U.S. patent application publication Ser. No. 10/360,854, incorporated herein by reference.

Figure 2:
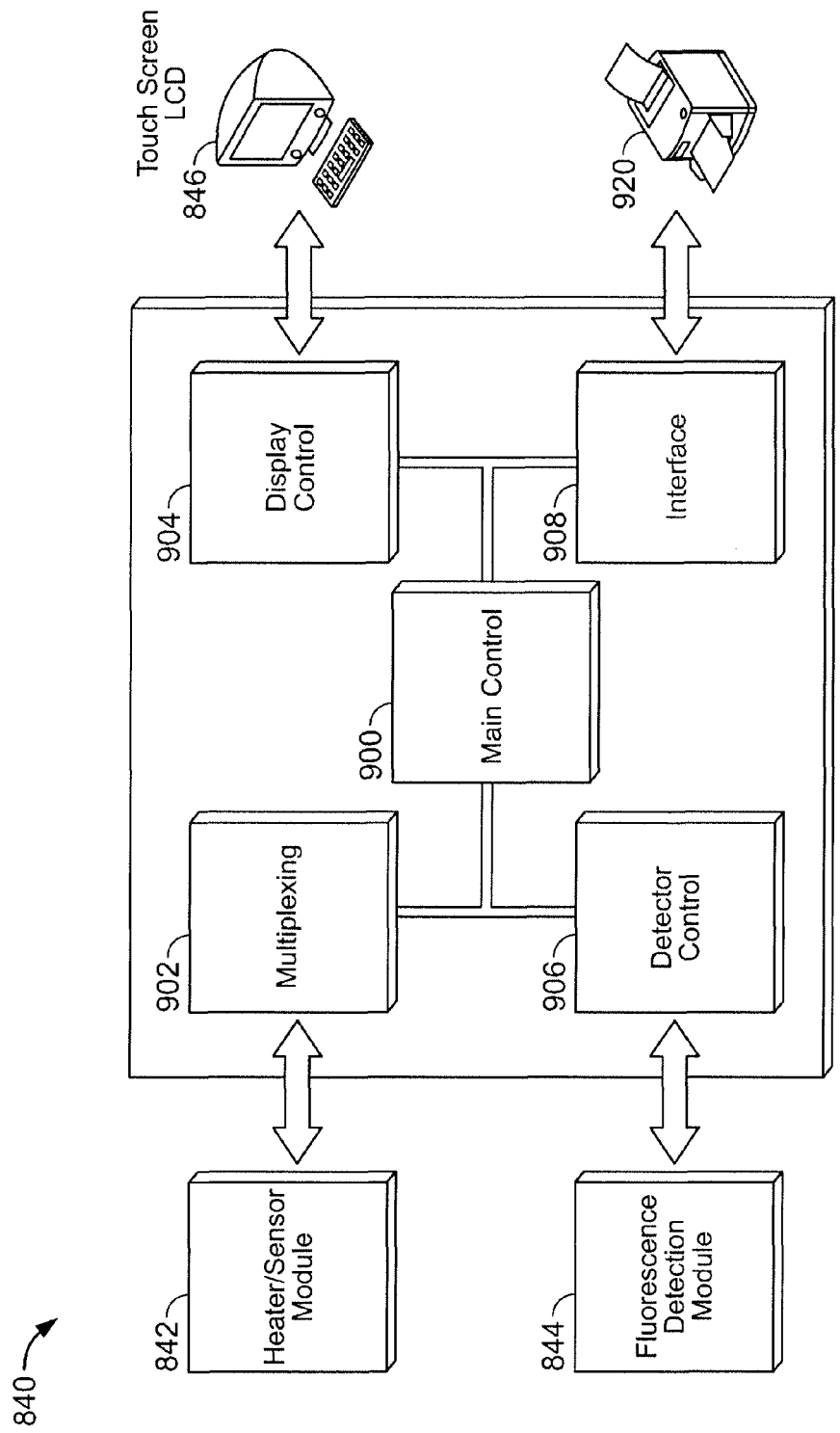

Control electronics 840 implemented into apparatus 971 or 981, shown schematically in the block diagram in FIG. 2, can include one or more functions in various embodiments, for example, for main control 900, multiplexing 902, display control 904, detector control 906, and the like. The main control function may serve as the hub of control electronics 840 in the apparatuses of FIGS. 1A and 1B, and can manage communication and control of the various electronic functions. The main control function can also support electrical and communications interface 908 with a user or an output device such as a printer 920, as well as optional diagnostic and safety functions. In conjunction with main control function 900, multiplexer function 902 can control sensor data 914 and output current 916 to help control heater assembly 977. The display control function 904 can control output to and, if applicable, interpret input from touch screen LCD 846, which can thereby provide a graphical interface to the user in certain embodiments. The detector function 906 can be implemented in control electronics 840 using typical control and processing circuitry to collect, digitize, filter, and/or transmit the data from a detector 999 such as one or more fluorescence detectors. Additional functions, not shown in FIG. 2, include but are not limited to control functions for controlling elements in FIGS. 1A and 1B such as a liquid dispense head, a separator, a cooler, and to accept data from a sample reader.

Figure 3A:
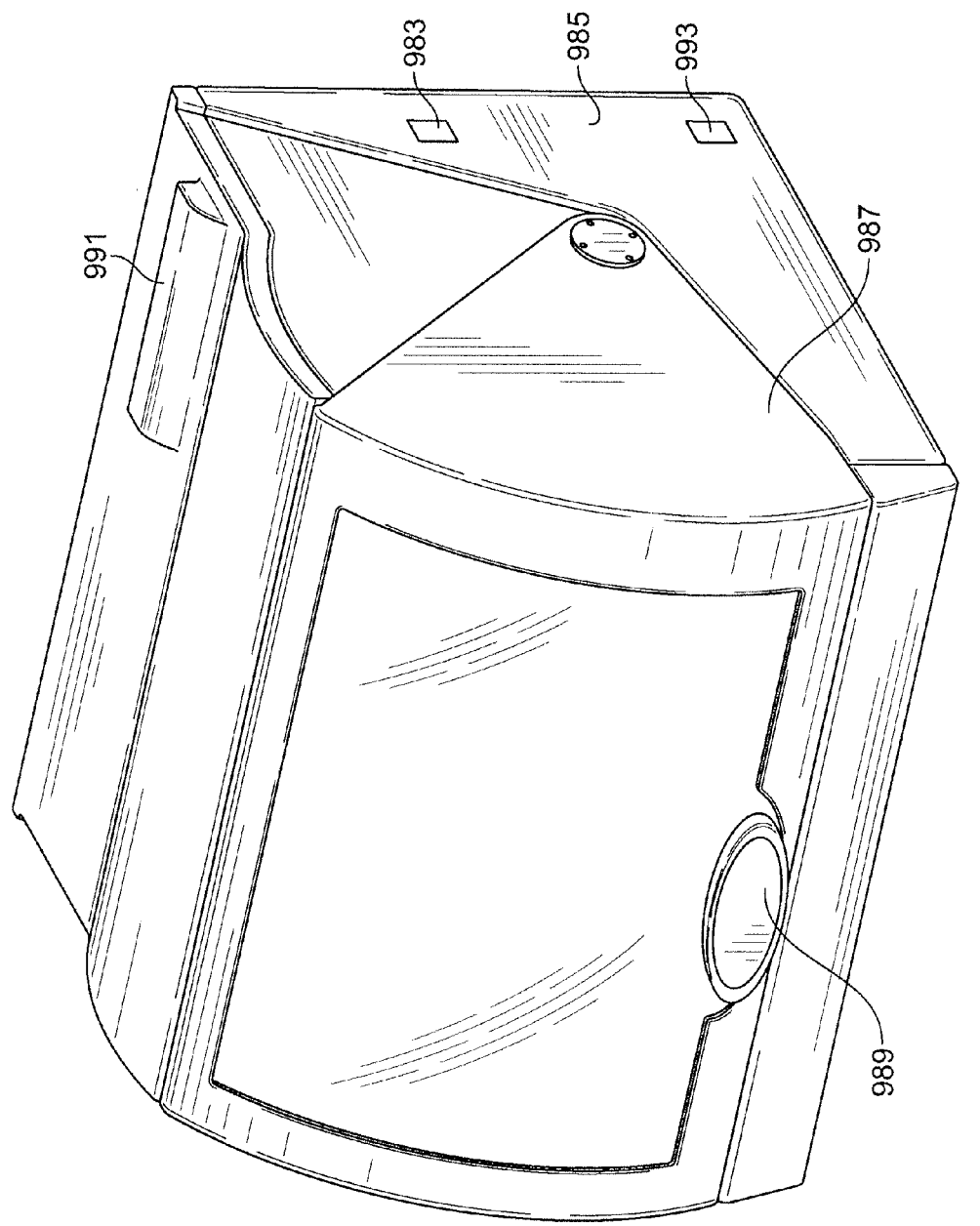
Figure 3B:
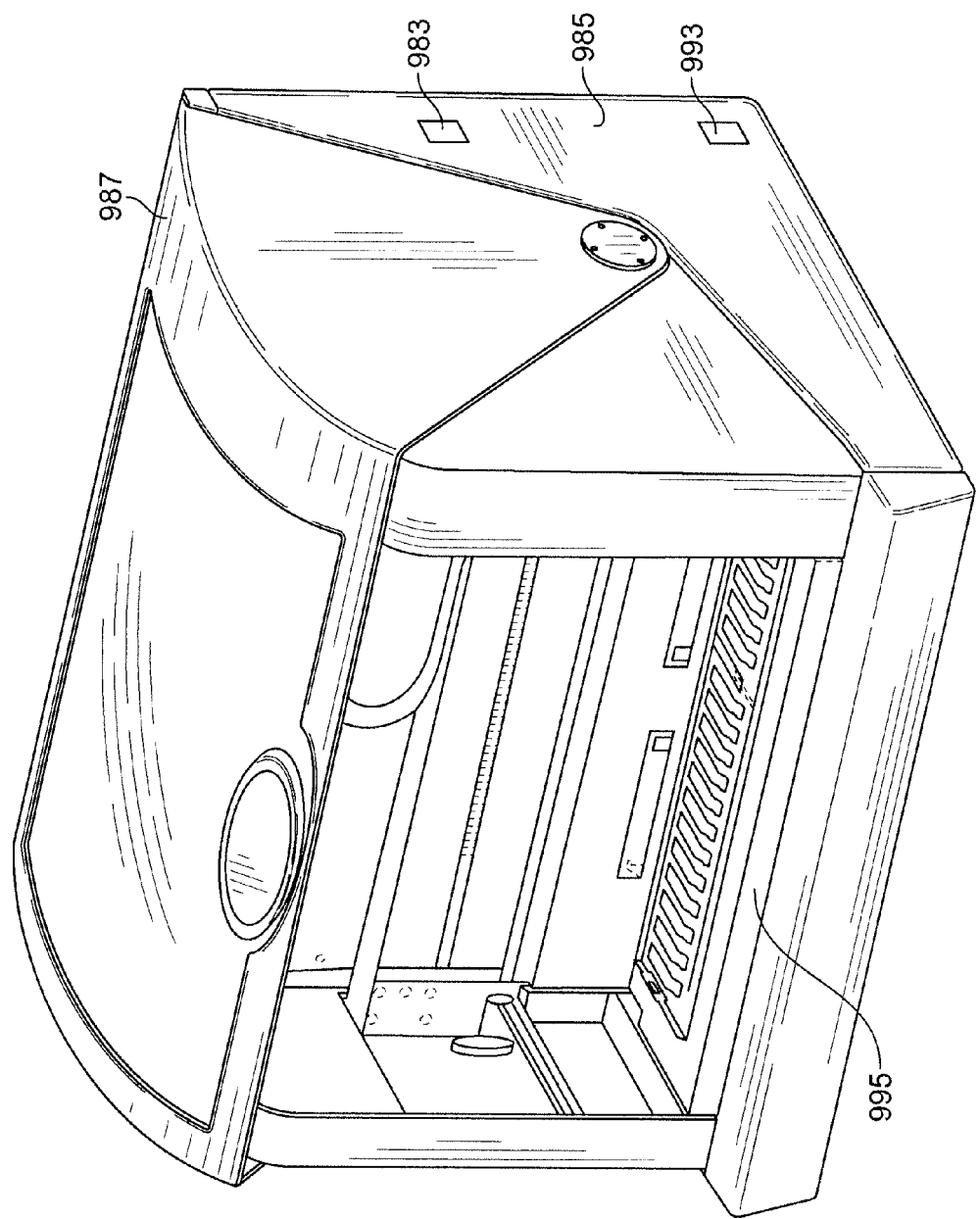

An exemplary apparatus, having functions according to FIG. 1A or 1B, is shown in FIGS. 3A and 3B. The exemplary apparatus in FIGS. 3A and 3B has a housing 985, and a cover 987, shown in a closed position in FIG. 3A, and in an open position in FIG. 3B to reveal interior features 995. Cover 987 optionally has a handle 989, shown as oval and raised from the surface of the cover, but which may be other shapes such as square, rectangular, or circular, and which may be recessed in, or flush with, the surface of the cover. Cover 987 is shown as having a hinge, though other configurations such as a sliding cover are possible. Bumper 991 serves to prevent the cover from falling too far backwards and/or provides a point that holds cover 987 steady in an open position. Housing 985 is additionally shown as having one or more communications ports 983, and one or more power ports 993, which may be positioned elsewhere, such as on the rear of the instrument.

The apparatus of FIGS. 1A and 1B may optionally comprise one or more stabilizing feet that cause the body of the device to be elevated above a surface on which system 100 is disposed, thereby permitting ventilation underneath system 100, and also providing a user with an improved ability to lift system 100. There may be 2, 3, 4, 5, or 6, or more feet, depending upon the size of system 100. Such feet are preferably made of rubber, or plastic, or metal, and in some embodiments may elevate the body of system 10 by from about 2 to about 10 mm above a surface on which it is situated.

Figure 4:
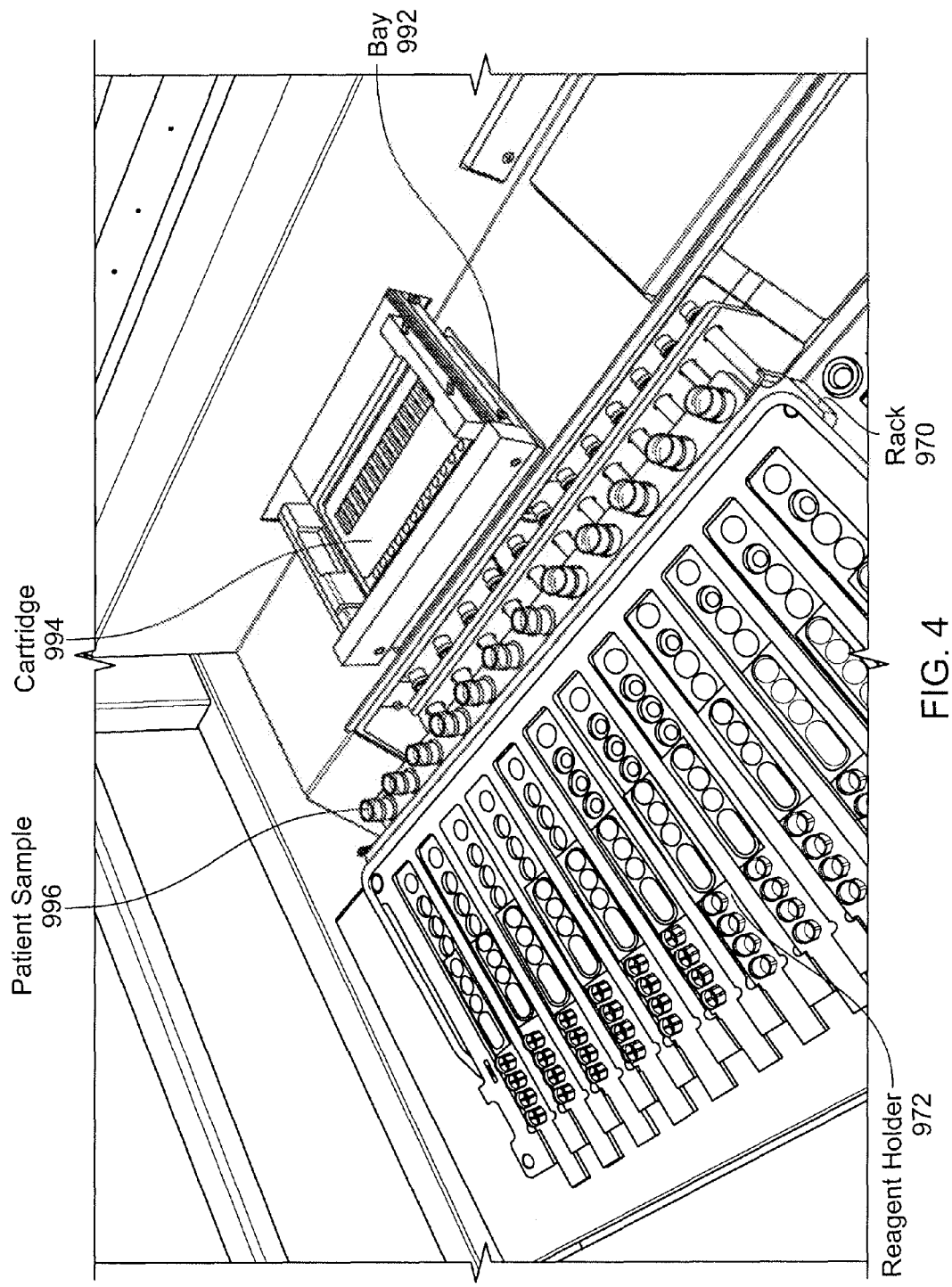

FIG. 4 shows an exemplary configuration of a portion of an interior of an exemplary apparatus, such as that shown in FIGS. 3A and 3B. In FIG. 4 are shown a rack 970, containing a number of reagent holders 972 and patient samples 996, as well as, in close proximity thereto, a receiving bay 992 having a cartridge 994, for performing PCR on polynucleotides extracted from the samples.

Rack

The apparatus further comprises one or more racks configured to be insertable into, and removable from, the apparatus, each of the racks being further configured to receive a plurality of reagent holders, and to receive a plurality of sample tubes, wherein the reagent holders are in one-to-one correspondence with the sample tubes, and wherein the reagent holders each contain sufficient reagents to extract polynucleotides from a sample and place the polynucleotides into a PCR-ready form. Exemplary reagent holders are further described elsewhere herein.

An apparatus may comprise 1, 2, 3, 4, or 6 racks, and each rack may accept 2, 4, 6, 8, 10, 12, 16, or 20 samples such as in sample tubes 802, and a corresponding number of holders 804, each at least having one or more pipette tips, and one or more containers for reagents.

A rack is typically configured to accept a number of reagent holders 804, such as those further described herein, the rack being configured to hold one or more such holders, either permitting access on a laboratory benchtop to reagents stored in the holders, or situated in a dedicated region of the apparatus permitting the holders to be accessed by one or more other functions of the apparatus, such as automated pipetting, heating of the process tubes, and magnetic separating of affinity beads.

Figure 5:
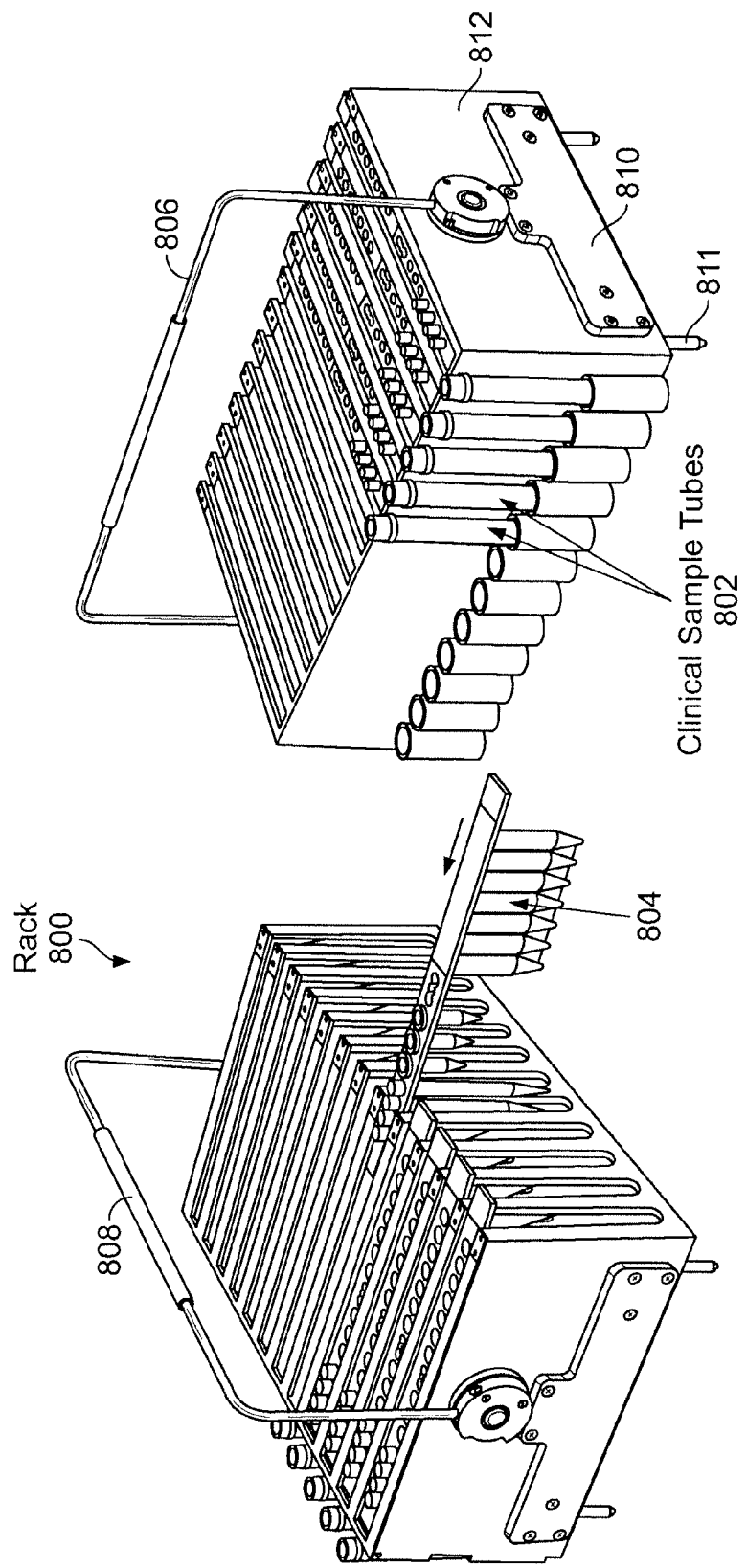

Two perspective views of an exemplary rack 800, configured to accept 12 sample tubes and 12 corresponding reagent holders, in 12 lanes, are shown in FIG. 5. A lane, as used herein in the context of a rack, is a dedicated region of the rack designed to receive a sample tube and corresponding reagent holder. Two perspective views of the same exemplary rack, in conjunction with a heater unit, are shown in FIG. 6.

Figure 7:
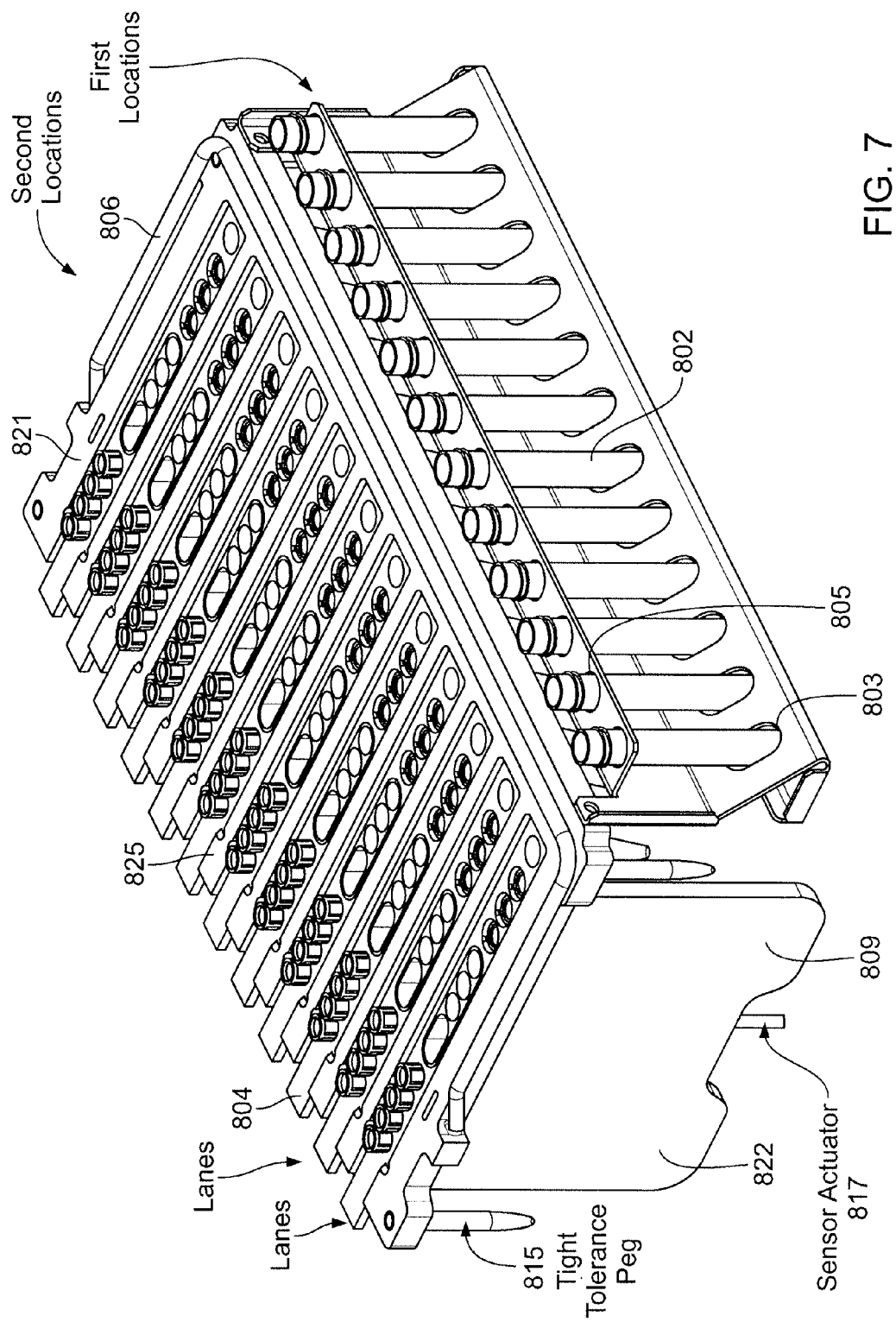
Figure 8A:
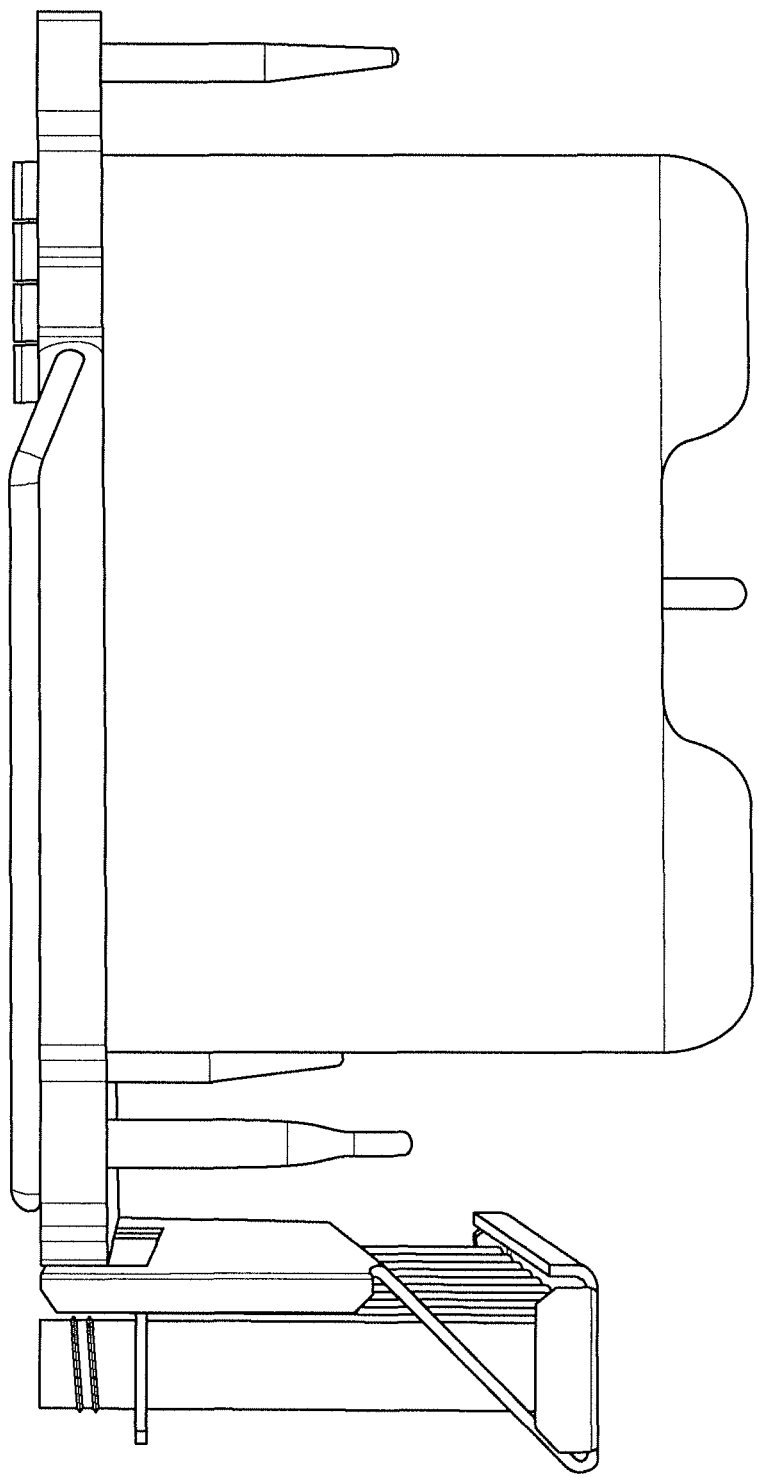
Figure 8B:
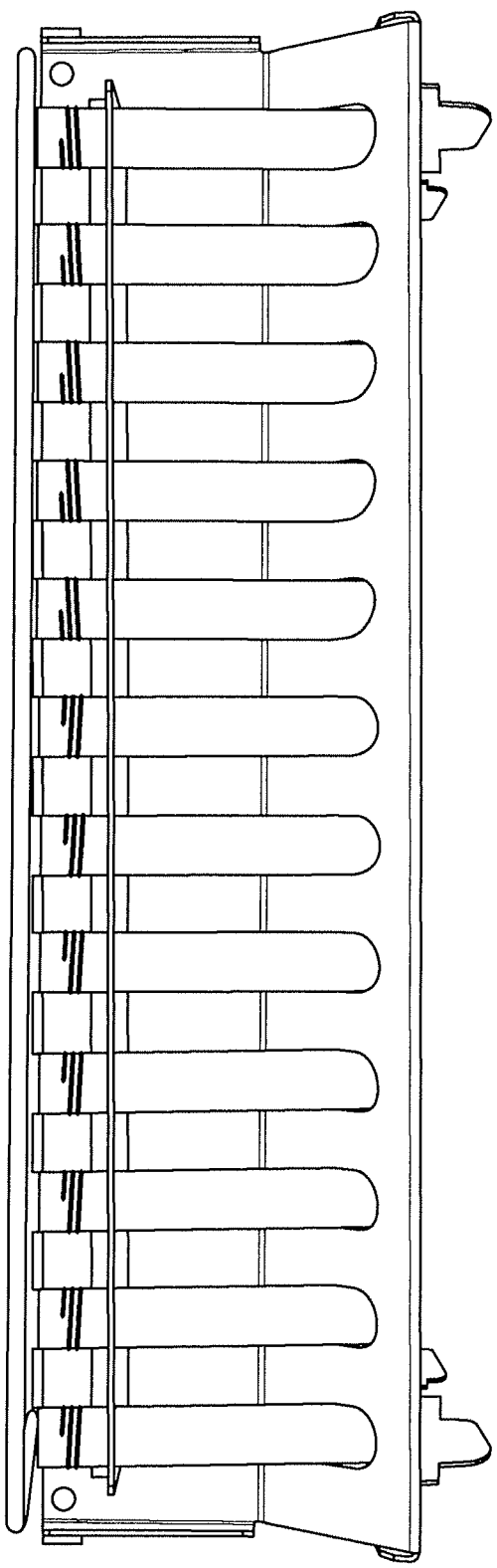
Figure 8C:
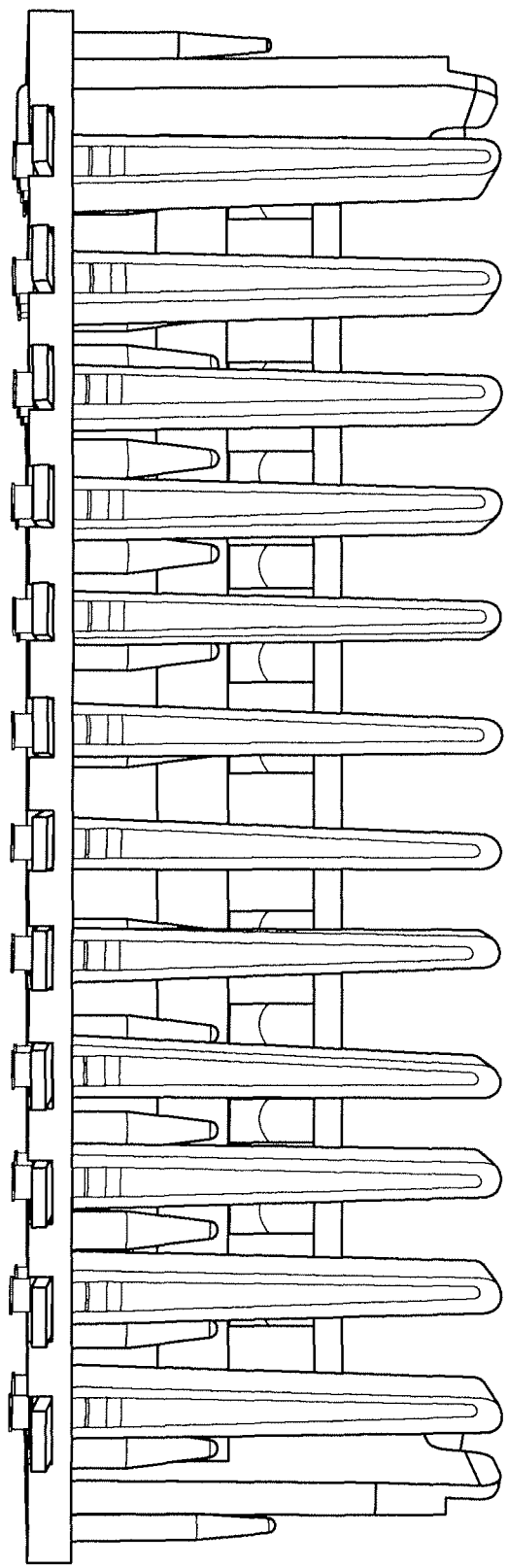
Figure 8D:
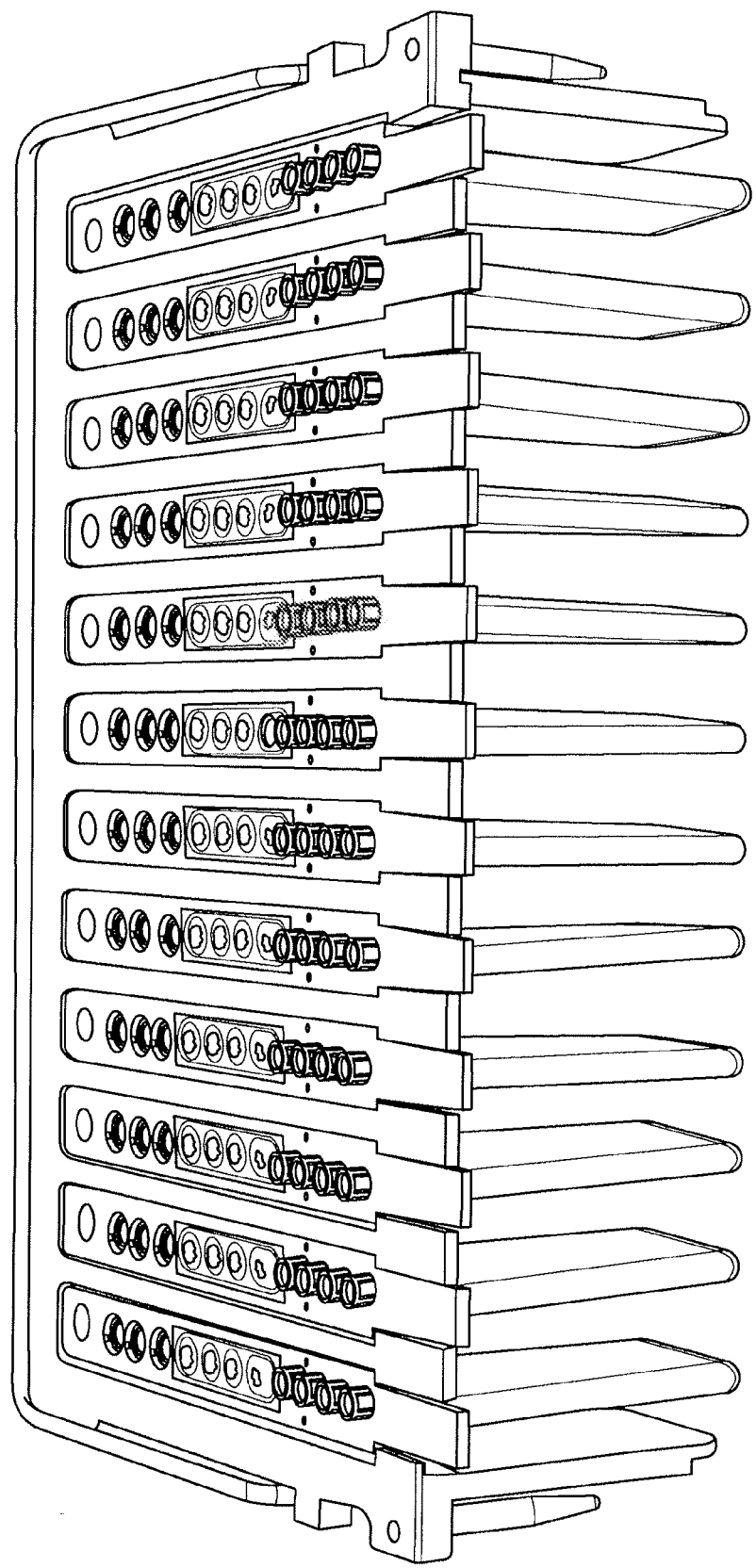
Figure 8E:
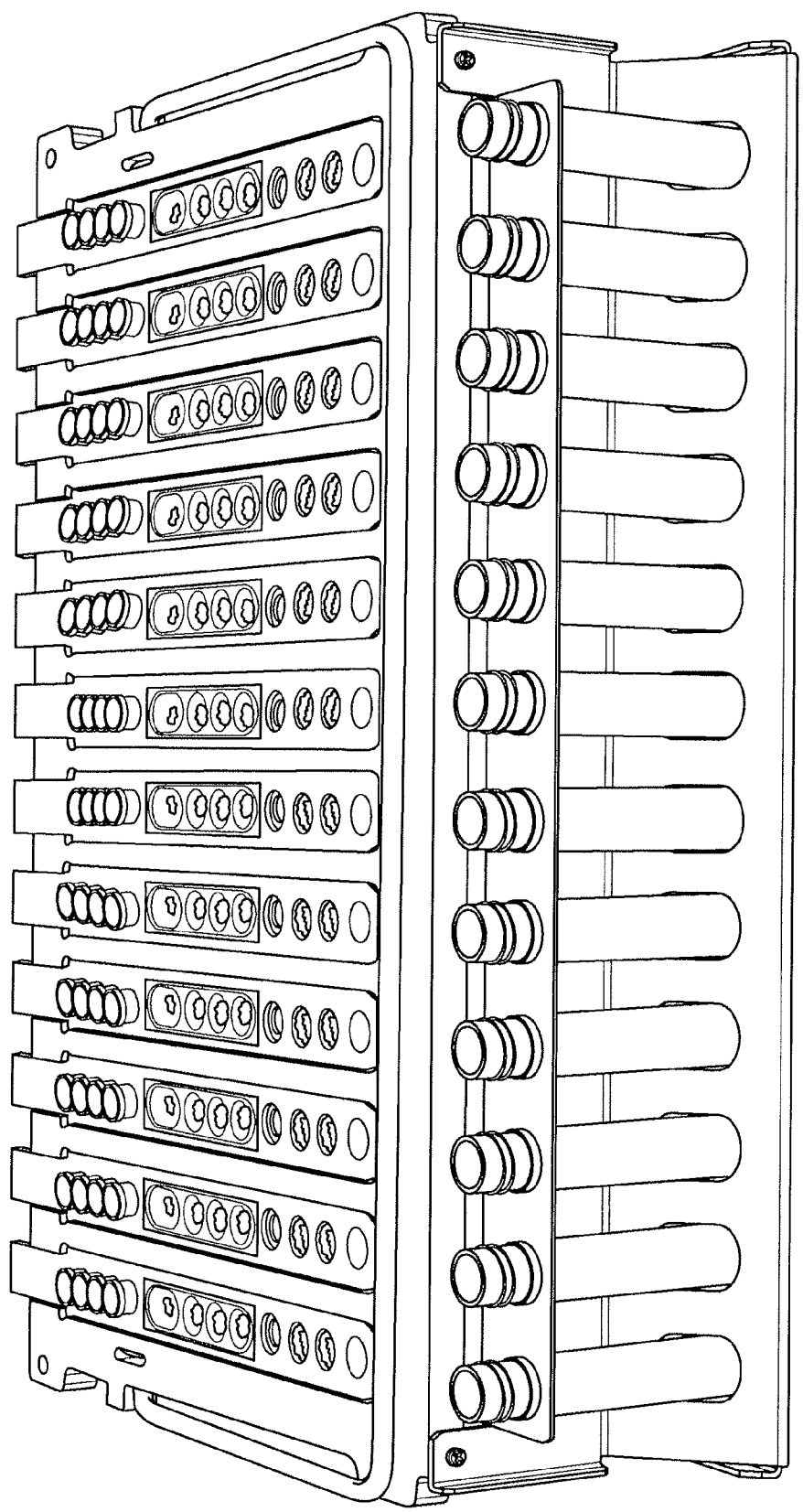
Figure 8F:
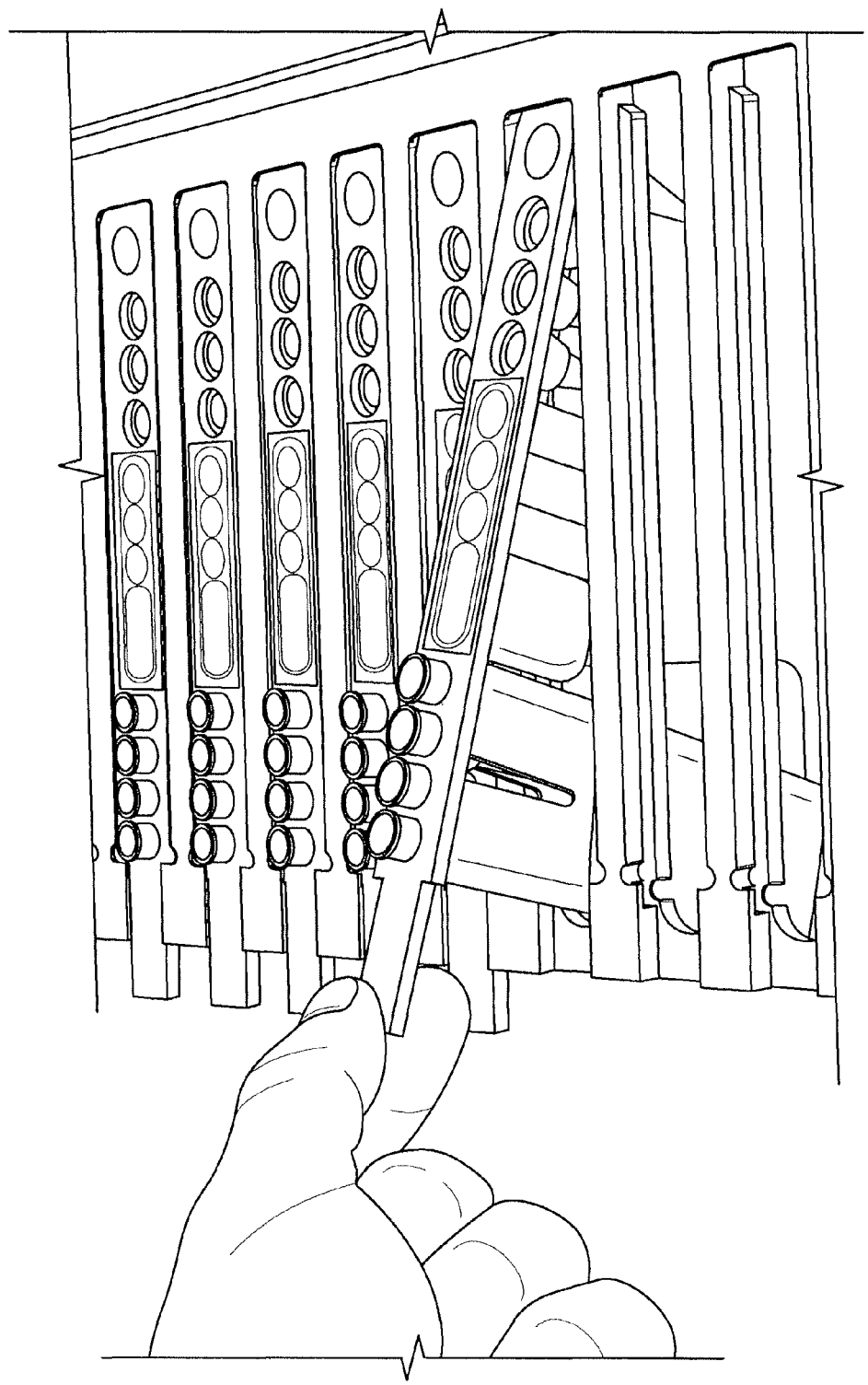
Figure 8G:
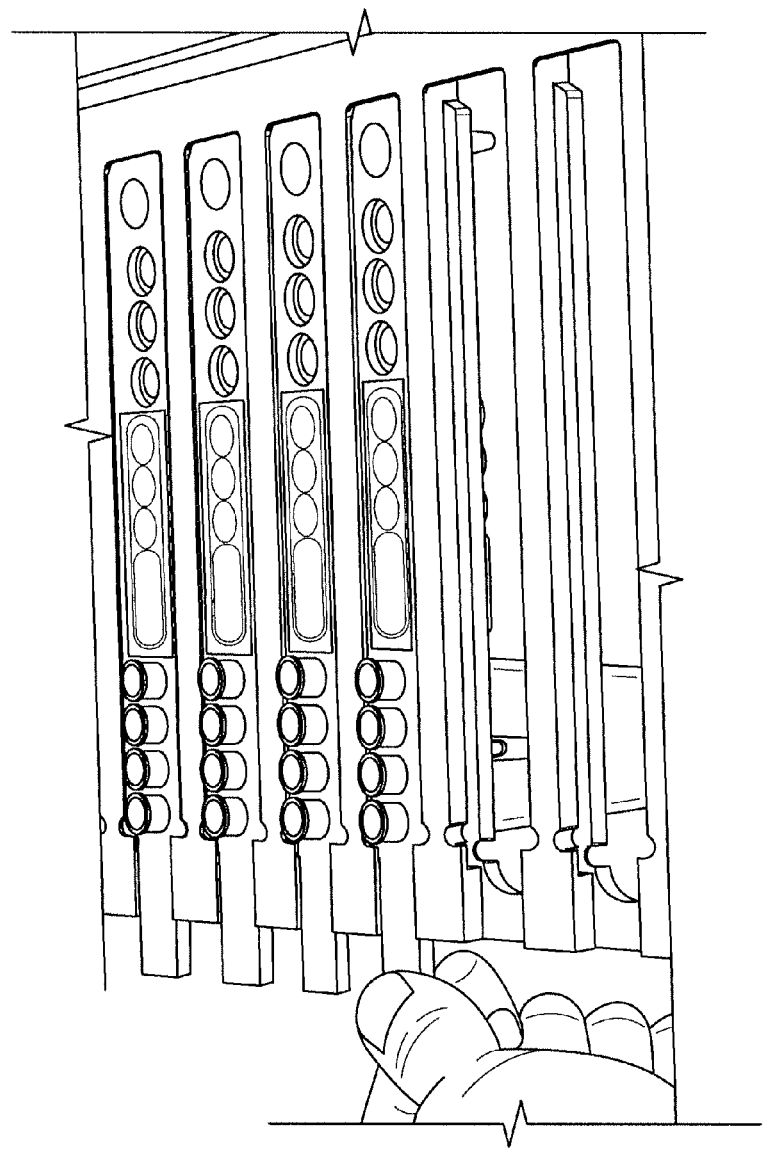
Figure 8H:
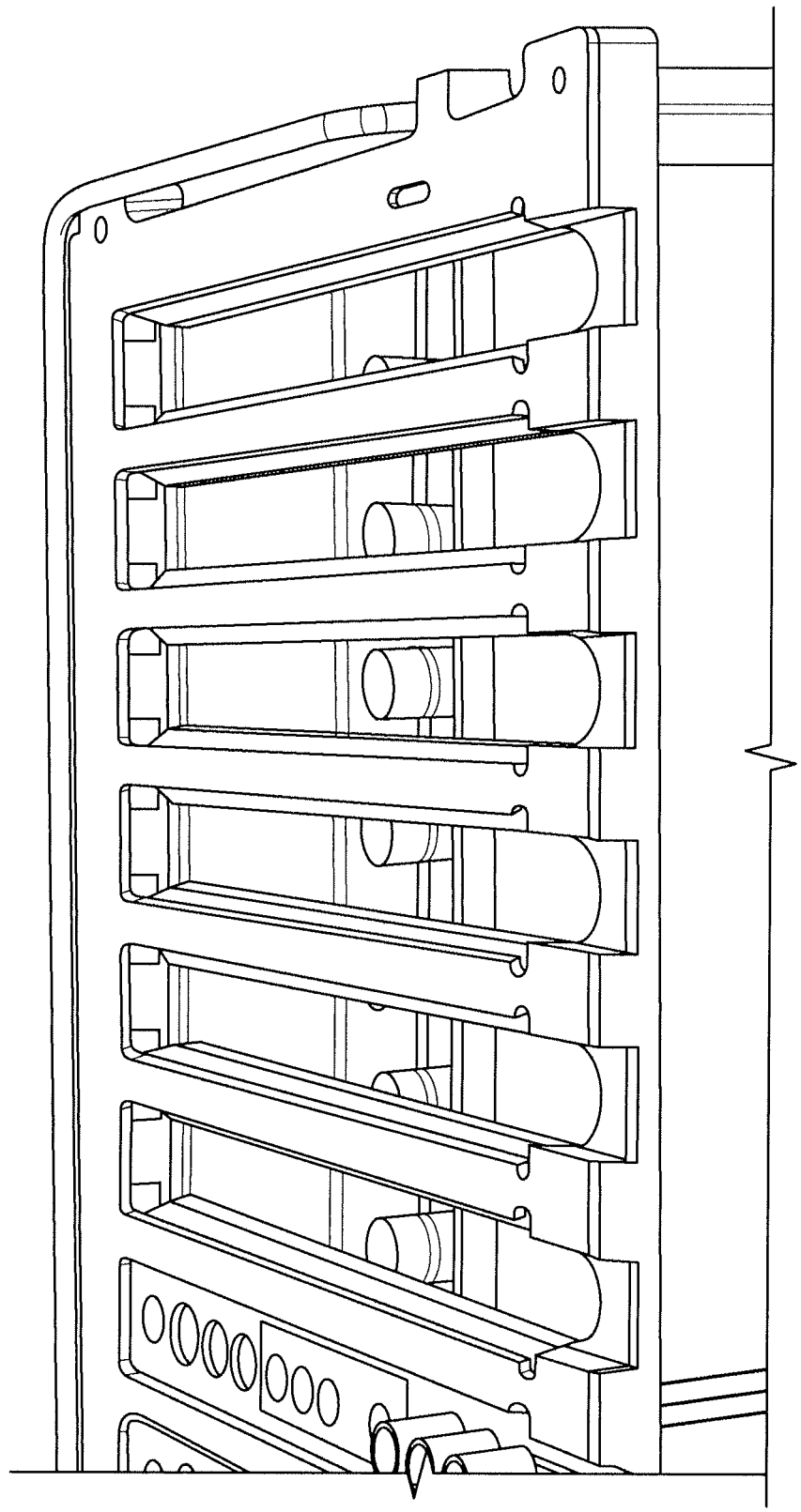
Figure 8I:
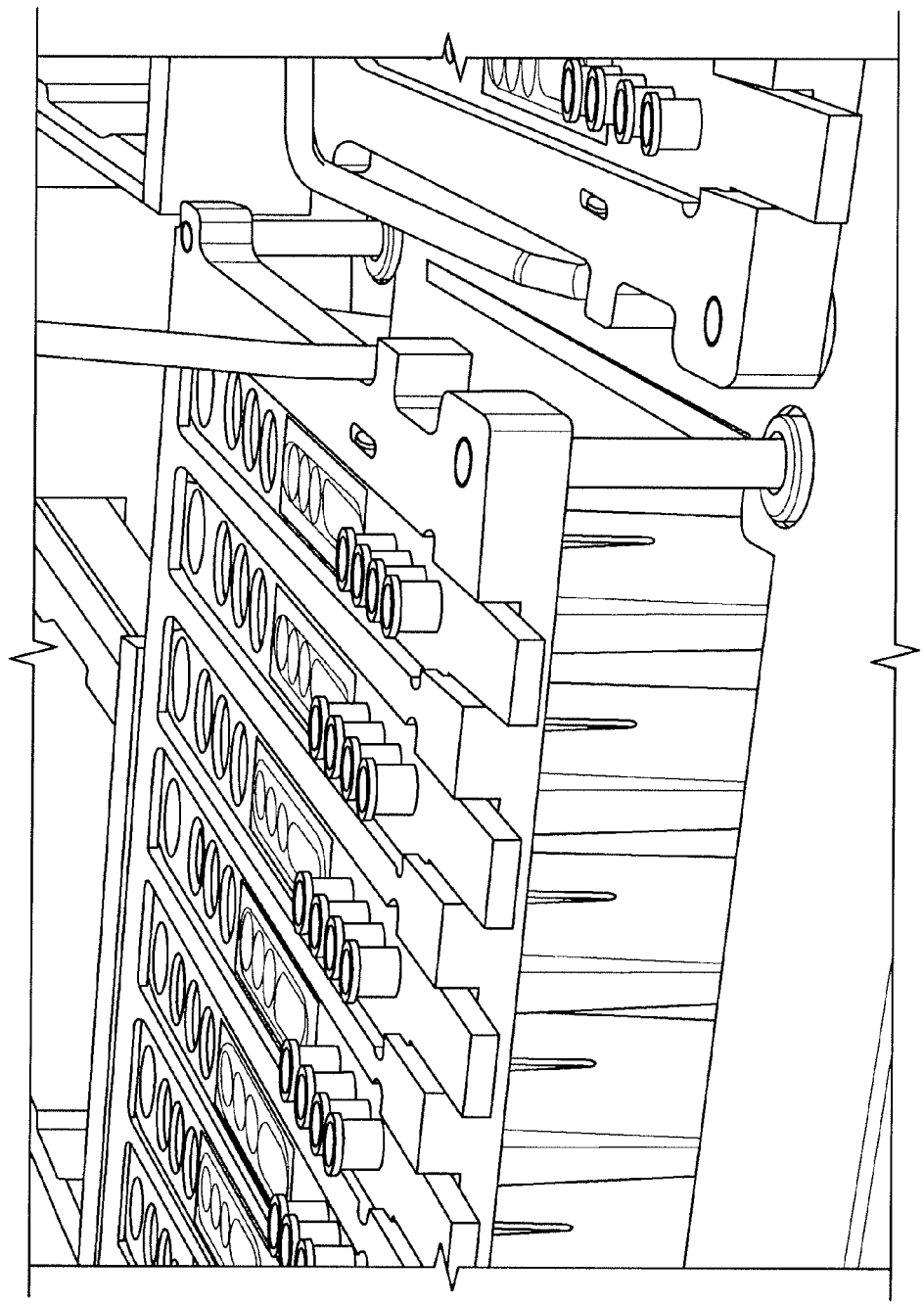
Figure 8J:
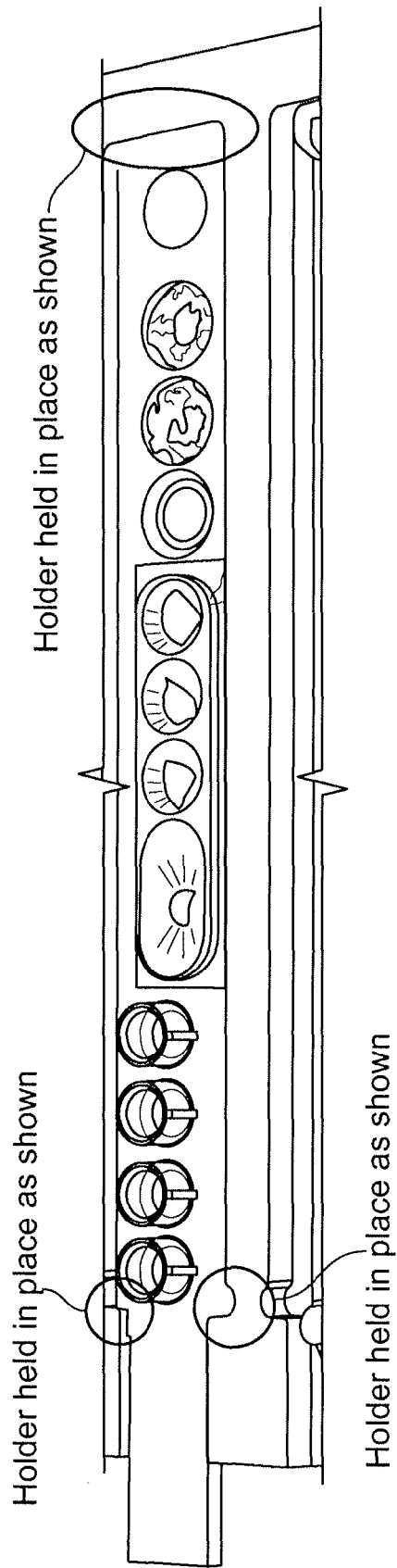
Figure 8K:
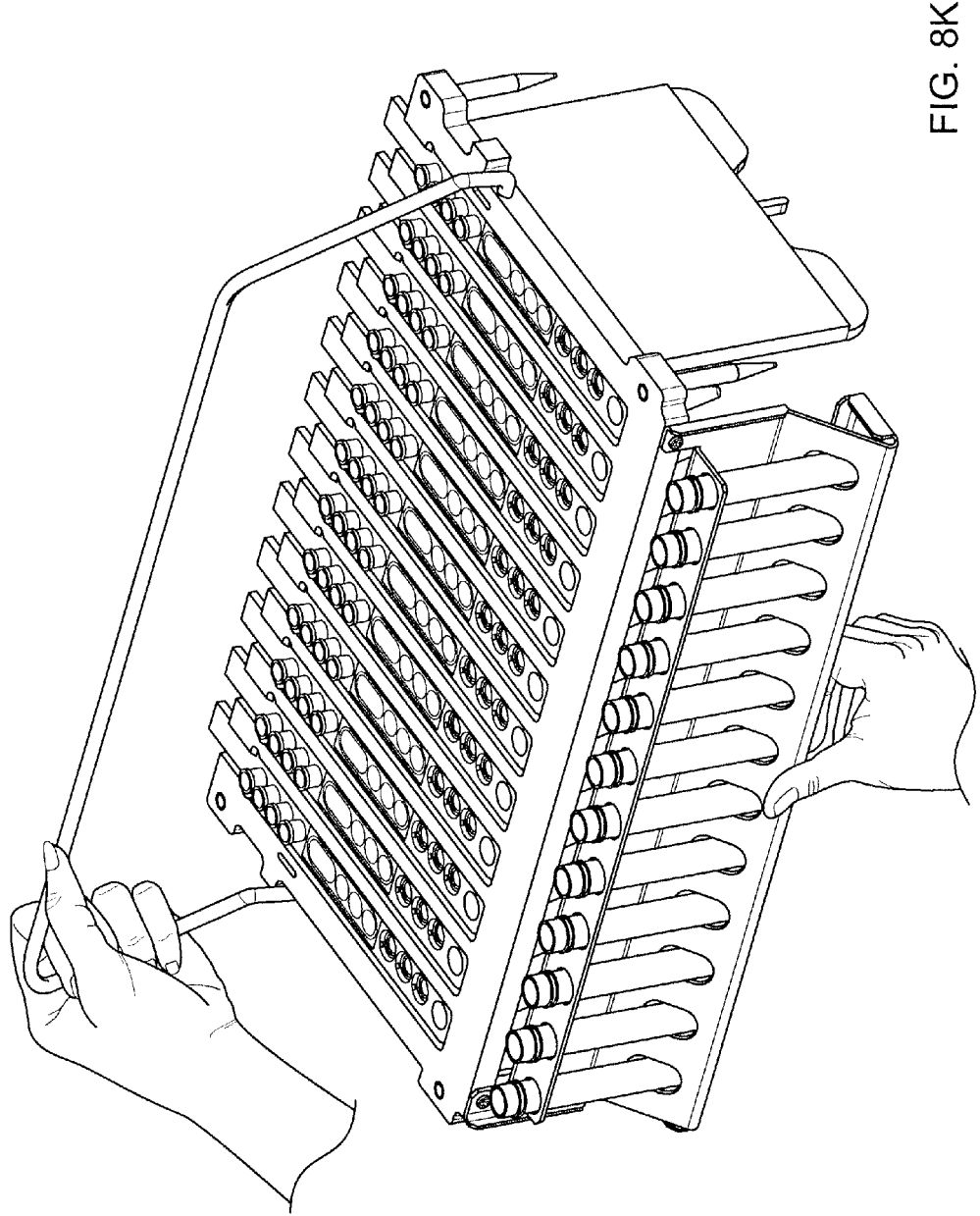
Figure 9:
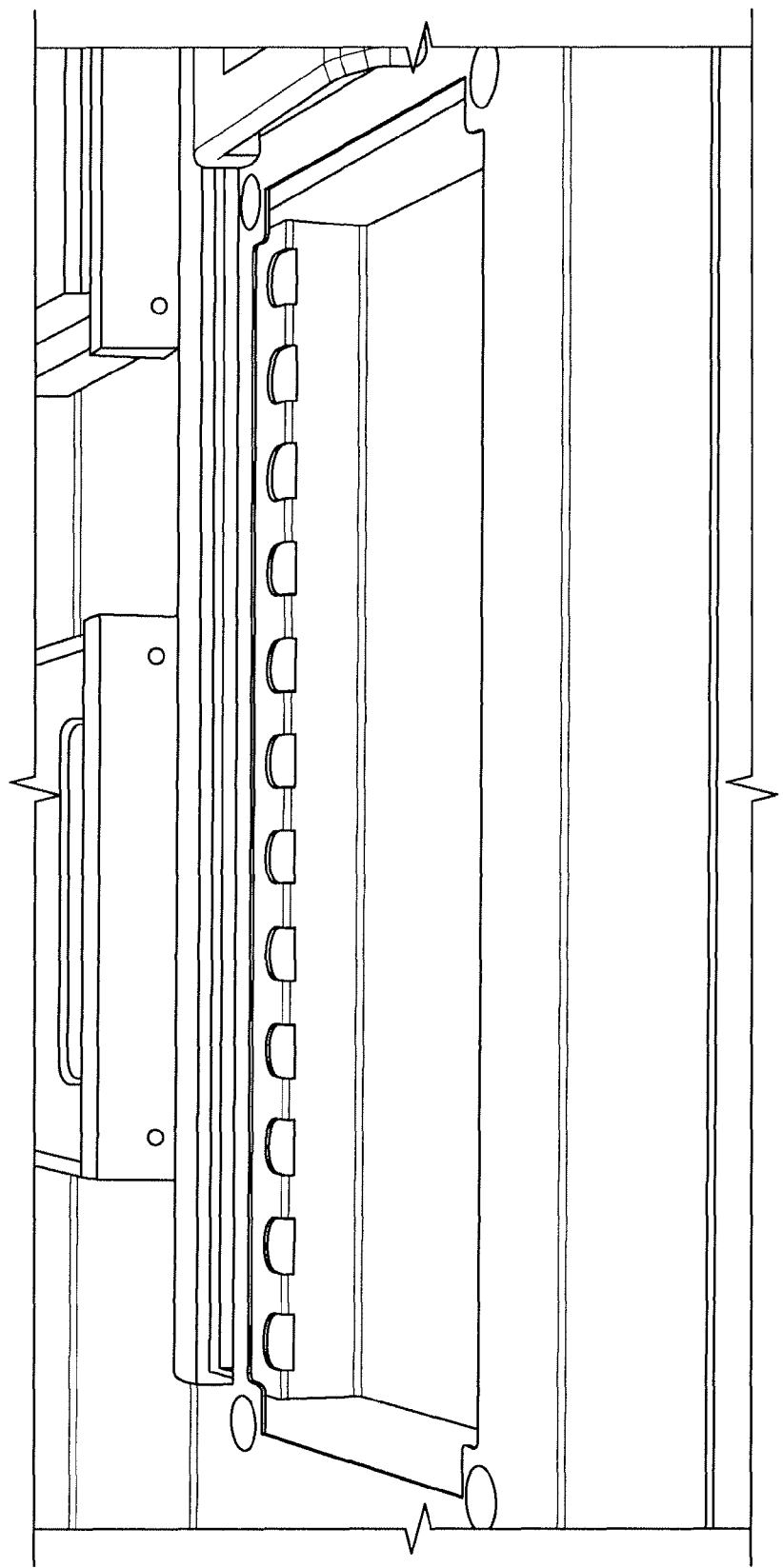

Various views of a second exemplary rack 800, also configured to accept 12 sample tubes and 12 reagent holders, are shown in FIG. 7, and FIGS. 8A-8K. Thus, the following views are shown: side plan (FIG. 8A); front plan, showing sample tubes (FIG. 8B); rear plan, showing reagent holders (FIG. 8C); rear elevation, showing reagent holders (FIG. 8D); front elevation, showing sample tubes (FIG. 8E); top, showing insertion of a reagent holder (FIGS. 8F and 8G); top showing slot for inserting a reagent holder (FIG. 8H); top view showing registration of reagent holder (FIG. 8I); close up of rack in state of partial insertion/removal from apparatus (FIG. 8J); and rack held by handle, removed from apparatus (FIG. 8K). A recessed area in a diagnostic or preparatory apparatus, as further described herein, for accepting the exemplary removable rack of FIG. 7 is shown in FIG. 9. Other suitably configured recessed areas for receiving other racks differing in shape, appearance, and form, rather than function, are consistent with the description herein.

The two exemplary racks shown in the figures being non-limiting, general features of racks contemplated herein are now described using the two exemplary racks as illustrative thereof. For example, the embodiments shown here, at least the first lane and the second lane are parallel to one another, a configuration that increases pipetting efficiency. Typically, when parallel to one another, pairs of adjacent sample lanes are separated by 24 mm at their respective midpoints. (Other distances are possible, such as 18 mm apart, or 27 mm apart. The distance between the midpoints in dependent on the pitch of the nozzles in the liquid dispensing head, as further described herein. Keeping the spacing in multiples of 9 mm enables easy loading from the rack into a 96 well plate (where typically wells are spaced apart by 9 mm). Typically, also, the rack is such that plurality of reagent holders in the plurality of lanes are maintained at the same height relative to one another.

The rack is configured to accept a reagent holder in such a way that the reagent holder snaps or locks reversibly into place, and remains steady while reagents are accessed in it, and while the rack is being carried from one place to another or is being inserted into, or removed from, the apparatus. In each embodiment, each of the second locations comprises a mechanical key configured to accept the reagent holder in a single orientation. In FIG. 5, it is shown that the reagent holder(s) slide horizontally into vertically oriented slots, one per holder, located in the rack. In such an embodiment, the edge of a connecting member on the holder engages with a complementary groove in the upper portion of a slot. In FIGS. 8F, 8G, and 8I, it is shown that the reagent holder(s) can engage with the rack via a mechanical key that keeps the holders steady and in place. For example, the mechanical key can comprise a raised or recessed portion that, when engaging with a complementary portion of the reagent holder, permits the reagent holder to snap into the second location. It can also be seen in the embodiments shown that the reagent holder has a first end and a second end, and the mechanical key comprises a first feature configured to engage with the first end, and a second feature configured to engage with the second end in such a way that a reagent holder cannot be inserted the wrong way around.

In certain embodiments the reagent holders each lock into place in the rack, such as with a cam locking mechanism that is recognized as locked audibly and/or physically, or such as with a mechanical key. The rack can be configured so that the holders, when positioned in it, are aligned for proper pipette tip pick-up using a liquid dispenser as further described herein. Furthermore, the second location of each lane can be deep enough to accommodate one or more pipette tips, such as contained in a pipette tip sheath.

In certain embodiments, the rack is configured to accept the samples in individual sample tubes 802, each mounted adjacent to a corresponding holder 804, for example on one side of rack 800. The sample tubes can be accessible to a sample identification verifier such as a bar code reader, as further described herein. In FIG. 5, a sample tube is held at its bottom by a cylindrical receiving member. In FIG. 7, it is shown that a sample tube can be held at both its top and bottom, such as by a recessed portion 803 configured to receive a bottom of a sample tube, and an aperture 805 configured to hold an upper portion of the sample tube. The aperture can be a ring or an open loop, or a hole in a metal sheet. The recessed portion can be as in FIG. 7, wherein it is an angled sheet of metal housing having a hole large enough to accommodate a sample tube.

The rack can be designed so that it can be easily removed from the apparatus and carried to and from the laboratory environment external to the apparatus, such as a bench, and the apparatus, for example, to permit easy loading of the sample tube(s) and the reagent holder(s) into the rack. In certain embodiments, the rack is designed to be stable on a horizontal surface, and not easily toppled over during carriage, and, to this end, the rack has one or more (such as 2, 3, 4, 6, 8) feet 809. In certain embodiments, the rack has a handle 806 to ease lifting and moving, and as shown in FIG. 5, the handle can be locked into a vertical position, during carriage, also to reduce risk of the rack being toppled over. The handle can optionally have a soft grip 808 in its middle. In the embodiment of FIG. 7, the carrying handle is positioned about an axis displaced from an axis passing through the center of gravity of the rack when loaded, and is free to fall to a position flush with an upper surface of the rack, under its own weight.

The embodiment of FIG. 5 has a metallic base member 810 having 4 feet 811 that also serve as position locators when inserting the rack into the dedicated portion of the apparatus. The handle is attached to the base member. The portion of the rack 812 that accepts the samples and holders can be made of plastic, and comprises 12 slots, and may be disposable.

In the embodiment of FIG. 7, the rack comprises a housing, a plurality of lanes in the housing, and wherein each lane of the plurality of lanes comprises: a first location configured to accept a sample tube; and a second location, configured to accept a reagent holder; and a registration member complementary to a receiving bay of a diagnostic apparatus. Typically, the housing is made of a metal, such as aluminum, that is both light but also can be machined to high tolerance and is sturdy enough to ensure that the rack remains stable when located in the diagnostic apparatus. The registration member in FIG. 7 comprises four (4) tight tolerance pegs 815, located one per corner of the rack. Such pegs are such that they fit snugly and tightly into complementary holes in the receiving bay of the apparatus and thereby stabilize the rack. Other embodiments having, for example, 2, or 3, or greater than 4 such pegs are consistent with the embodiments herein.

In particular, the housing in the embodiment of FIG. 7 comprises a horizontal member 821, and two or more vertical members 822 connected to the horizontal member, and is such that the second location of each respective lane is a recessed portion within the horizontal member. The two or more vertical members 809 in the embodiment of FIG. 7 are configured to permit the rack to free stand thereon. The housing may further comprise two or more feet or runners, attached symmetrically to the first and second vertical members and giving the rack additional stability when positioned on a laboratory bench top.

Furthermore, in the embodiment of FIG. 7, the housing further comprises a plurality of spacer members 825, each of which is disposed between a pair of adjacent lanes. Optionally, such spacer members may be disposed vertically between the lanes.

Although not shown in the FIGS., a rack can further comprise a lane identifier associated with each lane. A lane identifier may be a permanent or temporary marking such as a unique number or letter, or can be an RFID, or bar-code, or may be a colored tag unique to a particular lane.

A rack is configured so that it can be easily placed at the appropriate location in the instrument and gives the user positive feedback, such as audibly or physically, that it is placed correctly. In certain embodiments, the rack can be locked into position. It is desirable that the rack be positioned correctly, and not permitted to move thereafter, so that movement of the liquid dispenser will not be compromised during liquid handling operations. The rack therefore has a registration member to ensure proper positioning. In the embodiment of FIG. 7, the registration member comprises two or more positioning pins configured to ensure that the rack can only be placed in the diagnostic apparatus in a single orientation; and provide stability for the rack when placed in the diagnostic apparatus. The embodiment of FIG. 7 has, optionally, a sensor actuator 817 configured to indicate proper placement of the rack in the diagnostic apparatus. Such a sensor may communicate with a processor 980 to provide the user with a warning, such as an audible warning, or a visual warning communicated via an interface, if the rack is not seated correctly. It may also be configured to prevent a sample preparation process from initiating or continuing if a seating error is detected.

In certain embodiments, the interior of the rack around the location of process tubes in the various holders is configured to have clearance for a heater assembly and/or a magnetic separator as further described herein. For example, the rack is configured so that process chambers on the individual holders are accepted by heater units in a heater assembly as further described herein.

Having a removable rack enables a user to keep a next rack loaded with samples and in line while a previous rack of samples is being prepared by the apparatus, so that the apparatus usage time is maximized.

The rack can also be conveniently cleaned outside of the instrument in case of any sample spills over it or just as a routine maintenance of laboratory wares.

In certain embodiments the racks have one or more disposable parts.

Holder

Figure 10A:
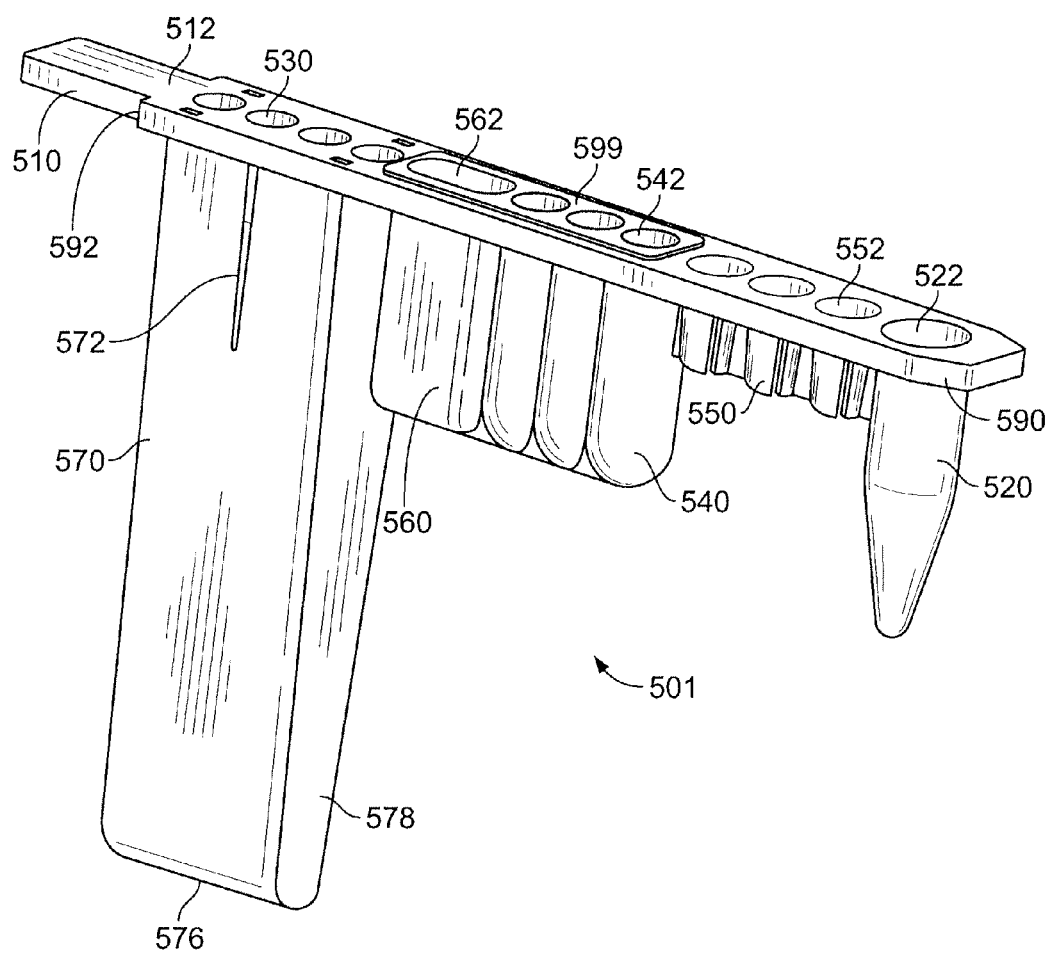
Figure 10B:
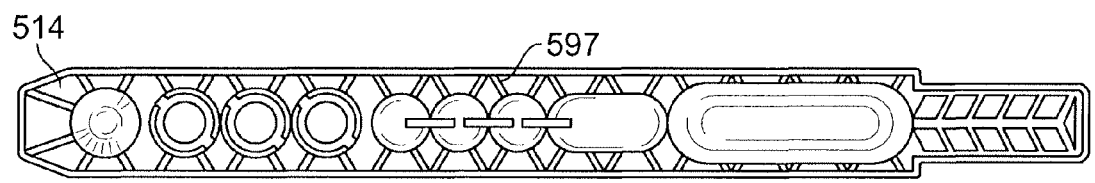
Figure 11:
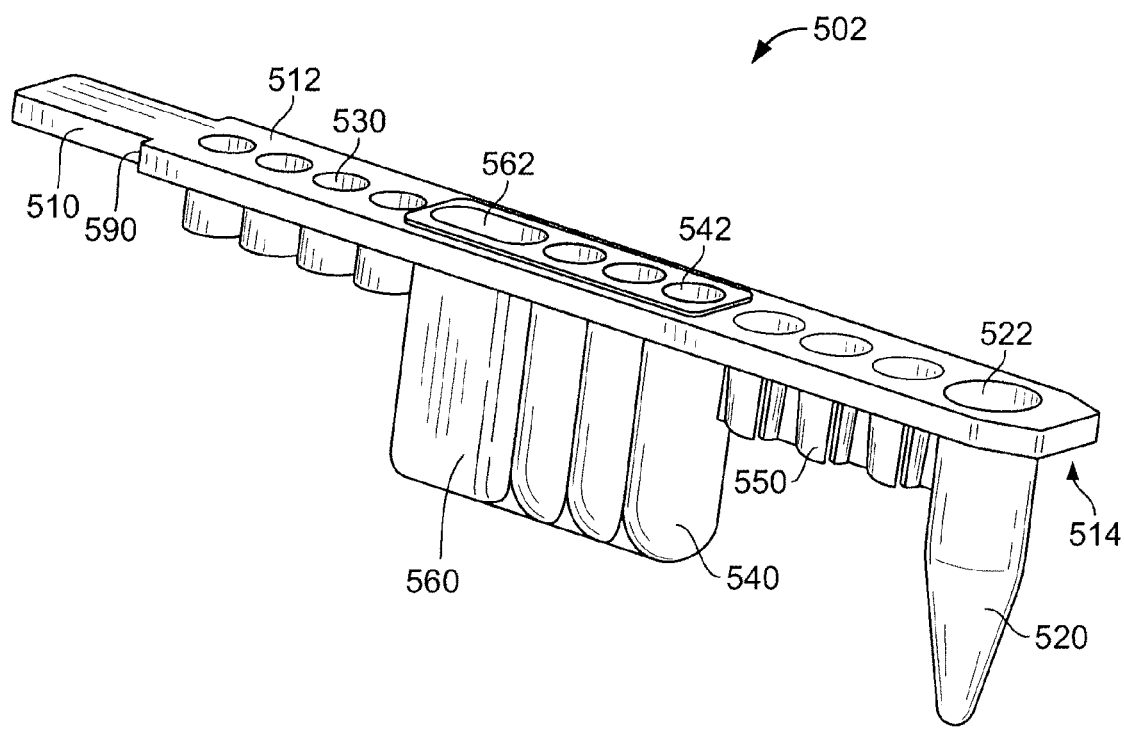
Figure 12C:
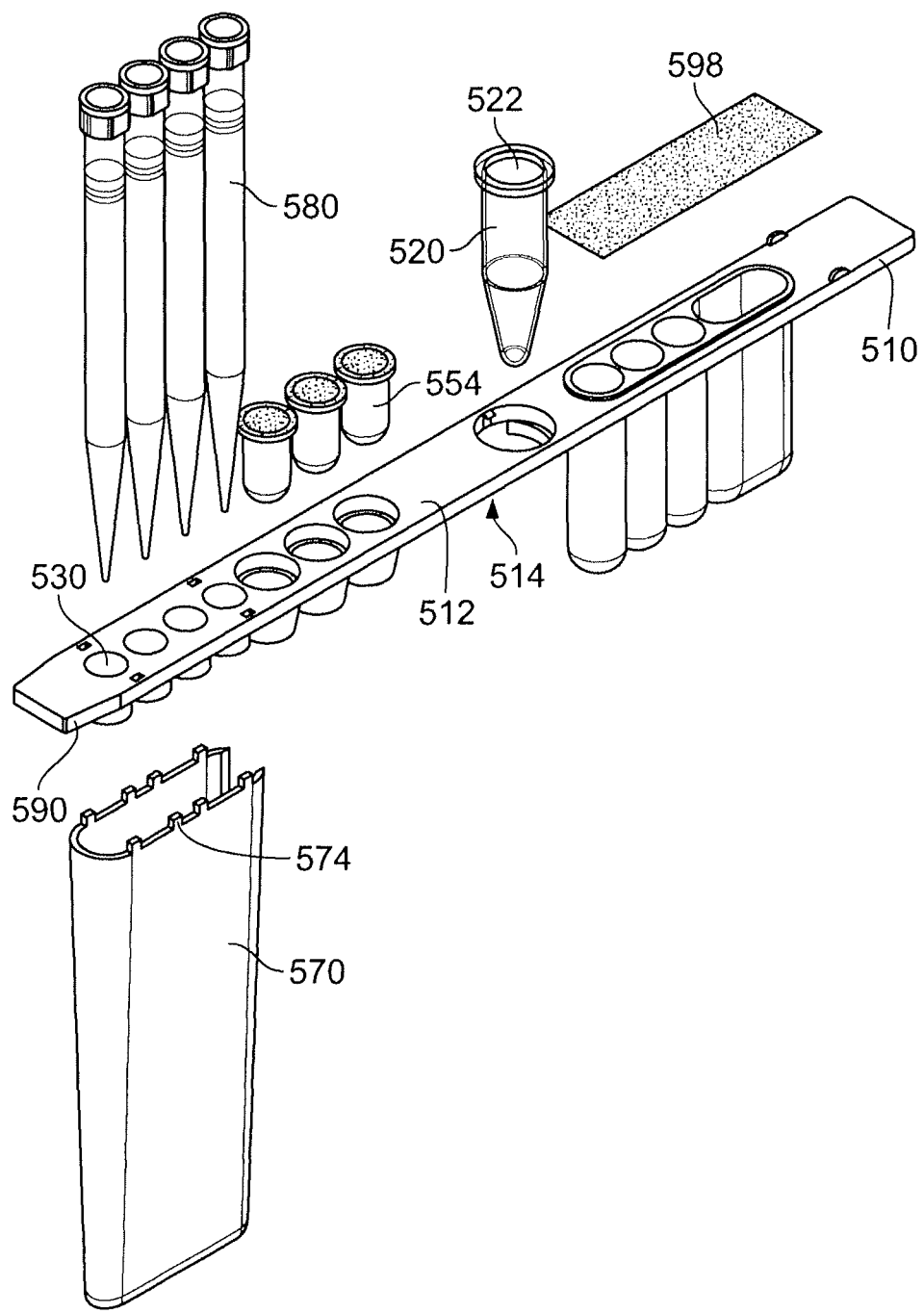

FIGS. 10A and 10B show views of an exemplary holder 501 as further described herein. FIG. 11 shows a plan view of another exemplary holder 502, as further described herein. FIG. 12A shows an exemplary holder 503 in perspective view, and FIG. 12B shows the same holder in cross-sectional view. FIG. 12C shows an exploded view of the same holder as in FIGS. 12A and 12B. All of these exemplary holders, as well as others consistent with the written description herein though not shown as specific embodiments, are now described.

The exemplary holders shown in FIGS. 10A, 10B, 11, 12A, 12B, and 12C can each be referred to as a "unitized disposable strip", or a "unitized strip", because they are intended to be used as a single unit that is configured to hold all of the reagents and receptacles necessary to perform a sample preparation, and because they are laid out in a strip format. It is consistent with the description herein, though, that other geometric arrangements of the various receptacles are contemplated, so that the description is not limited to a linear, or strip, arrangement, but can include a circular or grid arrangement.

Some of the reagents contained in the holder are provided as liquids, and others may be provided as solids. In some embodiments, a different type of container or tube is used to store liquids from those that store the solids.

The holder can be disposable, such as intended for a single use, following which it is discarded.

The holder is typically made of a plastic such as polypropylene. The plastic is such that it has some flexibility to facilitate placement into a rack, as further described herein. The plastic is typically rigid, however, so that the holder will not significantly sag or flex under its own weight and will not easily deform during routine handling and transport, and thus will not permit reagents to leak out from it.

The holder comprises a connecting member 510 having one or more characteristics as follows. Connecting member 510 serves to connect various components of the holder together. Connecting member 510 has an upper side 512 and, opposed to the upper side, an underside 514. In FIG. 10B, a view of underside 514 is shown, having various struts 597 connecting a rim of the connecting member with variously the sockets, process tube, and reagent tubes. Struts 597 are optional, and may be omitted all or in part, or may be substituted by, in all or in part, other pieces that keep the holder together.

The holder is configured to comprise: a process tube 520 affixed to the connecting member and having an aperture 522 located in the connecting member; at least one socket 530, located in the connecting member, the socket configured to accept a disposable pipette tip 580; two or more reagent tubes 540 disposed on the underside of the connecting member, each of the reagent tubes having an inlet aperture 542 located in the connecting member; and one or more receptacles 550, located in the connecting member, wherein the one or more receptacles are each configured to receive a complementary container such as a reagent tube (not shown) inserted from the upper side 512 of the connecting member.

The holder is typically such that the connecting member, process tube, and the two or more reagent tubes are made from a single piece, such as a piece of polypropylene.

The holder is also typically such that at least the process tube, and the two or more reagent tubes are translucent.

The one or more receptacles 550 are configured to accept reagent tubes that contain, respectively, sufficient quantities of one or more reagents typically in solid form, such as in lyophilized form, for carrying out extraction of nucleic acid from a sample that is associated with the holder. The receptacles can be all of the same size and shape, or may be of different sizes and shapes from one another. Receptacles 550 are shown as having open bottoms, but are not limited to such topologies, and may be closed other than the inlet 552 in the upper side of connecting member 510. Preferably the receptacles 550 are configured to accept commonly used containers in the field of laboratory analysis, or containers suitably configured for use with the holder herein. The containers are typically stored separately from the holders to facilitate sample handling, since solid reagents normally require different storage conditions from liquid reagents. In particular many solid reagents may be extremely moisture sensitive.

The snapped-in reagent tubes containing different reagents may be of different colors, or color-coded for easy identification by the user. For example they may be made of different color material, such as tinted plastic, or may have some kind of identifying tag on them, such as a color stripe or dot. They may also have a label printed on the side, and/or may have an identifier such as a barcode on the sealing layer on the top.

The containers 554 received by the receptacles 550 may alternatively be an integrated part of the holder and may be the same type of container as the waste chamber and/or the reagent tube(s), or may be different therefrom.

Figure 13B:
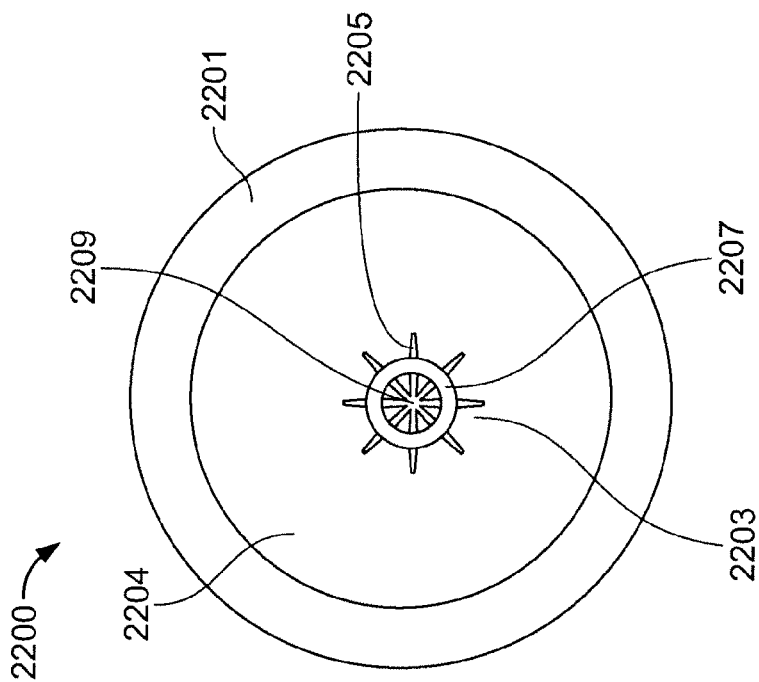

In one embodiment, the containers 554 containing lyophilized reagents, disposed in the receptacles 550 (shown, e.g., in FIGS. 12A and 12C), are 0.3 ml tubes that have been further configured to have a star pattern (see FIGS. 13A and 13B) on their respective bottom interior surfaces. This is so that when a fluid has been added to the lyophilized reagents (which are dry in the initial package), a pipette tip can be bottomed out in the tube and still be able to withdraw almost the entire fluid from the tube, as shown in FIG. 14, during the process of nucleic acid extraction. The design of the star-pattern is further described elsewhere herein.

The reagent tubes, such as containing the lyophilized reagents, can be sealed across their tops by a metal foil, such as an aluminum foil, with no plastic lining layer, as further described herein.

The embodiments 501, 502, and 503 are shown configured with a waste chamber 560, having an inlet aperture 562 in the upper side of the connecting member. Waste chamber 560 is optional and, in embodiments where it is present, is configured to receive spent liquid reagents. In other embodiments, where it is not present, spent liquid reagents can be transferred to and disposed of at a location outside of the holder, such as, for example, a sample tube that contained the original sample whose contents are being analyzed. Waste chamber 560 is shown as part of an assembly comprising additionally two or more reagent tubes 540. It would be understood that such an arrangement is done for convenience, e.g., of manufacture; other locations of the waste chamber are possible, as are embodiments in which the waste chamber is adjacent a reagent tube, but not connected to it other than via the connecting member.

The holder is typically such that the connecting member, process tube, the two or more reagent tubes, and the waste chamber (if present) are made from a single piece, made from a material such as polypropylene.

The embodiments 501 and 503 are shown having a pipette sheath 570. This is an optional component of the holders described herein. It may be permanently or removably affixed to connecting member 510, or may be formed, e.g., moulded, as a part of a single piece assembly for the holder. For example, exploded view of holder 503 in FIG. 12C shows lug-like attachments 574 on the upper surface of a removable pipette sheath 570 that engage with complementary recessed portions or holes in the underside 514 of connecting member 510. Other configurations of attachment are possible. Pipette sheath 570 is typically configured to surround the at least one socket and a tip and lower portion of a pipette tip when the pipette tip is stationed in the at least one socket. In some embodiments, the at least one socket comprises four sockets. In some embodiments the at least one socket comprises two, three, five, or six sockets.

Pipette sheath 570 typically is configured to have a bottom 576 and a walled portion 578 disposed between the bottom and the connecting member. Pipette sheath 570 may additionally and optionally have one or more cut-out portions 572 in the wall 578, or in the bottom 576. Such cutouts provide ventilation for the pipette tips and also reduce the total amount of material used in manufacture of the holder. Embodiment 503 has a pipette sheath with no such cutouts. In embodiment 501, such a cutout is shown as an isosceles triangle in the upper portion of the sheath; a similar shaped cutout may be found at a corresponding position in the opposite side of the sheath, obscured from view in FIG. 10A. Other cutouts could have other triangular forms, circular, oval, square, rectangular, or other polygonal or irregular shapes, and be several, such as many, in number. The wall 578 of pipette sheath 570 may also have a mesh or frame like structure having fenestrations or interstices. In embodiments having a pipette sheath, a purpose of the sheath is to catch drips from used pipette tips, and thereby to prevent cross-sample contamination, from use of one holder to another in a similar location, and/or to any supporting rack in which the holder is situated. Typically, then, the bottom 576 is solid and bowl-shaped (concave) so that drips are retained within it. An embodiment such as 502, having no pipette sheath, could utilize, e.g., a drip tray or a drainage outlet, suitably placed beneath pipette tips located in the one or more sockets, for the same purpose. In addition to catching drips, the pipette tip sheath prevents or inhibits the tips of other reagent holders—such as those that are situated adjacent to the one in question in a rack as further described herein—from touching each other when the tips are picked up and/or dropped off before or after some liquid processing step. Contact between tips in adjacent holders is generally not intended by, for example, an automated dispensing head that controls sample processing on holders in parallel, but the pipette tips being long can easily touch a tip in a nearby strip if the angle when dropping off of the tip deviates slightly from vertical.

The holders of embodiments 501, 502, and 503, all have a connecting member that is configured so that the at least one socket, the one or more receptacles, and the respective apertures of the process tube, and the two or more reagent tubes, are all arranged linearly with respect to one another (i.e., their midpoints lie on the same axis). However, the holders herein are not limited to particular configurations of receptacles, waste chamber, process tube, sockets, and reagent tubes. For example, a holder may be made shorter, if some apertures are staggered with respect to one another and occupy 'off-axis' positions. The various receptacles, etc., also do not need to occupy the same positions with respect to one another as is shown in FIGS. 12A and 12B, wherein the process tube is disposed approximately near the middle of the holder, liquid reagents are stored in receptacles mounted on one side of the process tube, and receptacles holding solid reagents are mounted on the other side of the process tube. Thus, in FIGS. 10A, 10B, and 11, the process tube is on one end of the connecting member, and the pipette sheath is at the other end, adjacent to, in an interior position, a waste chamber and two or more reagent tubes. Still other dispositions are possible, such as mounting the process tube on one end of the holder, mounting the process tube adjacent the pipette tips and pipette tip sheath (as further described herein), and mounting the waste tube adjacent the process tube. It would be understood that alternative configurations of the various parts of the holder give rise only to variations of form and can be accommodated within other variations of the apparatus as described, including but not limited to alternative instruction sets for a liquid dispensing pipette head, heater assembly, and magnetic separator, as further described herein.

Process tube 520 can also be a snap-in tube, rather than being part of an integrated piece. Process tube 520 is typically used for various mixing and reacting processes that occur during sample preparation. For example, cell lysis can occur in process tube 520, as can extraction of nucleic acids. Process tube 520 is then advantageously positioned in a location that minimizes, overall, pipette head moving operations involved with transferring liquids to process tube 520.

Reagent tubes 540 are typically configured to hold liquid reagents, one per tube. For example, in embodiments 501, 502, and 503, three reagent tubes are shown, containing respectively wash buffer, release buffer, and neutralization buffer, each of which is used in a sample preparation protocol.

Reagent tubes 540 that hold liquids or liquid reagents can be sealed with a laminate structure 598. The laminate structure typically has a heat seal layer, a plastic layer such as a layer of polypropylene, and a layer of metal such as aluminum foil, wherein the heat seal layer is adjacent the one or more reagent tubes. The additional plastic film that is used in a laminate for receptacles that contain liquid reagents is typically to prevent liquid from contacting the aluminum.

Figure 15:
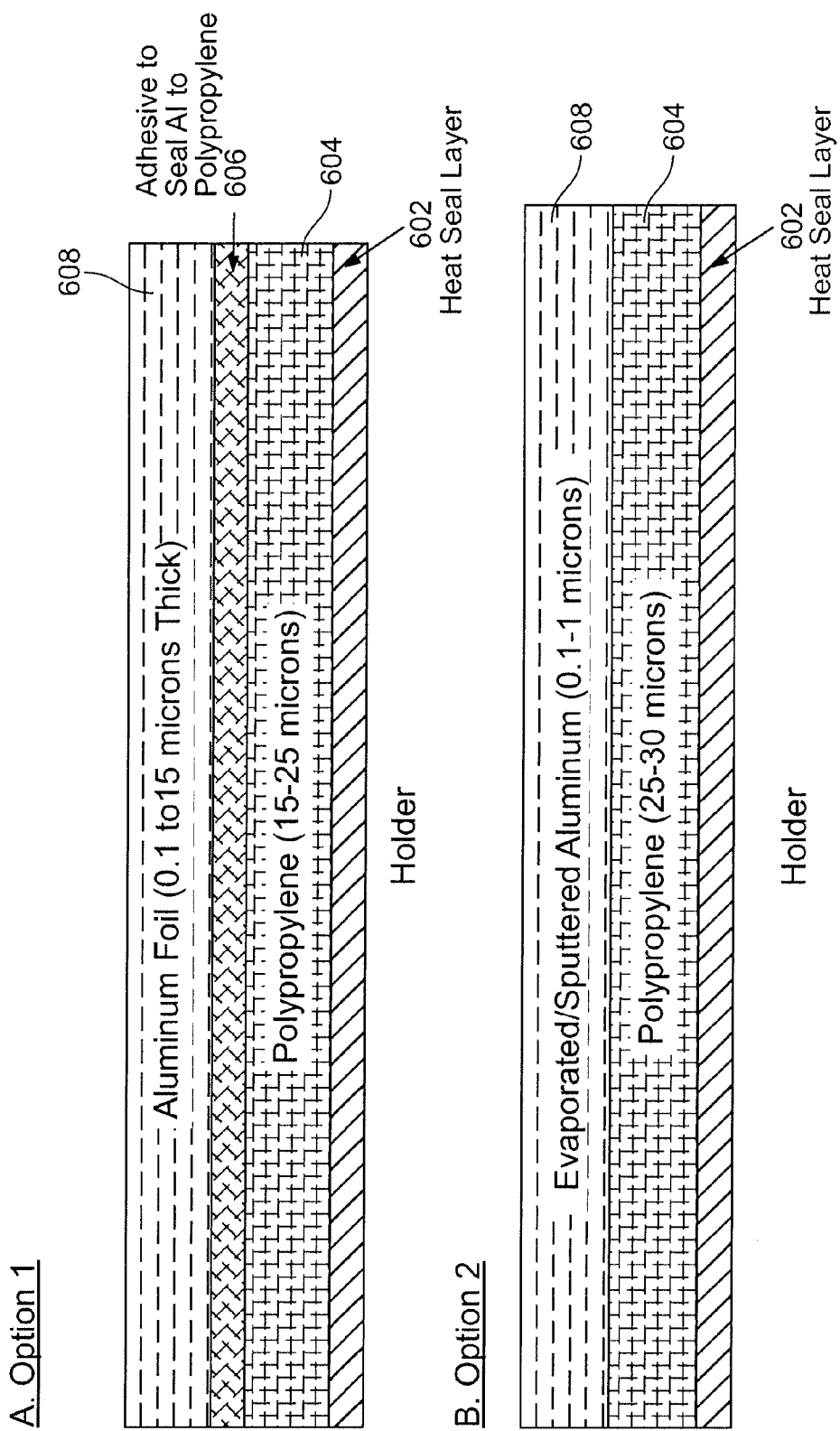

Two embodiments of a laminate structure, differing in their layer structures, are shown in FIG. 15. In both embodiments, the heat seal layer 602, for example made of a laquer or other such polymer with a low melting point, is at the bottom, adjacent to the top of the holder, when so applied. The plastic layer 604 is typically on top of the heat seal layer, and is typically made of polypropylene, having a thickness in the range 10-50 microns. The metal layer 608 is typically on top of the plastic layer and may be a layer of Al foil bonded to the plastic layer with a layer of adhesive 606, as in the first embodiment in FIG. 15, or may be a layer of metal that is evaporated or sputtered into place directly on to the plastic layer. Exemplary thicknesses for the respective layers are shown in FIG. 15, where it is to be understood that variations of up to a factor of 2 in thickness are consistent with the technology herein. In particular, the aluminum foil is 0.1-15 microns thick, and the polymer layer is 15-25 microns thick in one embodiment. In another embodiment, the aluminum is 0.1-1 microns thick, and the polymer layer is 25-30 microns thick.

The laminates deployed herein make longer term storage easier because the holder includes the presence of sealed lyophilized reagents as well as liquids sealed in close proximity, which is normally hard to achieve.

In one embodiment, the tops of the reagent tubes have beveled edges so that when an aluminum foil is heat bonded to the top, the plastic melt does not extend beyond the rim of the tube. This is advantageous because, if the plastic melt reduces the inner diameter of the tube, it will cause interference with the pipette tip during operation. In other embodiments, a raised flat portion 599 facilitates application and removal of laminate 598. Raised surface 599, on the upper side of the connecting member, and surrounding the inlet apertures to the reagent tubes and, optionally, the waste chamber, is an optional feature of the holder.

Figure 16:
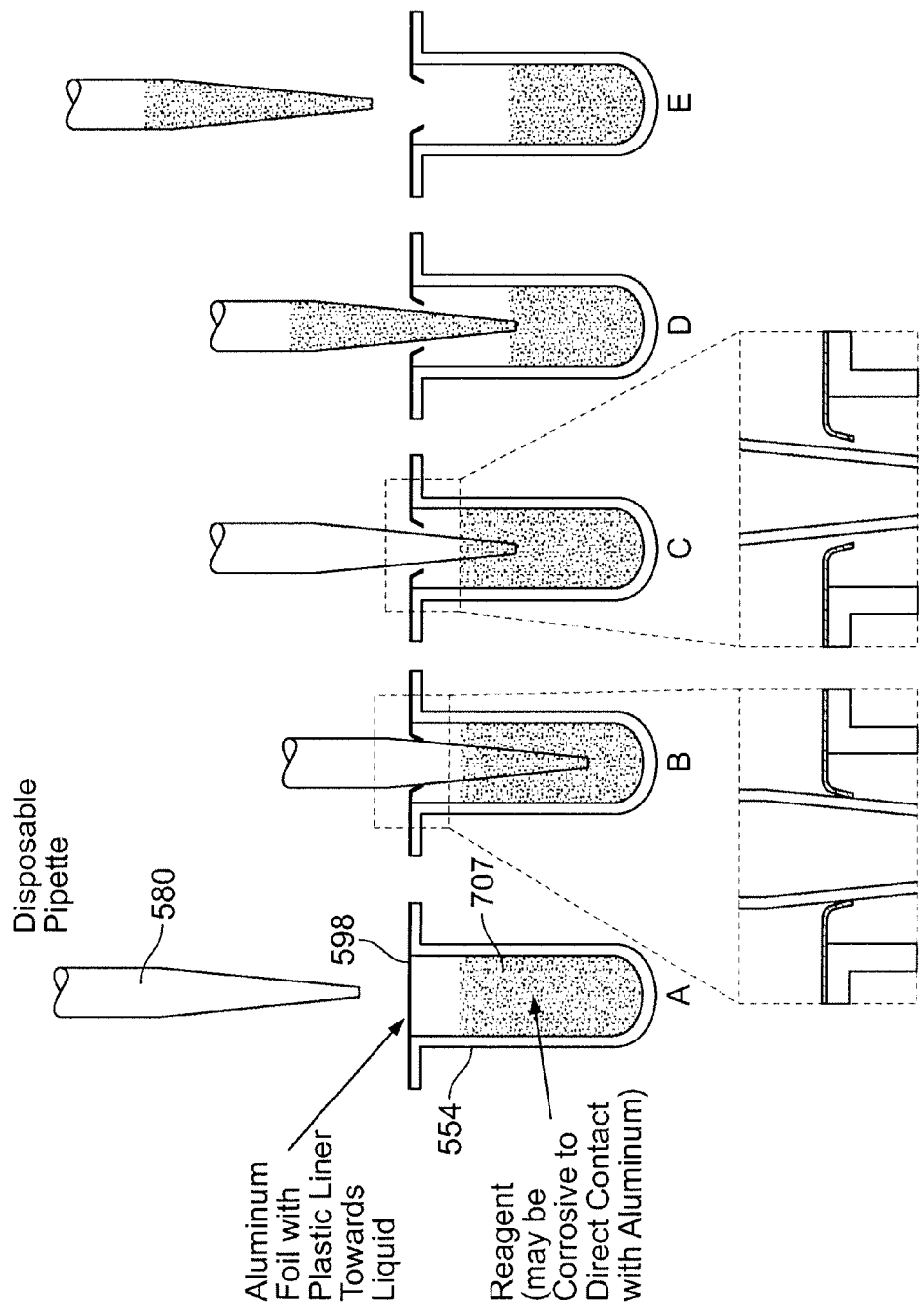
Figure 17A:
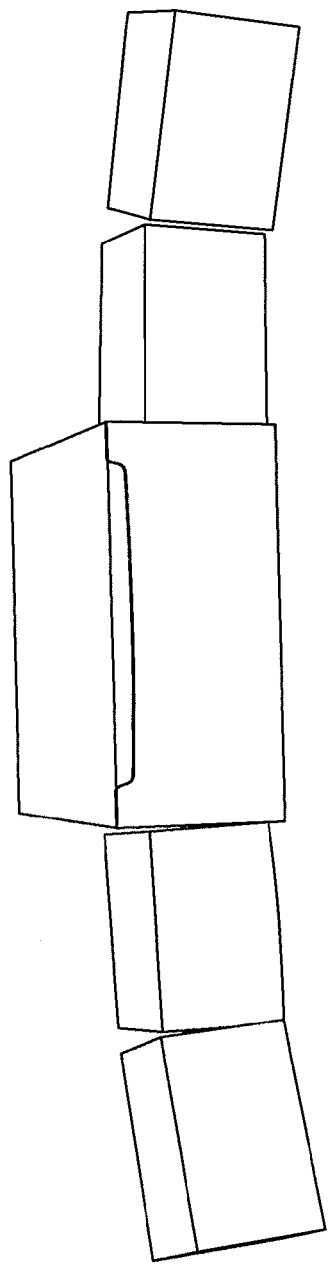
Figure 17B:
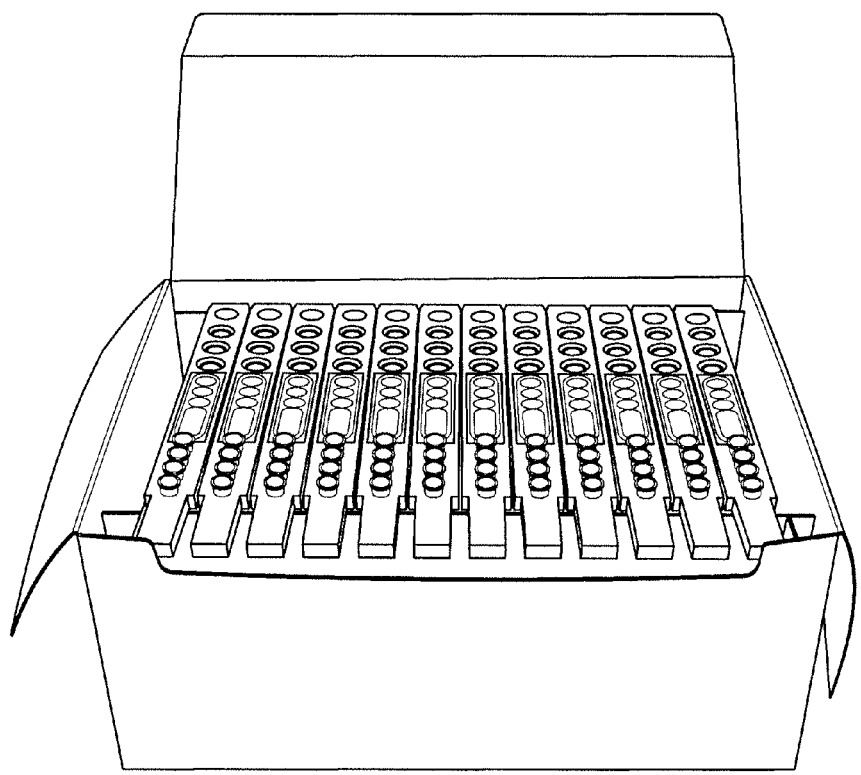
Figure 17C:
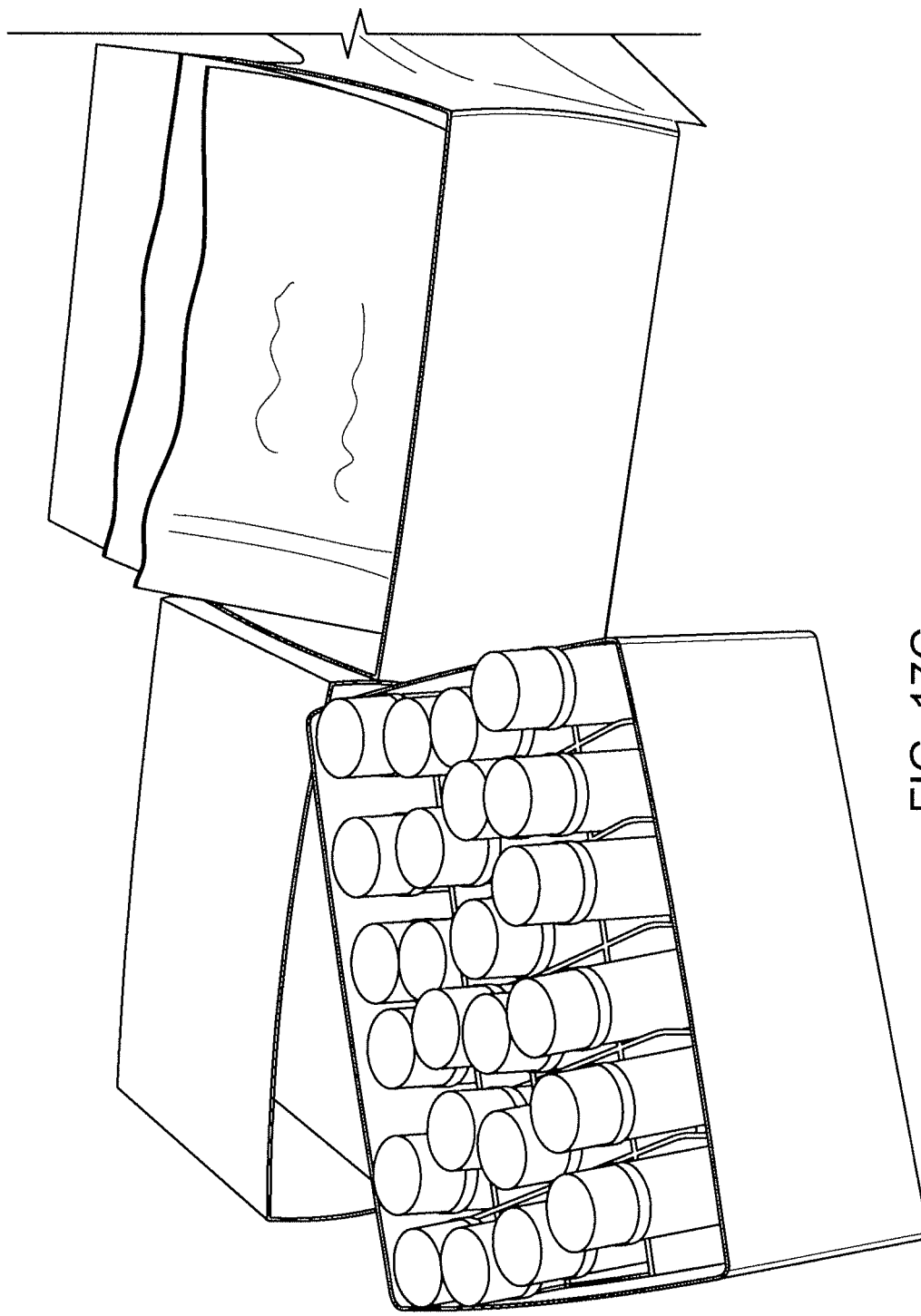
Figure 17D:
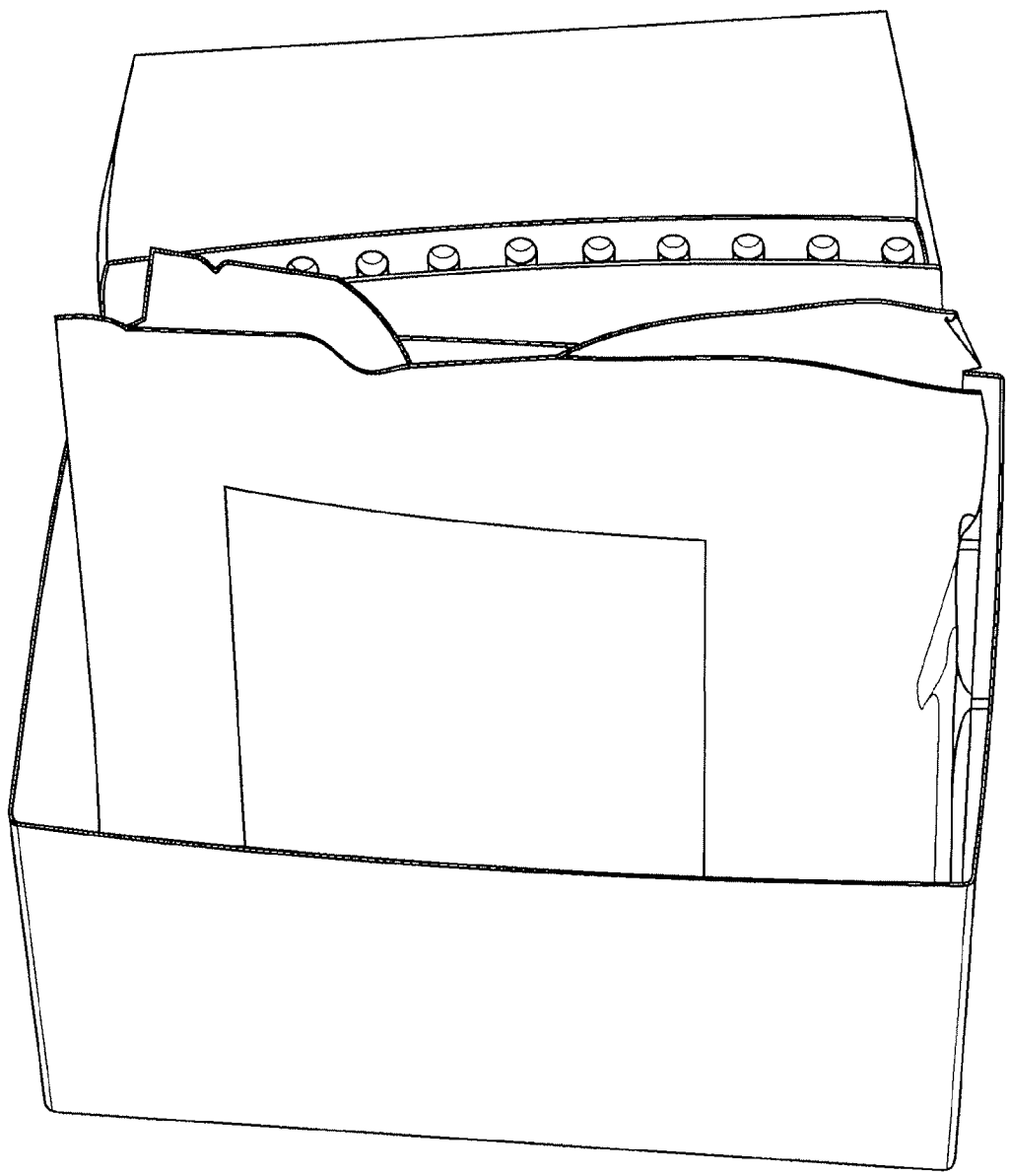

The manner in which liquid is pipetted out is such that a pipette tip piercing through the foil rips through without creating a seal around the pipette tip, as in FIG. 16. Such a seal around the tip during pipetting would be disadvantageous because a certain amount of air flow is desirable for the pipetting operation. In this instance, a seal is not created because the laminate structure causes the pierced foil to stay in the position initially adopted when it is pierced. The upper five panels in FIG. 16 illustrate the pipetting of a reagent out from a reagent tube sealed with a laminate as further described herein. At A, the pipette tip is positioned approximately centrally above the reagent tube that contains reagent 707. At B, the pipette tip is lowered, usually controllably lowered, into the reagent tube, and in so doing pierces the foil 598. The exploded view of this area shows the edge of the pierced laminate to be in contact with the pipette tip at the widest portion at which it penetrates the reagent tube. At C, the pipette tip is withdrawn slightly, maintaining the tip within the bulk of the reagent 707. The exploded view shows that the pierced foil has retained the configuration that it adopted when it was pierced and the pipette tip descended to its deepest position within the reagent tube. At D, the pipette tip sucks up reagent 707, possibly altering its height as more and more older people undergo such tests. At E, the pipette tip is removed entirely from the reagent tube.

The materials of the various tubes and chambers may be configured to have at least an interior surface smoothness and surface coating to reduce binding of DNA and other macromolecules thereto. Binding of DNA is unwanted because of the reduced sensitivity that is likely to result in subsequent detection and analysis of the DNA that is not trapped on the surface of the holder.

The process tube also may have a low binding surface, and allows magnetic beads to slide up and down the inside wall easily without sticking to it. Moreover, it has a hydrophobic surface coating enabling low stiction of fluid and hence low binding of nucleic acids and other molecules.

In some embodiments, the holder comprises a registration member such as a mechanical key. Typically such a key is part of the connecting member 510. A mechanical key ensures that the holder is accepted by a complementary member in, for example, a supporting rack or a receiving bay of an apparatus that controls pipetting operations on reagents in the holder. A mechanical key is normally a particular-shaped cut-out that matches a corresponding cutout or protrusion in a receiving apparatus. Thus, embodiment 501 has a mechanical key 592 that comprises a pair of rectangular-shaped cut-outs on one end of the connecting member. This feature as shown additionally provides for a tab by which a user may gain a suitable purchase when inserting and removing the holder into a rack or another apparatus. Embodiments 501 and 502 also have a mechanical key 590 at the other end of connecting member 510. Key 590 is an angled cutout that eases insertion of the holder into a rack, as well as ensures a good registration therein when abutting a complementary angled cut out in a recessed area configured to receive the holder. Other variations of a mechanical key are, of course, consistent with the description herein: for example, curved cutouts, or various combinations of notches or protrusions all would facilitate secure registration of the holder.

In some embodiments, not shown in FIG. 10A, 10B, 11, or 12A-C, the holder further comprises an identifier affixed to the connecting member. The identifier may be a label, such as a writable label, a bar-code, a 2-dimensional bar-code, or an RFID tag. The identifier can be, e.g., for the purpose of revealing quickly what combination of reagents is present in the holder and, thus, for what type of sample preparation protocol it is intended. The identifier may also indicate the batch from which the holder was made, for quality control or record-keeping purposes. The identifier may also permit a user to match a particular holder with a particular sample.

It should also be considered consistent with the description herein that a holder additionally can be configured to accept a sample, such as in a sample tube. Thus, in embodiments described elsewhere herein, a rack accepts a number of sample tubes and a number of corresponding holders in such a manner that the sample tubes and holders can be separately and independently loaded from one another. Nevertheless, in other embodiments, a holder can be configured to also accept a sample, for example in a sample tube. And thus, a complementary rack is configured to accept a number of holders, wherein each holder has a sample as well as reagents and other items. In such an embodiment, the holder is configured so that the sample is accessible to a sample identification verifier.

Kits

The holder described herein may be provided in a sealed pouch, to reduce the chance of air and moisture coming into contact with the reagents in the holder. Such a sealed pouch may contain one or more of the holders described herein, such as 2, 4, 6, 8, 10, 12, 16, 20, or 24 holders.

The holder may also be provided as part of a kit for carrying out sample preparation, wherein the kit comprises a first pouch containing one or more of the holders described herein, each of the holders configured with liquid reagents for, e.g., lysis, wash, and release, and a second pouch, having an inert atmosphere inside, and one or more reagent tubes containing lyophilized PCR reagents, as shown in FIG. 17. Such a kit may also be configured to provide for analysis of multiple samples, and contain sufficient PCR reagents (or other amplification reagents, such as for RT-PCR, transcription mediated amplification, strand displacement amplification, NASBA, helicase dependent amplification, and other familiar to one of ordinary skill in the art, and others described herein) to process such samples, and a number of individual holders such as 2, 4, 6, 8, 10, 12, 16, 20, or 24 holders.

Reagent Tubes

As referenced elsewhere herein, the containers 554 that contain lyophilized reagents are 0.3 ml tubes that have been further configured to have a star-shaped—or stellated—pattern (see FIGS. 13A and 13B) on their respective bottom interior surfaces. Still other tubes for use herein, as well as for other uses not herein described, can be similarly configured. Thus, for example, the benefits afforded by the star-shaped pattern also accrue to reagent tubes that contain liquid samples that are directly pipetted out of the tubes (as well as to those tubes that initially hold solids that are constituted into liquid form prior to pipetting). Other size tubes that would benefit from such a star-shaped pattern have sizes in the range 0.1 ml to 0.65 ml. for example.

The star-shaped pattern ensures that when a fluid is withdrawn from the tube, a pipette tip can be bottomed out in the tube and still be able to withdraw the entire, or almost the entire fluid from the tube, as shown in FIG. 14. This is important because, when working with such small volumes, and when target DNA can be present in very few copies, sample loss due to imperfections of pipetting is to be minimized to every extent possible.

The design of the star shaped pattern is important, especially when using for recovery of DNA/RNA present in very small numbers in the clinical sample. The stellated pattern should enable pipetting of most of the liquid (residual volume <1 microliter) when used with a pipette bottomed out with the bottom of the tube. Additionally, the stellated pattern should be designed to minimize surface area as well as dead-end grooves that tend to have two undesirable effects—to trap liquid as well as to increase undesirable retention of polynucleotides by adsorption.

FIG. 14 is now described, as follows. FIG. 14 has a number of panels, A-G, each representing, in sequence, a stage in a pipetting operation. At A, a pipette tip 2210, containing a liquid 2211 (such as a buffer solution), is positioned directly or approximately above the center of reagent tube 2200. The tube contains a number of lyophilized pellets 2212, and is sealed by a layer 2214, such as of foil. The foil may be heat-sealed on to the top of the tube. Although a laminate layer, as further described herein, can be placed on the reagent tube, typically a layer of aluminum foil is adequate, where the tube contents are solid, e.g., lyophilized, reagents. In some embodiments, the top of the reagent tube has chamfer edges to reduce expansion of the top rim of the tube during heat sealing of a foil on the top of the tube. The tube may further comprise an identifiable code, such as a 1-D or a 2-D bar-code on the top. Such a code is useful for identifying the composition of the reagents stored within, and/or a batch number for the preparation thereof, and/or an expiry date. The code may be printed on with, for example, an inkjet or transfer printer.

Stellated pattern 2203 on the bottom interior surface of the tube 2200 is shown. At B, the pipette tip is lowered, piercing seal 2214, and brought into a position above the particles 2212. At C the liquid 2211 is discharged from the pipette tip on to the particles, dissolving the same, as shown at D. After the particles are fully dissolved, forming a solution 2218, the pipette tip is lowered to a position where it is in contact with the stellated pattern 2203. A E, the pipette tip is caused to suck up the solution 2218, and at F, the tip may optionally discharge the solution back into the tube. Steps E and F may be repeated, as desired, to facilitate dissolution and mixing of the lyophilized components into solution. At step G, after sucking up as much of the solution 2218 as is practicable into the pipette tip, the pipette tip is withdrawn from the tube. Ideally, 100% by volume of the solution 2218 is drawn up into the pipette tip at G. In other embodiments, and depending upon the nature of solution 2218, at least 99% by volume of the solution is drawn up. In still other embodiments, at least 98%, at least 97%, at least 96%, at least 95%, and at least 90% by volume of the solution is drawn up.

The design of the stellated or star-shaped pattern can be optimized to maximize the flow rate of liquid through the gaps in-between a bottomed out pipette, such as a p1000 pipette, and the star pattern, and is further described in U.S.

provisional patent application Ser. No. 60/959,437, filed Jul. 13, 2007, incorporated herein by reference. It would be understood that, although the description herein pertains to pipettes and pipette tips typically used in sample preparation of biological samples, the principles and detailed aspects of the design are as applicable to other types of pipette and pipette tip, and may be so-adapted.

Figure 13A:
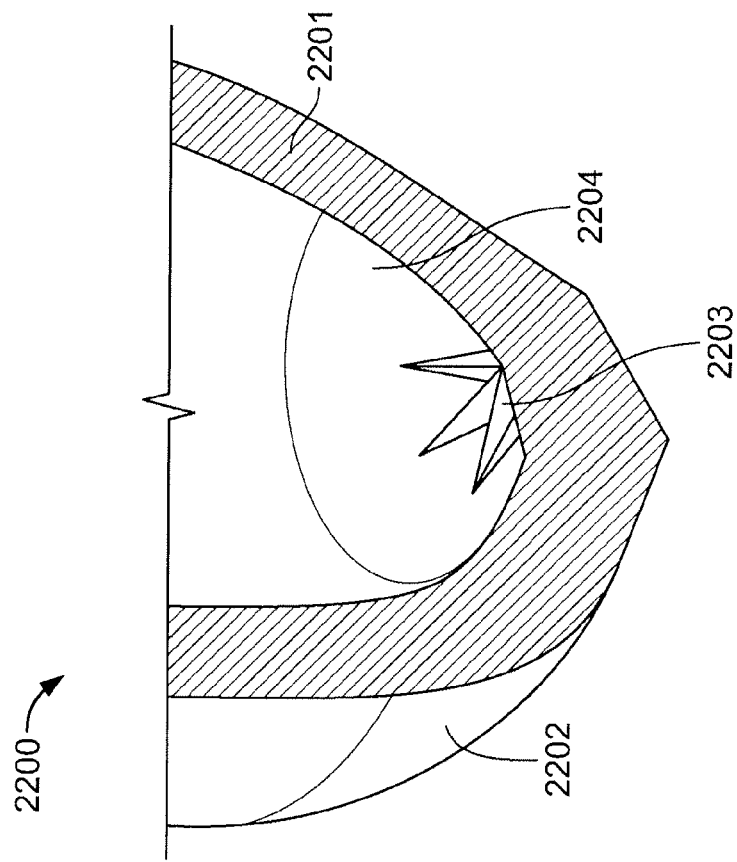
Figure 14:
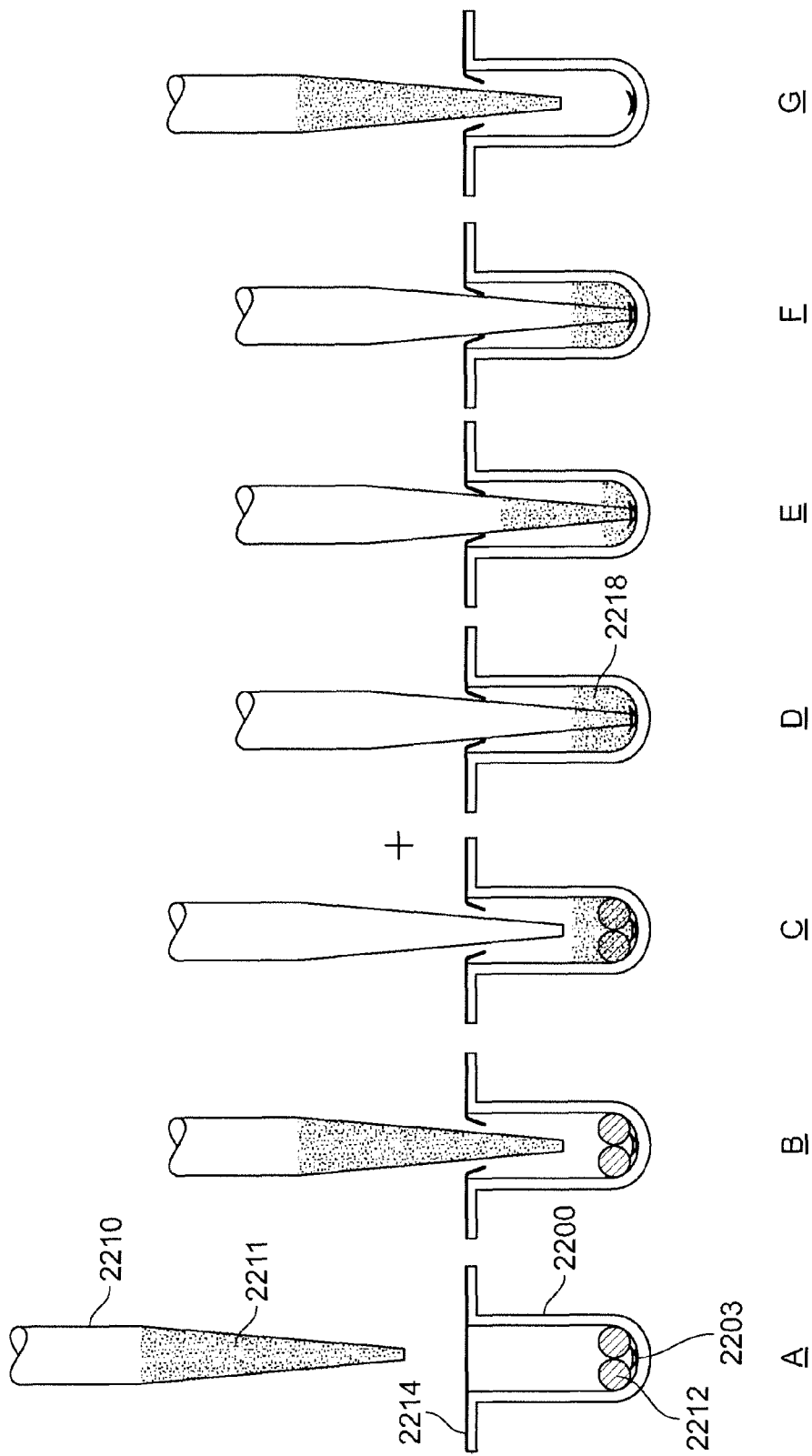

FIG. 13A shows a cross sectional perspective view of a reagent tube 2200 having side wall 2201 and bottom 2202. Interior surface 2204 of the bottom is visible. A star-shaped cutout 2203 is shown in part, as three apical grooves.

Typically the star-shaped pattern is present as a raised portion on the lower interior surface of the tube. Thus, during manufacture of a reagent tube, such as by injection moulding, an outer portion of the mould is a cavity defining the exterior shape of the tube. An interior shape of the tube is formed by a mould positioned concentrically with the outer portion mould, and having a star-shaped structure milled out of its tip. Thus, when liquid plastic is injected into the space between the two portions of the mould, the star-shape is formed as a raised portion on the bottom interior surface of the tube.

The exemplary star pattern 2203 shown in FIG. 13B in plan view resembles a "ship's wheel" and comprises a center 2209, a circular ring 2207 centered on center 2209, and 8 radial segments configured as radial grooves 2205. Each groove meets the other grooves at center 2209, and has a radial end, also referred to as an apex or vertex. Star pattern 2203 has 8 grooves, but it would be understood that a star pattern having fewer or a greater number of grooves, such as 3, 4, 6, 10, or 12, would be consistent with the design herein. The number of grooves of the star should be minimum consistent with effective liquid pipetting and also spaced apart enough not to trap the tip of any of the pipette tips to be used in the liquid handling applications.

Center 2209 is typically positioned coincidentally with the geometric center of the bottom of reagent tube 2200. The tube is typically circular in cross-section, so identifying its center (e.g., at a crossing point of two diameters) is normally straightforward. Center 2209 may be larger than shown in FIG. 13B, such as may be a circular cutout or raised portion that exceeds in diameter of the region formed by the meeting point of grooves 2205.

Ring 2207 is an optional feature of star-shaped pattern 2203. Typically ring 2207 is centered about center 2209, and typically it also has a dimension that corresponds to the lower surface of a pipette tip. Thus, when a pipette tip 'bottoms out' in the bottom of reagent tube 2200, the bottom of the pipette tip rests in contact with ring 2207. Ring 2207 is thus preferably a cut-our or recessed feature that can accommodate the pipette tip and assist in guiding its positioning centrally at the bottom of the tube. In other embodiments more than one, such as 2, 3, or 4 concentric rings 2207 are present.

The star pattern is configured to have dimensions that give an optimal flow-rate of liquid out of the reagent tube into a suitably positioned pipette tip. The star pattern is shown in FIG. 13B as being significantly smaller in diameter than the diameter of the tube at its widest point. The star pattern may have, in various embodiments, a diameter (measured from center 2209 to apex of a groove 2205) from 5-20% of the diameter of the reagent tube, or from 10-25% of the diameter of the reagent tube, or from 15-30% of the diameter of the reagent tube, or from 20-40% of the diameter of the reagent tube, or from 25-50% of the diameter of the reagent tube, or from 30-50% the diameter of the reagent tube, or from 40-60% the diameter of the reagent tube, or from 50-75% the diameter of the reagent tube, or from 65-90% the diameter of the reagent tube.

The grooves 2205 are thus separated by ridges (occupying the space in between adjacent grooves). In the embodiment shown, the grooves are narrower (occupy a smaller radial angle) than the gaps between them. In other embodiments, the grooves may be proportionately wider than the gaps between them. In such embodiments, it may be more appropriate to describe them as having ridges instead of grooves. In other embodiments, the grooves and ridges that separate them are of equal widths at each radial distance from the center.

The grooves that form the apices of the star may be rounded in their lower surfaces, such as semi-circular in cross section, but are typically V-shaped. They may also be trapezoid in cross-section, such as having a wider upper portion than the bottom, which is flat, the upper portion and the bottom being connected by sloping walls.

In some embodiments, for ease of manufacture, the grooves end on the same level in the bottom of the tube. Thus the radial ends are all disposed on the circumference of a circle. In other embodiments, the grooves do not all end on the same level. For example, grooves may alternately end on different levels, and thus the ends are alternately disposed on the respective circumferences of two circles that occupy different planes in space from one another.

Grooves 2205 are shown in FIG. 13B as having equal lengths (as measured from center 2209 to apex). This need not be so. In alternative embodiments, grooves may have different lengths from one another, for example, as alternating lengths on alternating grooves, where there are an even number of grooves. Furthermore, apices may be rounded, rather than pointed.

Typically the grooves taper uniformly in width and depth from center 2209 to each respective apex. Still other configurations are possible, such as a groove that follows a constant width, or depth, out to a particular radial extent, such as 30-60% of its length, and then narrows or becomes shallower towards its apex. Alternatively, a groove may start narrow at center 2209, widen to a widest region near its midpoint of length, and then narrow towards its apex. Still other possibilities, not described herein, are consistent with the stellated pattern.

In a 0.3 ml tube, the width of each groove 2205 at its widest point is typically around 50 microns, and the width typically tapers uniformly from a widest point, closest to or at center 2209, to the apex.

In a 0.3 ml tube, the depth of a groove at the deepest point is typically around 25-50 microns and the depth typically tapers uniformly from a deepest point, closest to or at center 2209, to an apex.

In a 0.3 ml tube, the radius of the star formed from the grooves, measured as the shortest distance from center 2209 to apex, is typically around 0.5 mm, but may be from 0.1-1 mm, or from 0.3-2 mm.

In another embodiment, in a 0.3 ml tube, the grooves should be rounded off and less than 100 microns deep, or less than 50 microns deep, or less than 25 microns deep.

The stellated pattern typically has a rotation axis of symmetry, the axis disposed perpendicular to the bottom of the tube and through center 2209, so that the grooves are disposed symmetrically about the rotation axis. By this is meant that, for n grooves, a rotation of $2\pi/n$ about the central (rotational) axis can bring each groove into coincidence with the groove adjacent to it.

The stellated shape shown in FIG. 13B is not limiting in that it comprises a number of radially disposed grooves 2205, and an optional circular ring 2207. Other star-shaped geometries may be used, and, depending upon ease of manufacture, may be preferred. For example, a star can be created simply be superimposing two or more polygons having a common center, but offset rotationally with respect to one another about the central axis. (See, for example "star polygons" described at the Internet site mathworld.wolfram.com/Star-Polygon.html.) Such alternative manners of creating star-shaped patterns are utilizable herein.

Liquid Dispenser

In various embodiments, preparation of a PCR-ready sample for use in subsequent diagnosis using the apparatus as further described herein, can include one or more of the following steps: contacting a neutralized polynucleotide sample with a PCR reagent mixture comprising a polymerase enzyme and a plurality of nucleotides (in some embodiments, the PCR reagent mixture can further include a positive control plasmid and a fluorogenic hybridization probe selective for at least a portion of the plasmid); in some embodiments, the PCR reagent mixture can be in the form of one or more lyophilized pellets, as stored in a receptacle on a holder, and the method can further include reconstituting the PCR pellet with liquid to create a PCR reagent mixture solution. Various, such as one or more, of the liquid transfer operations associated with the foregoing steps can be accomplished by an automated pipette head.

A suitable liquid dispenser for use with the apparatus herein comprises one or more sensors; a manifold; one or more pumps in fluid communication with the manifold; one or more dispense heads in fluid communication with the manifold; and electrical connections that accept electrical signals from an external controller, wherein the liquid dispenser has no inlet or outlet for fluids, other than through the one or more pumps.

Figure 18:
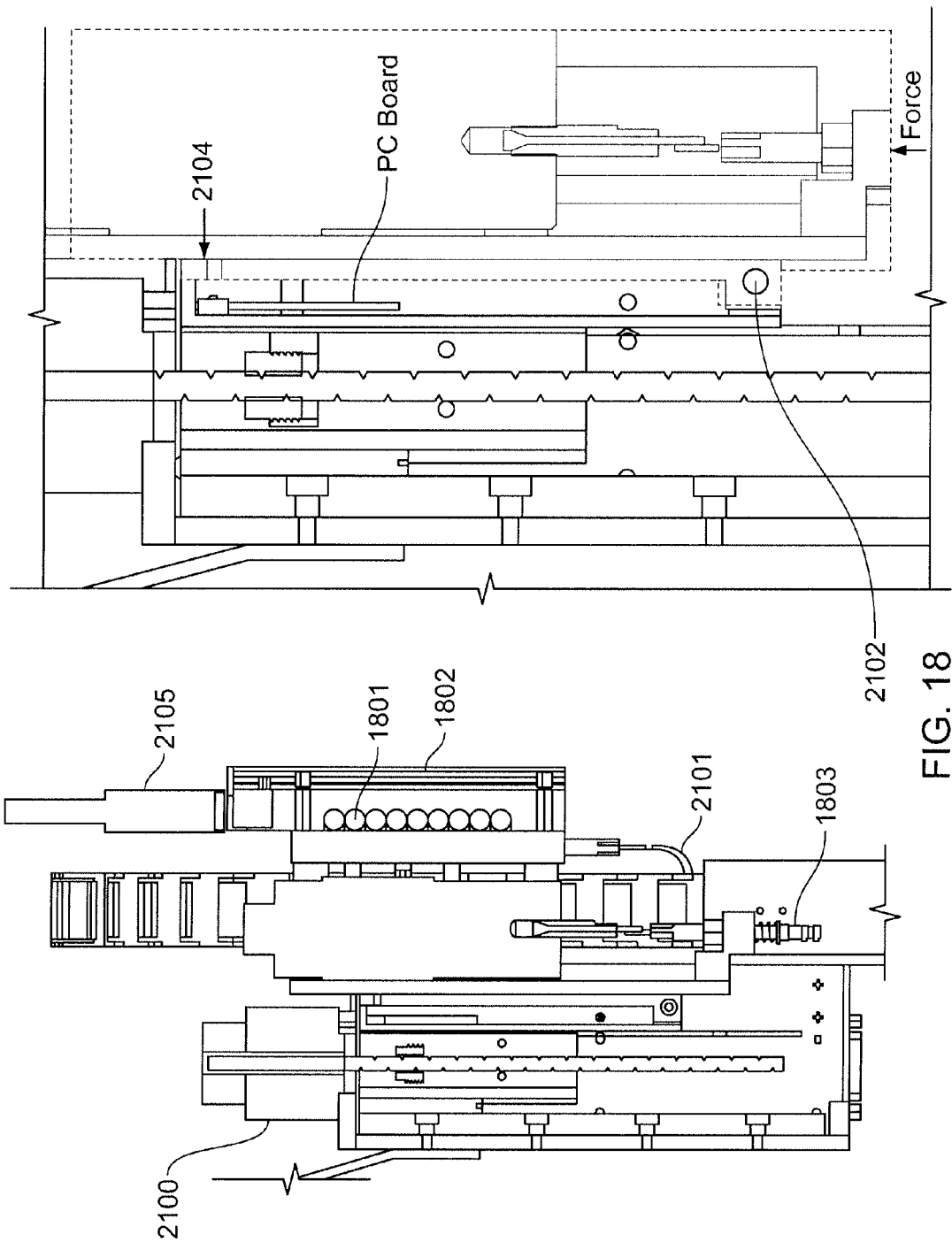

A cross-sectional view of an exemplary liquid dispenser is shown in FIG. 18. The liquid dispenser is configured to carry out fluid transfer operations on two or more holders simultaneously. As shown in FIG. 18, liquid dispenser 2105 can be mounted on a gantry having three degrees of translational freedom. Further embodiments can comprise a gantry having fewer than three degrees of translational freedom. The manner of mounting can be by a mechanical fastening such as one or more screws, as shown on the left hand side of FIG. 18. A suitable gantry comprises three axes of belt-driven slides actuated by encoded stepper motors. The gantry slides can be mounted on a framework of structural angle aluminum or other equivalent material, particularly a metal or metal alloy. Slides aligned in x- and y-directions (directed out of and in the plane of FIG. 18 respectively) facilitate motion of the gantry across an array of holders, and in a direction along a given holder, respectively.

The z-axis of the gantry can be associated with a variable force sensor which can be configured to control the extent of vertical motion of the head during tip pick-up and fluid dispensing operations. Shown in FIG. 18, for example, a pipette head 1803 can be mounted such that a force acting upwardly against the head can be sensed through a relative motion between the head and a force sensor. For example, when pipette head 1803 forces against a disposable pipette in the rack below it, an upward force is transmitted causing head 1803 to torque around pivot point 2102, causing set screw 2104 to press against a force sensor. In turn, the force sensor is in communication with a processor or controller that controls at least the vertical motion of the liquid dispenser so that, thereby, the processor or controller can send instructions to arrest the vertical motion of the liquid dispenser upon receiving an appropriate signal from the force sensor. An exemplary force sensor suitable for use herein is available from Honeywell; its specification is shown in an appendix hereto. The force sensor mechanism shown in FIG. 18 is exemplary and one of many possible mechanisms capable of commanding the head during up pick-up and fluid dispensing operations. For example, as an alternative to a force sensor, a stall sensor that senses interruption in vertical motion of the one or more dispense heads upon contact with a sample tube or reagent holder may be used. Accordingly, as would be understood by one of ordinary skill in the art, the liquid dispenser as described herein is not limited to the specific mechanism shown in FIG. 18.

Figure 19C:
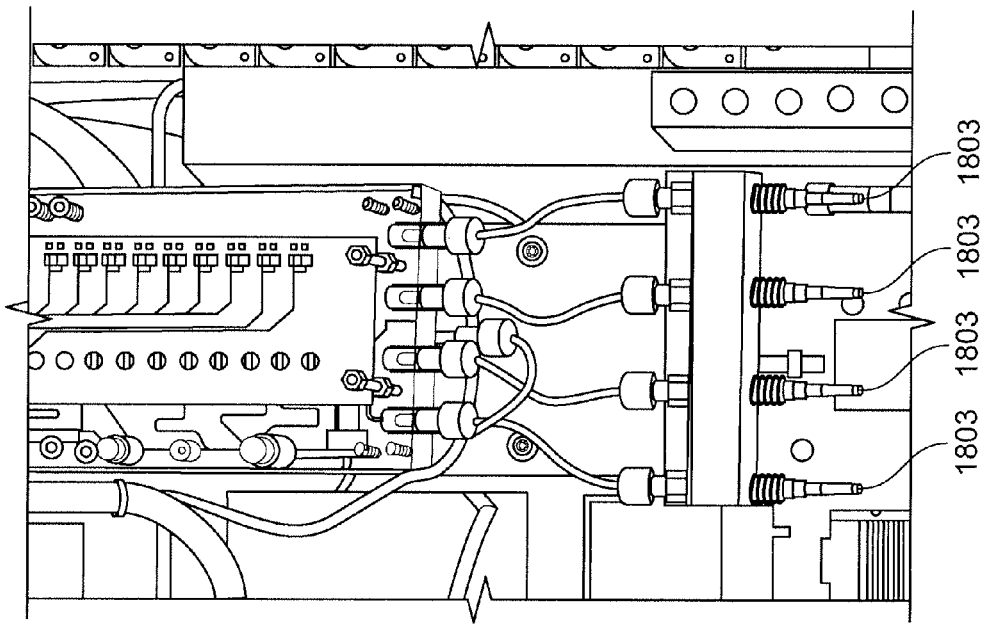

The liquid dispenser further comprises a number of individually sprung heads 1803, wherein each head is configured to accept a pipette tip from the one or more pipette tips in a holder. The liquid dispenser can be further configured such that no two heads accept pipette tips from the same holder. FIGS. 19A-C, for example, depicts four individually sprung heads 1803, but it is to be understood that the dispenser is not limited to this number. For example, other numbers include 2, 3, 5, 6, 8, 10, or 12. Furthermore, the individually sprung heads 1803 are shown arranged in parallel to one another, but may be configured in other arrangements.

The liquid dispenser can further comprise computer-controlled pump 2100 connected to distribution manifold 1802 with related computer controlled valving. Distribution manifold 1802 can comprise a number of valves, such as solenoid valves 1801 configured to control the flow of air through the pipette tips: in an exemplary embodiment, there are two valves for each pipette, and one additional valve to vent the pump. Thus, for a liquid dispenser having four pipette heads, there are nine valves. In another embodiment there is only one valve for each pipette, and one additional valve to vent the pump. However, the distribution manifold is not limited to comprising exactly nine solenoid valves.

The liquid dispenser is further configured to aspirate or dispense fluid in connection with analysis or preparation of solutions of two or more samples. The liquid dispense is also configured to dispense liquid into a microfluidic cartridge. Additionally, the liquid dispenser is configured to accept or dispense, in a single operation, an amount of 1.0 ml of fluid or less, such as an amount of fluid in the range 10 nl-1 ml.

Figure 20:
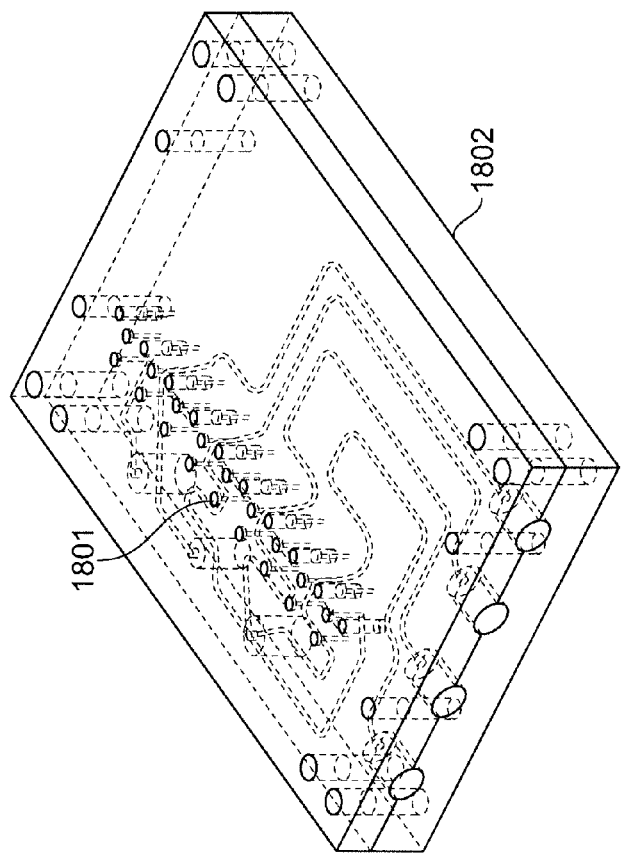

The liquid dispenser is configured such that pump 2100 pumps air in and out of the distribution manifold. The distribution manifold comprises a microfluidic network that distributes air evenly amongst the one or more valves. Thus, by controlling flow of air through the manifold and various valves, pressure above the pipette heads can be varied so that liquid is drawn up into or expelled from a pipette tip attached to the respective pipette heads. In this way it is not necessary to supply compressed air via an air hose to the liquid dispenser. Neither is it necessary to provide liquid lines to the dispense head. Furthermore, no liquid reagents or liquid samples from the holders enters any part of the liquid dispenser, including the manifold. This aspect reduces complications from introducing air bubbles into samples or liquid reagents. An exemplary configuration of a distribution manifold is shown in FIG. 20.

As shown in the various figures, the entire liquid dispenser that moves up and down the z-axis is a self-contained unit having only electrical connections to a processor or controller, and mechanical connections to the gantry. The translational motions in three dimensions of the liquid dispenser can be controlled by a microprocessor, such as processor 980. No fluid handling lines are associated with the dispenser. This design enables simplification of assembly of the instrument, minimizes contamination of the instrument and cross-contamination of samples between different instances of operation of the apparatus, increases efficiency of pumping (minimal dead volume) and enables easy maintenance and repair of the device. This arrangement also enables easy upgrading of features in the dispensing device, such as individual and independent pump control for each dispenser, individual pipette attachment or removal, ability to control the pitch of the pipettes, etc.

Figure 21:
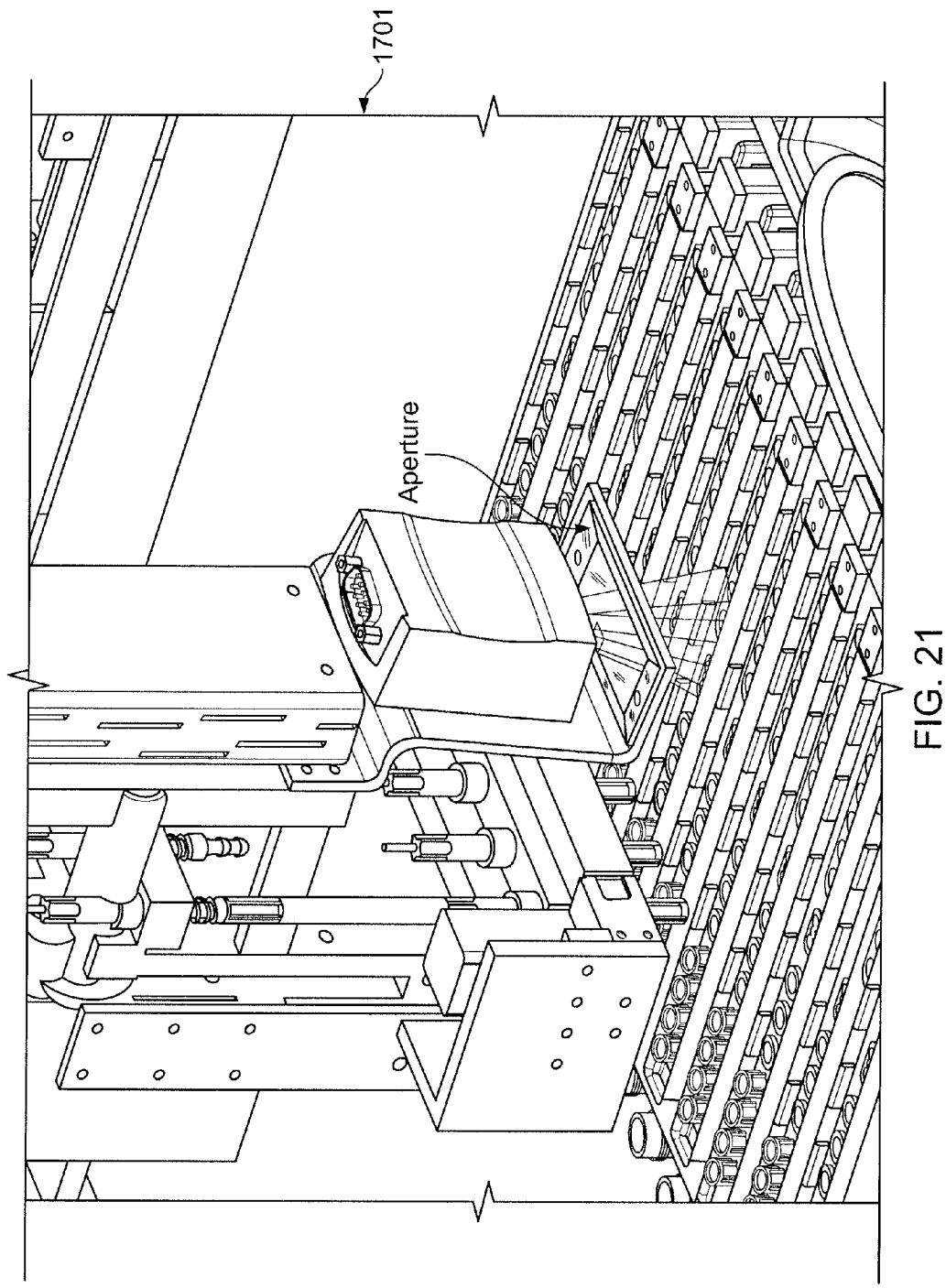
Figure 22:
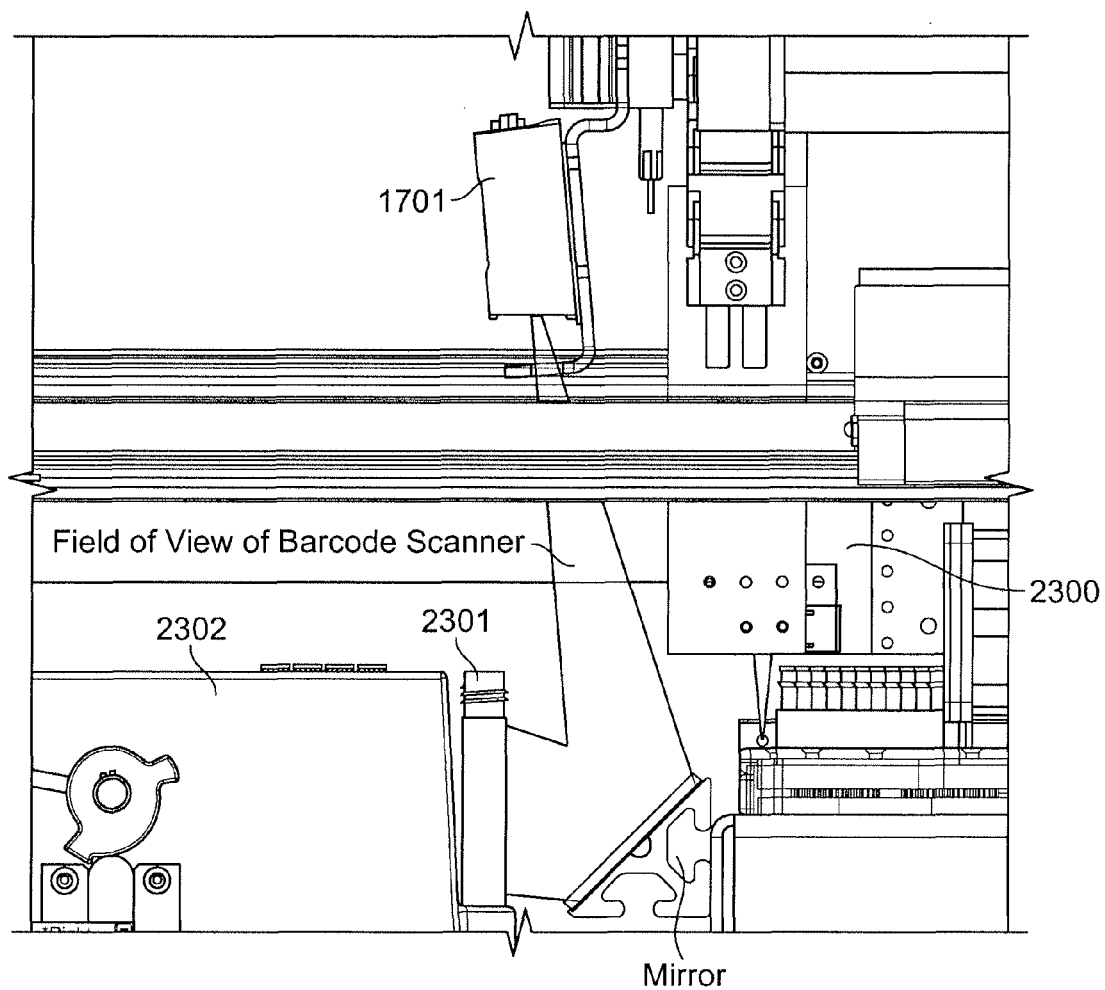

Another aspect of the apparatus relates to a sample identification verifier configured to check the identity of each of the number of nucleic-acid containing samples. Such sample identification verifiers can be optical character readers, bar code readers, or radio frequency tag readers, or other suitable readers, as available to one of ordinary skill in the art. A sample identification verifier can be mounted on the gantry, or attached to the liquid dispenser so that it moves in concert with the liquid dispenser. Alternatively, the sample identification verifier can be separately mounted and can move independently of the liquid dispenser. In FIGS. 21 and 22, for example, sample identification verifier 1701 is a bar-code reader attached to the liquid dispenser. The field of view of barcode scanner 1701 is non-linear, enabling it to detect light reflected by mirror 2300 from the barcoded clinical sample tube 2301 in disposable rack 2302. The barcode scanner reads the barcode on the clinical sample tube thus identifying the presence and specifics of the sample tube. Because of use of a mirror, the scanner is configured either to read a bar-code printed in mirror image form (that is thus reflected into normal form), or to read a mirror image of a normal bar-code and to convert the mirror image to unreflected form via a computer algorithm.

Sample identification verifier is configured to communicate details of labels that it has detected or read to a processor or controller in the apparatus, thereby permitting sample identifying information to be associated with diagnostic results and other information relating to sample preparation, and extraction and amplification of nucleic acid therein.

Figure 23:
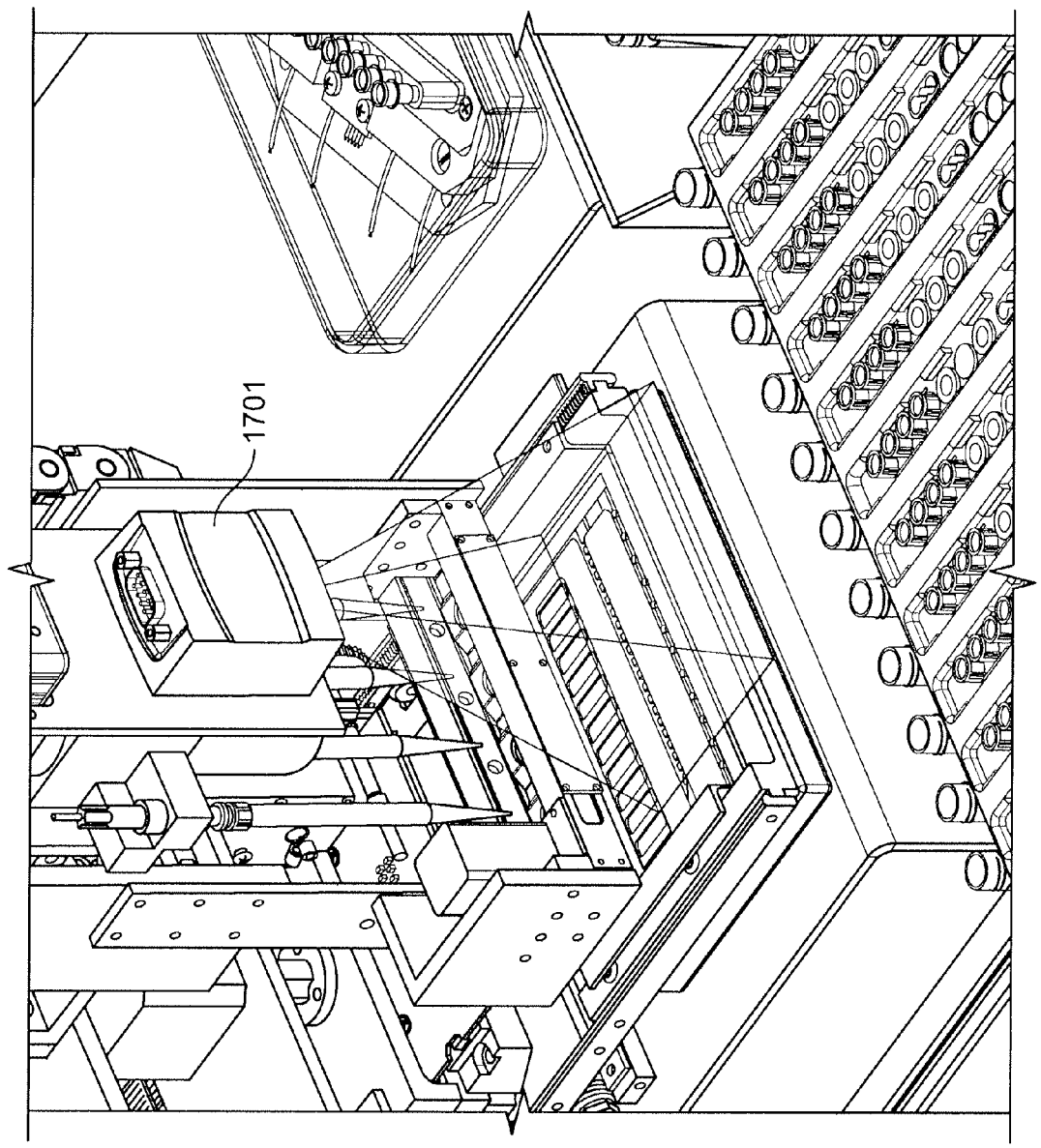

In FIG. 23, the sample identification verifier is positioned to read indicia from a microfluidic cartridge.

Figure 24:
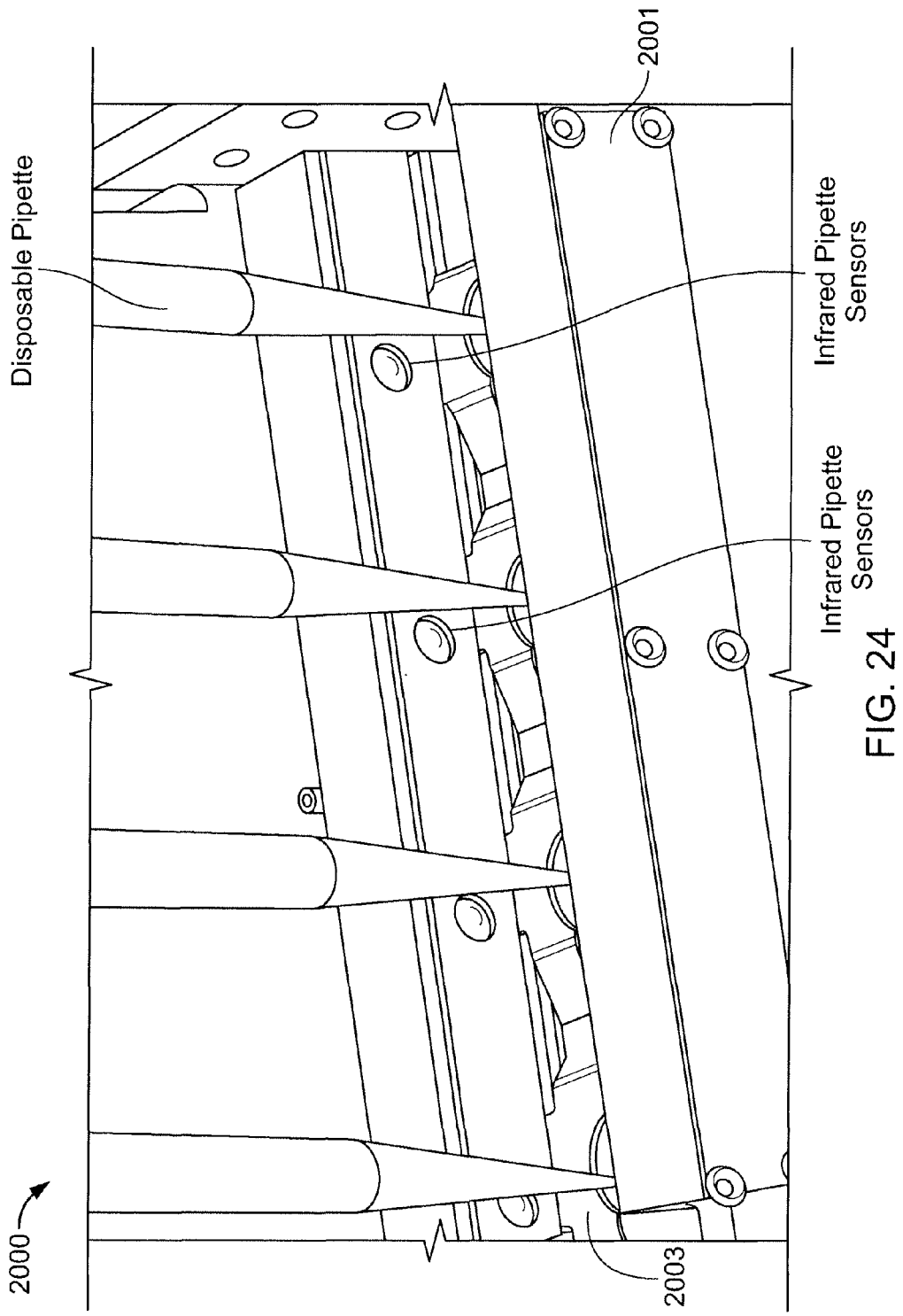

In certain embodiments, the liquid dispenser can also comprise one or more sensors 2001 (e.g., infra-red sensors) each of which detects the presence of a pipette tip in a rack. In FIG. 24, for example, an infra-red sensor 2001 can have an infra-red emitter placed opposed to it, and the presence of disposable pipette tip 2000 obstructs the line of sight between the emitter and the detector, thus enabling determination of the presence or absence of the pipette tip. The disposal pipettes are configured perpendicular to pipette stripper-alignment plate 2003 as further described herein.

The liquid dispenser can also operate in conjunction with a motorized plate configured to strip the pipettes and align the pipettes during dispensing of fluid into a microfluidic cartridge, as further described herein.

Figure 25B:
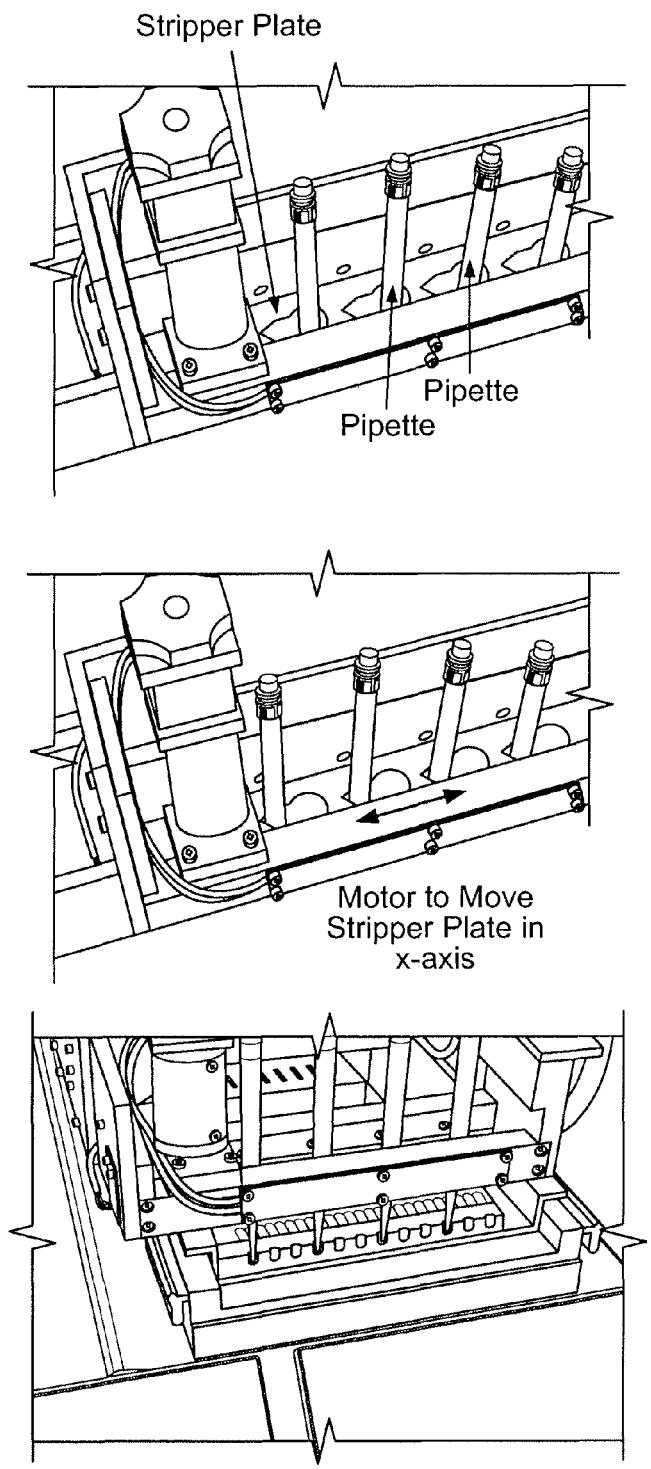

FIGS. 25A and 25B show an exemplary device for stripping pipette tips from a liquid dispenser as further described herein. The pipette tips are aligned, all at the same pitch, above respective sockets (over a pipette tip sheath) in a holder. A metal plate having elongated holes lies over the sockets. The pipette tips are inserted part way down into the sheath through the elongated holes, and the metal plate is moved along in such a manner that the pipette tips are clamped by the elongated portion of the holes. When the liquid dispenser is moved up, the pipette tips become detached from their respective heads. When the metal plate is subsequently moved back to its initial position, the pipette tips remain in place in their respective sockets.

Heater Assembly & Magnetic Separator

A cross-sectional view of a heater unit of an exemplary heater assembly 1401 is shown in FIG. 18 (right hand panel). The heater assembly comprises one or more independently, controllable heater units, each of which comprises a heat block. In certain embodiments there are 2, 3, 4, 5, 6, 8, 10, 12, 16, 20, 24, 25, 30, 32, 36, 40, 48, or 50 heater units in a heater assembly. Still other numbers of heater units, such as any number between 6 and 100 are consistent with the description herein. The one or more heat blocks may be fashioned from a single piece of metal or other material, or may be made separately from one another and mounted independently of one another or connected to one another in some way. Thus, the term heater assembly connotes a collection of heater units but does not require the heater units or their respective heat blocks to be attached directly or indirectly to one another. The heater assembly can be configured so that each heater unit independently heats each of the one or more process tubes 1402, for example by permitting each of the one or more heat blocks to be independently controllable, as further described herein. In the configuration of FIG. 26, the heater assembly comprises one or more heat blocks 1403 each of which is configured to align with and to deliver heat to a process tube 1402. Each heat block 1403 can be optionally secured and connected to the rest of the apparatus using a strip 1408 and one or more screws 1407 or other adhesive device. This securing mechanism is not limited to such a configuration.

Although a cross-sectional view of one heat block 1403 is shown in FIG. 26, it should be understood that this is consistent with having multiple heat blocks aligned in parallel to one another and such that their geometric midpoints all lie on a single linear axis, though it is not so limited in configuration. Thus, the one or more heat blocks may be positioned at different heights from one another, in groups or, alternately, individually, or may be staggered with respect to one another from left to right in FIG. 26 (right hand panel), in groups or alternately, or individually. Additionally, and in other embodiments, the heat blocks are not aligned parallel to one another but are disposed at angles relative to one another, the angles being other than 180°. Furthermore, although the heat block shown in FIG. 26 may be one of several that are identical in size, it is consistent with the technology herein that one or more heat blocks may be configured to accept and to heat process tubes of different sizes.

The exemplary heat block 1403 in FIG. 26 (right hand panel) is configured to have an internal cavity that partially surrounds a lower portion of process tube 1402. In the heat block of FIG. 26, the internal cavity surrounds the lower portion of process tube 1402 on two sides but not the front side (facing away from magnet 1404) and not the rear side (adjacent to magnet 1404). In other embodiments, heat block 1403 is configured to surround the bottom of process tube 1402 on three sides, including the front side. Still other configurations of heat block 1403 are possible, consistent with the goals of achieving rapid and uniform heating of the contents of process tube 1402. In certain embodiments, the heat block is shaped to conform closely to the shape of process tube 1402 so as to increase the surface area of the heat block that is in contact with the process tube during heating of the process tube. Thus, although exemplary heat block 1403 is shown having a conical, curve-bottomed cavity in which a complementary process tube is seated, other embodiments of heat block 1403 have, for example, a cylindrical cavity with a flat bottom. Still other embodiments of heat block 1403 may have a rectilinear internal cavity such as would accommodate a cuvette.

Moreover, although heat block 1403 is shown as an L-shape in FIG. 26, which aids in the transmittal of heat from heating element 1501 and in securing the one or more heat blocks to the rest of the apparatus, it need not be so, as further described herein. For example, in some embodiments heating element 1501 may be positioned directly underneath process tube 1402.

Each heat block 1403 is configured to have a low thermal mass while still maintaining high structural integrity and allowing a magnet to slide past the heat blocks and the process tubes with ease. A low thermal mass is advantageous because it allows heat to be delivered or dissipated rapidly, thus increasing the heating and cooling efficiency of the apparatus in which the heater assembly is situated. Factors that contribute to a low thermal mass include the material from which a heat block is made, and the shape that it adopts. The heat blocks 1403 can therefore be made of such materials as aluminum, silver, gold, and copper, and alloys thereof, but are not so limited.

In one embodiment, the heat block 1403 has a mass of ~0 grams and is configured to heat up liquid samples having volumes between 1.2 ml and 10 μl. Heating from room temperature to 65° C. for a 1 ml biological sample can be achieved in less than 3 minutes, and 10 μl of an aqueous liquid such as a release buffer up to 85° C. (from 50° C.) in less than 2 minutes. The heat block 1403 can cool down to 50° C. from 85° C. in less than 3 minutes. The heat block 1403 can be configured to have a temperature uniformity of 65±4° C. for heating up 1 ml of sample and 85±3° C. for heating up 10 μl of release buffer. These ranges are typical, but the heat block can be suitably scaled to heat other volumes of liquid at rates that are slower and faster than those described. This aspect of the technology is one aspect that contributes to achieving rapid nucleic acid extraction of multiple samples by combination of liquid processing steps, rapid heating for lysis, DNA capture and release and magnetic separation, as further described herein.

Not shown in FIG. 26, the heater assembly 1401 can also optionally be contained in an enclosure that surrounds the heat blocks 1403. The enclosure can be configured to enable sufficient air flow around the process tubes and so as not to significantly inhibit rate of cooling. The enclosure can have a gap between it and the heat blocks to facilitate cooling. The enclosure can be made of plastic, but is not so limited. The enclosure is typically configured to appear aesthetic to a user.

As shown in FIG. 26, the heater assembly 1401 can also comprise one or more heating elements (e.g., a power resistor) 1501 each of which is configured to thermally interface to a heat block 1403 and dissipate heat to it. For example, in one embodiment, a power resistor can dissipate up to 25 Watts of power. A power resistor is advantageous because it is typically a low-cost alternative to a heating element. Other off-the-shelf electronic components such as power transistors may also be used to both sense temperature and heat. Although the heating element 1501 is shown placed at the bottom of the heat block 1403, it would be understood that other configurations are consistent with the assembly described herein: for example, the heating element 1501 might be placed at the top or side of each heat block 1403, or directly underneath process tube 1402. In other embodiments, the heating element has other shapes and is not rectangular in cross section but may be curved, such as spherical or ellipsoidal. Additionally, the heating element may be moulded or shaped so that it conforms closely or approximately to the shape of the bottom of the process tube. Not shown in FIG. 26, the heater assembly can also comprise an interface material (e.g., Berquist q-pad, or thermal grease) between the heating element 1501 and the heat block 1403 to enable good thermal contact between the element and the heat block.

In the embodiment shown in FIG. 26, the heater assembly further comprises one or more temperature sensors 1502, such as resistive temperature detectors, to sense the respective temperatures of each heat block 1403. Although a temperature sensor 1502 is shown placed at the bottom of the heat block 1403, it would be understood that other configurations are consistent with the assembly described herein: for example, the temperature sensor might be placed at the top or side of each heat block 1403, or closer to the bottom of process tube 1402 but not so close as to impede uniform heating thereof. As shown in the embodiment of FIG. 26, the heater assembly can further comprise an interface material (e.g., Berquist q-pad) 1503 configured to enable good thermal contact between the sensor 1502 and the heat block 1403, to thereby ensure an accurate reading.

Certain embodiments of the diagnostic or preparatory apparatus herein have more than one heater assembly as further described herein. For example, a single heater assembly may be configured to independently heat 6 or 12 process tubes, and an apparatus may be configured with two or four such heater assemblies.

The disclosure herein further comprises a magnetic separator, configured to separate magnetic particles, the separator comprising: one or more magnets affixed to a supporting member; a motorized mechanism configured to move the supporting member in such a manner that the one or more magnets move backwards and forwards along a fixed axis, and during at least a portion of the motion, the one or more magnets maintain close proximity to one or more receptacles which contain the magnetic particles in solution; and control circuitry to control the motorized mechanism.

The disclosure herein still further includes an integrated magnetic separator and heater, comprising: a heater assembly, wherein the heater assembly comprises a plurality of independently controllable heater units, each of which is configured to accept and to heat one of a plurality of process tubes; one or more magnets affixed to a supporting member; a motorized mechanism configured to move the supporting member in such a manner that the one or more magnets move backwards and forwards along a fixed axis, and during at least a portion of the motion the one or more magnets maintain close proximity to one or more of the process tubes in the heater assembly, wherein the one or more process tubes contain magnetic particles; and control circuitry to control the motorized mechanism and to control heating of the heater units.

Typically, each of the one or more receptacles is a process tube, such as for carrying out biological reactions. In some embodiments, close proximity can be defined as a magnet having a face less than 2 mm away from the exterior surface of a process tube without being in contact with the tube. It can still further be defined to be less than 1 mm away without being in contact with the tube, or between 1 and 2 mm away.

Typically the magnetic particles are microparticles, beads, or microspheres capable of binding one or more biomolecules, such as polynucleotides. Separating the particles, while in solution, typically comprises collecting and concentrating, or gathering, the particles into one location in the inside of the one or more receptacles.

Figure 27:
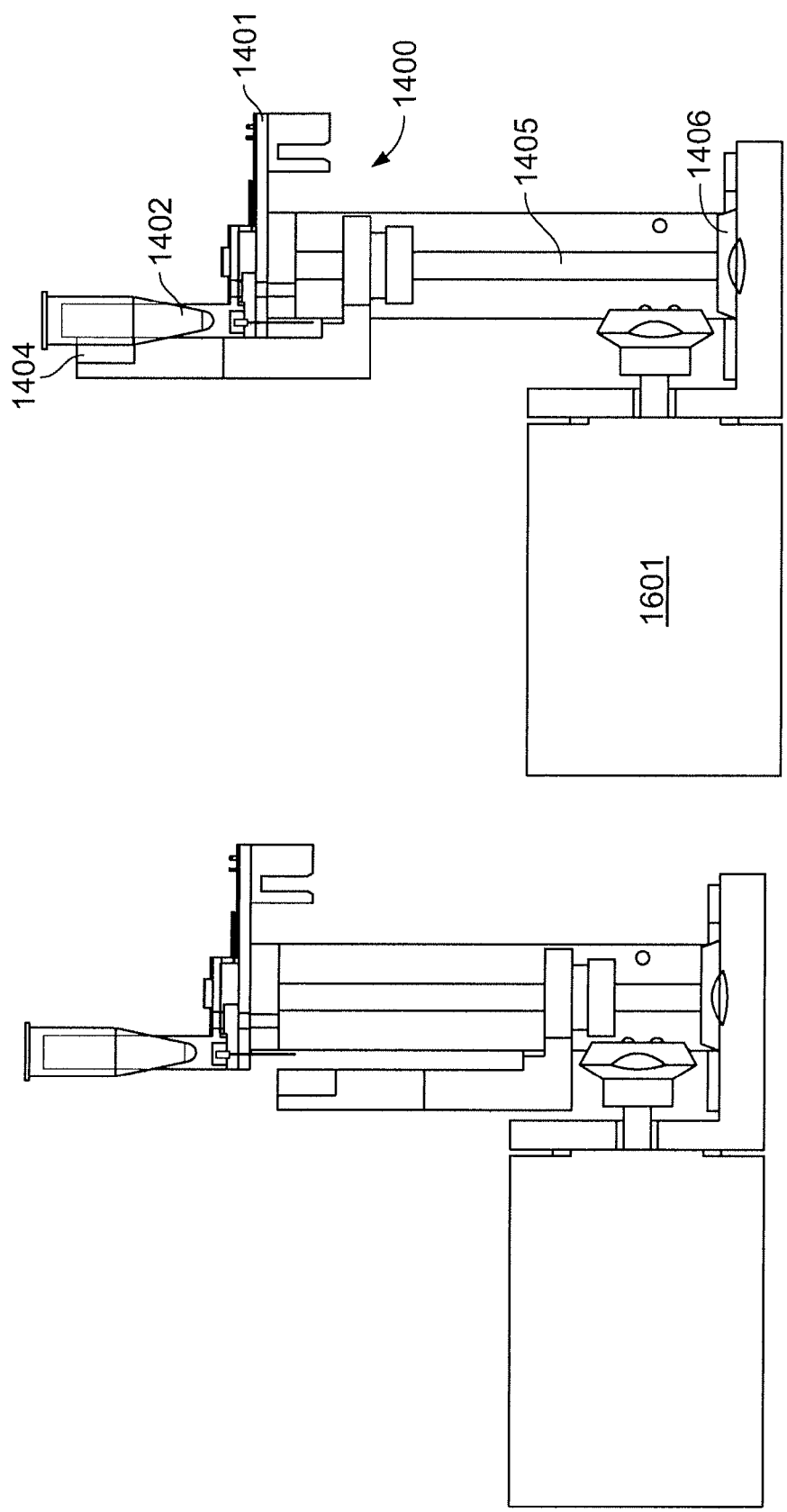

An exemplary magnetic separator 1400 is shown in FIG. 27, configured to operate in conjunction with heater assembly 1401. The magnetic separator 1400 is configured to move one or more magnets relative to the one or more process tubes 1402. While the magnet 1404 shown in FIG. 27 is shown as a rectangular block, it is not so limited in shape. Moreover, the configuration of FIG. 27 is consistent with either having a single magnet that extends across all heat blocks 1403 or having multiple magnets operating in concert and aligned to span a subset of the heat blocks, for example, aligned collinearly on the supporting member. The magnet 1404 can be made of neodymium (e.g., from K &J Magnetics, Inc.) and can have a magnetic strength of 5,000-15,000 Gauss (Brmax). The poles of the magnets 1404 can be arranged such that one pole faces the heat blocks 1403 and the other faces away from the heat blocks.

Further, in the embodiment shown in FIG. 27, the magnet 1404 is mounted on a supporting member 1505 that can be raised up and down along a fixed axis using a motorized shaft 1405. The fixed axis can be vertical. In the embodiment shown in FIG. 27, a geared arrangement 1406 enables the motor 1601 to be placed perpendicular to the shaft 1405, thereby saving space in the apparatus in which magnetic separator 1400 is situated. In other embodiments, the motor is placed underneath shaft 1405. It would be understood that other configurations are consistent with the movement of the magnet relative to the process tubes, including, but not limited to, moving the magnet from side-to-side, or bringing the magnet down from above. The motor can be computer controlled to run at a particular speed; for example at a rotational speed that leads to vertical motion of the magnet in the range 1-20 mm/s. The magnetic separator can thus be configured to move repetitively, e.g., up an down, from side to side, or backwards and forwards, along the same axis several times. In some embodiments there is more than one shaft that operates under motorized control. The presence of at least a second shaft has the effect of making the motion of the separator more smooth. In some embodiments, the supporting member rides on one more guiding members to ensure that the supporting member does not, for example, tip, twist, or yaw, or undergo other internal motions while moving (other than that of controlled motion along the axis) and thereby reduce efficacy of the separation.

The supporting member can also be configured to move the magnets between a first position, situated away from the one or more receptacles, and a second position situated in close proximity to the one or more receptacles, and is further configured to move at an amplitude about the second position where the amplitude is smaller than a distance between the first position and the second position as measured along the shaft.

Shown in FIGS. 26 and 27, the heater assembly 1401 and the magnetic separator 1400 can be controlled by electronic circuitry such as on printed circuit board 1409. The electronic circuitry 1409 can be configured to cause the heater assembly 1401 to apply heat independently to the process tubes 1402 to minimize the cost of heating and sensing. It can also be configured to cause the magnetic separator 1400 to move repetitively relative to the process tubes 1402. The electronic circuitry 1409 can be integrated into a single printed circuit board (PCB). During assembly, a plastic guide piece can help maintain certain spacing between individual heat blocks 1403. This design can benefit from use off-the-shelf electronics to control a custom arrangement of heat blocks 1403.

Not shown in FIGS. 26 and 27, an enclosure can cover the magnetic separator 1400 and the heater assembly 1401 for protection of sub-assemblies below and aesthetics. The enclosure can also be designed to keep the heat blocks 1403 spaced apart from one another to ensure efficiency of heating and cooling. The magnetic separator and heater assembly can, alternatively, be enclosed by separate enclosures. The one or more enclosures can be made of plastic.

Advantageously, the heater assembly and magnetic separator operate together to permit successive heating and separation operations to be performed on liquid materials in the one or more process tubes without transporting either the liquid materials or the process tubes to different locations to perform either heating or separation. Such operation is also advantageous because it means that the functions of heating and separation which, although independent of one another, are both utilized in sample preparation may be performed with a compact and efficient apparatus.

Cartridge Autoloader

Figure 28:
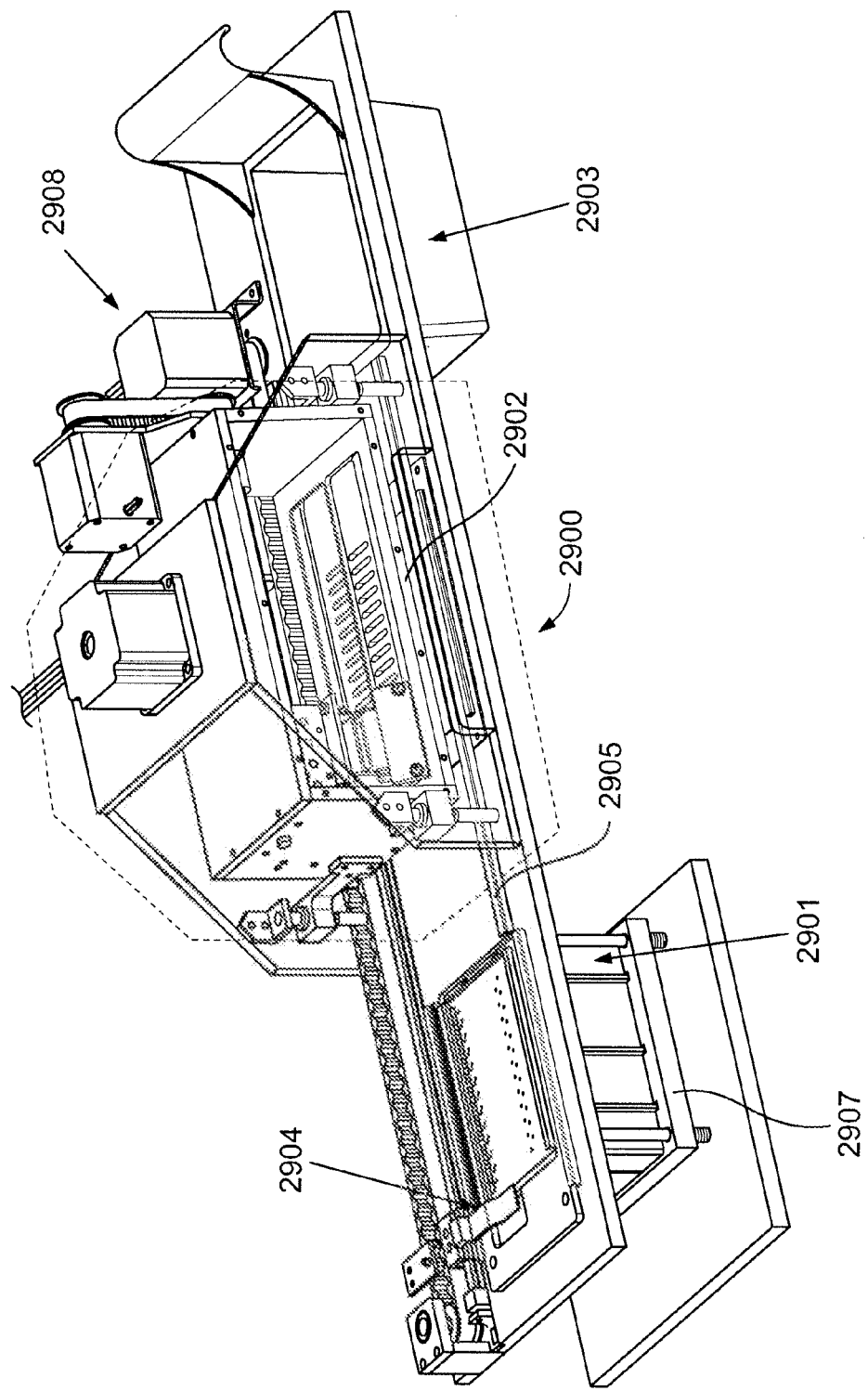

An exemplary embodiment of a PCR amplification-detection system 2900 for use with a microfluidic cartridge is shown in FIG. 28. The system 2900 performs and automates the process of PCR on multiple nucleic-acid containing samples in parallel. The system 2900 comprises a depository 2907 for unused microfluidic cartridges, a cartridge autoloader, a receiving bay for a microfluidic cartridge, a detector, and a waste tray 2903 configured to receive used microfluidic cartridges. In one embodiment, the cartridge autoloader comprises a cartridge pack 2901, and a cartridge pusher 2904.

The system 2900, for illustration purposes, is configured so that a microfluidic cartridge moves in a plane and in a linear manner from the depository to the receiving bay, to the waste bin, but it need not be so arranged. For example, the waste cartridge bin 2903 can be aligned orthogonally, or any angle thereof, to the receiving bay, such as disposed behind it. Alternatively, each element (cartridge autoloader 2901, receiving bay 2902, and waste cartridge bin 2903) can be configured in a step-wise manner where the cartridge pack 2901 is on the same, higher or lower level than the microfluidic PCR amplification-detection system 2902 and the microfluidic PCR amplification-detection system 2902 is on the same, higher or lower level than the waste cartridge bin 2903. Another configuration could be that each of the three elements is not arranged linearly but at an angle to one another, although within the same plane.

FIG. 28 illustrates the cartridge pack 2901 and the waste cartridge bin 2903 below the plane of the receiving bay, and a detection system 2908 above the plane. This configuration is exemplary and it would be understood that these elements may be positioned above or below the plane in other embodiments.

Figure 29:
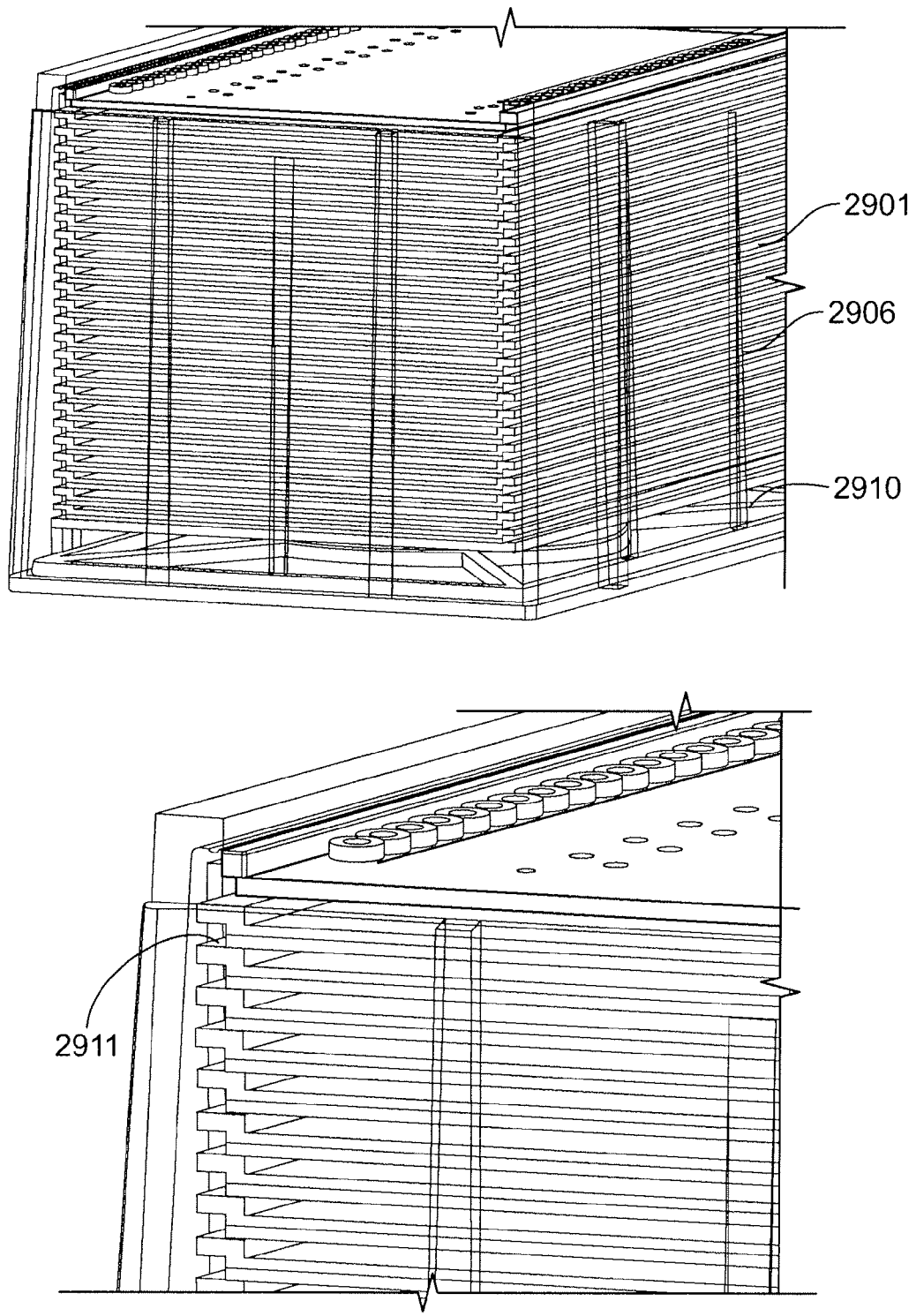

FIG. 29 illustrates a depository for unused microfluidic cartridges. The depository can be configured to accept a number of individually stacked and individually loaded cartridges, or can be configured to accept a pack of cartridges. An exemplary cartridge pack has 24 cartridges. The depository may consist of a cage 2910 of any material that may or may not be transparent. For example it may be made of metal or plastic. The cartridge pack 2901 is not limited to twenty-four cartridges 106 per pack but may contain any number from 2 to 100. For example, other numbers such as 2, 4, 8, 10, 12, 16, 20, 30, 36, 40, 48, 50, or 64 are possible numbers of cartridges 106 per pack. Similarly, the depository may be configured to accept those numbers of cartridges, when individually stacked. In one embodiment, as in FIG. 29, each cartridge 2906, individually stacked, rests on ledges 2911 that protrude from the cage 2910. However, other configurations are possible. For example, a cartridge 2906 may rest on recessed grooves made within the interior surfaces of cage 2910. Furthermore, the cartridge pack 2901 may not need to be placed in a cage 2910. The cartridge pack 2901 may itself include the necessary connections to bind securely to the apparatus to load the cartridges 2906.

Figure 30:
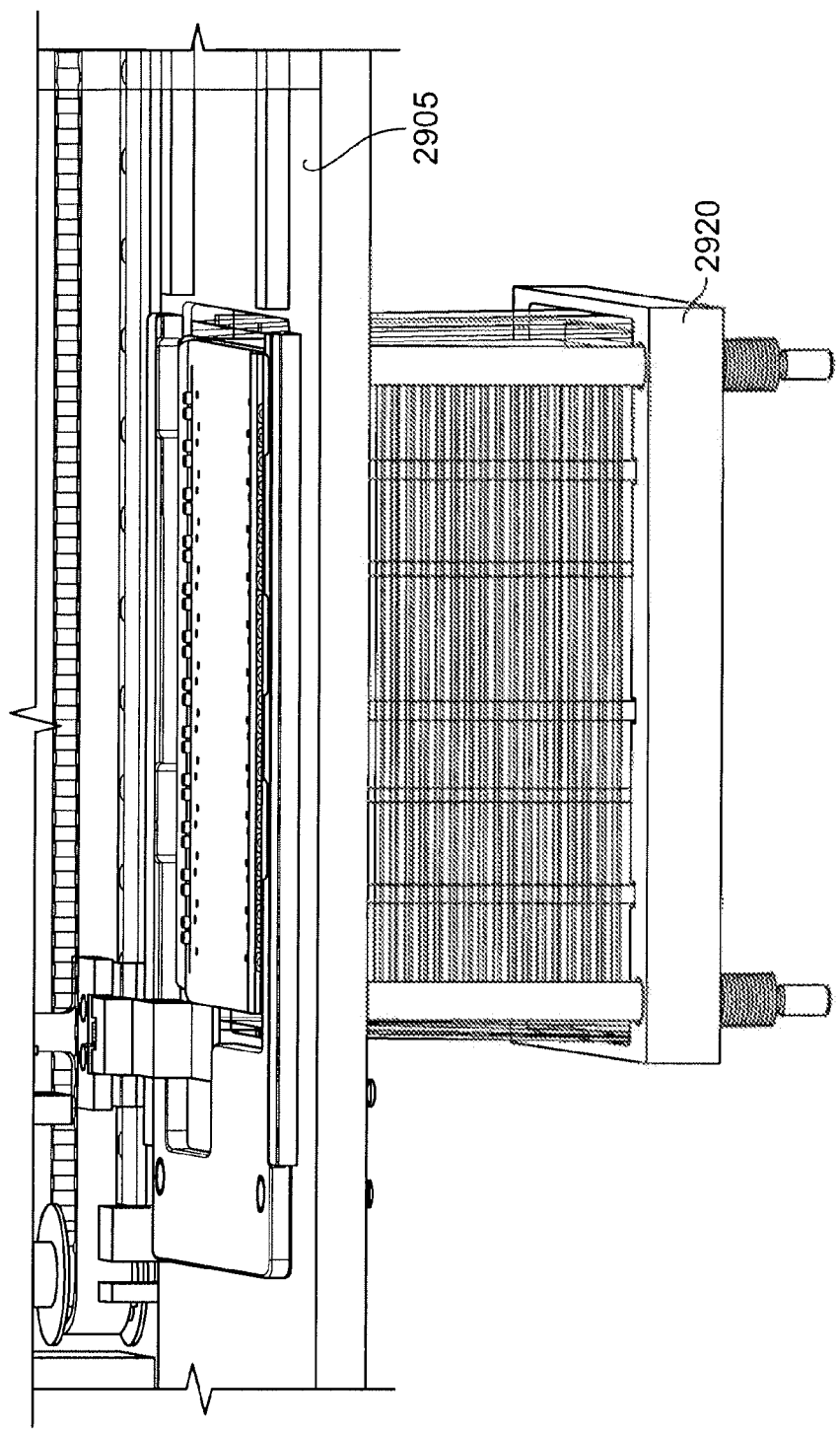

FIG. 30 is an illustration of an exemplary initial loading position of a cartridge pack 2901 in a depository when samples are loaded in the topmost cartridge in the pack. FIG. 30 shows the cartridge pack 2901 below a plane that contains a cartridge pusher. In other embodiments, the cartridge pack

2901 may be above the plane of a cartridge pusher where the pusher pushes the lowest cartridge out from the holder; or partly above and partly below in a holder 2920 where a cartridge pusher pushes a cartridge from the middle of the cartridge pack 2901. In the embodiment shown, a topmost cartridge 106 is pushed along two guide rails 2905. Alternatively, there may be more or fewer guide rails (such as one or three) or no guide rails at all so long as a cartridge 2906 can be caused to move to other required positions.

Figure 31:
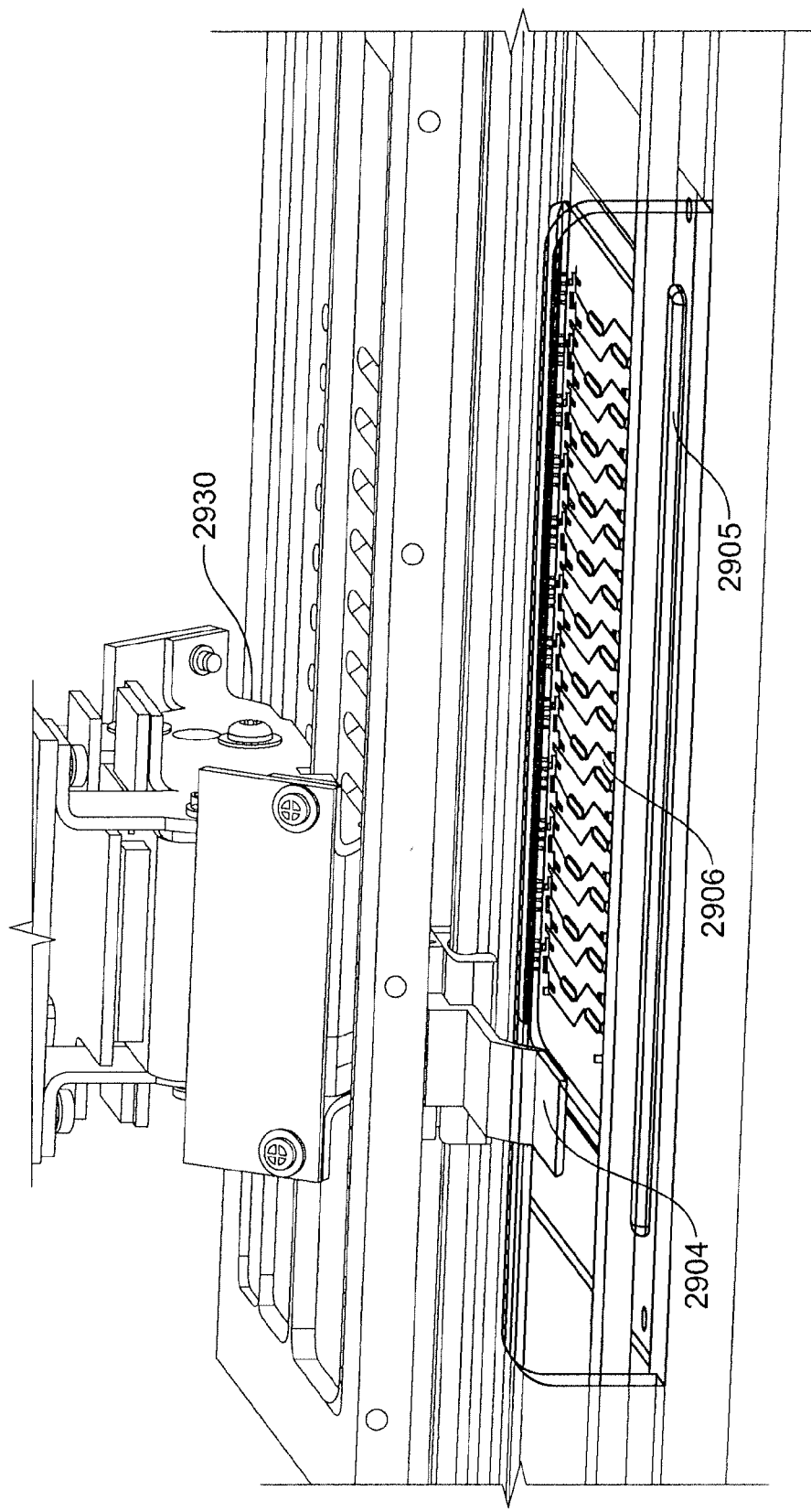

An exemplary cartridge pusher 2904 is shown in FIG. 31. The cartridge pusher 2904 pushes a cartridge 2906 along guide rails 2905, which allows a cartridge 2906 to travel to pre-calibrated positions by the mechanism of a stepper motor 2930. However, it would be understood that the mechanism of transporting the cartridge 2906 is not limited to a stepper motor 2930 and thus other mechanisms are also consistent with the cartridge pusher 2904 as described herein.

Figure 32:
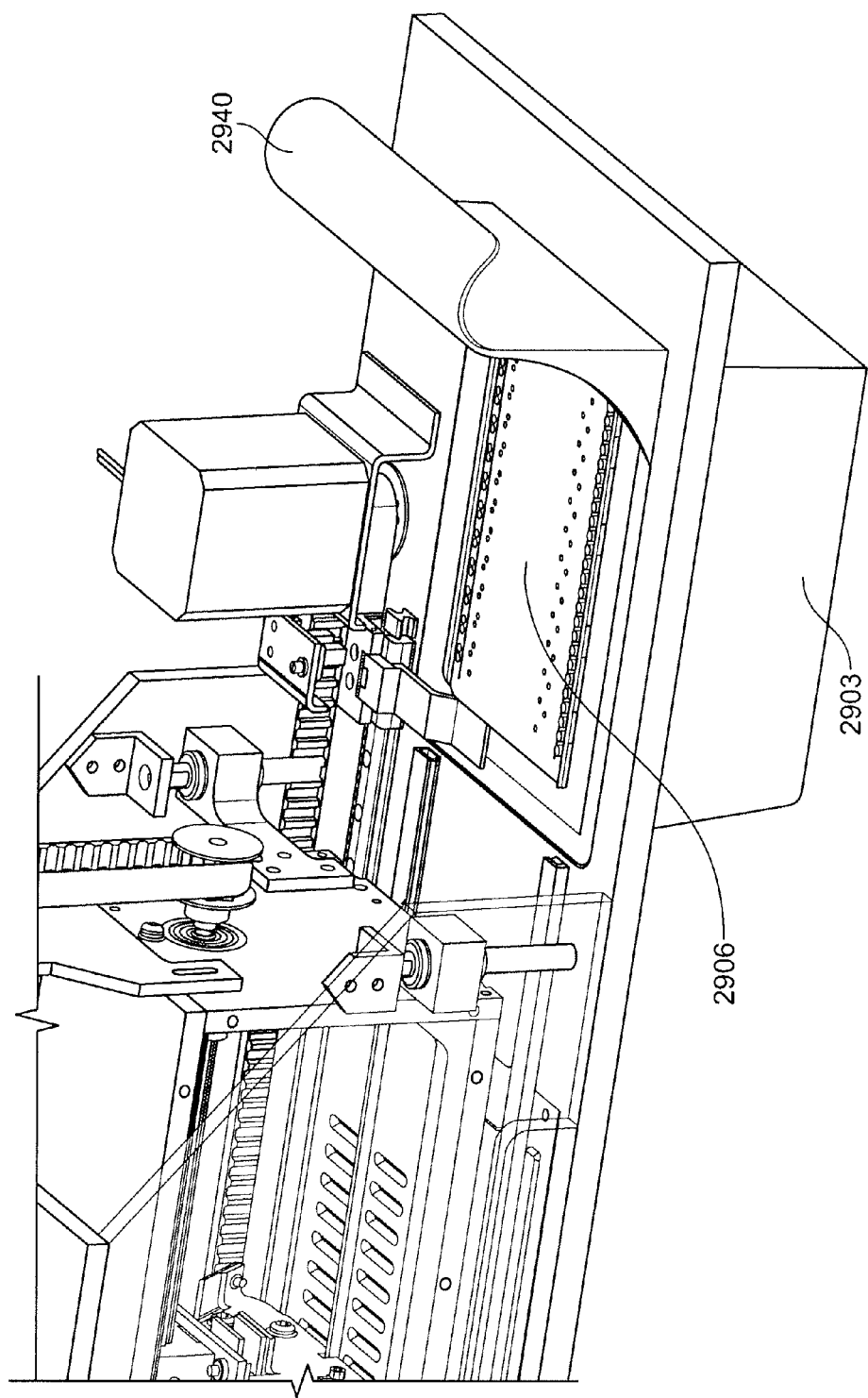

FIG. 32 shows a used cartridge 2906 that has been pushed by the cartridge pusher 2904 into the waste cartridge bin 2903 after a PCR process has been completed. The embodiment shows a lipped handle 2940 that facilitates easy handling, such as emptying, of the bin 2903. However, it would be understood that the handle 2904 is not limited to the style and shape shown.

Figure 33:
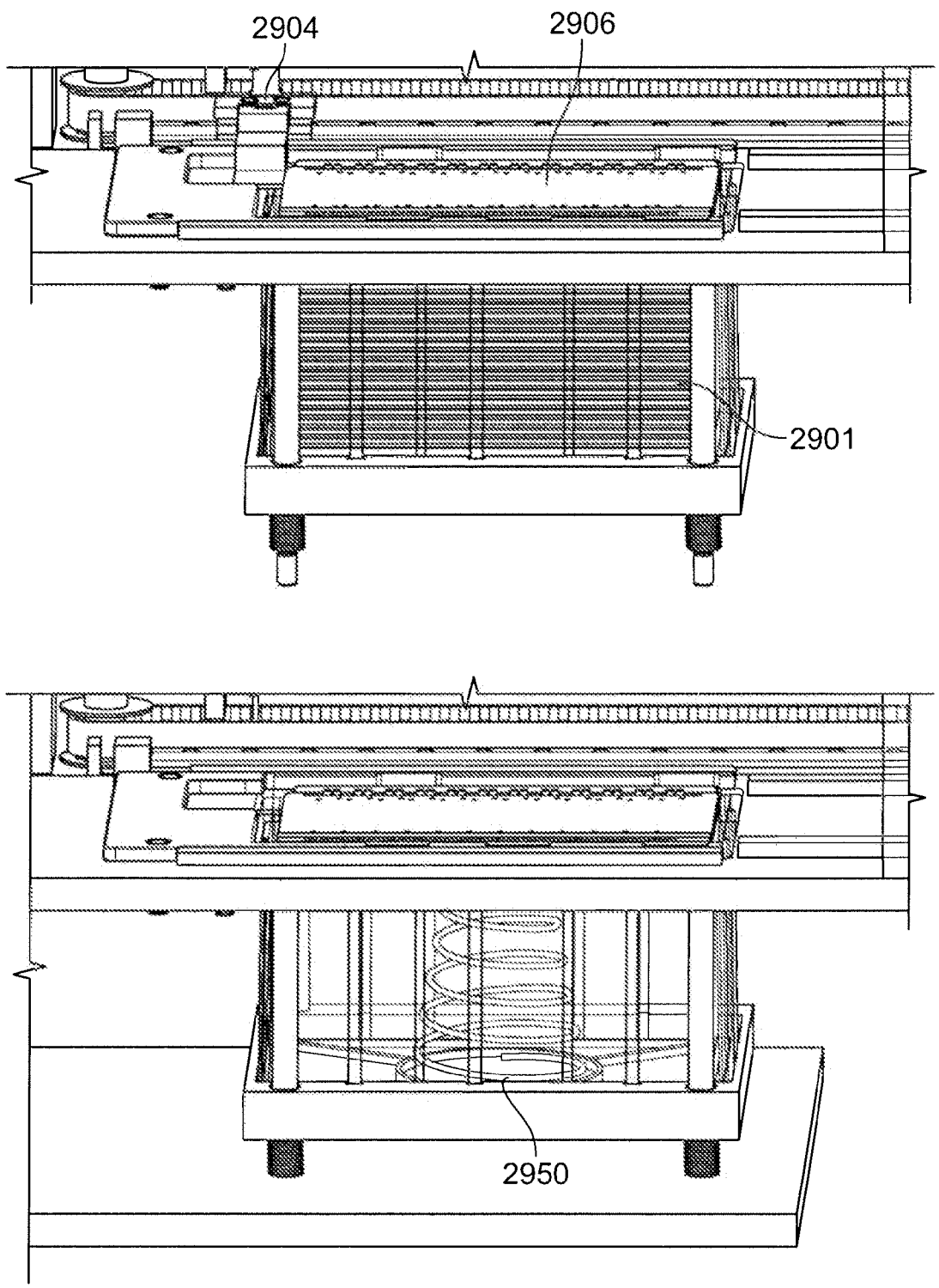
FIG. 33 shows a cartridge stacker in full and empty configurations.

An exemplary cartridge pack 2901, before and after multiple PCR processes are completed are shown in FIG. 33. After the cartridge pusher 2904 pushes a cartridge 2906 out of the cartridge pack 2901, a spring 2950 at the bottom of the cartridge pack pushes against the lower surface of the stack of cartridges and causes the topmost cartridge to be made available for sample injection. The spring 2950 is not limited in number or type. Thus although a single helical or coiled spring is shown, it is consistent with the description herein that more than one helical or coiled springs could be used, such as 2, 3, or 4, and that alternatively a sprung metal strip, or several strips, could be used. Alternatively another mechanism for forcing the cartridges upwards could be deployed, such as a pneumatic, hydraulic, or inflatable pressurized container, could be utilized.

It is to be noted that microfluidic cartridges, as further described herein, that have a raised lip along their edges to permit ease of stacking and/or storage in a pack or an autoloader are particularly advantageous because the raised lips also introduce a stiffness into the cartridges and assist in keeping the fluid inlets on one cartridge away from those on another cartridge during storage and transport. The raised regions, which need not only be lips along each edge of a cartridge, also help minimize friction between the lower surface of one cartridge and the upper surface of another.

Cartridge Receiving Bay

The present technology relates to an apparatus and related methods for amplifying, and carrying out diagnostic analyses on, nucleotides from biological samples. The apparatus is configured to act on a disposable microfluidic cartridge containing multiple sample lanes in parallel, and comprises a reusable instrument platform that can actuate on-cartridge operations, can detect and analyze the products of the PCR amplification in each of the lanes separately, in all simultaneously, or in groups simultaneously, and, optionally, can display the results on a graphical user interface.

Figure 34:
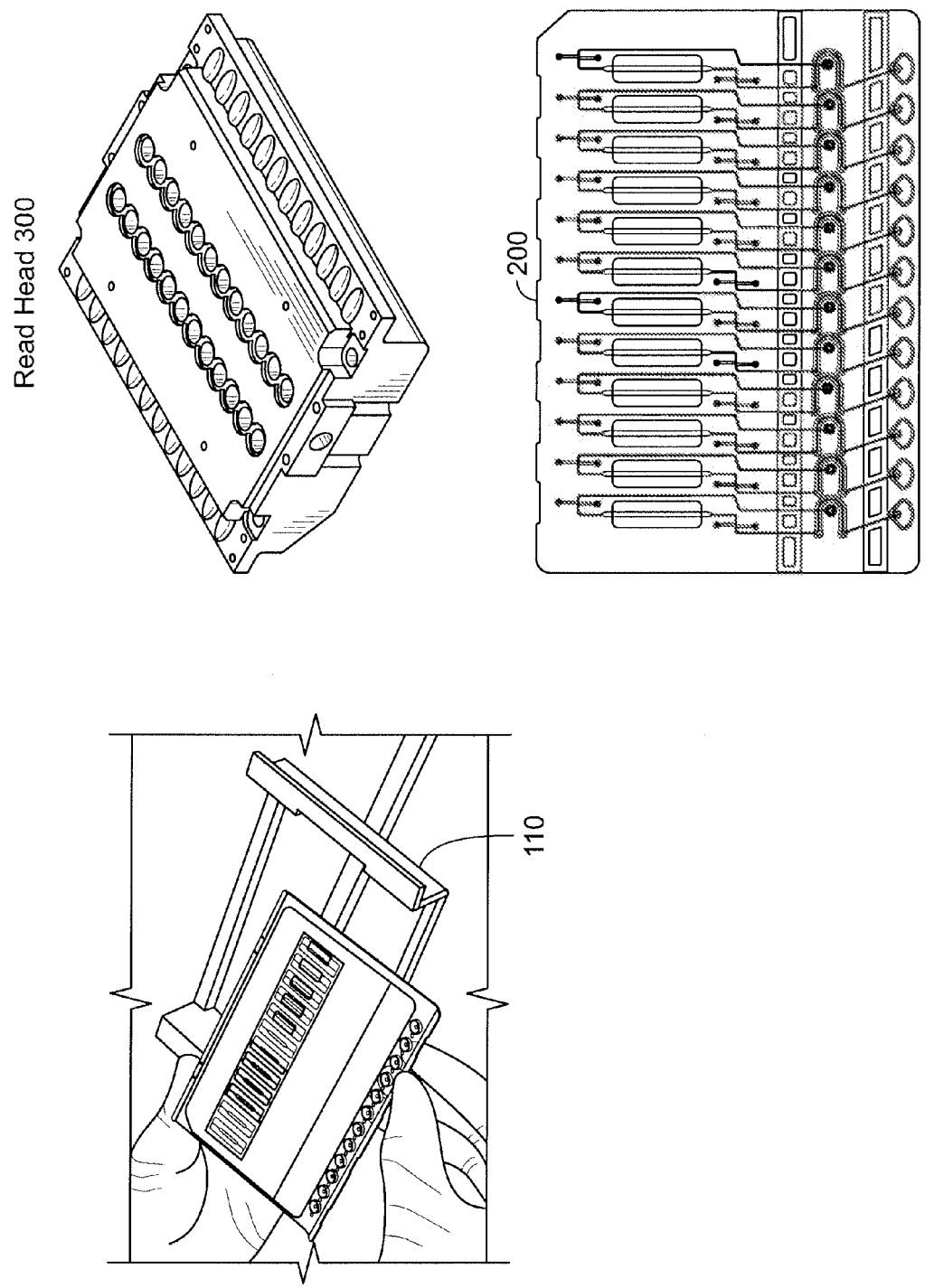
FIG. 34 shows a microfluidic cartridge, a read-head, and a cartridge tray.

FIG. 34 shows a perspective view of an exemplary cartridge 200 that contains multiple sample lanes, and exemplary read head 300 that contains detection apparatus for reading signals from cartridge 200. Also shown in FIG. 34 is a tray 110 that, optionally, can accommodate cartridge 200 prior to insertion of the cartridge in a receiving bay. The apparatus described herein is able to carry out real-time PCR on a number of samples in cartridge 200 simultaneously. Preferably the number of samples is 12 samples, as illustrated with exemplary cartridge 200, though other numbers of samples such as 4, 8, 10, 16, 20, 24, 25, 30, 32, 36, 40, and 48 are within the scope of the present description. In preferred operation of the apparatus, a PCR-ready solution containing the sample, and, optionally, one or more analyte-specific reagents (ASR's) using other components of the apparatus, as further described herein, prior to introduction into cartridge 200.

In some embodiments, an apparatus includes a bay configured to selectively receive a microfluidic cartridge; at least one heat source thermally coupled to the bay; and coupled to a processor as further described herein, wherein the heat source is configured to heat individual sample lanes in the cartridge, and the processor is configured to control application of heat to the individual sample lanes, separately, in all simultaneously, or in groups simultaneously.

In some embodiments, an apparatus further includes at least one detector configured to detect a polynucleotide (nucleic acid) in a sample in one or more of the individual sample lanes, separately or simultaneously; wherein the processor is coupled to the detector to control the detector and to receive signals from the detector.

The bay can be a portion of the apparatus that is configured to selectively receive the microfluidic cartridge. For example, the bay and the microfluidic cartridge can be complementary in shape so that the microfluidic cartridge is selectively received in, e.g., a single orientation. For example, the microfluidic cartridge can have a registration member that fits into a complementary feature of the bay. The registration member can be, for example, a cut-out on an edge of the cartridge, such as a corner that is cut-off, or one or more notches that are made on one or more of the sides. By selectively receiving the cartridge, the bay can help a user to place the cartridge so that the apparatus can properly operate on the cartridge. In this way, error-free alignment of cartridges can be achieved. Moreover, the cartridge can be designed to be slightly smaller than the receiving bay by approximately 200-300 micron for easy placement and removal of the cartridge. The apparatus can further include a sensor configured to sense whether the microfluidic cartridge is selectively received The bay can also be configured so that various components of the apparatus that can operate on the microfluidic cartridge (heat sources, detectors, force members, and the like) are positioned to properly operate on the microfluidic cartridge. For example, a contact heat source can be positioned in the bay such that it can be thermally coupled to a distinct location at a microfluidic cartridge that is selectively received in the receiving bay.

Alternatively, in connection with alignment of microheaters in the heater module with corresponding heat-requiring microcomponents (such as valves, pumps, gates, reaction chambers, etc), the microheaters can be designed to be slightly bigger than the heat requiring microfluidic components so that even though the cartridge may be off-centered from the heater, the individual components can still function effectively.

The detector 300 can be, for example, an optical detector, as further described herein. For example, the detector can include a light source that selectively emits light in an absorption band of a fluorescent dye, and a light detector that selectively detects light in an emission band of the fluorescent dye, wherein the fluorescent dye corresponds to a fluorescent polynucleotide probe or a fragment thereof. Alternatively, for example, the optical detector can include a bandpass-filtered diode that selectively emits light in the absorption band of the fluorescent dye and a bandpass filtered photodiode that selectively detects light in the emission band of the fluorescent dye; or for example, the optical detector can be configured to independently detect a plurality of fluorescent dyes having different fluorescent emission spectra, wherein each fluorescent dye corresponds to a fluorescent polynucleotide probe or a fragment thereof; or for example, the optical detector can be configured to independently detect a plurality of fluorescent dyes at a plurality of different locations on a microfluidic cartridge, wherein each fluorescent dye corresponds to a fluorescent polynucleotide probe or a fragment thereof in a different sample.

The heat source can be, for example, a heat source such as a resistive heater or network of resistive heaters, a reversible heat source such as a liquid-filled heat transfer circuit or a thermoelectric element, a radiative heat source such as a xenon lamp, and the like.

In preferred embodiments, the at least one heat source can be a contact heat source selected from a resistive heater (or network thereof), a radiator, a fluidic heat exchanger and a Peltier device. The contact heat source can be configured at the receiving bay to be thermally coupled to one or more distinct locations of a microfluidic cartridge received in the bay, whereby the distinct locations are selectively heated. At least one additional contact heat source can be included, wherein the contact heat sources are each configured at the bay to be independently thermally coupled to a different distinct location in a microfluidic cartridge received in the bay, whereby the distinct locations are independently heated. The contact heat source can be configured to be in direct physical contact with a distinct location of a microfluidic cartridge received in the bay. In various embodiments, each contact source heater can be configured to heat a distinct location having an average diameter in 2 dimensions from about 1 millimeter (mm) to about 15 mm (typically about 1 mm to about 10 mm), or a distinct location having a surface area of between about 1 mm$^2$ about 225 mm$^2$ (typically between about 1 mm$^2$ and about 100 mm$^2$, or in some embodiments between about 5 mm$^2$ and about 50 mm$^2$).

In various embodiments, at least one heat source can be a radiative heat source configured to direct heat to a distinct location of a microfluidic cartridge received in the receiving bay.

In various embodiments, the apparatus includes one or more force members that are configured to apply force to thermally couple the at least one heat source to at least a portion of the microfluidic cartridge received in the bay. The one or more force members can be configured to operate a mechanical member at the microfluidic cartridge. At least one force member can be manually operated. At least one force member can be mechanically coupled to a lid at the receiving bay, whereby operation of the lid operates the force member.

In various embodiments, the force applied by the one or more force members can result in an average pressure at an interface between a portion of the receiving bay and a portion of the microfluidic cartridge of about 1 psi. The application of force is important to ensure consistent thermal contact between the heater wafer and the PCR reactor and microvalves in the microfluidic cartridge.

In various embodiments, the apparatus can further include a lid at the receiving bay, the lid being operable to at least partially exclude ambient light from the bay. The lid can be, for example, a sliding lid. The lid can include the optical detector. A major face of the lid at the bay can vary from planarity by less than about 100 micrometers, for example, less than about 25 micrometers. The lid can be configured to be removable from the apparatus. The lid can include a latching member that ensures that the lid is securely closed before amplification reactions are applied to the samples in the cartridge.

Figure 35:
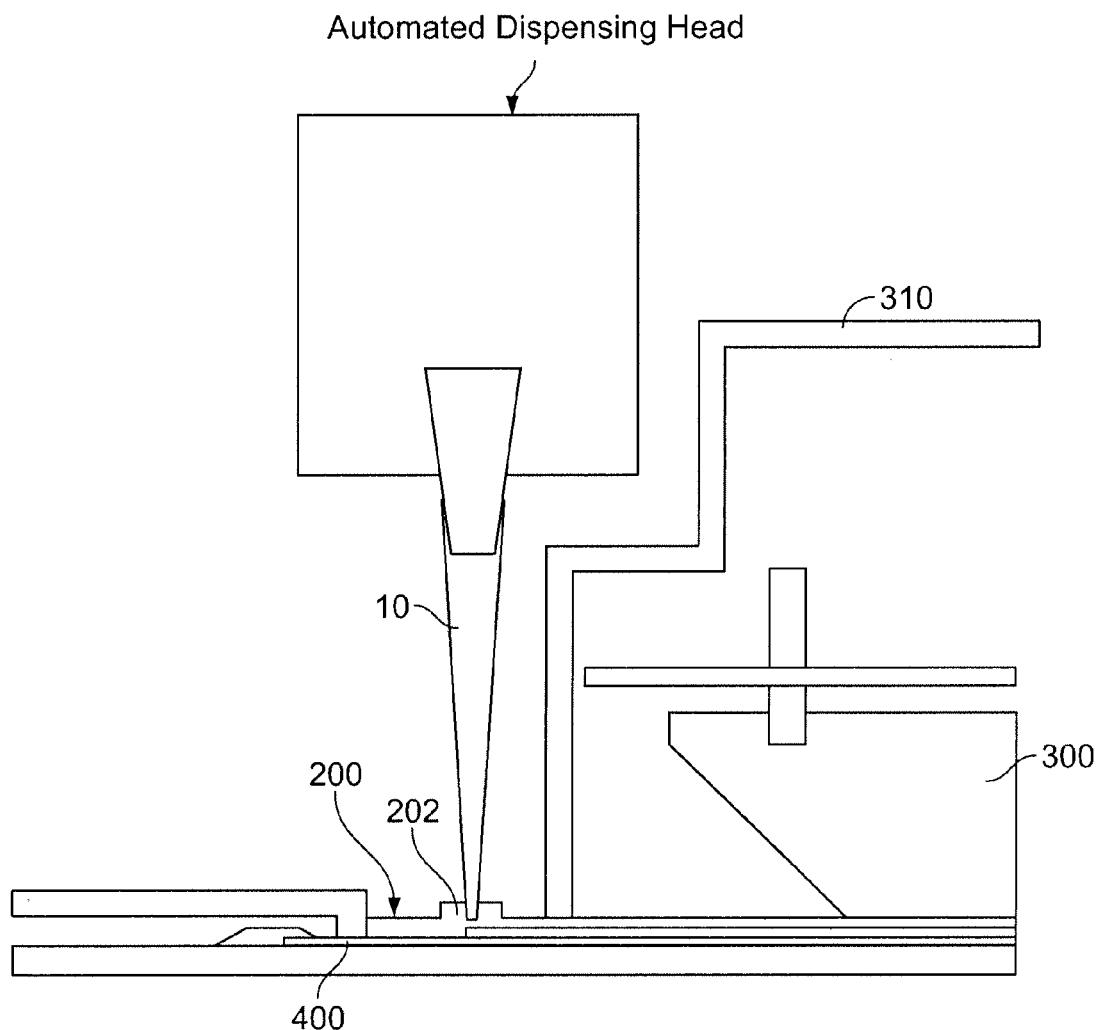
FIG. 35 shows a cross-section of a pipetting head and a cartridge in position in a microfluidic apparatus.

FIG. 35 shows a schematic cross-sectional view of a part of an apparatus as described herein, showing input of sample into a cartridge 200 via a pipette tip 10 (such as a disposable pipette) attached to an automated dispensing head, and an inlet 202. Although not shown, there are as many inlets 202 as samples to be input into cartridge 200. Inlet 202 is preferably configured to receive a pipette or the bottom end of a PCR tube and thereby accept sample for analysis with minimum waste, and with minimum introduction of air. Cartridge 200 is disposed on top of and in contact with a heater substrate 400. Read head 300 is positioned above cartridge 200 and a cover for optics 310 restricts the amount of ambient light that can be detected by the read head.

In various embodiments, a system as described herein can include both a microfluidic cartridge and the diagnostic apparatus.

Microfluidic Cartridge

Figure 36:
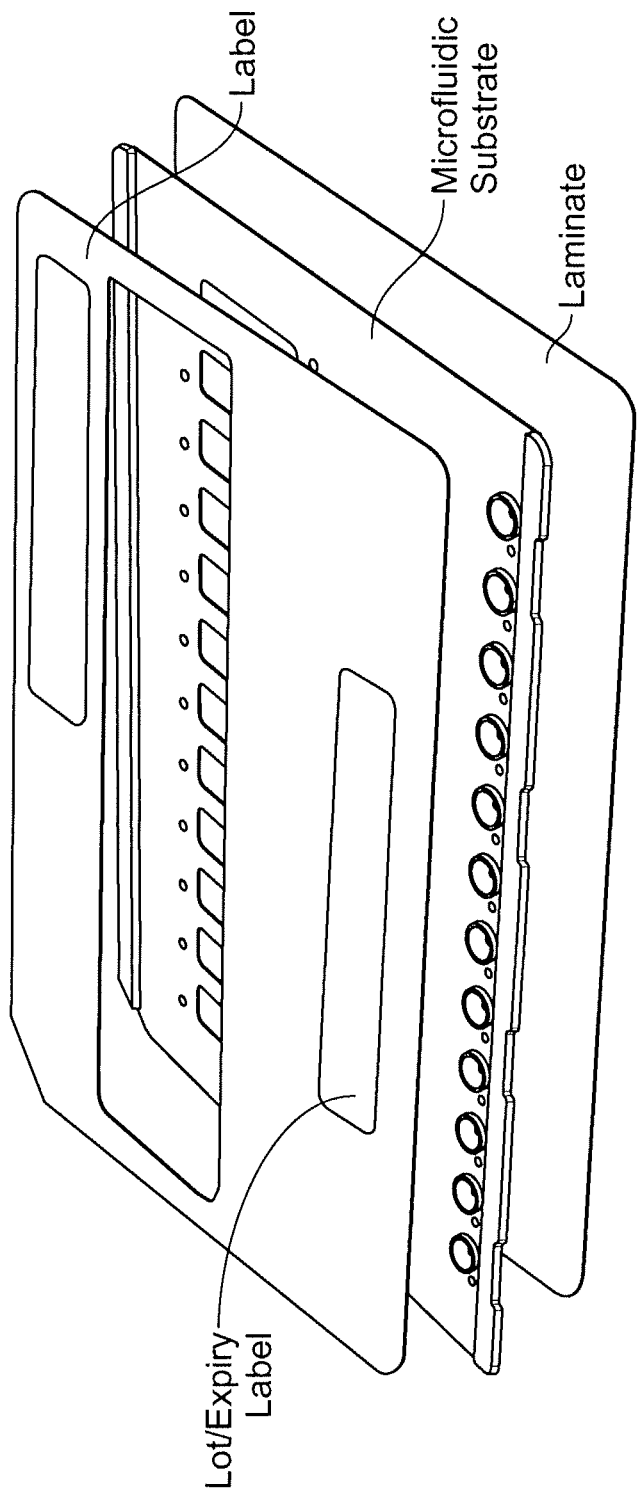
FIG. 36 shows an exemplary microfluidic cartridge having a 3-layer construction.

One aspect of the present technology relates to a microfluidic cartridge including a first, second, and third, layers that together define a plurality of microfluidic networks, each network having various components configured to carry out PCR on a sample having one or more polynucleotides whose presence is to be determined. The cartridge includes one or more sample lanes in parallel, wherein each lane is independently associated with a given sample for simultaneous processing, and each lane contains an independently configured microfluidic network. An exemplary cartridge having such a construction is shown in FIG. 36. Such a cartridge is simple to manufacture, and permits PCR in a concentrated reaction volume (~4 μl) and enables rapid thermocycling, at ~20 seconds per cycle.

Although other layers may be found in cartridges having comparable performance and ease of manufacture, the cartridge herein includes embodiments having only three layers in their construction: a substrate having an upper side and an opposed lower side, wherein the substrate comprises a microfluidic network having a plurality of sample lanes; a laminate attached to the lower side to seal the components of the microfluidic network, and provide an effective thermal transfer layer between a dedicated heating element and components in the microfluidic network; and a label, attached to the upper side that also covers and seals holes that are used in the manufacturing process to load microfluidic components such as valves. Thus, embodiments herein include microfluidic cartridges consisting of three layers, a substrate, a laminate, and a label, though other, additional, features other than layers may be consistent with such characterizations. Embodiments herein further include microfluidic cartridges consisting essentially of three layers, a substrate, a laminate, and a label, though other, additional, features other than layers may be consistent with such characterizations. Furthermore, embodiments herein still further include microfluidic cartridges comprising three layers, a substrate, a laminate, and a label.

A microfluidic network can include, in fluidic communication, one or more components selected from the group consisting of: gates, valves such as thermally actuated valves, channels, vents, and reaction chambers. Particular components of exemplary microfluidic networks are further described elsewhere herein. The cartridge typically processes the sample by increasing the concentration of a polynucleotide to be determined.

A sample lane is a set of elements, controllable independently of those in another sample lane, by which a sample can be accepted and analyzed, according to methods described herein. A lane comprises at least a sample inlet, and a microfluidic component, as further described herein in connection with a microfluidic cartridge. In some embodiments, each microfluidic network additionally comprises an overflow reservoir to contain extra liquid dispensed into the cartridge.

Figure 37:
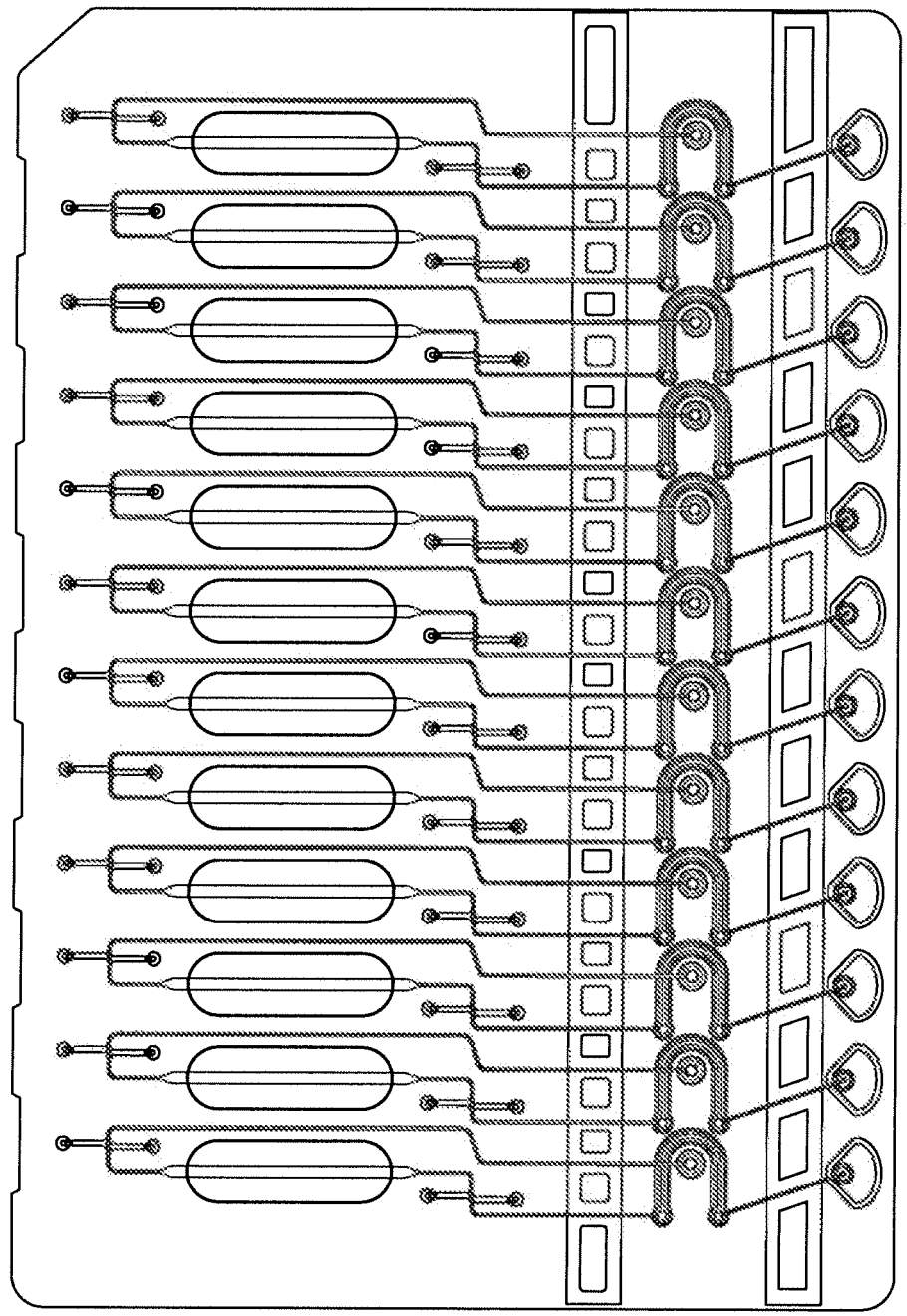
FIG. 37 shows a plan of microfluidic circuitry and inlets in an exemplary multi-lane cartridge.

In various embodiments, a lane can include a sample inlet port, a first thermally actuated valve, a second thermally actuated valve, a PCR reaction chamber, and channels connecting the inlet port to the PCR reaction chamber via the first valve, and channels connecting the PCR reaction chamber to an exit vent via the second valve. The sample inlet valve can be configured to accept a quantity of sample at a pressure differential compared to ambient pressure of between about 100 to 5000 Pa. It should be noted that the lower the loading pressure, the higher the fill time for a aliquot of reaction mix to fill the microfluidic network. Applying more pressure will reduce the fill time, but if the time for which the pressure is applied is not determined correctly, the sample could be blown out through the microfluidic cartridge (if an end hydrophobic vent is not present). Therefore the time for which the pressure is applied should be properly determined, such as by methods available to one of ordinary skill in the art, to prevent underfill or overfill. In general, the fill time is inversely proportional to the viscosity of the solution. For example, FIG. 37 shows a microfluidic cartridge containing twelve independent sample lanes capable of independent (simultaneous or successive) processing of samples.

The microfluidic network in each lane is typically configured to carry out PCR on a PCR-ready sample, such as one containing nucleic acid (DNA or RNA) extracted from a raw biological sample using other aspects of the apparatus as further described herein. A PCR-ready sample is thus typically a mixture comprising the PCR reagent(s) and the neutralized polynucleotide sample, suitable for subjecting to thermal cycling conditions that create PCR amplicons from the neutralized polynucleotide sample. For example, a PCR-ready sample can include a PCR reagent mixture comprising a polymerase enzyme, a positive control plasmid, a fluorogenic hybridization probe selective for at least a portion of the plasmid and a plurality of nucleotides, and at least one probe that is selective for a polynucleotide sequence.

Typically, the microfluidic network is configured so that the time required for a microdroplet of sample to pass from the inlet to the second valve is less than 50% of the time required for the sample to travel up to the exit vent. Typically, the microfluidic network is designed to have an increased flow resistance downstream of the two valves without increasing the total volume of the microfluidic network in comparison to the amount required to fill from the first valve to the end vent of the network.

Figure 38A:
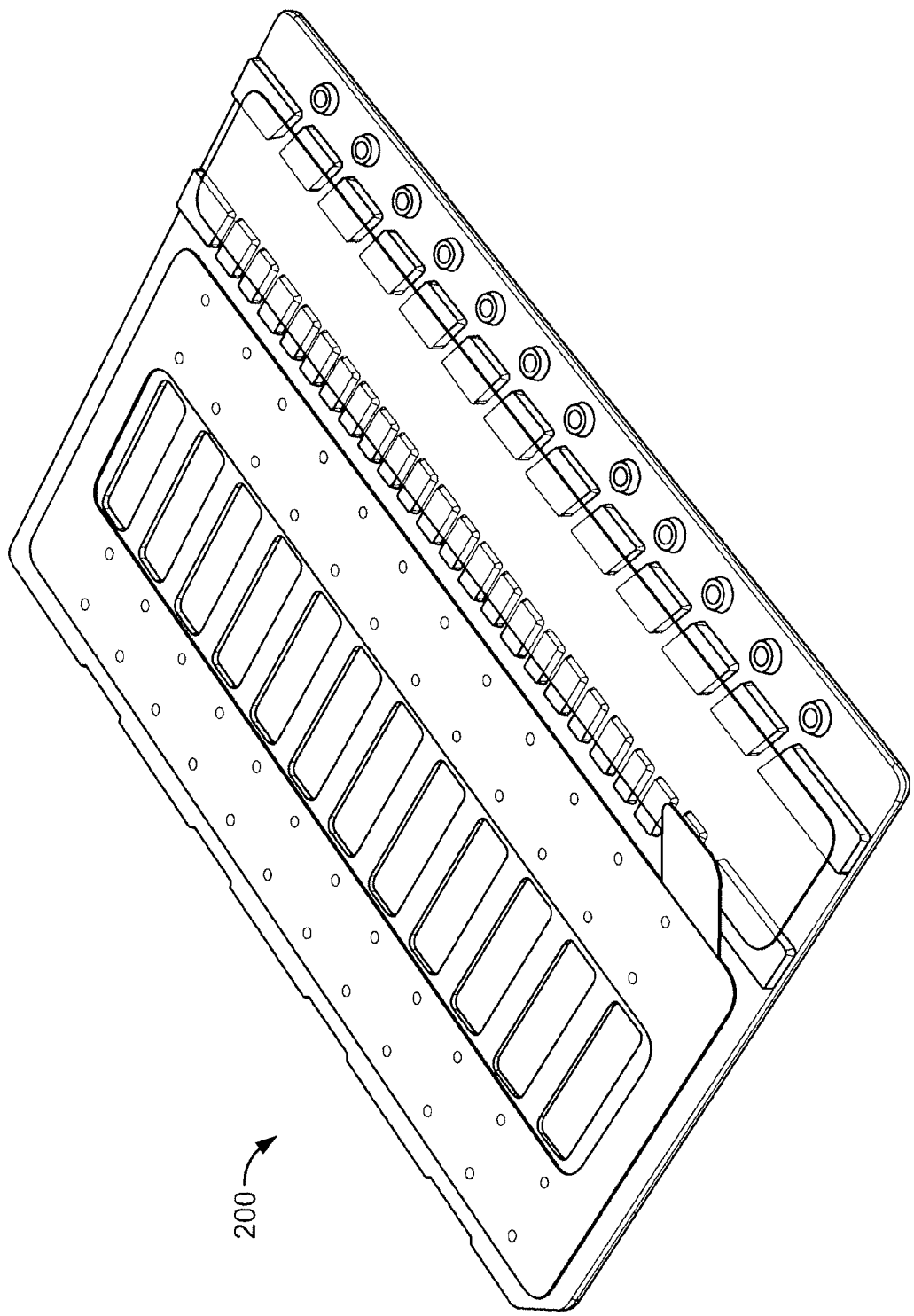
FIG. 38A shows an exemplary multi-lane cartridge.

FIG. 38A shows a perspective view of a portion of an exemplary microfluidic cartridge 200 according to the present technology. The cartridge may be referred to as a multi-lane PCR cartridge with dedicated pipette inlets 202. Shown in FIG. 38A are various representative components of cartridge 200. For example, sample inlet 202 is configured to accept a syringe, a pipette, or a PCR tube containing a PCR ready sample. More than one inlet 202 is shown, wherein one inlet operates in conjunction with a single lane. Various components of microfluidic circuitry in each lane are also visible. For example, microvalves 204, and 206, and vents 208, are parts of microfluidic circuitry in a given lane. Also shown is an ultrafast PCR reactor 210, which, as further described herein, is a microfluidic channel that is long enough to permit PCR to occur in a sample. Above PCR reactor 210 is a window 212 that permits optical detection, such as detection of fluorescence from a fluorescent substance, such as a fluorogenic hybridization probe, in PCR reactor 210 when a detector is situated above window 212.

A multi-lane cartridge is configured to accept a number of samples, in particular embodiments 12 samples, wherein the samples include at least a first sample and a second sample, wherein the first sample and the second sample each contain one or more polynucleotides in a form suitable for amplification. The polynucleotides in question may be the same as, or different from one another, in different lanes of a cartridge. The multi-sample cartridge comprises at least a first microfluidic network and a second microfluidic network, adjacent to one another, wherein each of the first microfluidic network and the second microfluidic network is as elsewhere described herein, and wherein the first microfluidic network accepts the first sample, and wherein the second microfluidic network accepts the second sample.

The sample inlets of adjacent lanes are reasonably spaced apart from one another to prevent any contamination of one sample inlet from another sample when a user introduces a sample into any one cartridge. In some embodiments, the sample inlets are configured so as to prevent subsequent inadvertent introduction of sample into a given lane after a sample has already been introduced into that lane.

In some embodiments, the multi-sample cartridge has a size substantially the same as that of a 96-well plate as is customarily used in the art. Advantageously, then, the cartridge may be used with plate handlers used elsewhere in the art. Still more preferably, however, the multi-sample cartridge is designed so that a spacing between the centroids of sample inlets is 9 mm, which is an industry-recognized standard. This means that, in certain embodiments the center-to-center distance between inlet holes in the cartridge that accept samples from PCR tubes, as further described herein, is 9 mm. The inlet holes are manufactured frusto-conical in shape with an appropriate conical angle so that industry-standard pipette tips (2 µl, 20 µl, 200 µl, volumes, etc.) fit snugly, entering from the widest point of the inlet. Thus, in certain embodiments, an inlet comprises an inverted frustoconical structure of at least 1 mm height, and having a diameter at its widest point that accepts entry of a pipette tip, of from 1-5 mm. The apparatus herein may be adapted to suit other, later-arising, industry standards for pipette tips not otherwise described herein. Typically the volume of sample accepted via an inlet into a microfluidic network in a sample lane is from 1-20 µl, and may be from 3-5 µl. The inlet hole can be designed to fit a pipette tip snugly and to create a good seal around the pipette tip, within the cone of the inlet hole. However, the cone is designed such that the sealing is reversible because it is undesirable if the seal is so tight that the cartridge can be pulled away from its tray, or location in the receiving bay, when the pipette tips are lifted after the dispensing operations.

FIG. 37 shows a plan view of an exemplary microfluidic cartridge having 12 lanes. The inlet ports have a 6 mm spacing, so that, when used in conjunction with an automated sample loader having 4 heads, spaced equidistantly at 9 mm apart, the inlets can be loaded in three batches of 4 inlets: e.g., inlets 1, 4, 7, and 10 together, followed by 2, 5, 8, and 11, then finally 3, 6, 9, and 12, wherein the 12 inlets are numbered consecutively from one side of the cartridge to the other.

Figure 38B:
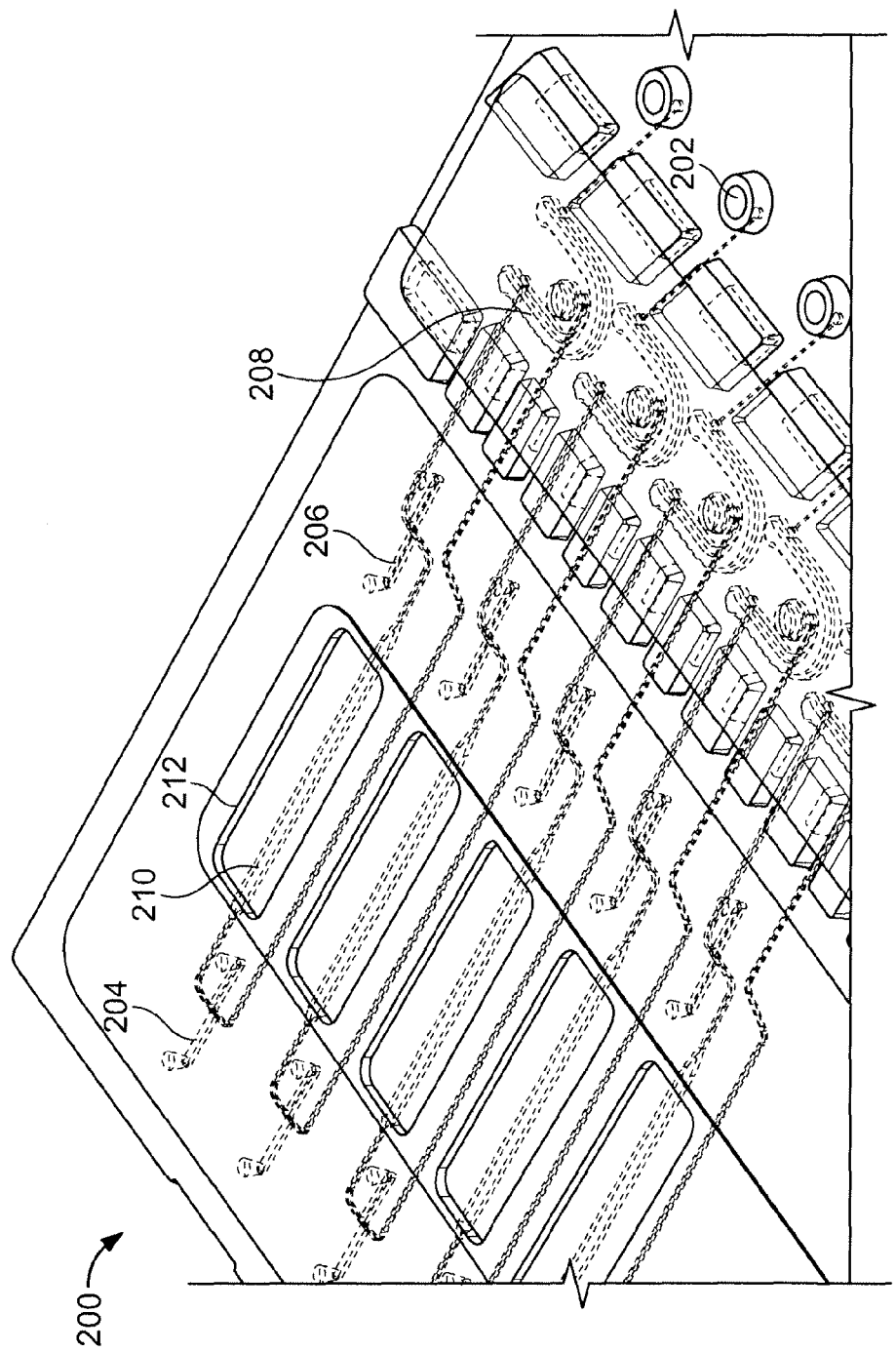
FIG. 38B shows a portion of an exemplary multi-lane cartridge.
Figure 39A:
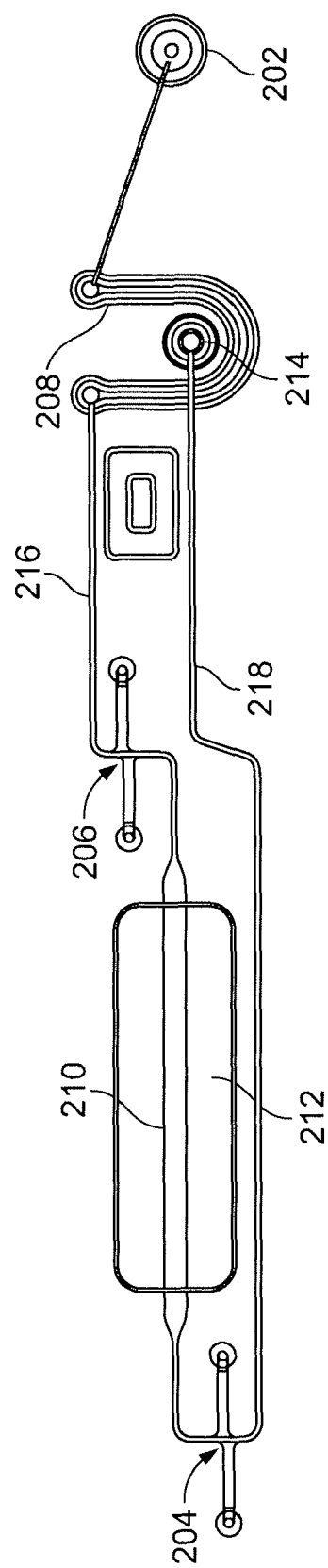
FIGS. 39A, 39B show an exemplary microfluidic network in a lane of a multi-lane cartridge.
Figure 39B:
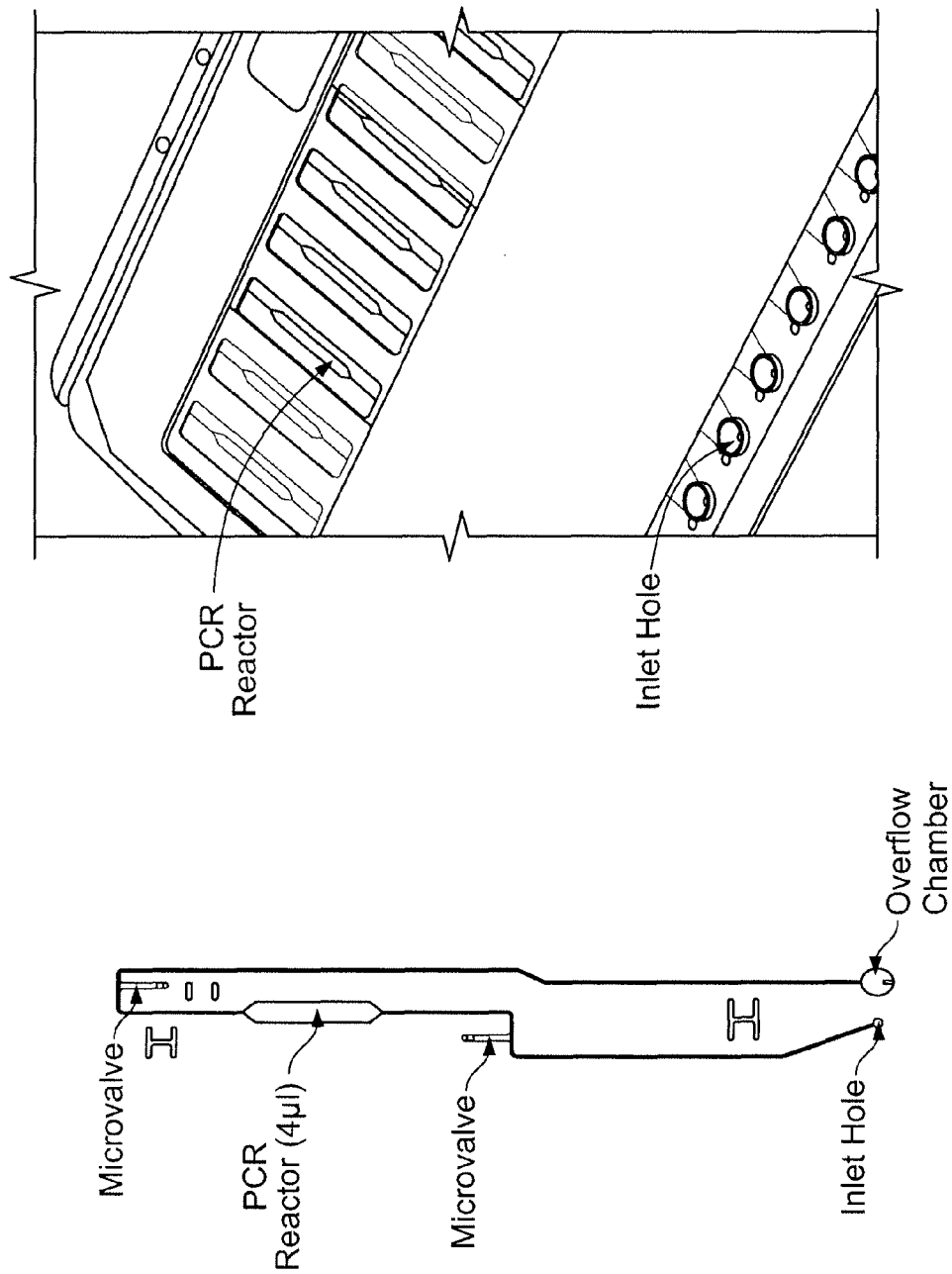

FIG. 39A shows a plan view of a representative microfluidic circuit found in one lane of a multi-lane cartridge such as shown in FIGS. 38A and 38B. FIG. 39B shows another plan view (left panel) of another representative microfluidic circuit found in one lane of a multi-lane cartridge such as shown in FIG. 36, and shows how the circuit is visible through the cartridge construction (right panel). Other configurations of microfluidic network would be consistent with the function of the cartridges and apparatus described herein. In sequence, sample is introduced through liquid inlet 202, and optionally flows into a bubble removal vent channel 208 (which permits adventitious air bubbles introduced into the sample during entry, to escape), and continues along a channel 216. Typically, when using a robotic dispenser of liquid sample, the volume is dispensed accurately enough that formation of bubbles is not a significant problem, and the presence of vent channel 208 is not necessary.

Throughout the operation of cartridge 200 the fluid is manipulated as a microdroplet (not shown in FIGS. 39A,B). Valves 204 and 206 are shown in FIG. 39A as double-valves, having a source of thermally responsive material (also referred to as a temperature responsive substance) on either side of the channel where they are situated. However, valves 204 and 206 may either or both be single valves that have a source of thermally responsive material on only one side of the respective channels. Valves 204 and 206 are initially open, so that a microdroplet of sample-containing fluid can be pumped into PCR reactor 210 from inlet hole 202. Upon initiating of processing, the detector present on top of the PCR reactor checks for the presence of liquid in the PCR reactor, and then closes valves 204 and 206 to isolate the PCR reaction mix from the channels on either side.

The PCR reactor 210 is a microfluidic channel that is heated through a series of cycles to carry out amplification of nucleotides in the sample, as further described herein. Typically the PCR reactor has a volume of 3-5 µl, in particular, 4 µl. The inside walls of the channel in the PCR reactor are made very smooth and polished to a shiny finish (for example, using a polish selected from SPI A1, SPI A2, SPI A3, SPI b1, or SPI B2) during manufacture. This is in order to minimize any microscopic air trapping in the surface of the PCR reactor, which would causing bubbling during the thermocycling steps. The presence of bubbles especially in the detection region of the PCR reactor might cause a false reading for the PCR reaction. Furthermore, the PCR reactor 210 is made shallow such that the temperature gradient across the depth of the channel is minimized. The region of the cartridge 212 above PCR reactor 210 permits a detector to monitor progress of the reaction and also to detect fluorescence from a probe that binds to a quantity of amplified nucleotide. The region 212 is made of thinner material than the rest of the cartridge so as to permit the PCR reactor to be more responsive to a heating cycle (for example, to rapidly heat and cool between temperatures appropriate for denaturing and annealing steps), and so as to reduce glare, autofluorescence, and undue absorption of fluorescence. Both valves 204 and 206 are closed prior to thermocycling to prevent any evaporation of liquid, bubble generation, or movement of fluid from the PCR reactor.

End vent 214 prevents a user from introducing any excess amount of liquid into the microfluidic cartridge, as well as playing a role of containing any sample from spilling over to unintended parts of the cartridge. A user may input sample volumes as small as an amount to fill from the bubble removal vent to the middle of the PCR reactor, or up to valve 204 or beyond valve 204. The use of microvalves prevents both loss of liquid or vapor thereby enabling even a partially filled reactor to successfully complete a PCR thermocycling reaction. The application of pressure (such as ~1 psi) to contact the cartridge to the heater of the instrument assists in achieving better thermal contact between the heater and the heat-receivable parts of the cartridge, and also prevents the bottom laminate structure from expanding, as would happen if the PCR channel was partially filled with liquid and the entrapped air would be thermally expanded during thermocycling.

In various embodiments, the microfluidic network can optionally include at least one hydrophobic vent additional to the end vent.

After PCR has been carried out on a sample, and presence or absence of a polynucleotide of interest has been determined, it is preferred that the amplified sample remains on the cartridge and that the cartridge is either used again (if one or more lanes remain open), or disposed of. Should a user wish to run a post amplification analysis, such as gel electrophoresis, the user may pierce a hole through the laminate of the cartridge, and recover an amount—typically about 1.5 microliter—of PCR product. The user may also place the individual PCR lane on a special narrow heated plate, maintained at a temperature to melt the wax in the valve, and then aspirate the reacted sample from the inlet hole of that PCR lane.

In various embodiments, the microfluidic network can optionally include at least one reservoir configured to contain waste.

In various embodiments, the microfluidic cartridge can further include a label, such as a computer-readable or scannable label. For example, the label can be a bar code, a radio frequency tag, or one or more computer-readable, or optically scannable, characters. The label can be positioned such that it can be read by a sample identification verifier as further described herein.

In various embodiments, during transport and storage, the microfluidic cartridge can be further surrounded by a sealed pouch. The microfluidic cartridge can be sealed in the pouch with an inert gas. The microfluidic cartridge can be disposable.

Microfluidic cartridge 200 can be fabricated as desired. Typically, the microfluidic cartridge layer includes a layer of polypropylene or other plastic label with pressure sensitive adhesive (typically between about 50 and 150 microns thick) configured to seal the wax loading holes of the valves, trap air used for valve actuation, and serve as a location for operator markings. This layer can be in two separate pieces, though it would be understood by one of ordinary skill in the art that in many embodiments a single piece layer would be appropriate.

The microfluidic substrate layer, is typically injection molded out of a plastic, preferably a zeonor plastic (cyclic olefin polymer), having a PCR channel and valve channels on a first side, and vent channels and various inlet holes, including wax loading holes and liquid inlet holes, on a second side (disposed toward the label). Typically, all of the microfluidic networks together, including the PCR reactors, the inlet holes and the valves for isolating the PCR reaction chambers, are defined in a single substrate. The substrate is made of a material that confers rigidity on the substrate and cartridge, and is impervious to air or liquid, so that entry or exit of air or liquid during operation of the cartridge is only possible through the inlet or the vent.

Channels of a microfluidic network in a lane of cartridge 200 typically have at least one sub-millimeter cross-sectional dimension. For example, channels of such a network may have a width and/or a depth of about 1 mm or less (e.g., about 750 microns or less, about 500 microns, or less, about 250 microns or less).

The cartridge can further include a heat sealable laminate layer 222 (typically between about 100 and about 125 microns thick) attached to the bottom surface of the microfluidic substrate using, for example, heat bonding, pressure bonding, or a combination thereof. The laminate layer 222 may also be made from a material that has an adhesive coating on one side only, that side being the side that contacts the underside of the microfluidic substrate. This layer may be made from a single coated tape having a layer of Adhesive 420, made by 3M. Exemplary tapes include single-sided variants of double sided tapes having product nos. 9783, 9795, and 9795B, and available from 3M. Other acceptable layers may include tapes based on micro-capsule based adhesives.

In use, cartridge 200 is typically thermally associated with an array of heat sources configured to operate the components (e.g., valves, gates, and processing region 210) of the device. In some embodiments, the heat sources are operated by an operating system, which operates the device during use. The operating system includes a processor (e.g., a computer) configured to actuate the heat sources according to a desired protocol. Processors configured to operate microfluidic devices are described in, e.g., U.S. application Ser. No. 09/819,105, filed Mar. 28, 2001, which application is incorporated herein by reference.

Table 1 outlines volumes, pumping pressures, and operation times associated with various components of a microfluidic cartridge.

TABLE 1

| Operation | Pumping Pressure | Displacement Volume | Time of Operation |
|---|---|---|---|
| Mixing displacements | ~2 psi | 10-25 µl | 1-2 minutes |
| Moving valve wax plugs | ~1-2 psi | <1 µl | 5-15 seconds |

| Operation | Pump Used | Pump Design | Pump Actuation |
|---|---|---|---|
| Mixing displacements | Expancel Pump | Same as above | Same as above |
| Moving valve wax plugs | Thermopneumatic pump | 1 µl of trapped air | Heat trapped air to ~70-90 C. |

In some embodiments, a microfluidic cartridge further comprises a registration member that ensures that the cartridge is received by a complementary diagnostic apparatus in a single orientation, for example, in a receiving bay of the apparatus. The registration member may be a simple cut-out from an edge or a corner of the cartridge (as shown in FIG. 38A), or may be a series of notches, or some other configuration of shapes that require a unique orientation of placement in the apparatus.

In some embodiments, the microfluidic cartridge comprises two or more positioning elements, or fiducials, for use when filling the valves with thermally responsive material. The positioning elements may be located on the substrate, typically the upper face thereof.

The microfluidic cartridges may also be stackable, such as for easy storage or transport, or may be configured to be received by a loading device, as further described herein, that holds a plurality of cartridges in close proximity to one another, but without being in contact. In order to accomplish either or both of these characteristics, the substrate may comprise two ridges, one of each situated along each of two opposite edges of the cartridge, the ridges disposed on the upper side of the substrate. Thus, where a cartridge has a rectangular aspect (ignoring any registration member or mechanical key), the two ridges may be situated along the long side, or along the short side, of the cartridge.

Valves

Figure 40A:
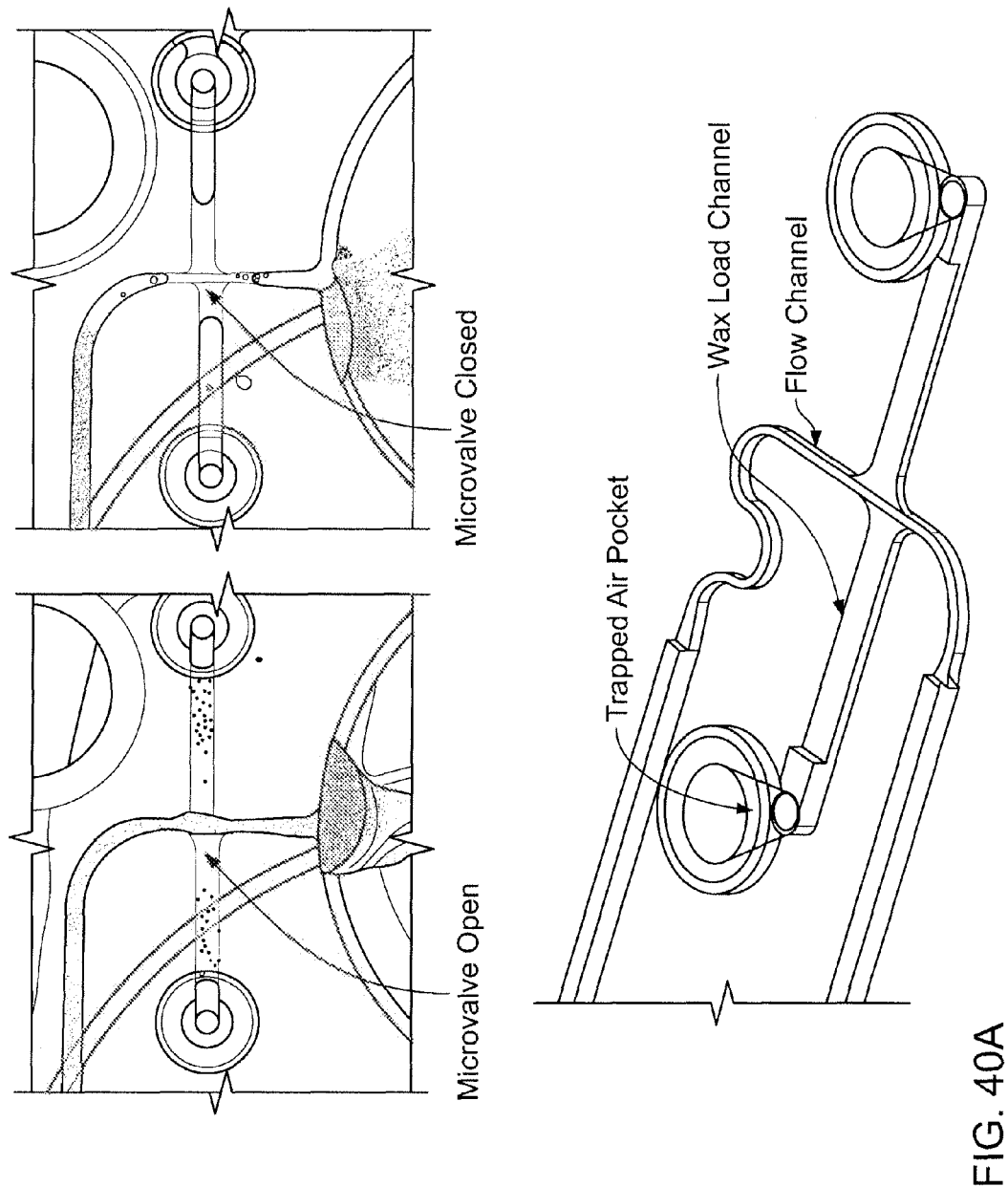
FIGS. 40A-40C show diagrams of exemplary microfluidic valves.

A valve is a microfluidic component that has a normally open state allowing material to pass along a channel from a position on one side of the valve (e.g., upstream of the valve) to a position on the other side of the valve (e.g., downstream of the valve). An exemplary double valve is shown in FIG. 40A. A double valve has two channels, one on either side of the channel whose flow it regulates, whereas a single valve has just one channel, disposed on one side of the channel whose flow it regulates.

Upon actuation, e.g., by application of heat, the valve transitions to a closed state that prevents material, such as a microdroplet of PCR-ready sample, from passing along the channel from one side of the valve to the other. For example, a valve includes one or more masses of a thermally responsive substance (TRS) that is relatively immobile at a first temperature and more mobile at a second temperature. A mass of TRS can be an essentially solid mass or an agglomeration of smaller particles that cooperate to obstruct the passage upon actuation. Examples of TRS's include a eutectic alloy (e.g., a solder), wax (e.g., an olefin), polymers, plastics, and combinations thereof. The first and second temperatures are insufficiently high to damage materials, such as polymer layers of a microfluidic cartridge in which the valve is situated. Generally, the second temperature is less than about 90° C. and the first temperature is less than the second temperature (e.g., about 70° C. or less).

For each mass associated with a valve, a chamber is in gaseous communication with the mass. Upon heating gas (e.g., air) in the chamber(s) and heating the one or more masses of TRS to the second temperature, gas pressure within a chamber moves the corresponding mass into the channel obstructing material from passing therealong. Other valves of the network have the same structure and operate in the same fashion as the valves described herein.

In order to make the valve sealing very robust and reliable, the flow channel at the valve junction is made narrow (150 µm wide and 150 µm deep or narrower) and the constricted channel is made at least 0.5 or 1 mm long such that the wax seals up a long narrow channel thereby reducing any leakage through the walls of the channel. In the case of a bad seal, there is leakage of fluid around the walls of the channel, past the wax. So the flow channel is narrowed as much as possible, and made longer, e.g., as long as ~1 mm. The valve operates by heating air in the wax-loading port, which forces the wax forwards in a manner so that it does not come back to its original position. In this way, both air and wax are heated during operation of the valve.

Figure 40B:
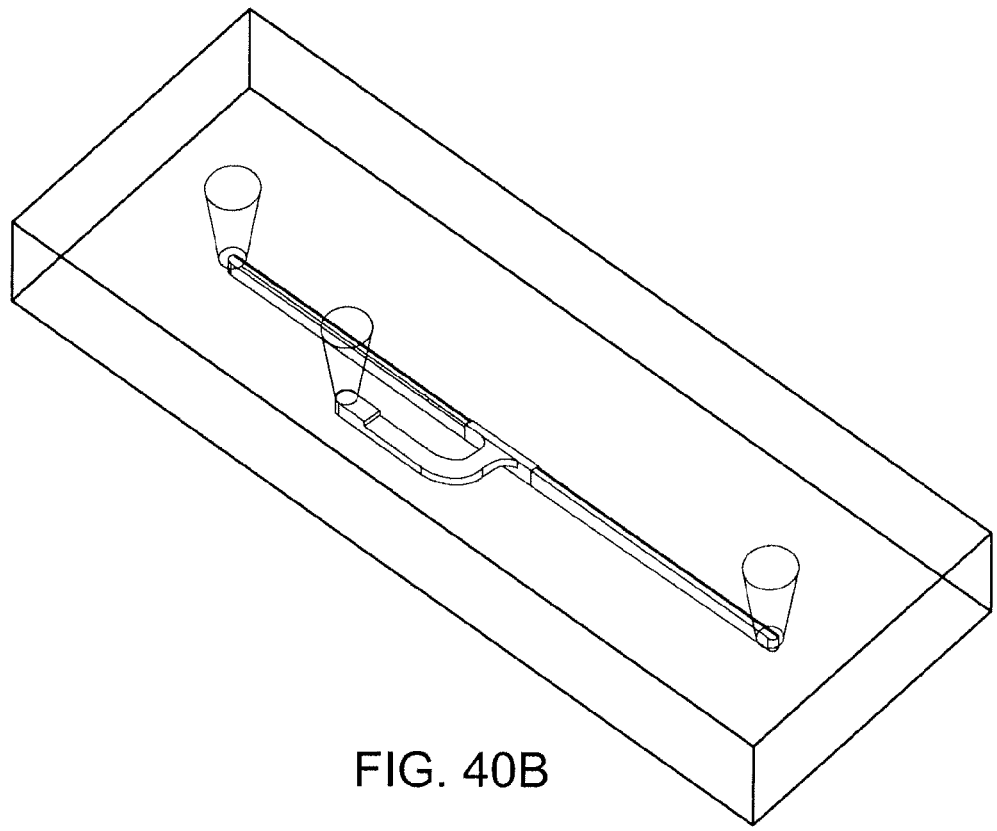

In various embodiments, the microfluidic network can include a bent valve as shown in FIG. 32B (as a single valve) to reduce the footprint of the valve on the cartridge and hence reduce cost per part for manufacturing highly dense microfluidic substrates. In the valve of FIG. 40B, the loading hole for TRS is in the center of the valve; the structures at either end are an inlet and an outlet and are shown for illustrative purposes only. Single valve shown.

Figure 40C:
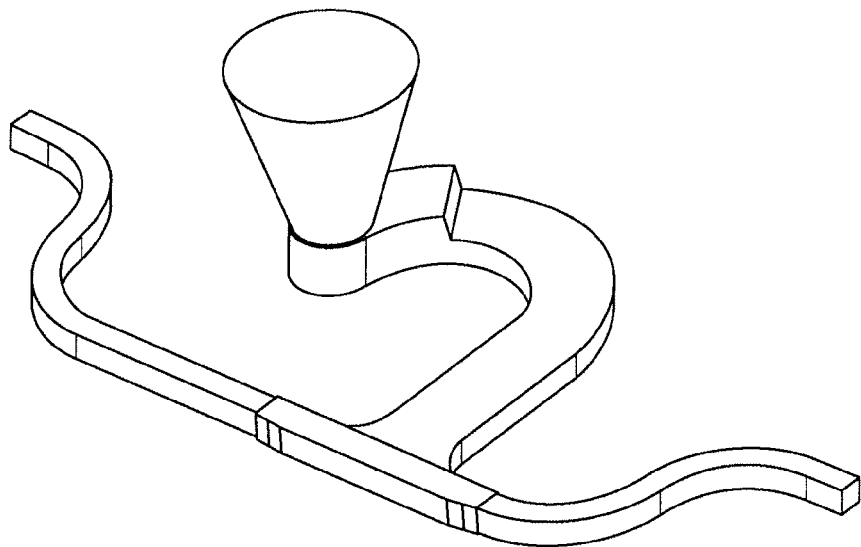

In various embodiments, the network can include a curved valve as shown in FIG. 40C, also as a single valve, in order to reduce the effective cross-section of the microvalve, enabling manufacture of cheaper dense microfluidic devices.

Vents

Figure 41:
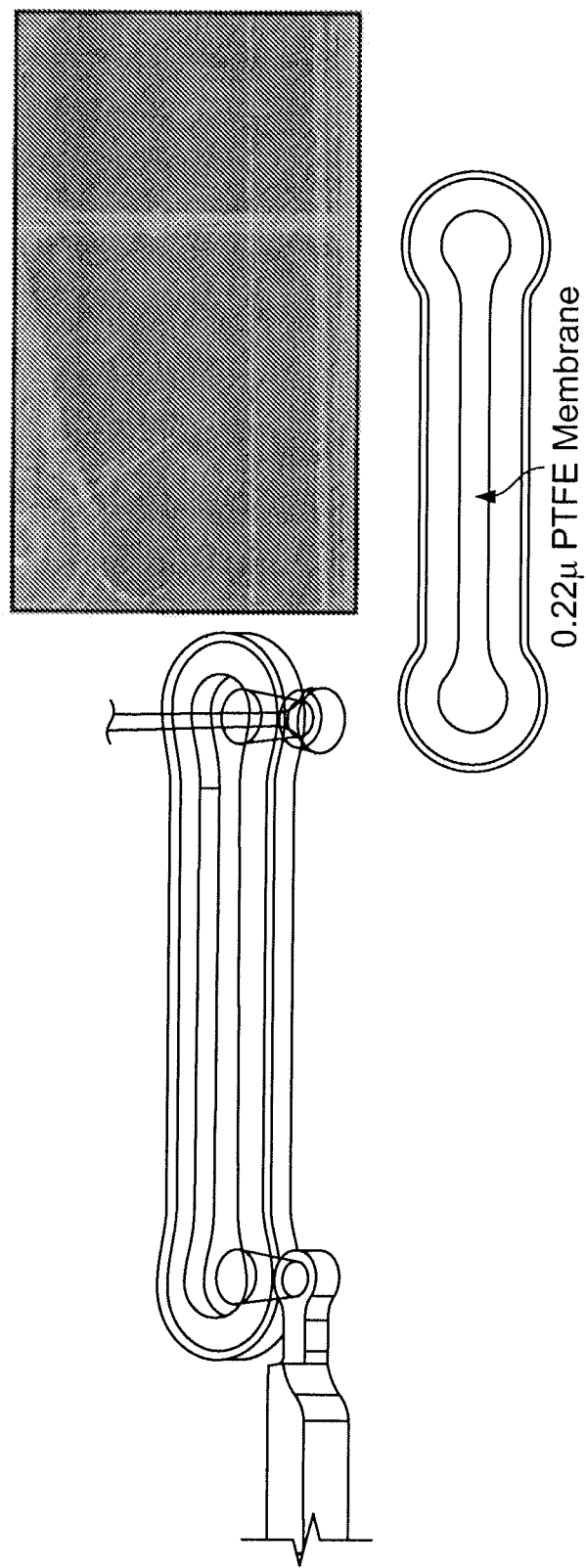
FIG. 41 shows a vent.

A hydrophobic vent (e.g., a vent in FIG. 41) is a structure that permits gas to exit a channel while limiting (e.g., preventing) liquid from exiting the channel. Typically, hydrophobic vents include a layer of porous hydrophobic material (e.g., a porous filter such as a porous hydrophobic membrane from Osmonics) that defines a wall of the channel. As discussed herein, hydrophobic vents can be used to position a microdroplet of sample at a desired location within a microfluidic network.

The hydrophobic vents of the cartridge are preferably constructed so that the amount of air that escapes through them is maximized while minimizing the volume of the channel below the vent surface. Accordingly, it is preferable that the vent is constructed so as to have a hydrophobic membrane of large surface area and a shallow cross section of the microchannel below the vent surface.

Bubble removal hydrophobic vents typically have a length of at least about 2.5 mm (e.g., at least about 5 mm, at least about 7.5 mm) along a channel. The length of the hydrophobic vent is typically at least about 5 times (e.g., at least about 10 times, at least about 20 times) larger than a depth of the channel within the hydrophobic vent. For example, in some embodiments, the channel depth within the hydrophobic vent is about 300 microns or less (e.g., about 250 microns or less, about 200 microns or less, about 150 microns or less). Bubble vents are optional in the microfluidic networks of the microfluidic cartridges described herein.

The depth of the channel within the hydrophobic vent is typically about 75% or less (e.g., about 65% or less, about 60% or less) of than the depth of the channel upstream and downstream of the hydrophobic vent. For example, in some embodiments the channel depth within the hydrophobic vent is about 150 microns and the channel depth upstream and downstream of the hydrophobic vent is about 250 microns.

A width of the channel within the hydrophobic vent is typically at least about 25% wider (e.g., at least about 50% wider) than a width of the channel upstream from the vent and downstream from the vent. For example, in an exemplary embodiment, the width of the channel within the hydrophobic vent is about 400 microns and the width of the channel upstream and downstream from the vent is about 250 microns.

Highly Multiplexed Embodiment

Embodiments of the apparatus and cartridge described herein may be constructed that have high-density microfluidic circuitry on a single cartridge that thereby permit processing of multiple samples in parallel, or in sequence, on a single cartridge. Preferred numbers of such multiple samples include 36, 40, 48, 50, 64, 72, 80, 96, and 100, but it would be understood that still other numbers are consistent with the apparatus and cartridge herein, where deemed convenient and practical.

Accordingly, different configurations of lanes, sample inlets, and associated heater networks are contemplated that can facilitate processing such numbers of samples on a single cartridge are within the scope of the instant disclosure. Similarly, alternative configurations of detectors for use in conjunction with such a highly multiplexed cartridge are also within the scope of the description herein.

Figure 43:
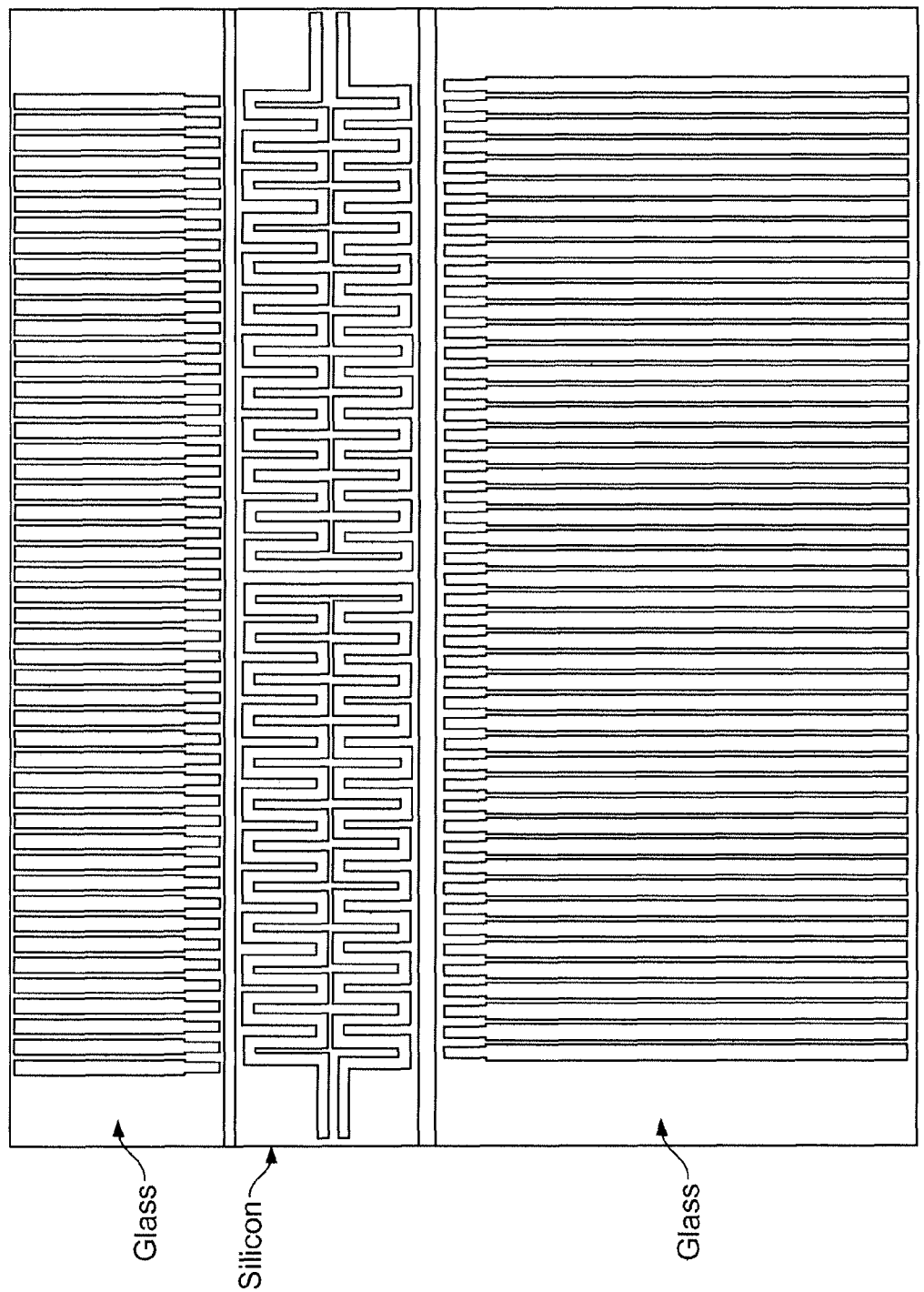
FIGS. 43-46 show various aspects of exemplary highly multiplexed microfluidic cartridges.

In an exemplary embodiment, a highly multiplexed cartridge has 48 PCR channels, and has independent control of each valve in the channel, with 2 banks of thermocycling protocol per channel, as shown in FIG. 43. In the embodiment in FIG. 43, the heaters are arranged in three arrays. Heaters in two separate glass regions only apply heat to valves in the microfluidic networks in each lane. Because of the low thermal conductivity of glass, the individual valves may be heated separately from one another. This permits samples to be loaded into the cartridge at different times, and passed to the PCR reaction chambers independently of one another. The PCR heaters are mounted on a silicon substrate—and are not readily heated individually, but thereby permit batch processing of PCR samples, where multiple samples from different lanes are amplified by the same set of heating/cooling cycles. It is preferable for the PCR heaters to be arranged in 2 banks (the heater arrays on the left and right are not in electrical communication with one another), thereby permitting a separate degree of sample control.

Figure 42:
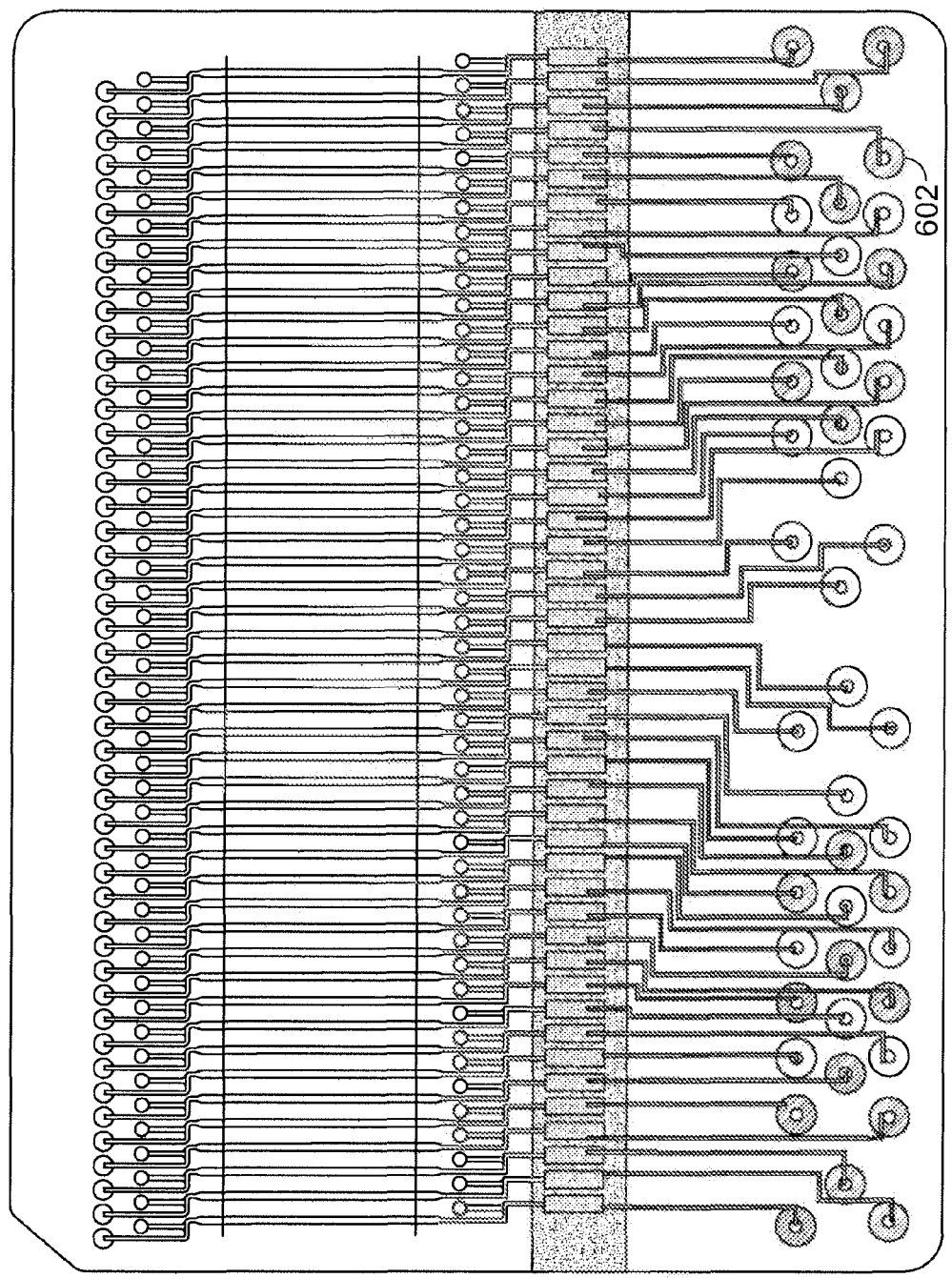
FIG. 42 shows an exemplary highly-multiplexed microfluidic cartridge.

FIG. 42 shows a representative cartridge, revealing an inlet configuration for a 48-sample cartridge. The inlet configuration is compatible with an automatic pipetting machine that has dispensing heads situated at a 9 mm spacing. For example, such a machine having 4 heads can load 4 inlets at once, in 12 discrete steps, for the cartridge of FIG. 42.

Figure 44:
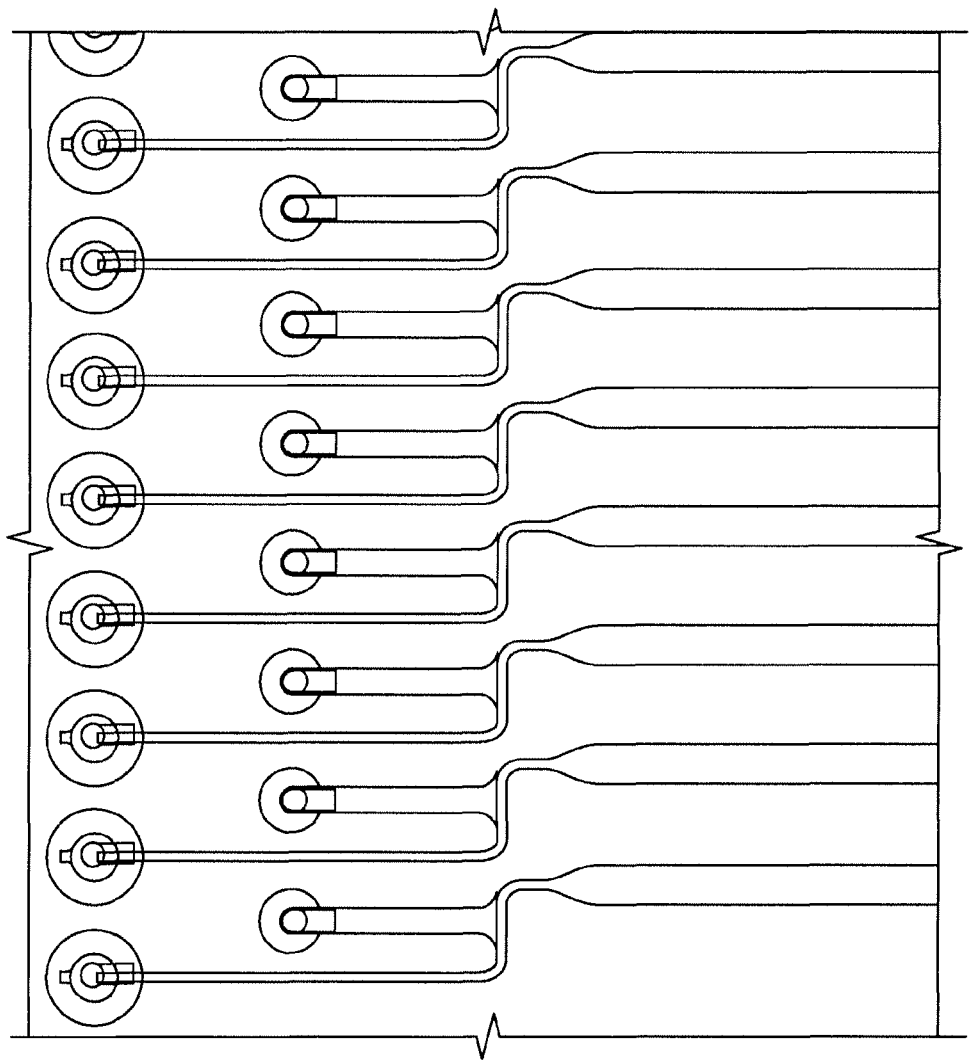

FIG. 44 shows, in close, up an exemplary spacing of valves and lanes in adjacent lanes of a multi-sample microfluidic cartridge.

Figure 45:
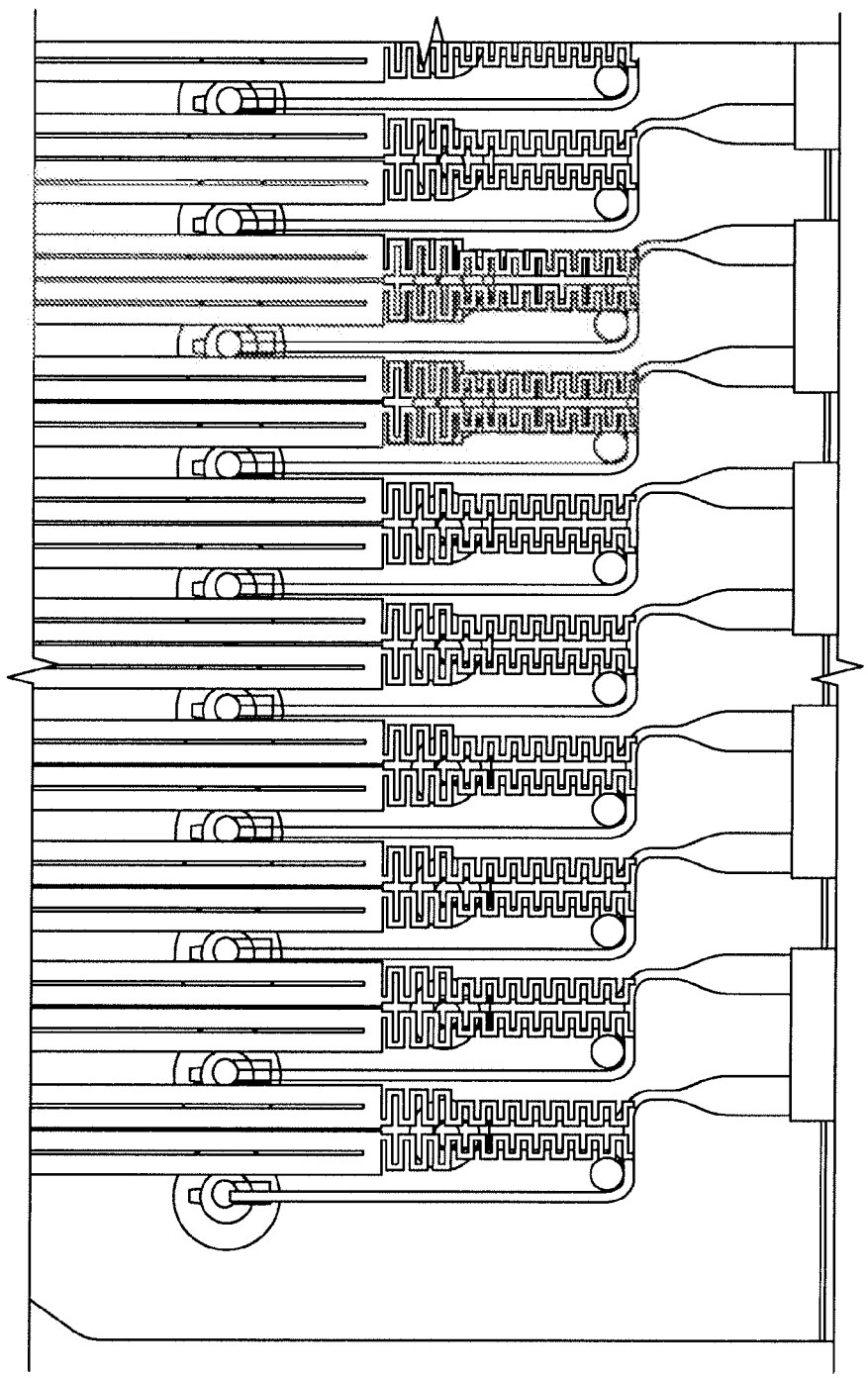
Figure 46:
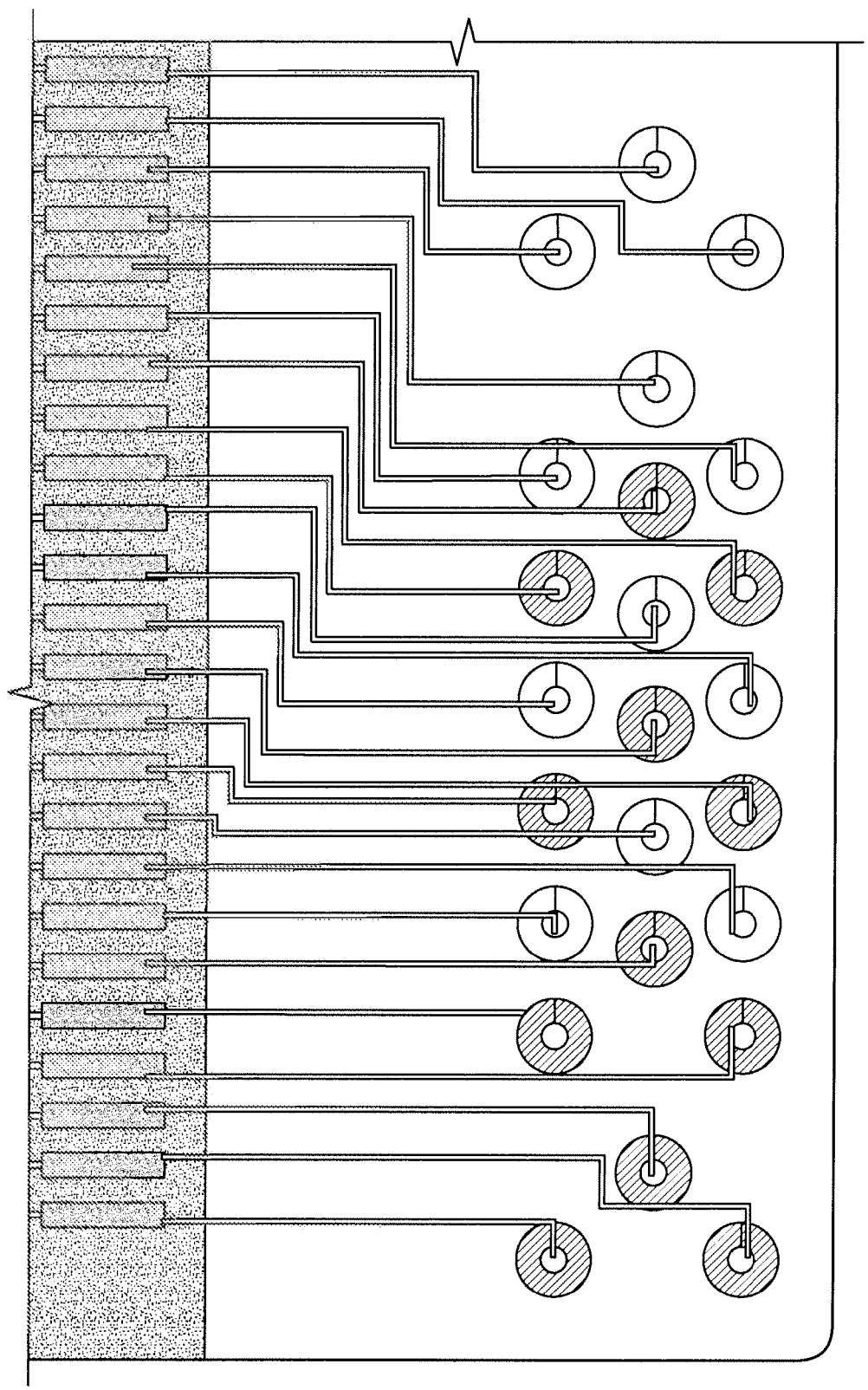

FIGS. 45 and 46 show close-ups of, respectively, heater arrays, and inlets, of the exemplary cartridge shown in FIG. 44.

Figure 47A:
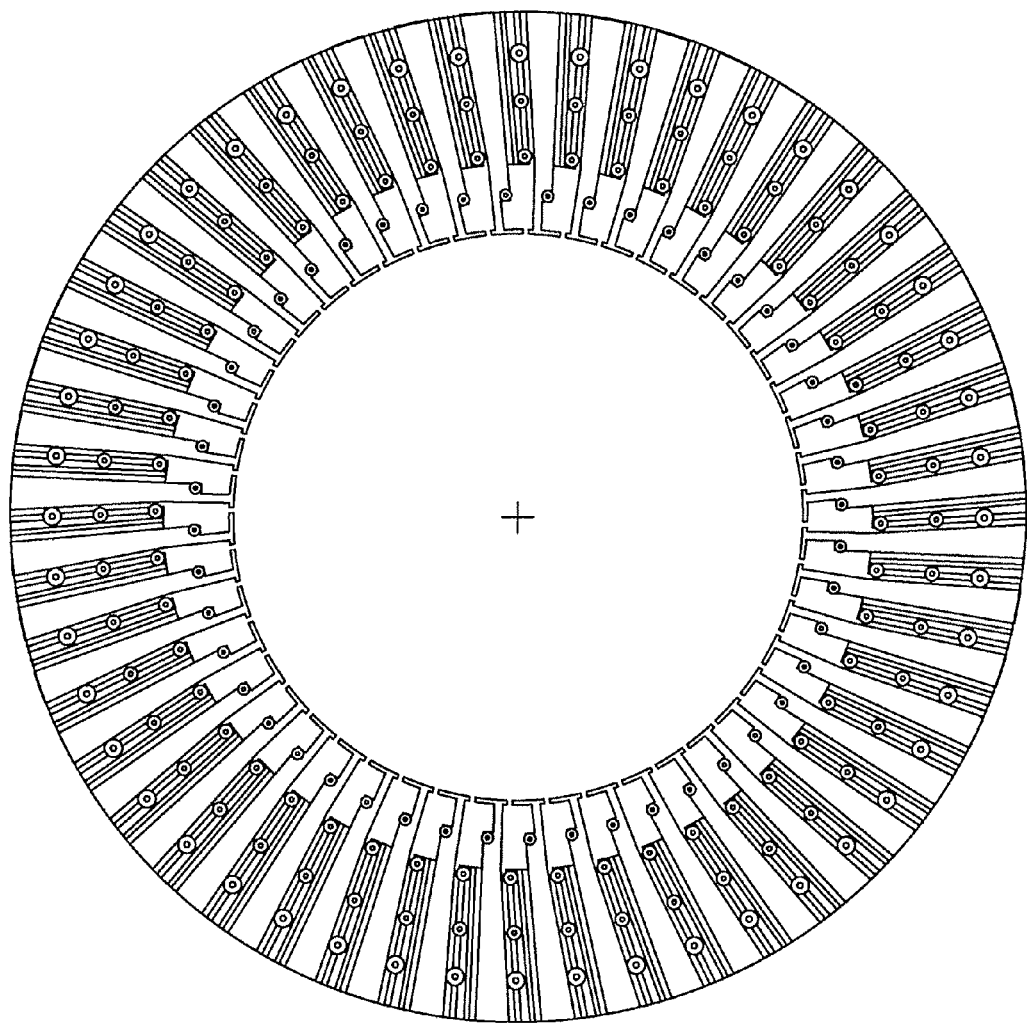
FIGS. 47A-C show various aspects of a radially configured highly multiplexed microfluidic cartridge.
Figure 47B:
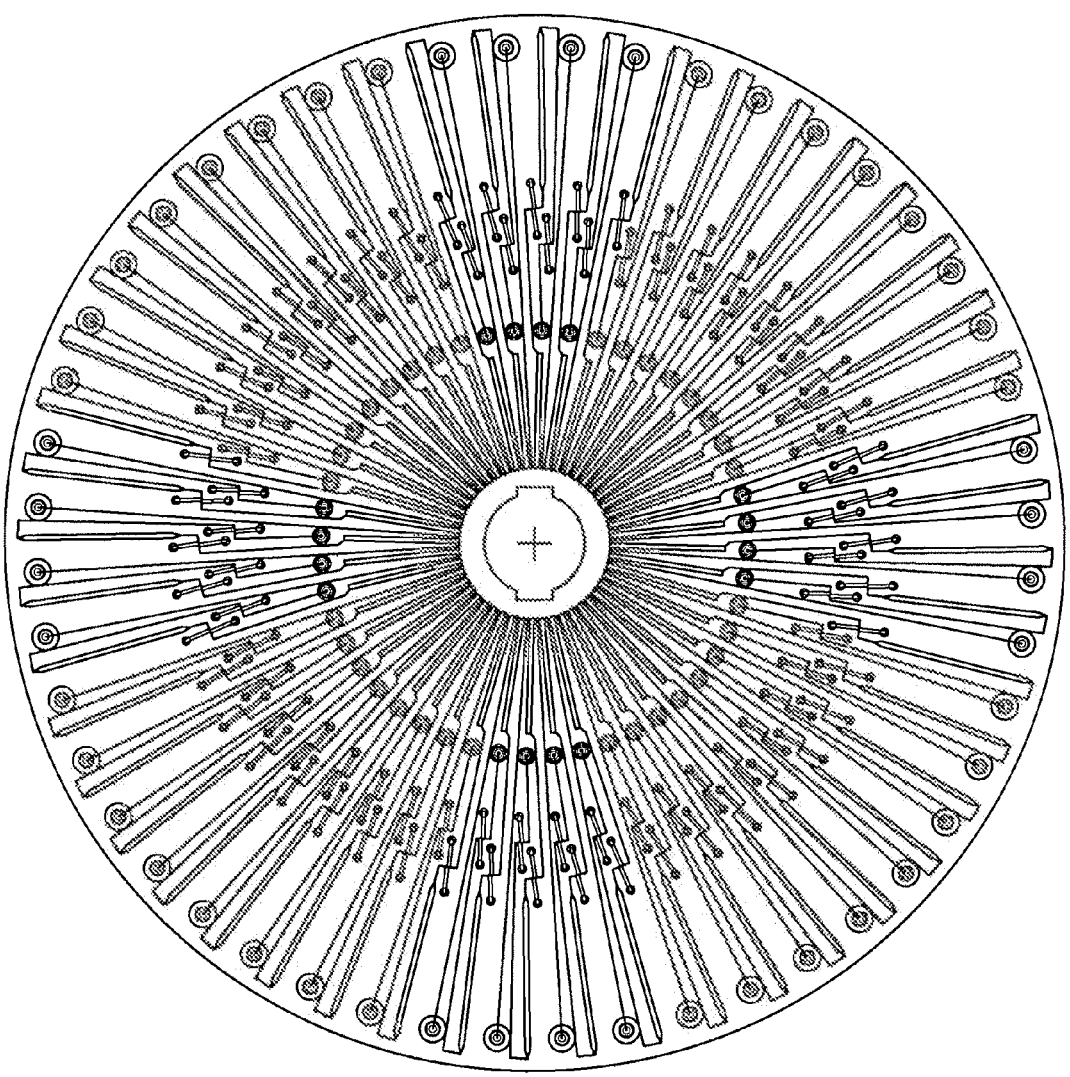
Figure 47C:
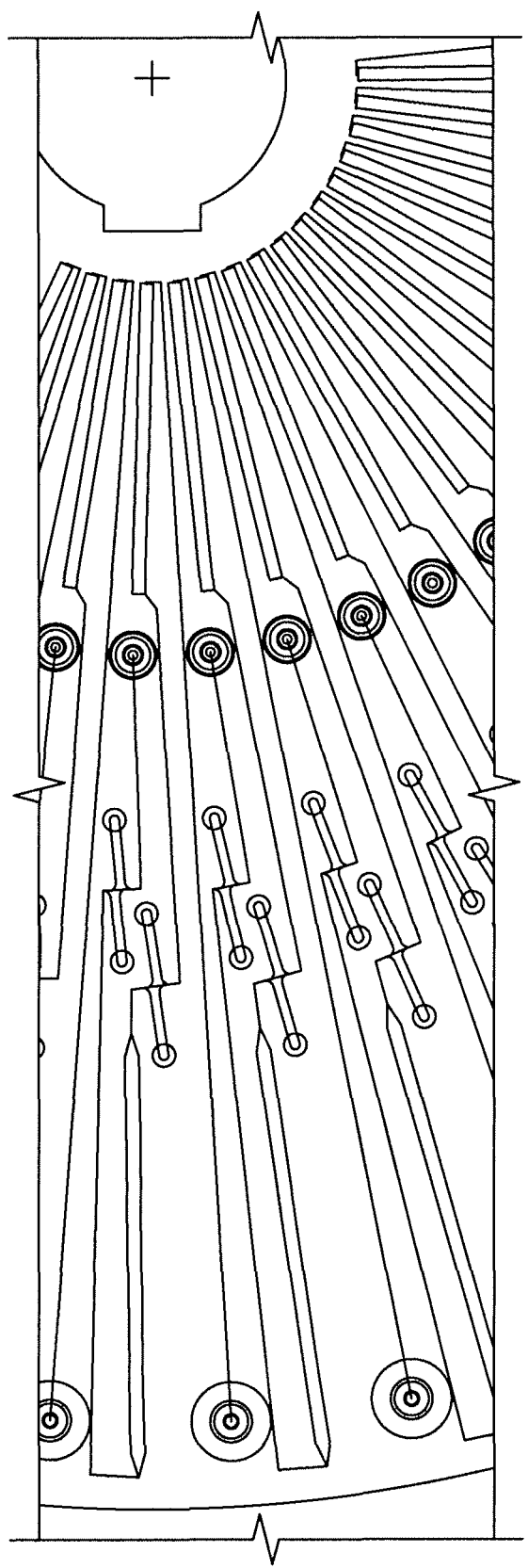

FIGS. 47A-47C show various views of an embodiment of a radially-configured highly-multiplexed cartridge, having a number of inlets, microfluidic lanes, and PCR reaction zones.

The various embodiments shown in FIGS. 42-47C are compatible with liquid dispensers, receiving bays, and detectors that are configured differently from the specific examples described herein.

In another preferred embodiment (not shown in the FIGS.), a cartridge and apparatus is configured so that the read-head does not cover the sample inlets, thereby permitting loading of separate samples while other samples are undergoing PCR thermocycling.

Heater Configurations to Ensure Uniform Heating of a Region

Another aspect of the apparatus described herein relates to a method and apparatus for uniformly controlling the heating of a region of a microfluidic network that includes but is not limited to one or more microfluidic components. In an exemplary embodiment, multiple heaters can be configured to simultaneously and uniformly heat a region, such as the PCR reaction zone, of the microfluidic cartridge.

In preferred embodiments, a microfluidic cartridge having a microfluidic network comprising one or more microfluidic components is brought into contact with a heat source, within a suitably configured apparatus. The heat source is configured so that particular heating elements are situated to heat specific components of the microfluidic network of the cartridge.

FIG. 48 shows a cross-sectional view of an exemplary microfluidic cartridge to show relative location of PCR channel in relation to the heaters when the cartridge is placed in the instrument. The view in FIG. 48 is also referred to as a sectional-isometric view of the cartridge lying over the heater wafer. A window 903 above the PCR channel in the cartridge is shown in perspective view. PCR channel 901 (for example, 150μ deep×700μ wide), is shown in an upper layer of the cartridge. A laminate layer 905 of the cartridge (for example, 125μ thick) is directly under the PCR channel 901. A further layer of thermal interface laminate 907 on the cartridge (for example, 125μ thick) lies directly under the laminate layer 905. Heaters are situated in a further layer 913 directly under the thermal interface laminate. The heaters are photolithographically defined and etched metal layers of gold (typically about 3,000 Å thick). Layers of 400 Å of TiW are deposited on top and bottom of the gold layer to serve as an adhesion layer. The substrate used is glass, fused silica or quartz wafer having a thickness of 0.4 mm, 0.5 mm or 0.7 mm or 1 mm. A thin electrically-insulative layer of 2 μm silicon oxide serves as an insulative layer on top of the metal layer. Additional thin electrically insulative layers such as 2-4 μm of Parylene may also be deposited on top of the Silicon oxide surface. Two long heaters 909 and 911, as further described herein, are also shown.

Figure 49A:
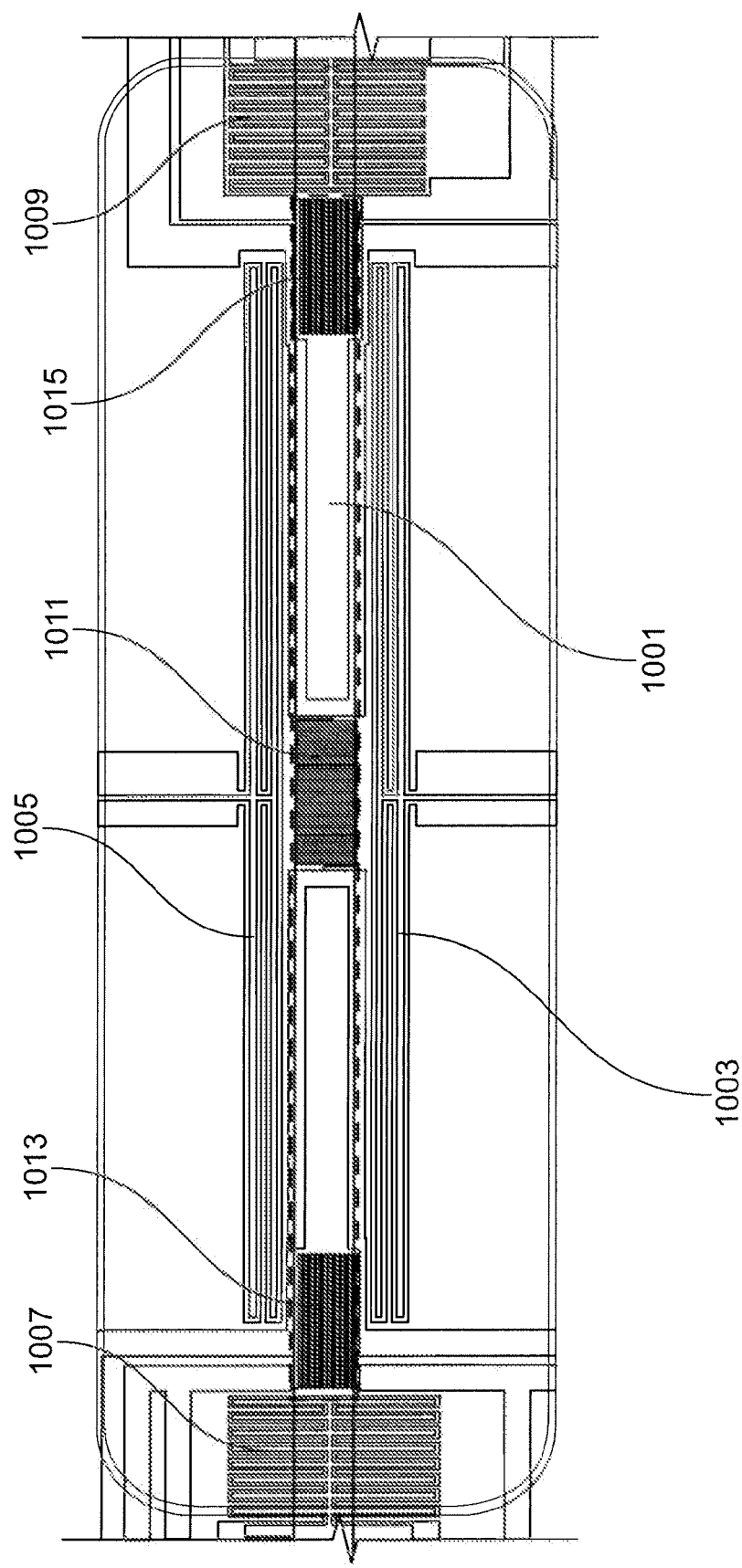
FIGS. 49A, 49B show a PCR reaction chamber and associated heaters.
Figure 49B:
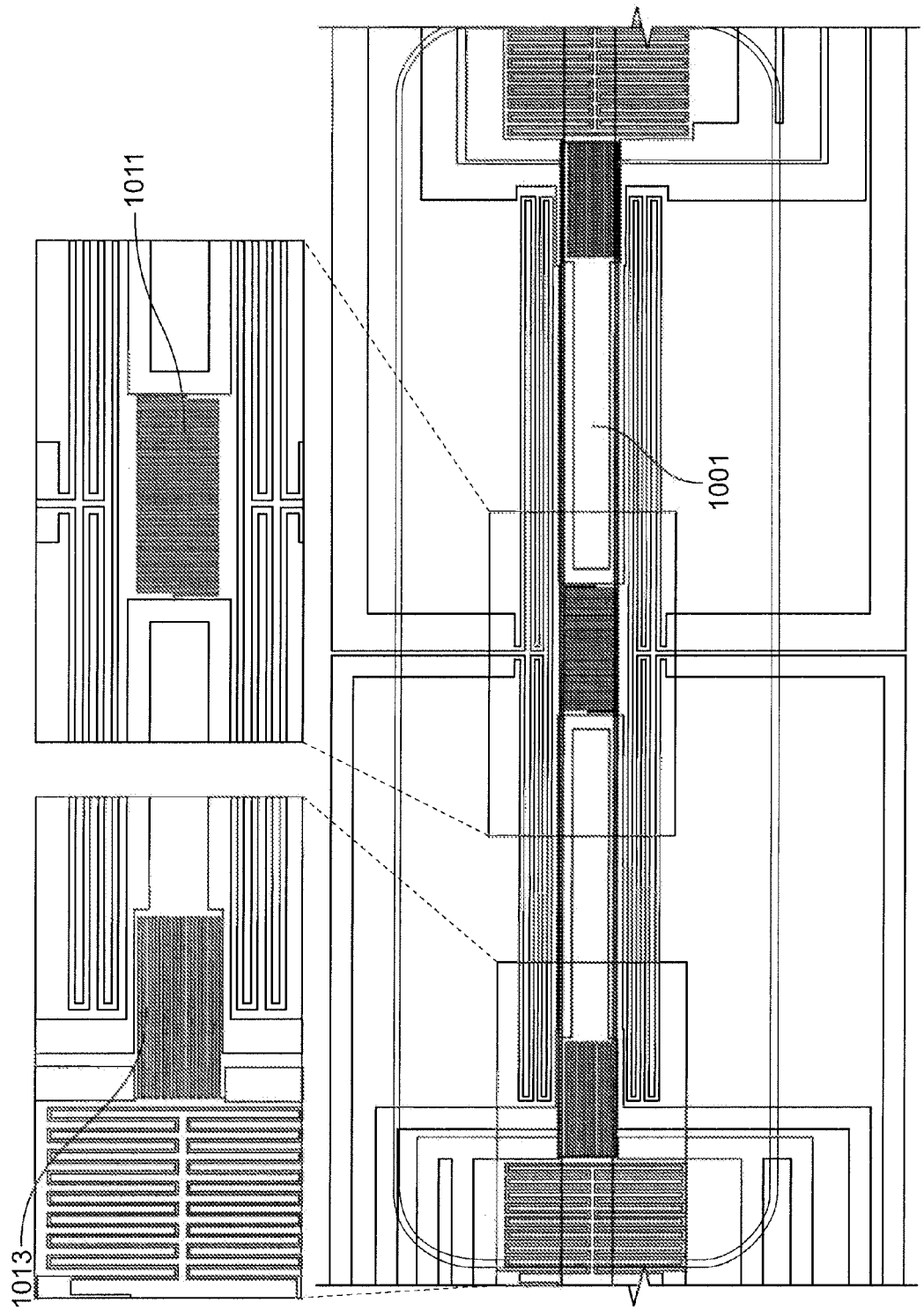

Referring to FIGS. 49A and 49B, the PCR reaction zone 1001, typically having a volume ~1.6 μl, is configured with a long side and a short side, each with an associated heating element. The apparatus therefore preferably includes four heaters disposed along the sides of, and configured to heat, the PCR reaction zone, as shown in the exemplary embodiment of FIG. 38A: long top heater 1005, long bottom heater 1003, short left heater 1007, and short right heater 1009. The small gap between long top heater 1005 and long bottom heater 1003 results in a negligible temperature gradient (less than 1° C. across the width of the PCR channel at any point along the length of the PCR reaction zone) and therefore an effectively uniform temperature throughout the PCR reaction zone. The heaters on the short edges of the PCR reactor provide heat to counteract the gradient created by the two long heaters from the center of the reactor to the edge of the reactor. It would be understood by one of ordinary skill in the art that still other configurations of one or more heater(s) situated about a PCR reaction zone are consistent with the methods and apparatus described herein. For example, a 'long' side of the reaction zone can be configured to be heated by two or more heaters. Specific orientations and configurations of heaters are used to create uniform zones of heating even on substrates having poor thermal conductivity because the poor thermal conductivity of glass, or quartz, or fused silica substrates is utilized to help in the independent operation of various microfluidic components such as valves and independent operation of the various PCR lanes.

In preferred embodiments, each heater has an associated temperature sensor. In the embodiment of FIG. 49A, a single temperature sensor 1011 is used for both long heaters. A temperature sensor 1013 for short left heater, and a temperature sensor 1015 for short right heater are also shown. The temperature sensor in the middle of the reactor is used to provide feedback and control the amount of power supplied to the two long heaters, whereas each of the short heaters has a dedicated temperature sensor placed adjacent to it in order to control it. As further described herein, temperature sensors are preferably configured to transmit information about temperature in their vicinity to the processor at such times as the heaters are not receiving current that causes them to heat. This can be achieved with appropriate control of current cycles.

In order to reduce the number of sensor or heater elements required to control a PCR heater, we may use the heaters to sense as well as heat, and thereby obviate the need to have a separate dedicated sensor for each heater. In another embodiment, each of the four heaters may be designed to have an appropriate wattage, and connect the four heaters in series or in parallel to reduce the number of electronically-controllable elements from 4 to just 1, thereby reducing the burden on the electronics.

FIG. 49B shows expanded views of heaters and temperature sensors used in conjunction with a PCR reaction zone of FIG. 49A. Temperature sensors 1001 and 1013 are designed to have a room temperature resistance of approximately 200-300 ohms. This value of resistance is determined by controlling the thickness of the metal layer deposited (e.g., a sandwich of 400 Å TiW/3000 Å Au/400 Å TiW), and etching the winding metal line to have a width of approximately 10-25 μm and 20-40 mm length. The use of metal in this layer gives it a temperature coefficient of resistivity of the order of 0.5-20° C./ohms, preferably in the range of 1.5-3° C./ohms. Measuring the resistance at higher temperatures will enable determination of the exact temperature of the location of these sensors.

The configuration for uniform heating, shown in FIG. 49A for a single PCR reaction zone, can be applied to a multi-lane PCR cartridge in which multiple independent PCR reactions occur.

Figure 50:
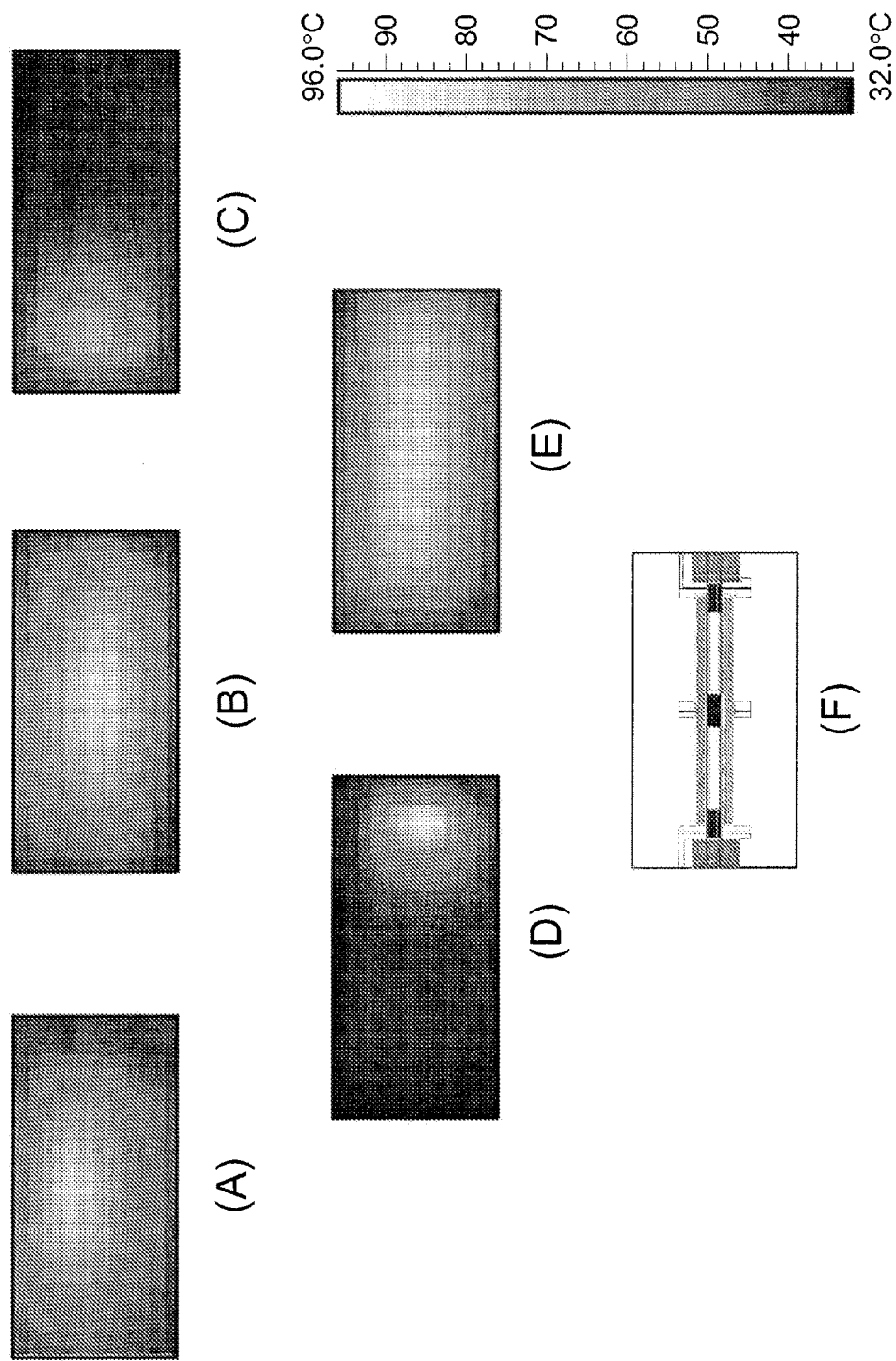
FIG. 50 shows thermal images of heater circuitry in operation.

Each heater can be independently controlled by a processor and/or control circuitry used in conjunction with the apparatus described herein. FIG. 50 shows thermal images, from the top surface of a microfluidic cartridge having heaters configured as in FIGS. 49A and 49B, when each heater in turn is activated, as follows: (A): Long Top only; (B) Long Bottom only; (C) Short Left only; (D) Short Right only; and (E) All Four Heaters on. Panel (F) shows a view of the reaction zone and heaters on the same scale as the other image panels in FIG. 50. Also shown in the figure is a temperature bar.

Use of Cutaways in Cartridge Substrate to Improve Rate of Cooling During PCR Cycling During a PCR amplification of a nucleotide sample, a number of thermal cycles are carried out. For improved efficiency, the cooling between each application of heat is preferably as rapid as possible. Improved rate of cooling can be achieved with various modifications to the heating substrate, as shown in FIGS. 51A-51C.

Figure 51A:
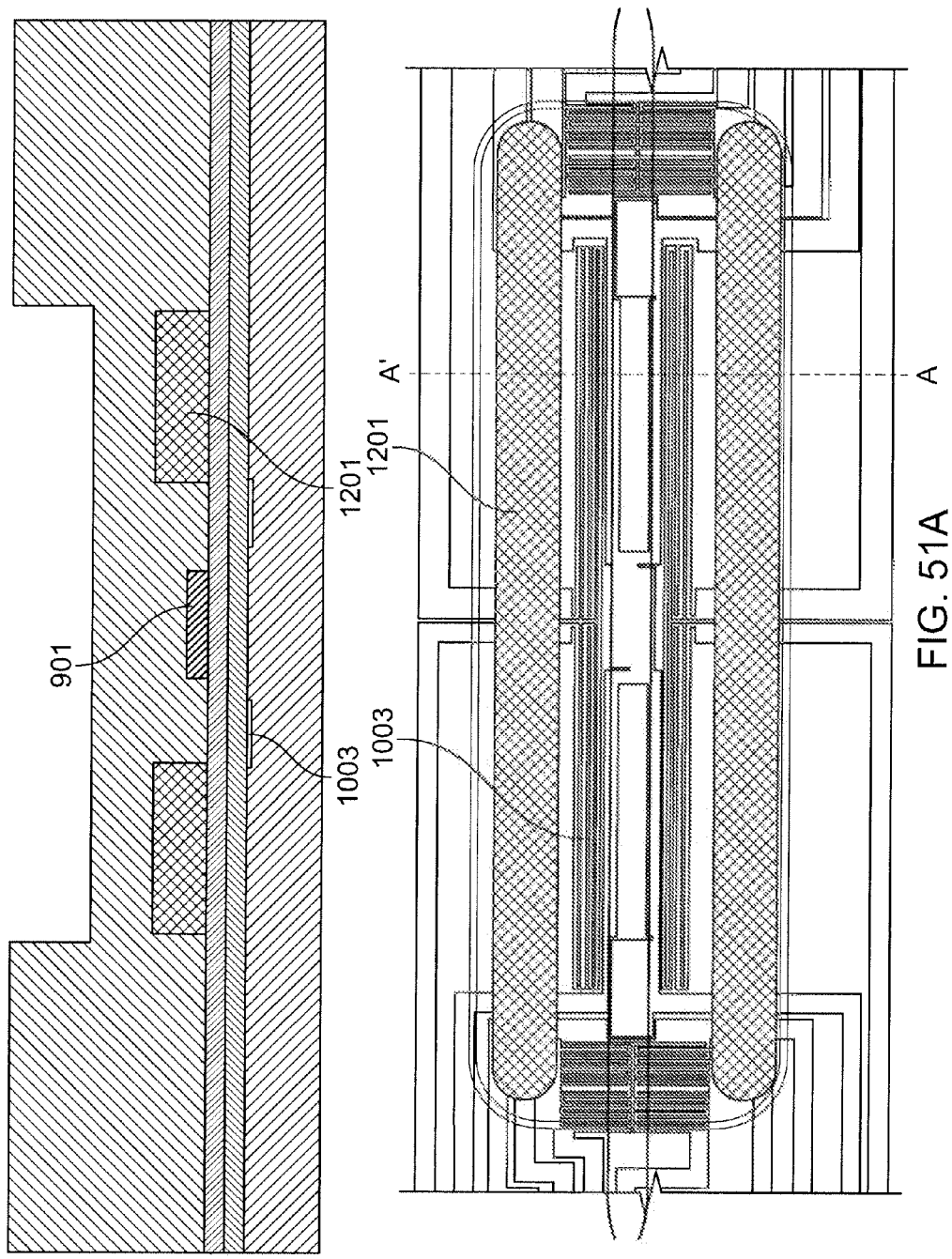
FIGS. 51A-51C shows various cut-away sections that can be used to improve cooling rates during PCR thermal cycling.

One way to achieve rapid cooling is to cutaway portions of the microfluidic cartridge substrate, as shown in FIG. 51A. The upper panel of FIG. 51A is a cross-section of an exemplary microfluidic cartridge taken along the dashed line A-A' as marked on the lower panel of FIG. 51A. PCR reaction zone 901, and representative heaters 1003 are shown. Also shown are two cutaway portions, one of which labeled 1201, that are situated alongside the heaters that are situated along the long side of the PCR reaction zone. Cutaway portions such as 1201 reduce the thermal mass of the cartridge, and also permit air to circulate within the cutaway portions. Both of these aspects permit heat to be conducted away quickly from the immediate vicinity of the PCR reaction zone. Other configurations of cutouts, such as in shape, position, and number, are consistent with the present technology.

Figure 51B:
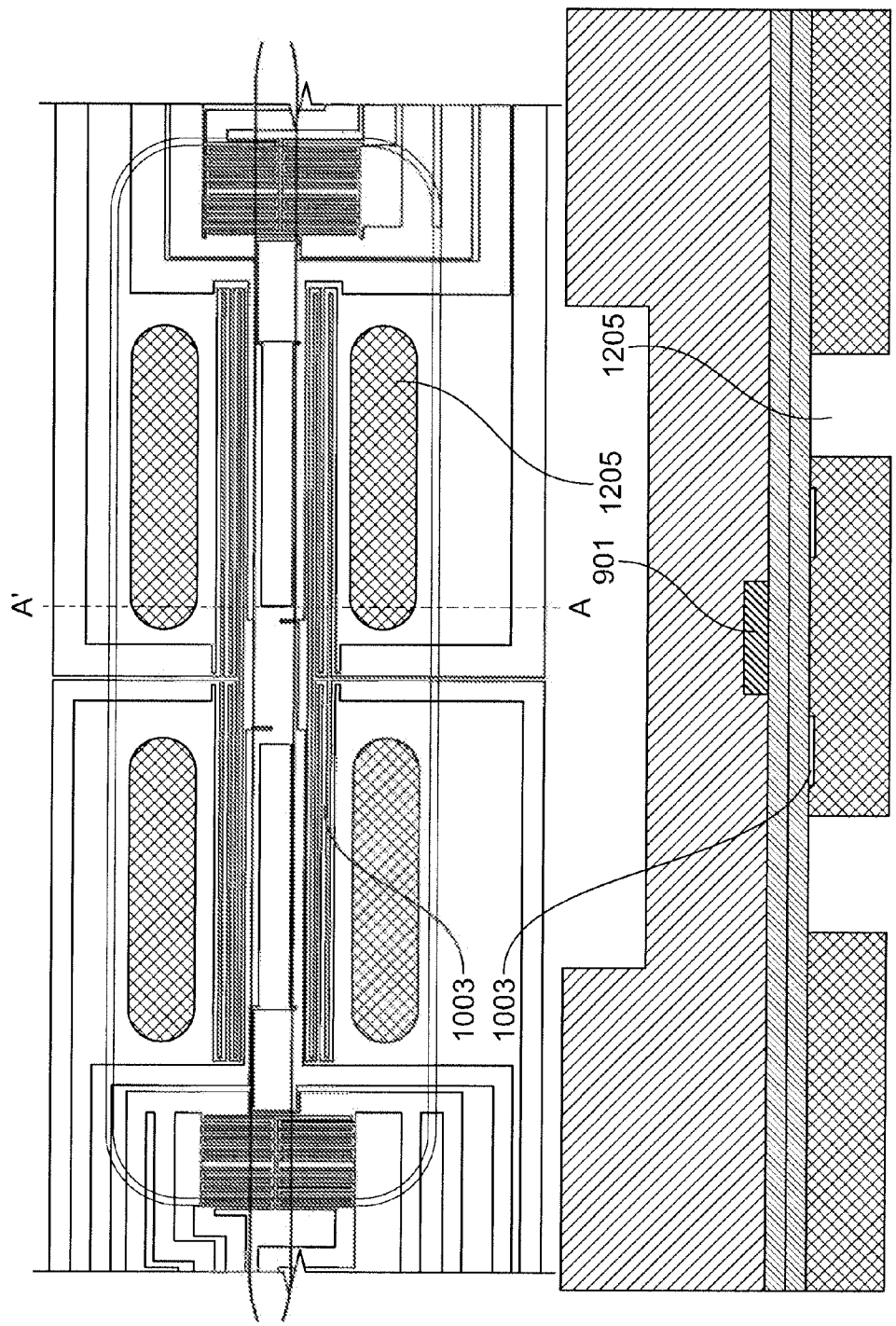

Another way to achieve rapid cooling is to cutaway portions of the heater substrate, as shown in FIG. 51B. The lower panel of FIG. 51B is a cross-section of an exemplary microfluidic cartridge and heater substrate taken along the dashed line A-A' as marked on the upper panel of FIG. 51B. PCR reaction zone 901, and representative heaters 1003 are shown. Also shown are four cutaway portions, one of which labeled 1205, that are situated alongside the heaters that are situated along the long side of the PCR reaction zone. Cutaway portions such as 1205 reduce the thermal mass of the heater substrate, and also permit air to circulate within the cutaway portions. Both of these aspects permit heat to be conducted away quickly from the immediate vicinity of the PCR reaction zone. Four separate cutaway portions are shown in FIG. 51B so that control circuitry to the various heaters is not disrupted. Other configurations of cutouts, such as in shape, position, and number, are consistent with the present technology. These cutouts may be created by a method selected from: selective etching using wet etching processes, deep reactive ion etching, selective etching using $CO_2$ laser or femtosecond laser (to prevent surface cracks or stress near the surface), selective mechanical drilling, selective ultrasonic drilling, or selective abrasive particle blasting. Care has to be taken to maintain mechanically integrity of the heater while reducing as much material as possible.

Figure 51C:
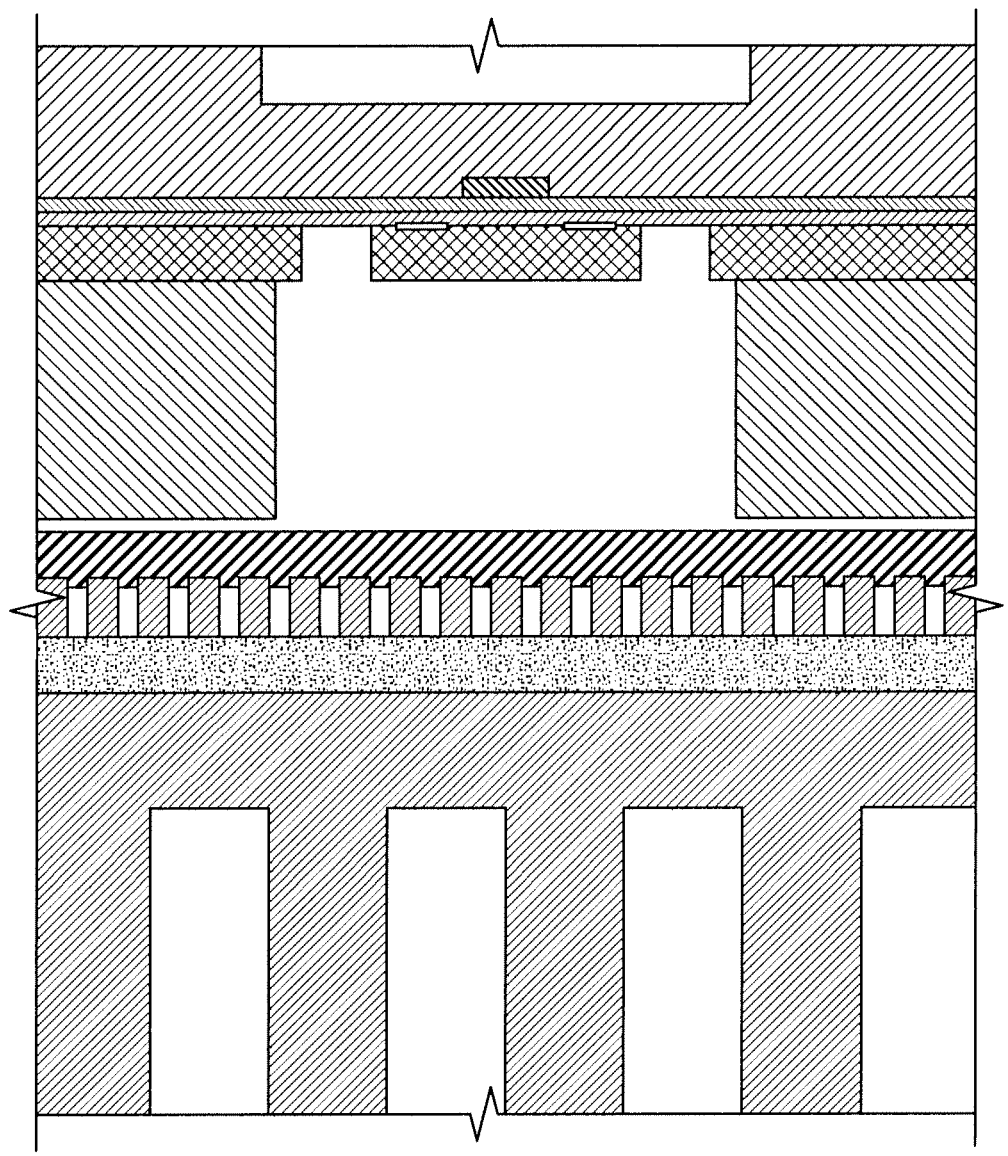

FIG. 51C shows a combination of cutouts and use of ambient air cooling to increase the cooling rate during the cooling stage of thermocycling. A substantial amount of cooling happens by convective loss from the bottom surface of the heater surface to ambient air. The driving force for this convective loss is the differential in temperatures between the glass surface and the air temperature. By decreasing the ambient air temperature by use of, for example, a peltier cooler, the rate of cooling can be increased. The convective heat loss may also be increased by keeping the air at a velocity higher than zero.

Figure 52:
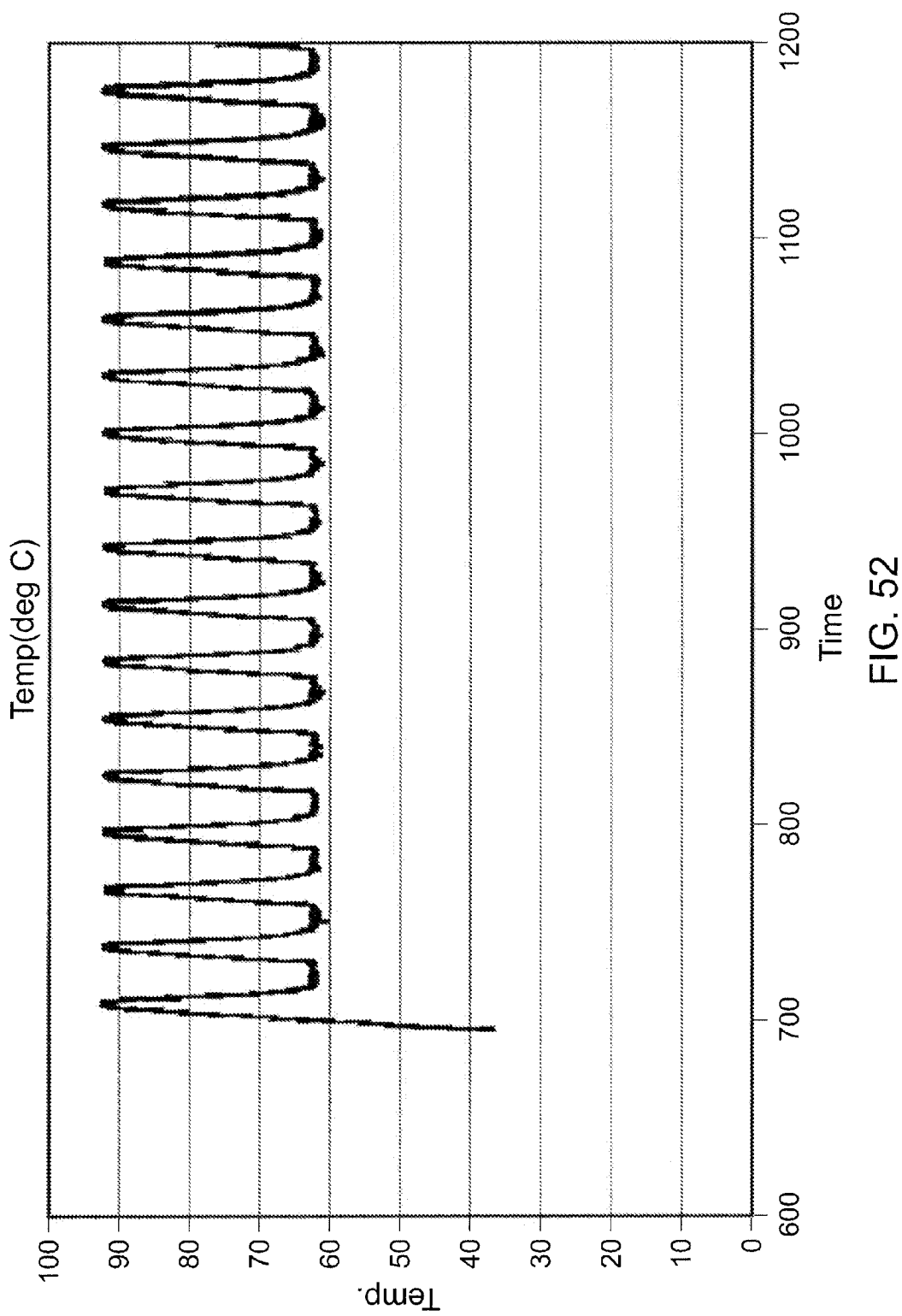
FIG. 52 shows a plot of temperature against time during a PCR process, as performed on a microfluidic cartridge as described herein.

An example of thermal cycling performance obtained with a configuration as described herein, is shown in FIG. 52 for a protocol that is set to heat up to 92° C., and stay there for 1 second, then cool to 62° C., and stay for 10 seconds. Cycle time is about 29 seconds, with 8 seconds required to heat from 62° C. and stabilize at 92° C., and 10 seconds required to cool from 92° C., and stabilize at 62° C.

Manufacturing Process for Cartridge

Figure 53:
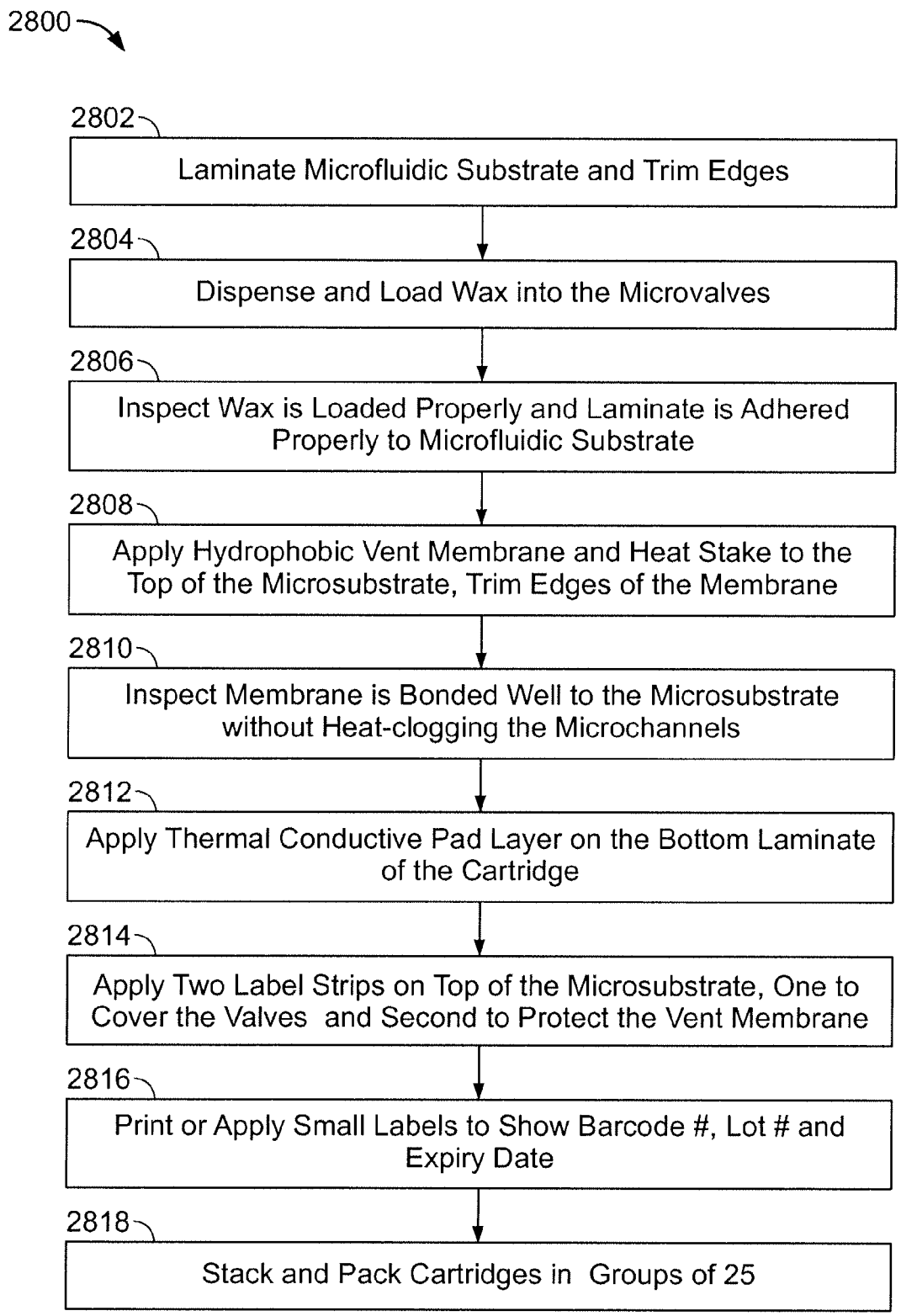
FIG. 53 shows an assembly process for a cartridge as further described herein.

FIG. 53 shows a flow-chart 2800 for an assembly process for an exemplary cartridge as further described herein. It would be understood by one of ordinary skill in the art, both that various steps may be performed in a different order from that set forth in FIG. 53, and additionally that any given step may be carried out by alternative methods to those set forth in the figure. It would also be understood that, where separate steps are illustrated for carrying out two or more functions, such functions may be performed synchronously and combined into single steps and be consistent with the overall process described herein.

At 2802, a laminate layer is applied to a microfluidic substrate that has previously been engineered to have a microfluidic network constructed in it; edges are trimmed from the laminate where they spill over the bounds of the substrate.

At 2804, wax is dispensed and loaded into the microvalves of the microfluidic network in the microfluidic substrate. An exemplary process for carrying this out is further described herein.

At 2806, the cartridge is inspected to ensure that wax from step 2804 is loaded properly and that the laminate from step 2802 adheres properly to the microfluidic substrate. If a substrate does not satisfy either or both of these tests, it is discarded. If substrates repeatedly fail either or both of these tests, then the wax dispensing, or laminate application steps, as applicable, are reviewed.

At 2808, a hydrophobic vent membrane is applied to, and heat bonded to, the top of the microfluidic substrate over the wax valves, and on the opposite face of the substrate from the laminate. Edges of the membrane that are in excess of the boundary of the substrate are trimmed.

At 2810, the assembly is inspected to ensure that the hydrophobic vent membrane is bonded well to the microfluidic substrate without heat-clogging the microfluidic channels. If any of the channels is blocked, or if the bond between the membrane and the substrate is imperfect, the assembly is discarded, and, in the case of repeated discard events, the foregoing process step is reviewed.

At 2812, a thermally conductive pad layer is applied to the bottom laminate of the cartridge.

At 2814, two label strips are applied to the top of the microfluidic substrate, one to cover the valves, and a second to protect the vent membranes. It would be understood that a single label strip may be devised to fulfill both of these roles.

At 2816, additional labels are printed or applied to show identifying characteristics, such as a barcode #, lot # and expiry date on the cartridge. Preferably one or more of these labels has a space and a writable surface that permits a user to make an identifying annotation on the label, by hand.

At 2818, to facilitate transport and delivery to a customer, assembled and labeled cartridges are stacked and pack cartridges in groups, such as groups of 25, or groups of 10, or groups of 20, or groups of 50. Preferably the packaging is via an inert and/or moisture-free medium.

Exemplary Wax-Deposition Process

Figure 54A:
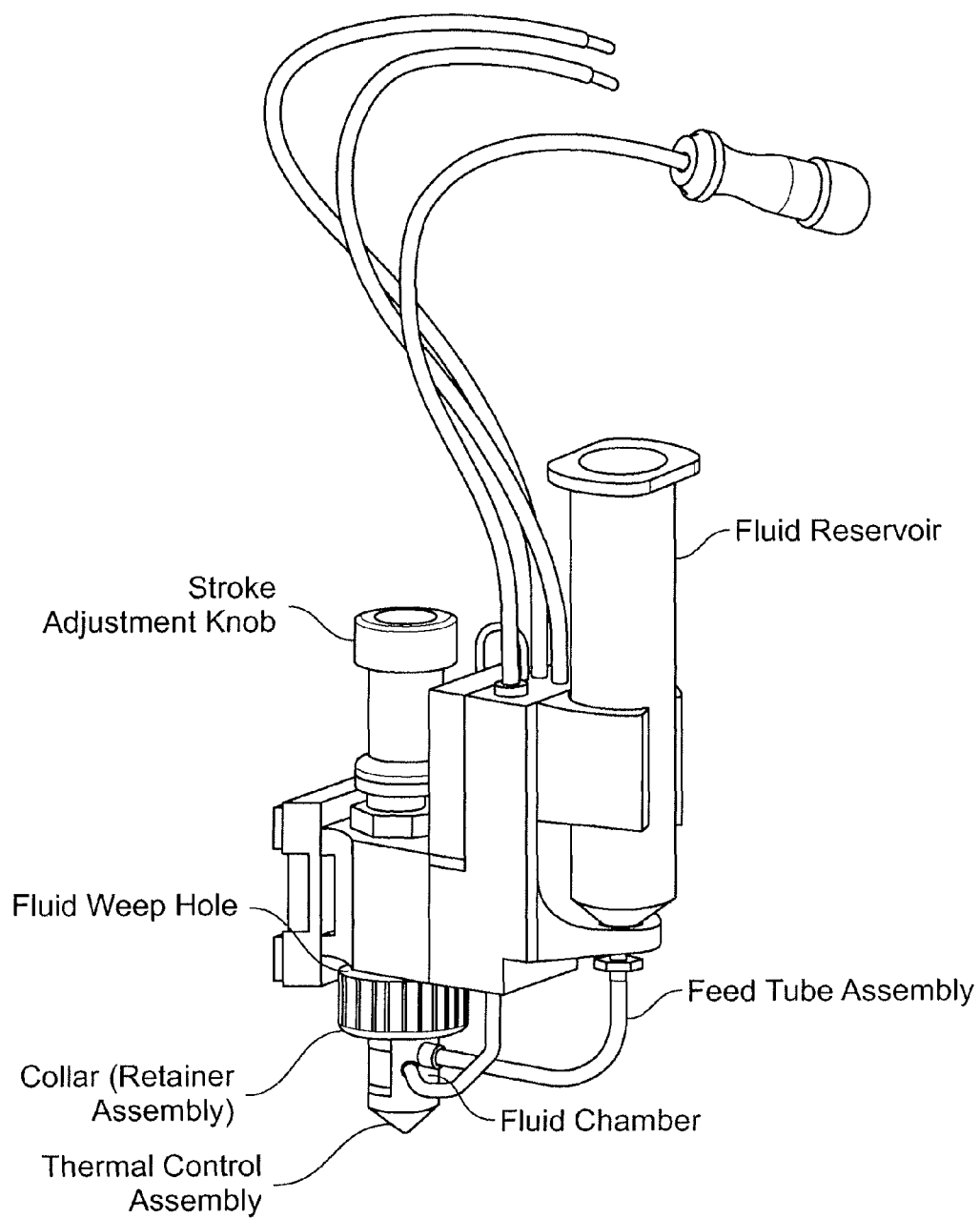
FIGS. 54A and 54B show exemplary apparatus for carrying out wax deposition.
Figure 54B:
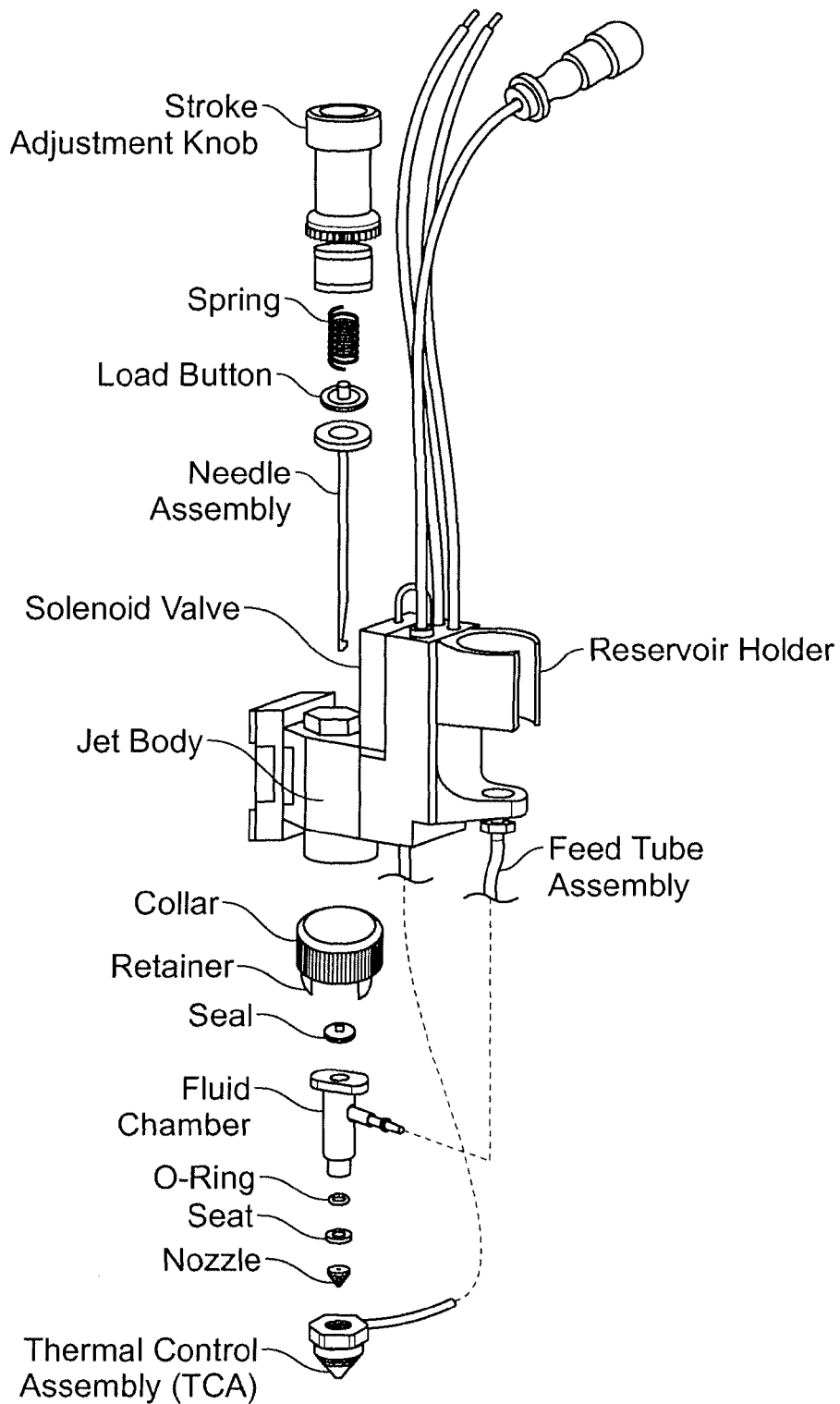

Deposition of wax in valves of the microfluidic network, as at step 2804 may be carried out with the exemplary equipment shown in FIGS. 54A and 54B. The DispenseJet Series DJ-9000 (FIGS. 54A and 54B) is a non-contact dispenser that provides high-speed delivery and exceptional volumetric control for various fluids, including surface mount adhesive, underfill, encapsulants, conformal coating, UV adhesives, and silver epoxy. The DJ-9000 jets in tight spaces as small as 200 micrometers and creates fillet wet-out widths as small as 300 micrometers on the dispensed side of a substrate such as a die. It dispenses fluid either as discrete dots or a rapid succession of dots to form a 100-micron (4 mil) diameter stream of fluid from the nozzle. It is fully compatible with other commercially available systems such as the Asymtek Century C-718/C-720, Millennium M-2000, and Axiom X-1000 Series Dispensing Systems.

A DJ-9000 is manufactured by Asymtek under manufacturing quality control standards aim to provide precise and reliable performance. Representative specifications of the apparatus are as follows.

| Characteristic | Specification |
| --- | --- |
| Size | Width: 35 mm |
| | Height: 110 mm |
| | Depth: 100 mm |
| Weight | 400 grams - dry |
| Feed Tube Assembly | Nylon -Fitting |
| | Polyurethane - Tube |
| Fluid Chamber | Type 303 Stainless Steel |
| Seat and Nozzle | 300/400 Series S/S, Carbide |
| Needle Assembly | 52100 Bearing Steel - Shaft |
| | Hard Chrome Plate |
| | Carbide - Tip |
| Fluid Seal | PEEK/Stainless Steel |
| Fluid Chamber 0-Ring | Ethylene Propylene |
| Jet Body | 6061-T6 Aluminum |
| | Nickel Plated |
| Needle Assembly Bearings | PEEK |
| Thermal Control Body | 6061-T6 Aluminum |
| | Nickel Plated |
| Reservoir Holder | Acetyl |
| Reservoir Size | 5, 10, or 30 cc (0.17, 0.34, or 1.0 oz) |
| Feed Tube Assembly Fitting | Female Luer per ANSI/HIMA MD70.1-1983 |
| Maximum Cycle Frequency | 200 Hz. |
| Minimum Valve Air Pressure | 5.5 bar (80 psi) |
| Operating Noise Level | 70 db* |
| Solenoid | 24 VDC, 12.7 Watts |
| Thermal Control Heater | 24 VDC, 14.7 Watts, 40 ohms |
| Thermal Control RTD | 100 ohm, platinum |
| Maximum Heater Set Point | 80 C. |

*At Maximum Cycle Rate

An exploded view of this apparatus is shown in FIG. 54B.

Theory of Operation of DJ-9000

The DJ-9000 has a normally closed, air-actuated, spring-return mechanism, which uses momentum transfer principles to expel precise volumes of material. Pressurized air is regulated by a high-speed solenoid to retract a needle assembly from the seat. Fluid, fed into the fluid chamber, flows over the seat. When the air is exhausted, the needle travels rapidly to the closed position, displacing fluid through the seat and nozzle in the form of a droplet. Multiple droplets fired in succession can be used to form larger dispense volumes and lines when combined with the motion of a dispenser robot.

The equipment has various adjustable features: The following features affect performance of the DJ-9000 and are typically adjusted to fit specific process conditions.

Fluid Pressure should be set so that fluid fills to the seat, but should not be influential in pushing the fluid through the seat and nozzle. In general, higher fluid pressure results in a larger volume of material jetted.

The Stroke Adjustment controls the travel distance of the Needle Assembly. The control is turned counterclockwise to increase needle assembly travel, or turned clockwise to decrease travel. An increase of travel distance will often result in a larger volume of material jetted.

The Solenoid Valve controls the valve operation. When energized, it allows air in the jet air chamber to compress a spring and thereby raise the Needle Assembly. When de-energized, the air is released and the spring forces the piston down so that the needle tip contacts the seat.

The seat and nozzle geometry are typically the main factors controlling dispensed material volume. The seat and nozzle size are determined based on the application and fluid properties. Other parameters are adjusted in accordance with seat and nozzle choices. Available seat and nozzle sizes are listed in the table hereinbelow.

Thermal Control Assembly: Fluid temperature often influences fluid viscosity and flow characteristics. The DJ-9000 is equipped with a Thermal Control Assembly that assures a constant fluid temperature.

Dot and Line Parameters: In addition to the DJ-9000 hardware configuration and settings, Dot and Line Parameters are set in a software program (referred to as FmNT) to control the size and quality of dots and lines dispensed.

Wax Loading in Valves

Figure 55A:
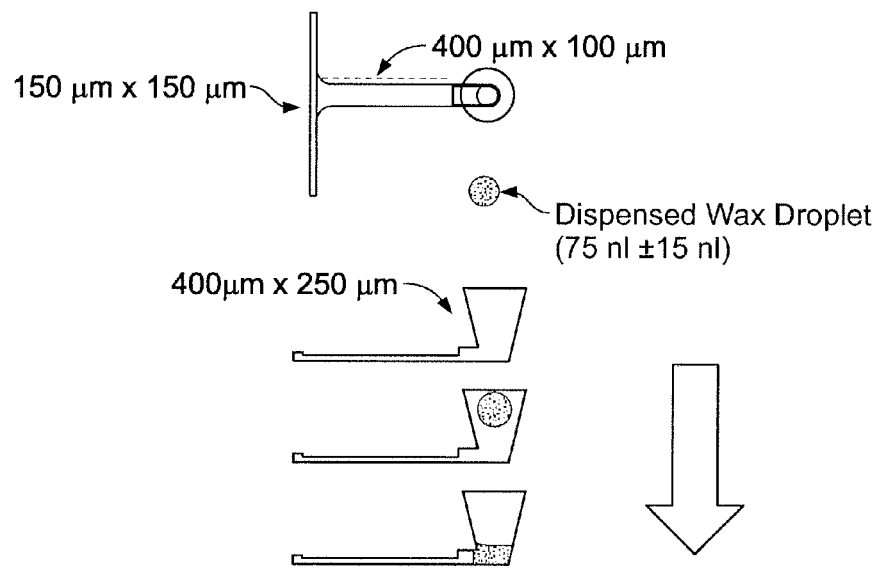
FIGS. 55A and 55B show exemplary deposition of wax droplets into microfluidic valves.
Figure 55B:
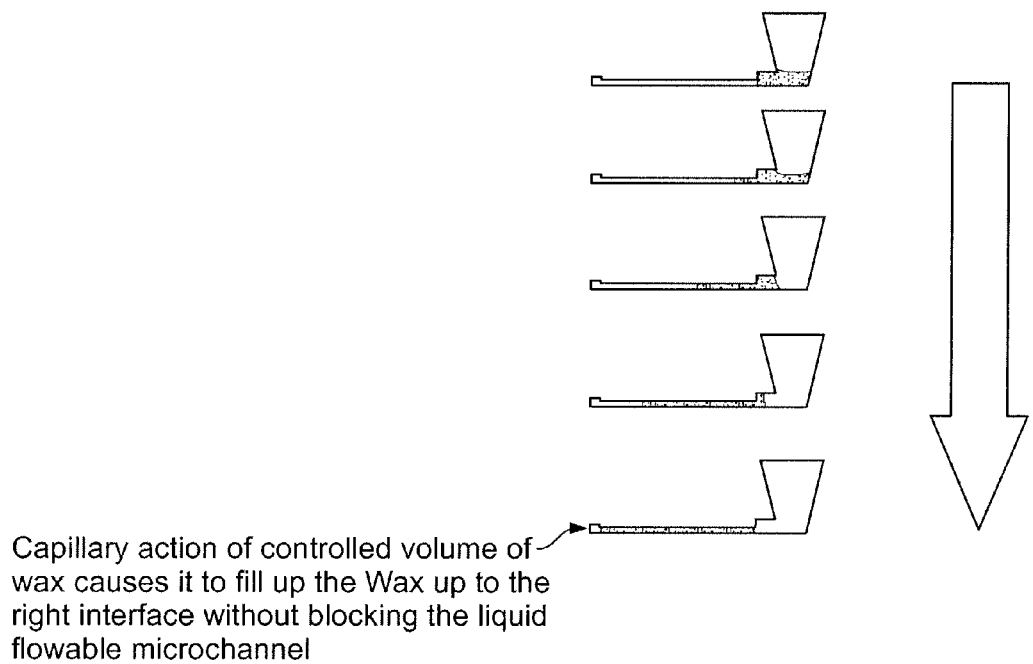

FIGS. 55A and 55B show how a combination of controlled hot drop dispensing into a heated microchannel device of the right dimensions and geometry is used to accurately load wax into a microchannel of a microfluidic cartridge to form a valve. The heated dispenser head can be accurately position over an inlet hole of the microchannel in the microfluidic device, and can dispense molten wax drops in volumes as small as 75 nanoliters with an accuracy of 20%. The inlet hole of the microchannel device is dimensioned in such a way that the droplet of 75 nl can be accurately shot to the bottom of the inlet hole using, for example, compressed air, or in a manner similar to an inkjet printing method. The microchannel device is maintained at a temperature above the melting point of the wax thereby permitting the wax to stay in a molten state immediately after it is dispensed. After the drop falls to the bottom of the inlet hole, the molten wax is drawn into the narrow channel by capillary action. The volume of the narrow section is designed to be approximately equal to a maximum typical amount that is dispensed into the inlet hole.

Heater Multiplexing (Under Software Control)

Figure 56:
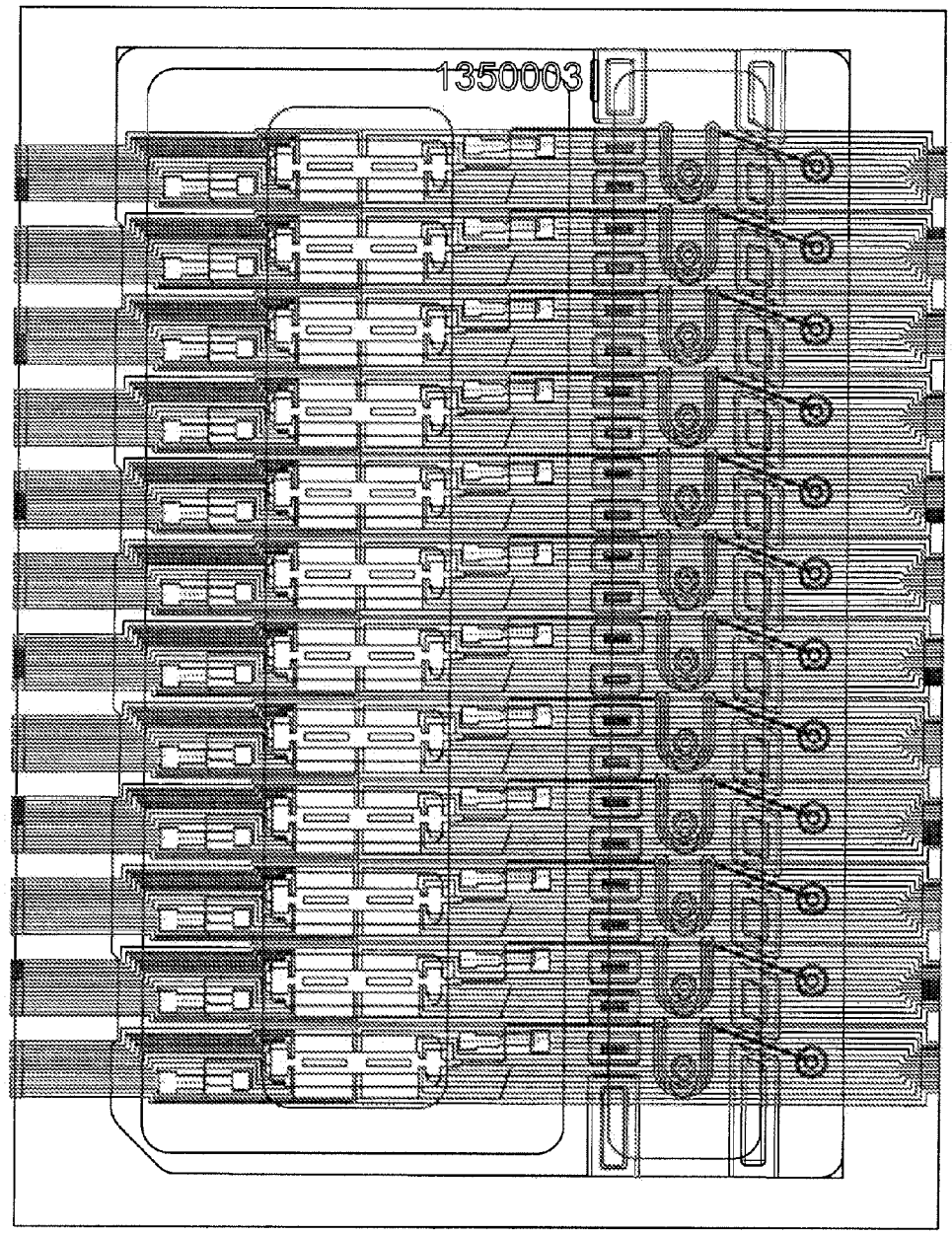
FIG. 56 shows an overlay of an array of heater elements on an exemplary multi-lane microfluidic cartridge, wherein various microfluidic networks are visible.

Another aspect of the apparatus described herein, relates to a method for controlling the heat within the system and its components, as illustrated in FIG. 56. The method leads to a greater energy efficiency of the apparatus described herein, because not all heaters are heating at the same time, and a given heater is receiving current for only part of the time.

Generally, the heating of microfluidic components, such as a PCR reaction zone, is controlled by passing currents through suitably configured microfabricated heaters. The heating can be further controlled by periodically turning the current on and off with varying pulse width modulation (PWM), wherein pulse width modulation refers to the on-time/off-time ratio for the current. The current can be supplied by connecting a microfabricated heater to a high voltage source (for example, 30V), which can be gated by the PWM signal. In some embodiments, the device includes 48 PWM signal generators. Operation of a PWM generator includes generating a signal with a chosen, programmable period (the end count) and granularity. For instance, the signal can be 4000 μs (micro-seconds) with a granularity of 1 us, in which case the PWM generator can maintain a counter beginning at zero and advancing in increments of 1 μs until it reaches 4000 μs, when it returns to zero. Thus, the amount of heat produced can be adjusted by adjusting the end count. A high end count corresponds to a greater length of time during which the microfabricated heater receives current and therefore a greater amount of heat produced.

In various embodiments, the operation of a PWM generator can also include a programmable start count in addition to the aforementioned end count and granularity. In such embodiments, multiple PWM generators can produce signals that can be selectively non-overlapping (e.g., by multiplexing the on-time of the various heaters) such that the current capacity of the high voltage power is not exceeded. Multiple heaters can be controlled by different PWM signal generators with varying start and end counts. The heaters can be divided into banks, whereby a bank defines a group of heaters of the same start count. For example, 36 PWM generators can be grouped into six different banks, each corresponding to a certain portion of the PWM cycle (500 ms for this example). The end count for each PWM generator can be selectively programmed such that not more than six heaters will be on at any given time. A portion of a PWM cycle can be selected as dead time (count 3000 to 4000 for this example) during which no heating takes place and sensitive temperature sensing circuits can use this time to sense the temperature. The table below represents a PWM cycle for the foregoing example:

|  | Start Count | End Count | Max End count |
|---|---|---|---|
| Bank 1 | | | |
| PWM generator#1 | 0 | 150 | 500 |
| PWM generator#2 | 0 | 220 | 500 |
| ... | ... | ... | ... |
| PWM generator#6 | 0 | 376 | 500 |
| Bank 2 | | | |
| PWM generator#7 | 500 | 704 | 1000 |
| PWM generator#8 | 500 | 676 | 1000 |
| ... | ... | ... | ... |
| PWM generator#12 | 500 | 780 | 1000 |
| Bank 3 | | | |
| PWM generator#13 | 1000 | 1240 | 1500 |
| PWM generator#14 | 1000 | 1101 | 1500 |
| ... | ... | ... | ... |
| PWM generator#18 | 1000 | 1409 | 1500 |
| Bank 4 | | | |
| PWM generator#19 | 1500 | 1679 | 2000 |
| PWM generator#20 | 1500 | 1989 | 2000 |
| ... | ... | ... | ... |
| PWM generator#24 | 1500 | 1502 | 2000 |
| Bank 5 | | | |
| PWM generator#25 | 2000 | 2090 | 2500 |
| PWM generator#26 | 2000 | 2499 | 2500 |
| ... | ... | ... | ... |
| PWM generator#30 | 2000 | 2301 | 2500 |
| Bank 6 | | | |
| PWM generator#31 | 2500 | 2569 | 3000 |
| PWM generator#32 | 2500 | 2790 | 3000 |
| ... | ... | ... | ... |
| PWM generator#36 | 2500 | 2678 | 3000 |

Use of Detection System to Measure/Detect Fluid in PCR Chamber

The apparatus optionally has a very sensitive fluorescence detector that is able to collect fluorescence light from the PCR chamber 210 of a microfluidic cartridge. This detector is used to detect the presence of liquid in the chamber, a measurement that determines whether or not to carry out a PCR cycle. A background reading is taken prior to filling the chamber with liquid. Another reading is taken after microfluidic operations have been performed that should result in filling the PCR chamber with liquid. The presence of liquid alters the fluorescence reading from the chamber. A programmable threshold value is used to tune an algorithm programmed into the processor (for example, the second reading has to exceed the first reading by 20%). If the two readings do not differ beyond the programmed margin, the liquid is deemed to not have entered the chamber, and a PCR cycle is not initiated for that chamber. Instead, a warning is issued to a user.

Computer Program Product

In various embodiments, a computer program product for use with the apparatus herein includes computer readable instructions thereon for operating the apparatus.

In various embodiments, the computer program product can include one or more instructions to cause the system to: output an indicator of the placement of the microfluidic cartridge in the bay; read a sample label or a microfluidic cartridge label; output directions for a user to input a sample identifier; output directions for a user to load a sample transfer member with the PCR-ready sample; output directions for a user to introduce the PCR-ready sample into the microfluidic cartridge; output directions for a user to place the microfluidic cartridge in the receiving bay; output directions for a user to close the lid to operate the force member; output directions for a user to pressurize the PCR-ready sample in the microfluidic cartridge by injecting the PCR-ready sample with a volume of air between about 0.5 mL and about 5 mL; and output status information for sample progress from one or more lanes of the cartridge.

In various embodiments, the computer program product can include one or more instructions to cause the system to: heat the PCR ready-sample under thermal cycling conditions suitable for creating PCR amplicons from the neutralized polynucleotide; contact the neutralized polynucleotide sample or a PCR amplicon thereof with at least one probe that is selective for a polynucleotide sequence; independently contact each of the neutralized polynucleotide sample and a negative control polynucleotide with the PCR reagent mixture under thermal cycling conditions suitable for independently creating PCR amplicons of the neutralized polynucleotide sample and PCR amplicons of the negative control polynucleotide; contact the neutralized polynucleotide sample or a PCR amplicon thereof and the negative control polynucleotide or a PCR amplicon thereof with at least one probe that is selective for a polynucleotide sequence; output a determination of the presence of a polynucleotide sequence in the biological sample, the polynucleotide sequence corresponding to the probe, if the probe is detected in the neutralized polynucleotide sample or a PCR amplicon thereof; and/or output a determination of a contaminated result if the probe is detected in the negative control polynucleotide or a PCR amplicon thereof.

In various embodiments, the computer program product can include one or more instructions to cause the system to automatically conduct one or more of the steps of the method.

In various embodiments, the microfluidic cartridge comprises two or more sample lanes, each including a sample inlet valve, a bubble removal vent, a thermally actuated pump, a thermally actuated valve, and a PCR reaction zone, wherein the computer readable instructions are configured to independently operate one or more components of each said lane in the system, independently of one another, and for causing a detector to measure fluorescence from the PCR reaction zones.

Sample

In various embodiments, the sample can include a PCR reagent mixture comprising a polymerase enzyme and a plurality of nucleotides. The PCR reagent mixture can be in the form of one or more lyophilized pellets and the steps by which the PCR-ready sample is prepared can involve contacting the PCR pellet with liquid to create a PCR reagent mixture solution. In yet another embodiment, each of the PCR lanes may have dried down or lyophilized ASR reagents preloaded such that the user only needs to input prepared polynucleotide sample into the PCR. In another embodiment, the PCR lanes may have only the application-specific probes and primers premeasured and preloaded, and the user inputs a sample mixed with the PCR reagents.

In various embodiments, the microfluidic network can be configured to couple heat from an external heat source to a sample mixture comprising PCR reagent and neutralized polynucleotide sample under thermal cycling conditions suitable for creating PCR amplicons from the neutralized polynucleotide sample.

In various embodiments, the PCR ready sample can further include a positive control plasmid and a fluorogenic hybridization probe selective for at least a portion of the plasmid. In various embodiments, the PCR-ready sample further includes a sample buffer, and at least one probe that is selective for a polynucleotide sequence, e.g., the polynucleotide sequence that is characteristic of a pathogen selected from the group consisting of gram positive bacteria, gram negative bacteria, yeast, fungi, protozoa, and viruses.

In various embodiments, the microfluidic cartridge can accommodate a negative control polynucleotide, wherein the microfluidic network can be configured to independently carry out PCR on each of a neutralized polynucleotide sample and a negative control polynucleotide with the PCR reagent mixture under thermal cycling conditions suitable for independently creating PCR amplicons of the neutralized polynucleotide sample and PCR amplicons of the negative control polynucleotide. Each lane of a multi-lane cartridge as described herein can perform two reactions because of the presence of two fluorescence detection systems per lane. A variety of combinations of reactions can be performed in the cartridge, such as two sample reactions in one lane, a positive control and a negative control in two other lanes; or a sample reaction and an internal control in one lane and a negative control in a separate lane.

In various embodiments, the sample can include at least one probe that can be selective for a polynucleotide sequence, wherein the steps by which the PCR-ready sample is prepared involve contacting the neutralized polynucleotide sample or a PCR amplicon thereof with the probe. The probe can be a fluorogenic hybridization probe. The fluorogenic hybridization probe can include a polynucleotide sequence coupled to a fluorescent reporter dye and a fluorescence quencher dye. The PCR reagent mixture can further include a positive control plasmid and a plasmid fluorogenic hybridization probe selective for at least a portion of the plasmid and the microfluidic cartridge can be configured to allow independent optical detection of the fluorogenic hybridization probe and the plasmid fluorogenic hybridization probe.

In various embodiments, the probe can be selective for a polynucleotide sequence that is characteristic of an organism, for example any organism that employs deoxyribonucleic acid or ribonucleic acid polynucleotides. Thus, the probe can be selective for any organism. Suitable organisms include mammals (including humans), birds, reptiles, amphibians, fish, domesticated animals, wild animals, extinct organisms, bacteria, fungi, viruses, plants, and the like. The probe can also be selective for components of organisms that employ their own polynucleotides, for example mitochondria. In some embodiments, the probe is selective for microorganisms, for example, organisms used in food production (for example, yeasts employed in fermented products, molds or bacteria employed in cheeses, and the like) or pathogens (e.g., of humans, domesticated or wild mammals, domesticated or wild birds, and the like). In some embodiments, the probe is selective for organisms selected from the group consisting of gram positive bacteria, gram negative bacteria, yeast, fungi, protozoa, and viruses.

In various embodiments, the probe can be selective for a polynucleotide sequence that is characteristic of an organism selected from the group consisting of *Staphylococcus* spp., e.g., *S. epidermidis, S. aureus*, Methicillin-resistant *Staphylococcus aureus* (MRSA), Vancomycin-resistant *Staphylococcus; Streptococcus*(e.g., α, β or γ-hemolytic, Group A, B, C, D or G) such as *S. pyogenes, S. agalactiae; E. faecalis, E. durans*, and *E. faecium* (formerly *S. faecalis, S. durans, S. faecium*); nonenterococcal group D streptococci, e.g., *S. bovis* and *S. equines; Streptococci viridans*, e.g., *S. mutans, S. sanguis, S. salivarius, S. mitior, A. milleri, S. constellatus, S. intermedius*, and *S. anginosus; S. iniae; S. pneumoniae; Neisseria*, e.g., *N. meningitides, N. gonorrhoeae*, saprophytic *Neisseria* sp; *Erysipelothrix*, e.g., *E. rhusiopathiae; Listeria* spp., e.g., *L. monocytogenes*, rarely *L. ivanovii* and *L. seeligeri; Bacillus*, e.g., *B. anthracis, B. cereus, B. subtilis, B. subtilus niger, B. thuringiensis; Nocardia asteroids; Legionella*, e.g., *L. pneumonophilia, Pneumocystis*, e.g., *P. carinii*; Enterobacteriaceae such as *Salmonella, Shigella, Escherichia* (e.g., *E. coli, E. coli*O157:H7); *Klebsiella, Enterobacter, Serratia, Proteus, Morganella, Providencia, Yersinia*, and the like, e.g., *Salmonella*, e.g., *S. typhi S. paratyphi* A, B (*S. schottmuelleri*), and C (*S. hirschfeldii*), *S. dublin S. choleraesuis, S. enteritidis, S. typhimurium, S. heidelberg, S. newport, S. infantis, S. agona, S. montevideo*, and *S. saint-paul; Shigella* e.g., subgroups: A, B, C, and D, such as *S. flexneri, S. sonnei, S. boydii, S. dysenteriae; Proteus (P. mirabilis, P. vulgaris*, and *P. myxofaciens*), *Morganella* (*M. morganii*); *Providencia* (*P. rettgeri, P. alcalifaciens*, and *P. stuartii*); *Yersinia*, e.g., *Y. pestis, Y. enterocolitica; Haemophilus*, e.g., *H. influenzae, H. parainfluenzae H. aphrophilus, H. ducreyi; Brucella*, e.g., *B. abortus, B. melitensis, B. suis, B. canis; Francisella*, e.g., *F. tularensis; Pseudomonas*, e.g., *P. aeruginosa, P. paucimobilis, P. putida, P. fluorescens, P. acidovorans, Burkholderia (Pseudomonas) pseudomallei, Burkholderia mallei, Burkholderia cepacia* and *Stenotrophomonas maltophilia; Campylobacter*, e.g., *C. fetus fetus, C. jejuni, C. pylori (Helicobacter pylori); Vibrio*, e.g., *V. cholerae, V. parahaemolyticus, V. mimicus, V. alginolyticus, V. hollisae, V. vulnificus*, and the nonagglutinable vibrios; *Clostridia*, e.g., *C. perfringens, C. tetani, C. difficile, C. botulinum; Actinomyces*, e.g., *A. israelii; Bacteroides*, e.g., *B. fragilis, B. thetaiotaomicron, B. distasonis, B. vutlgatus, B. ovatus, B. caccae*, and *B. merdae; Prevotella*, e.g., *P. melaminogenica*; genus *Fusobacterium; Treponema*, e.g. *T. pallidum* subspecies *endemicum, T. pallidum* subspecies *pertenue, T. carateum*, and *T. pallidum* subspecies *pallidum*; genus *Borrelia*, e.g., *B. burgdorferi*; genus *Leptospira; Streptobacillus*, e.g., *S. moniliformis; Spirillum*, e.g., *S. minus; Mycobacterium*, e.g., *M. tuberculosis, M. bovis, M. africanum, M. avium M. intracellulare, M. kansasii, M. xenopi, M. marinum, M. ulcerans*, the *M. fortuitum* complex (*M. fortuitum* and *M. chelonei*), *M. leprae, M. asiaticum, M. chelonei* subsp. *abscessus, M. fallax, M. fortuitum, M. malmoense, M. shimoidei, M. simiae, M. szulgai, M. xenopi; Mycoplasma*, e.g., *M. hominis, M. orale, M. salivarium, M. fermentans, M. pneumoniae, M. bovis, M. tuberculosis, M. avium, M. leprae; Mycoplasma*, e.g., *M. genitalium; Ureaplasma*, e.g., *U. urealyticum; Trichomonas*, e.g., *T. vaginalis; Cryptococcus*, e.g., *C. neoformans; Histoplasma*, e.g., *H. capsulatum; Candida*, e.g., *C. albicans; Aspergillus* sp; *Coccidioides*, e.g., *C. immitis; Blastomyces*, e.g. *B. dermatitidis; Paracoccidioides*, e.g., *P. brasiliensis; Penicillium*, e.g., *P. manmeffei; Sporothrix*, e.g., *S. schenckii; Rhizopus, Rhizomucor, Absidia*, and *Basidiobolus*; diseases caused by *Bipolaris, Cladophialophora, Cladosporium, Drechslera, Exophiala, Fonsecaea, Phialophora, Xylohypha, Ochroconis, Rhinocladiella, Scolecobasidium*, and *Wangiella; Trichosporon*, e.g., *T. beigelii; Blastoschizomyces*, e.g., *B. capitatus; Plasmodium*, e.g., *P. falciparum, P. vivax, P. ovale*, and *P. malariae; Babesia* sp; protozoa of the genus *Trypanosoma*, e.g., *T. cruzi; Leishmania*, e.g., *L. donovani, L. major L. tropica, L. mexicana, L. braziliensis, L. viannia braziliensis; Toxoplasma*, e.g., *T. gondii; Amoebas* of the genera *Naegleria* or *Acanthamoeba; Entamoeba histolytica; Giardia lamblia*; genus *Cryptosporidium*, e.g., *C. parvum; Isospora belli; Cyclospora cayetanensis; Ascaris lumbricoides; Trichuris trichiura; Ancylostoma duodenale* or *Necator americanus; Strongyloides stercoralis Toxocara*, e.g., *T. canis, T. cati; Baylisascaris*, e.g., *B. procyonis; Trichinella*, e.g., *T. spiralis; Dracunculus*, e.g., *D. medinensis*; genus *Filarioidea; Wuchereria bancrofti; Brugia*, e.g., *B. malayi*, or *B. timori; Onchocerca volvulus; Loa loa; Dirofilaria immitis*; genus *Schistosoma*, e.g., *S. japonicum, S. mansoni, S. mekongi, S. intercalatum, S. haematobium; Paragonimus*, e.g., *P. Westermani, P. Skriabini; Clonorchis sinensis; Fasciola hepatica; Opisthorchis* sp; *Fasciolopsis buski; Diphyllobothrium latum; Taenia*, e.g., *T. saginata, T. solium; Echinococcus*, e.g., *E. granulosus, E. multilocularis*; Picornaviruses, rhinoviruses echoviruses, coxsackieviruses, influenza virus; paramyxoviruses, e.g., types 1, 2, 3, and 4; adnoviruses; Herpesviruses, e.g., HSV-1 and HSV-2; varicella-zoster virus; human T-lymphotrophic virus (type I and type II); Arboviruses and Arenaviruses; Togaviridae, Flaviviridae, Bunyaviridae, Reoviridae; Flavivirus; Hantavirus; Viral encephalitis (alphaviruses [e.g., Venezuelan equine encephalitis, eastern equine encephalitis, western equine encephalitis]); Viral hemorrhagic fevers (filoviruses [e.g., Ebola, Marburg] and arenaviruses [e.g., Lassa, Machupo]); Smallpox (variola); retroviruses e.g., human immunodeficiency viruses 1 and 2; human papillomavirus [HPV] types 6, 11, 16, 18, 31, 33, and 35.

In various embodiments, the probe can be selective for a polynucleotide sequence that is characteristic of an organisms selected from the group consisting of *Pseudomonas aeruginosa, Proteus mirabilis, Klebsiella oxytoca, Klebsiella pneumoniae, Escherichia coli, Acinetobacter Baumannii, Serratia marcescens, Enterobacter aerogenes, Enterococcus faecium*, vancomycin-resistant *enterococcus* (VRE), *Staphylococcus aureus*, methecillin-resistant *Staphylococcus aureus*(MRSA), *Streptococcus viridans, Listeria monocytogenes, Enterococcus* spp., *Streptococcus* Group B, *Streptococcus* Group C, *Streptococcus* Group G, *Streptococcus* Group F, *Enterococcus faecalis, Streptococcus pneumoniae, Staphylococcus epidermidis, Gardenerellca vaginalis, Micrococcus* sps., *Haemophilus influenzae, Neisseria gonorrhoeee, Moraxella catarrahlis, Salmonella* sps., *Chlamydia trachomatis, Peptostreptococcus productus, Peptostreptococcus anaerobius, Lactobacillus fermentum, Eubacterium lentum, Candida glabrata, Candida albicans, Chlamydia* spp., *Camplobacter* spp., *Salmonella* spp., smallpox (variola major), *Yersina Pestis*, Herpes Simplex Virus I (HSV I), and Herpes Simplex Virus II (HSV II).

In various embodiments, the probe can be selective for a polynucleotide sequence that is characteristic of Group B *Streptococcus*.

Carrying out PCR on a PCR-ready sample can include heating the PCR reagent mixture and the neutralized polynucleotide sample under thermal cycling conditions suitable for creating PCR amplicons from the neutralized polynucleotide sample; contacting the neutralized polynucleotide sample or a PCR amplicon thereof with at least one probe that is selective for a polynucleotide sequence; independently contacting each of the neutralized polynucleotide sample and a negative control polynucleotide with the PCR reagent mixture under thermal cycling conditions suitable for independently creating PCR amplicons of the neutralized polynucleotide sample and PCR amplicons of the negative control polynucleotide; and/or contacting the neutralized polynucleotide sample or a PCR amplicon thereof and the negative control polynucleotide or a PCR amplicon thereof with at least one probe that is selective for a polynucleotide sequence.

In various embodiments, a method of carrying out PCR on a sample can further include one or more of the following steps: heating the biological sample in the microfluidic cartridge; pressurizing the biological sample in the microfluidic cartridge at a pressure differential compared to ambient pressure of between about 20 kilopascals and 200 kilopascals, or in some embodiments between about 70 kilopascals and 110 kilopascals.

In various embodiments, a method of using the apparatus described herein can further include one or more of the following steps: determining the presence of a polynucleotide sequence in the biological sample, the polynucleotide sequence corresponding to the probe, if the probe is detected in the neutralized polynucleotide sample or a PCR amplicon thereof; determining a contaminated result if the probe is detected in the negative control polynucleotide or a PCR amplicon thereof; and/or in some embodiments, wherein the PCR reagent mixture further comprises a positive control plasmid and a plasmid probe selective for at least a portion of the plasmid, the method further including determining a PCR reaction has occurred if the plasmid probe is detected.

Fluorescence Detection System, Including Lenses and Filters, and Multiple Parallel Detection for a Multi-Lane Cartridge A miniaturized, highly sensitive fluorescence detection system can be incorporated for monitoring fluorescence from the biochemical reactions that are the basis of nucleic acid amplification methods such as PCR.

Accordingly, another aspect of the apparatus includes a system for monitoring fluorescence from biochemical reactions. The system can be, for example, an optical detector having a light source (for example an LED) that selectively emits light in an absorption band of a fluorescent dye, lenses for focusing the light, and a light detector (for example a photodiode) that selectively detects light in an emission band of the fluorescent dye, wherein the fluorescent dye corresponds to a fluorescent polynucleotide probe or a fragment thereof. Alternatively, the optical detector can include a bandpass-filtered diode that selectively emits light in the absorption band of the fluorescent dye (a fluorogenic probe) and a bandpass filtered photodiode that selectively detects light in the emission band of the fluorescent dye. For example, the optical detector can be configured to independently detect a plurality of fluorescent dyes having different fluorescent emission spectra, wherein each fluorescent dye corresponds to a fluorescent polynucleotide probe or a fragment thereof. For example, the optical detector can be configured to independently detect a plurality of fluorescent dyes at a plurality of different locations of, for example, a microfluidic cartridge, wherein each fluorescent dye corresponds to a fluorescent polynucleotide probe or a fragment thereof.

In some embodiments, a given detector for use with the apparatus described herein is capable of detecting a fluorescence signal from nanoliter scale PCR reactions. Advantageously, the detector is formed from inexpensive components, having no moving parts. The detector is also configured to mate with a microfluidic cartridge as further described herein, and is also preferably part of a pressure application system, such as a sliding lid, that keeps the cartridge in place. The detector further has potential for 2 or 3 color detection and is controlled by software, preferably custom software, configured to sample information from the detector.

Figure 57:
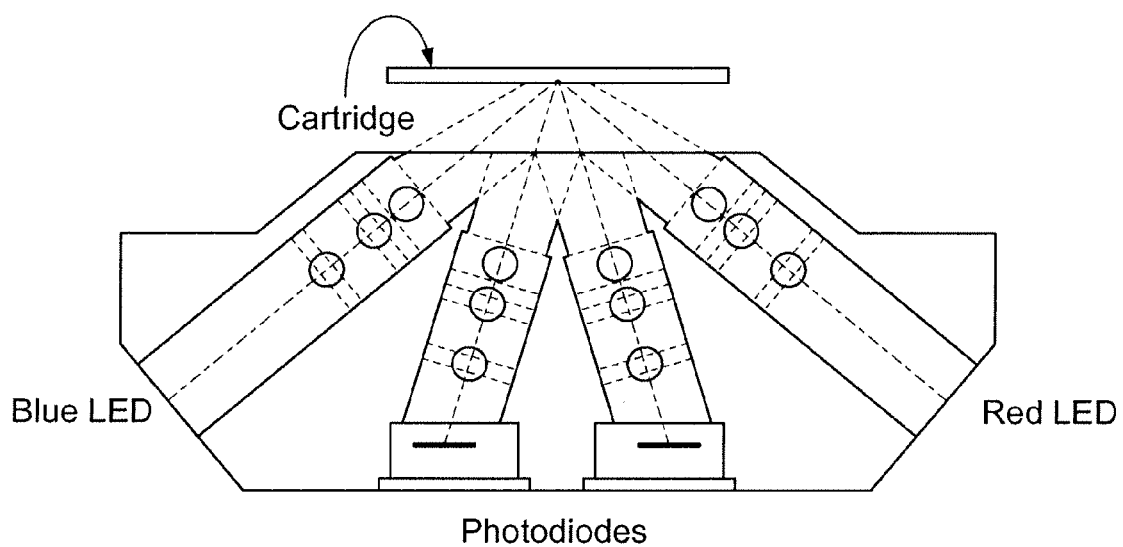
FIG. 57 shows a cross-sectional view of an exemplary detector.
Figure 58:
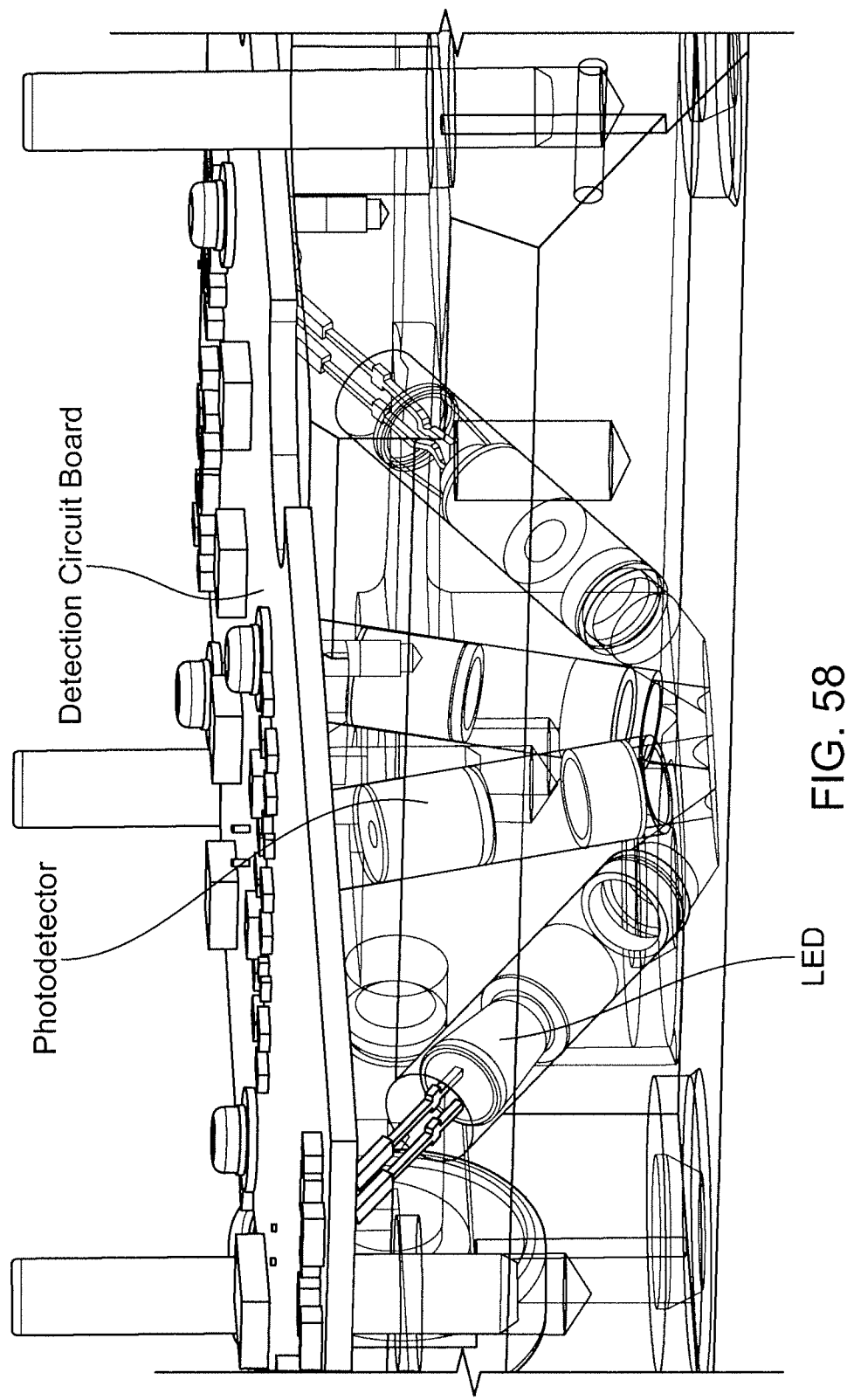
FIG. 58 shows a perspective view of a detector in a read-head.
Figure 59:
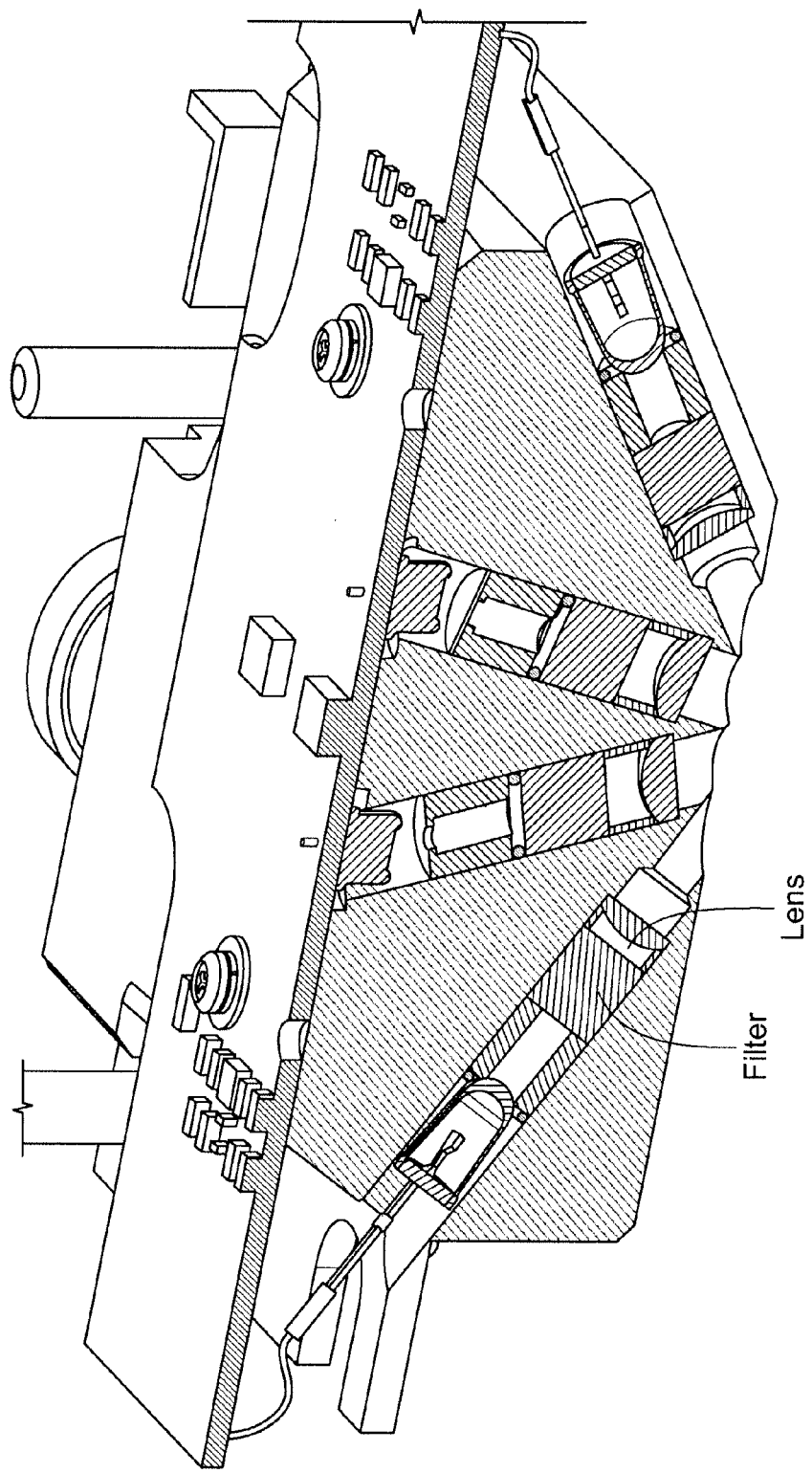
FIG. 59 shows a cutaway view of an exemplary detector in a read-head.

FIGS. 57-59 depict an embodiment of a highly sensitive fluorescence detection system including light emitting diodes (LED's), photodiodes, and filters/lenses for monitoring, in real-time, one or more fluorescent signals emanating from the microfluidic cartridge. The embodiment in FIGS. 57-59 has a two-color detection system having a modular design that mates with a single lane microfluidic cartridge. The detector comprises two LED's (blue and red, respectively) and two photodiodes. The two LED's are configured to transmit a beam of focused light on to a particular region of the cartridge. The two photodiodes are configured to receive light that is emitted from the region of the cartridge. One photodiode is configured to detect emitted red light, and the other photodiode is configured to detect emitted blue light.

Figure 60:
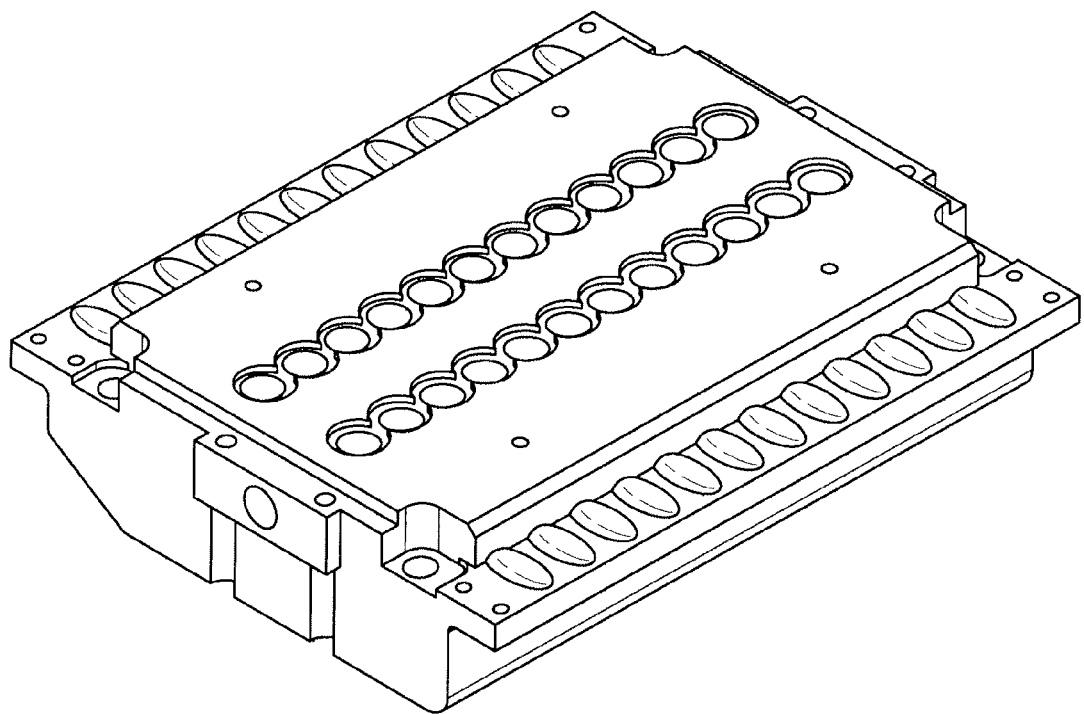
FIG. 60 shows an exterior view of an exemplary multiplexed read-head with an array of detectors therein.
Figure 61:
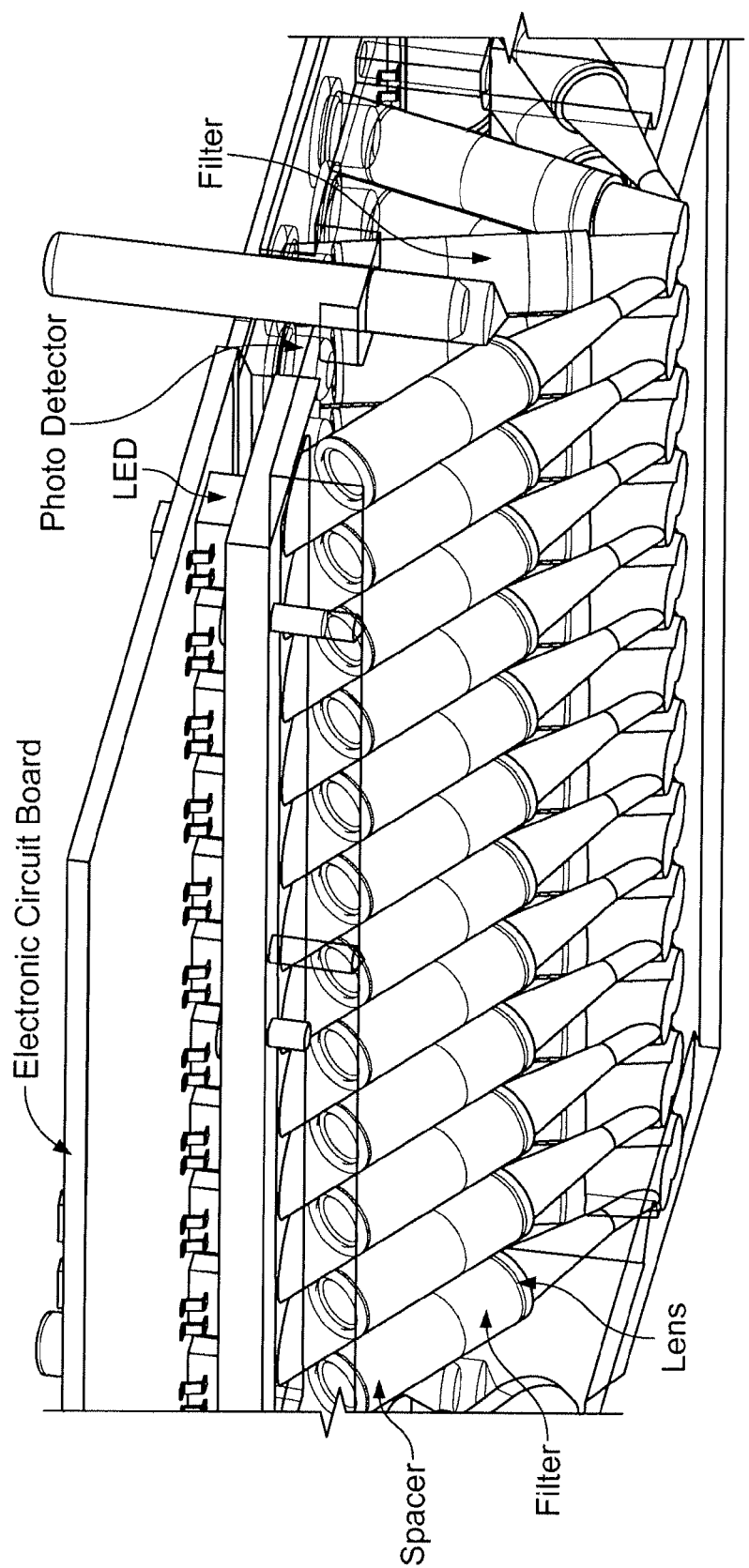
FIG. 61 shows an cutaway view of an exemplary multiplexed read-head with an array of detectors therein.

FIGS. 60 and 61 show an exemplary read-head comprising a multiplexed 2 color detection system, such as multiple instances of a detection system shown in FIGS. 57-59, that is configured to mate with a multi-lane microfluidic cartridge. FIG. 60 shows a view of the exterior of a multiplexed read-head. FIG. 61 is an exploded view that shows how various detectors are configured within an exemplary multiplexed read head, and in communication with an electronic circuit board.

The module in FIGS. 60 and 61 is configured to detect fluorescence from each lane of a 12-lane cartridge, and therefore comprises 24 independently controllable detectors, arranged as 12 pairs of identical detection elements. Each pair of elements is then capable of dual-color detection of a predetermined set of fluorescent probes. It would be understood by one of ordinary skill in the art that other numbers of pairs of detectors are consistent with the apparatus described herein. For example, 4, 6, 8, 10, 16, 20, 24, 25, 30, 32, 36, 40, and 48 pairs are also consistent and can be configured according to methods and criteria understood by one of ordinary skill in the art.

Exemplary Optics Assembly

In an exemplary embodiment, the optical chassis/pressure assembly is housed in an enclosure (made of plastic in certain embodiments) that can be positioned to cover a multi-lane microfluidic cartridge. The enclosure can optionally have a handle that can be easily grasped by a user, and is guided for smooth and easy pushing and pulling. The handle may also serves as a pressure-locking device. The enclosure's horizontal position is sensed in both the all-open and in the all-forward position, and reported to controlling software. The enclosure and optical chassis pressure assembly registers with a heater cassette module positioned underneath a microfluidic cartridge to within 0.010". A close fit is important for proper heater/cartridge interface connections. The enclosure assembly does not degrade in performance over a life of 10,000 cycles, where a cycle is defined as: beginning with the slider in the back position, and sliding forward then locking the handle down on a cartridge, unlocking the handle and returning it to the original back position. All optical path parts should be non-reflective (anodized, painted, molded, etc.) and do not lose this feature for 10,000 cycles. The optics unit is unaffected by a light intensity of <=9,000 foot-candles from a source placed 12" from the instrument at angles where light penetration is most likely to occur. No degradation of performance is measured at the photo-detector after 10,000 cycles.

When fabricating a detector assembly, a single channel is made that houses two LED sources (blue and amber) and two additional channels that house one photodiode detector each (four total bored holes). The two paired channels (source and detector) are oriented 43° from each other, measured from the optical axis and are in-line with the other paired channels that are at the same 43° orientation. The holes bored in the optical chassis contain filters and lenses with appropriate spacers, the specifications of which are further described herein. The LED's are held in place to prevent movement as the mechanical alignment is important for good source illumination. The LED's are preferably twisted until the two "hot spots" are aligned with the reading channels on the cartridge. This position must be maintained until the LED's cannot be moved. The optical chassis can be made of aluminum and be black anodized. The bottom pressure surface of the optical chassis is flat to ±0.001" across the entire surface. The optical chassis is center-balanced such that the center of the optical chassis force is close to the center of the reagent cartridge. The pressure assembly (bottom of the optical chassis) provides uniform pressure of a minimum of 1 psi across all heater sections of the reagent cartridge. The optical assembly can be moved away from the reagent cartridge area for cartridge removal and placement. Appropriate grounding of the optical chassis is preferred to prevent spurious signals to emanate to the optic PCB.

The LED light sources (amber and blue) are incident on a microfluidic cartridge through a band pass filter and a focusing lens. These LED light sources have a minimum output of 2800 millicandles (blue) and 5600 millicandles (Green), and the center wavelengths are 470 (blue) and 575 (amber) nanometers, with a half band width of no more than 75 nanometers.

The LED light excites at least one fluorescent molecule (initially attached to an oligonucleotide probe) in a single chamber on a cartridge, causing it to fluoresce. This fluorescence will normally be efficiently blocked by a closely spaced quencher molecule. DNA amplification via TAQ enzyme will separate the fluorescent and quenching molecules from the oligonucleotide probe, disabling the quenching. DNA amplification will only occur if the probe's target molecule (a DNA sequence) is present in the sample chamber. Fluorescence occurs when a certain wavelength strikes the target molecule. The emitted light is not the same as the incident light. Blue incident light is blocked from the detector by the green only emission filter. Green incident light similarly is blocked from the detector by the yellow emission filter. The fluorescent light is captured and travels via a pathway into a focusing lens, through a filter and onto a very sensitive photodiode. The amount of light detected increases as the amount of the DNA amplification increases. The signal will vary with fluorescent dye used, but background noise should be less than 1 mV peak-to-peak. The photo-detector, which can be permanently mounted to the optical chassis in a fixed position, should be stable for 5 years or 10,000 cycles, and should be sensitive to extremely low light levels, and have a dark value of no more than 60 mV. Additionally, the photo-detector must be commercially available for at least 10 years. The lenses are Plano-convex (6 mm detector, and 12 mm source focal length) with the flat side toward the test cartridge on both lenses. The filters should remain stable over normal operating humidity and temperature ranges.

The filters, e.g., supplied by Omega Optical (Brattleboro, Vt. 05301), are a substrate of optical glass with a surface quality of F/F per Mil-C-48497A. The individual filters have a diameter of 6.0±0.1 mm, a thickness of 6.0±0.1 mm, and the AOI and ½ cone AOI is 0 degrees and ±8 degrees, respectively. The clear aperture is >/=4 mm diameter and the edge treatment is blackened prior to mounting in a black, anodized metal ring. The FITC exciter filters is supplied by, e.g., Omega Optical (PN 481AF30-RED-EXC). They have a cut-off frequency of 466±4 nm and a cut-on frequency of 496±4 nm. Transmission is >/=65% peak and blocking is: >/=OD8 in theory from 503 to 580 nm, >/=OD5 from 501-650 nm, >/=OD4 avg. over 651-1000 nm, and >/=OD4 UV-439 nm. The FITC emitter filters is supplied by, e.g., Omega Optical (PN 534AF40-RED-EM). They will have a cut-off frequency of 514±2 nm and a cut-on frequency of 554±4 mm. Transmission is >/=70% peak and blocking is: >/=OD8 in theory from 400 to 504 nm, >/=OD5 UV-507 nm, and >/=OD4 avg. 593-765 nm. The amber exciter filters are supplied by, e.g., Omega Optical (PN 582AF25-RED-EXC). They have a cut-off frequency of 594±5 nm and a cut-on frequency of 569±5 nm. Transmission is >/=70% peak and blocking is: >/=OD8 in theory from 600 to 700 nm, >/=OD5 600-900 nm, and >/=OD4 UV-548 nm. The amber emitter filters are supplied by, e.g., Omega Optical (PN 627AF30-RED-EM). They have a cut-off frequency of 642±5 nm and a cut-on frequency of 612±5 nm. Transmission is >/=70% peak and blocking is: >/=OD8 in theory from 550 to 600 nm, >/=OD5 UV-605 nm, and >/=OD5 avg. 667-900 nm. The spacers should be inert and temperature stable throughout the entire operating range and should maintain the filters in strict position and alignment. The epoxy used should have optically black and opaque material and dry solid with no tacky residue. Additionally, it should have temperature and moisture stability, exert no pressure on the held components, and should mount the PCB in such a way that it is fixed and stable with no chances of rotation or vertical height changes. 50% of illumination shall fall on the sample plane within an area 0.1" (2.5 mm) wide by 0.3" (7.5 mm) along axis of the detection channel. Fluorescence of the control chip should not change more than 0.5% of the measured signal per 0.001" of height though a region ±0.010 from the nominal height of the control chip.

Figure 62:
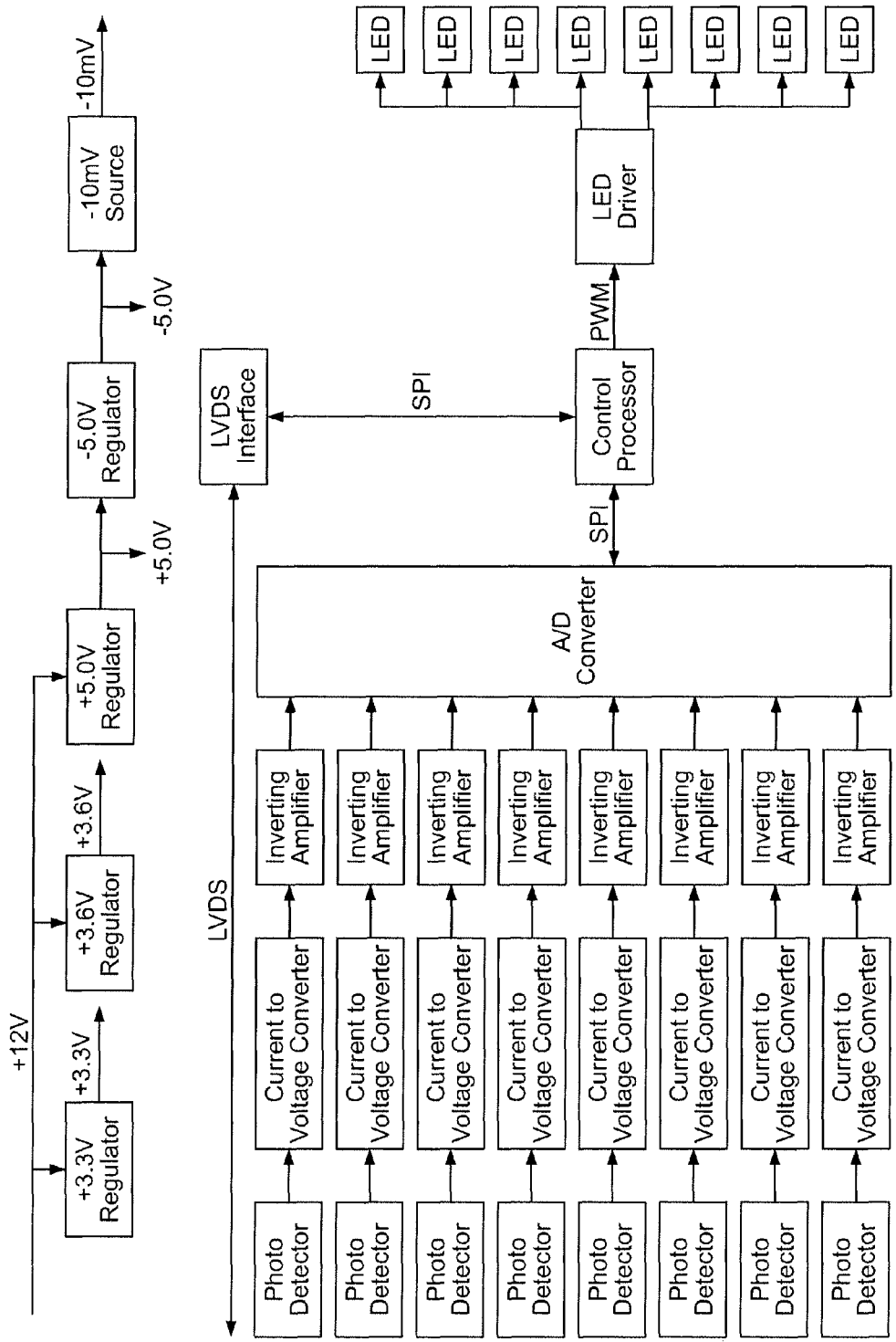
FIG. 62 shows a block diagram of exemplary electronic circuitry in conjunction with a detector as described herein.
Figure 63:
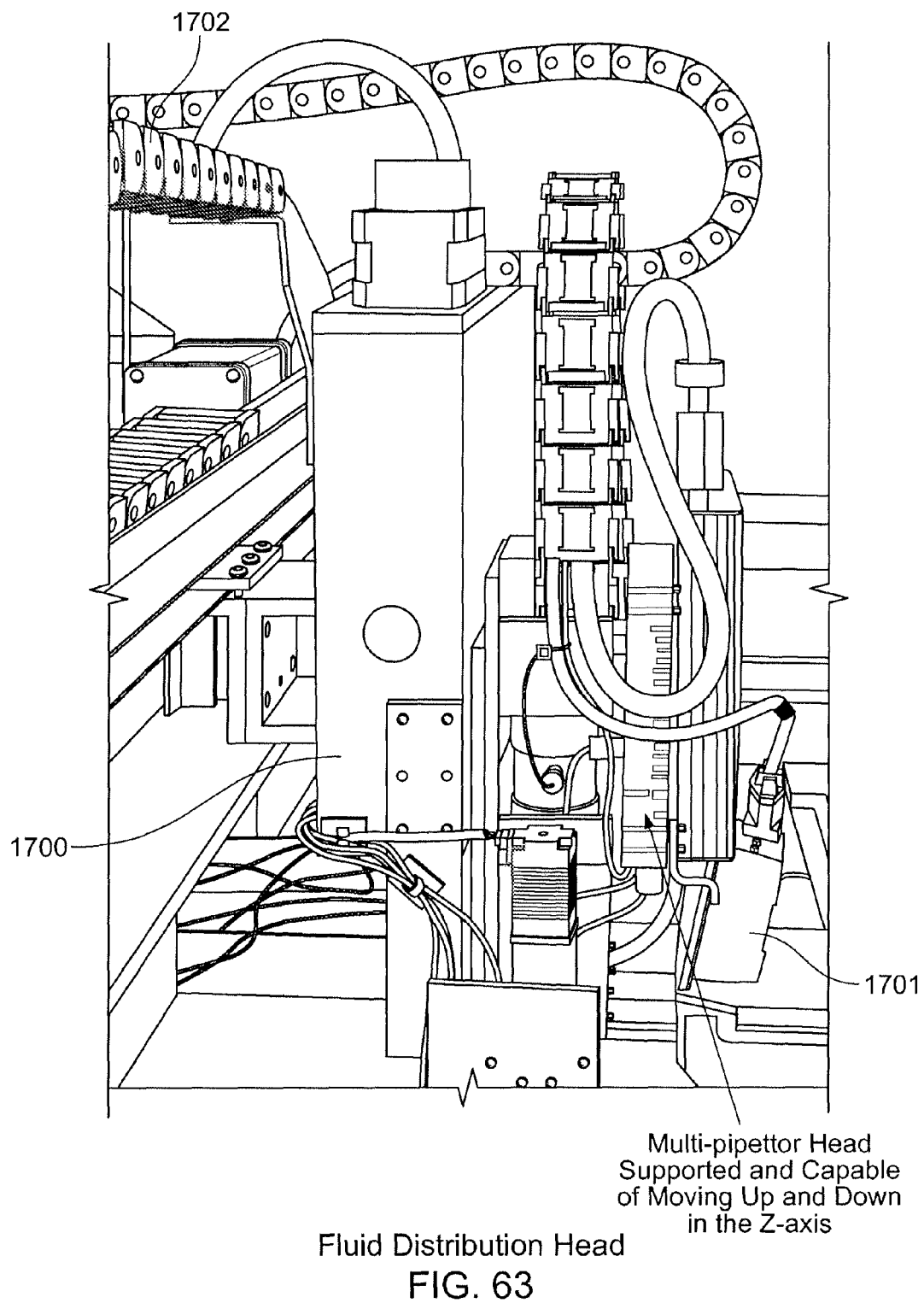
FIG. 63 shows an exemplary liquid dispensing system.

An exemplary optics board is shown in FIG. 62, and is used to detect and amplify the fluorescent signature of a successful chemical reaction on a micro-fluidic cartridge, and controls the intensity of LED's using pulse-width modulation (PWM) to illuminate the cartridge sample over up to four channels, each with two color options. Additionally, it receives instructions and sends results data back over an LVDS (low-voltage differential signaling) SPI (serial peripheral interface). The power board systems include: a +12V input; and +3.3V, +3.6V, +5V, and −5V outputs, configured as follows: the +3.3V output contains a linear regulator, is used to power the LVDS interface, should maintain a +/−5% accuracy, and supply an output current of 0.35 A; the +3.6V output contains a linear regulator, is used to power the MSP430, should maintain a +/−5% accuracy, and supply an output current of 0.35 A; the +5V output contains a linear regulator, is used to power the plus rail for op-amps, should maintain a +/−5% accuracy, and supply an output current of 0.35 A; the −5V output receives its power from the +5V supply, is used to power the minus rail for op-amps and for the photo-detector bias, should maintain a +/−1% voltage accuracy, and supply an output current of 6.25 mA +/−10%. Additionally, the power board has an 80 ohm source resistance, and the main board software can enable/disable the regulator outputs.

The main board interface uses a single channel of the LVDS standard to communicate between boards. This takes place using SPI signaling over the LVDS interface which is connected to the main SPI port of the control processor. The interface also contains a serial port for in-system programming.

The exemplary optical detection system of FIG. 62 consists of a control processor, LED drivers, and a photo-detection system. In the exemplary embodiment, the control processor is a TI MSP430F1611 consisting of a dual SPI (one for main board interface and one for ADC interface) and extended SRAM for data storage. It has the functions of power monitoring, PWM LED control, and SPI linking to the ADC and main board. The LED drivers contain NPN transistor switches, are connected to the PWM outputs of the control processor, can sink 10 mA @ 12V per LED (80 mA total), and are single channel with 2 LEDs (one of each color) connected to each. The photo-detection system has two channels and consists of a photo-detector, high-sensitivity photo-diode detector, high gain current to voltage converter, unity gain voltage inverting amplifier, and an ADC. Additionally it contains a 16 channel Sigma-delta (only utilizing the first 8 channels) which is connected to the second SPI port of the control processor. It would be understood by one of ordinary skill in the art that other choices and combinations of elements can be brought together to make a functioning detection system consistent with the description herein.

Additional Advantages and Features of the Technology Herein

The use of a disposable process chamber, having surface coating and material properties to allow low volume, and open tube heated release to maximize sample concentration in lowest volume possible.

The integrated magnetic heat separator that allows multiple samples to be heated independently but separated using a single moveable magnet platform.

A reader/tray design that allows easy placement of microfluidic cartridge and multiple sample pipetting of liquid using a robotic dispenser in one position; relative displacement to another location and pressure application for subsequent rapid heat incubation steps and optical detection. The bottom surface of the cartridge mates with the heating surface. Furthermore, it is typically easier to move a cartridge and heater in and out of position than a detector.

A moveable readhead design for fluorescence detection from microfluidic PCR channels.

Aspects of the holder, such as a unitized disposable strip, that include the presence of sealed lyophilized reagents as well as liquids sealed in close proximity, which is normally hard to achieve. The laminates deployed herein make storage easier.

The holder permits snapping of multiple ASR tubes, and associated liquid dispensing processes that minimizes cross-sample contamination but multiple PCR preparations to be performed from a single clinical sample.

Software features allow a user to either get results from all 24 samples as quickly as possible or the first 12 samples as quickly as possible and the next 12 later.

The preparatory and diagnostic instruments described herein enables different sample types (such as blood, urine, swab, etc.) to be all processed at the same time even though each may require different temperatures, times or chemical reagents. This is achieved in part by using individualized but compatible holders.

Automatic feeding of microfluidic cartridges into a PCR reader via a cartridge autoloader saves a user time and leads to increased efficiency of overall operation.

Piercing through foil over a liquid tube and reliable way of picking up liquid.

A moveable read-head that has the pumps, sensors (pipette detection, force sensing), sample identification verifier, etc., moving with it, and therefore minimizes the number of control lines that move across the instrument during use.

Accurate and rapid alignment of pipette tips with cartridge inlet holes using a motorized alignment plate.

EXAMPLES

Example 1

Reagent Holder

An exemplary reagent holder consistent with the description herein has the following dimensions and capacities:
180 mm long×22 mm wide×100 mm tall;
Made from Polypropylene.
One snapped-in low binding 1.7 ml tube that functions as a process tube.
3 built-in tubes that function as receptacles for reagents, as follows:
   One tube containing 200-1000 µl of wash buffer (0.1 mM Tris, pH 8).
   One tube containing 200-1000 µl of release solution (40 mM NaOH).
   One tube containing 200-1000 µl of neutralization solution (330 mM Tris, pH 8.0).
One built-in tube that functions as a waste chamber (will hold ~4 ml of liquid waste).
3 receptacles to accept containers for solid reagents. Snap-in 0.3 ml or 0.65 ml PCR tubes (which are typically stored separately from the reagent holder) are placed in each of these locations, and contain, respectively:
   lyophilized sample preparation reagents (lysis enzyme mix and magnetic affinity beads).
   First lyophilized PCR master mix, probes and primers for a first target analyte detection.
   Second lyophilized PCR master mix, probes and primers for a second target analyte detection (only offered in select cases, such as detection of *Chlamydia* and *Gonorrhea* from urine).
4 pipette tips located in 4 respective sockets.
Pipette tip Sheath: The pipette tips have a sheath/drip tray underneath to help capture any drip from the pipette tips after being used, and also to prevent unwanted contamination of the instrument.
Handle and Flex-Lock allows easy insertion, removal, and positive location of strip in rack.
One or more labels: positioned upward facing to facilitate ease of reading by eye and/or, e.g., a bar-code reader, the one or more labels containing human and machine readable information pertaining to the analysis to be performed.

It is to be understood that these dimensions are exemplary. However, it is particularly desirable to ensure that a holder does not exceed these dimensions so that a rack and an apparatus that accommodates the reagent holder(s) does not become inconveniently large, and can be suitably situated in a laboratory, e.g., on a bench-top.

Example 2

Disposable Reagent Holder Manufacturing

Simple fixtures can be designed and machined to enable handling and processing of multiple strips. There are five steps that can be performed to produce this component. The disposable reagent holder will be placed in a fixture and filled with liquids using manual/electric-multiple pipetting. Immediately after dispensing all liquids into the strip, foil will be heat sealed to the plastic using exemplary heat seal equipment (Hix FH-3000-D Flat Head Press) and the foil trimmed as required. After heat sealing liquids on board, all pellets in tubes can be snapped into the strip, pipette tips can be inserted in their respective sockets, and a barcode label can be affixed. Desiccant packs can be placed into the blow molded or thermoformed rack designed to house 12 holders. Twelve disposable strips will be loaded into the rack and then sealed with foil. The sealed bag will be placed into a carton and labeled for shipping.

Example 3

Foil-Sealing of Buffer Containing Reagent Tubes

Tubes containing buffers have to be sealed with high moisture vapor barrier materials in order to retain the liquid over a long period of time. Disposable holders may need to have a shelf life of 1-2 years, and as such, they should not lose more than say 10-15% of the liquid volume over the time period, to maintain required volume of liquid, and to maintain the concentration of various molecules present in the solution. Moreover, the materials used for construction of the tube as well as the sealing laminate should not react with the liquid buffer. Special plastic laminates may provide the moisture barrier but they may have to be very thick (more than 300 μm thick), causing the piercing force to go up tremendously, or of special, expensive polymer (such as Aclar). Aluminum foils, even a thin foil of a few hundred angstrom provides an effective moisture barrier but bare aluminum reacts with some liquid buffers, such as sodium hydroxide, even an aluminum foil with a sprayed coating of a non-reactive polymer may not be able to withstand the corrosive vapors over a long time. They may react through tiny pin holes present in the coating and may fail as a barrier over time.

For these reasons, aluminum foils with a laminate structure have beer; identified as a suitable barrier, exemplary properties of which are described below:
1. Sealing
   Heat seals to unitized polypropylene strip (sealing temp ~170-180° C.)
   No wrinkling, cracking and crazing of the foil after sealing
2. Moisture Vapor Transmission Rate (MVTR)
   Loss of less than 10% liquid (20 microliters from a volume of 200 microliter) for a period of 1 year stored at ambient temperature and pressure. (effective area of transport is ~63 mm$^2$); Approximate MVTR ~0.8 cc/m$^2$/day
3. Chemistry
   Ability to not react with 40 mM Sodium Hydroxide (pH<12.6): foil should have a plastic laminate at least 15 microns thick closer to the sealed fluid.
   Ability to not react with other buffers containing mild detergents
4. Puncture
   Ability to puncture using a p1000 pipette with a force less than 3 lb
   Before puncturing, a fully supported membrane 8 mm in diameter will not stretch more than 5 mm in the orthogonal direction
   After puncturing, the foil should not seal the pipette tip around the circumference of the pipette.
5. Other Features
   Pin-hole free
   No bubbles in case of multi-laminate structures.

Example 4

Mechanism of Piercing Through a Plasticized Laminate and Withdrawing Liquid Buffer The aluminum laminate containing a plastic film described elsewhere herein serves well for not reacting with corrosive reagents such as buffers containing NaOH, and having the favorable properties of pierceability and acting as a moisture barrier. However, it presents some additional difficulties during piercing. The aluminum foil tends to burst into an irregular polygonal pattern bigger than the diameter of the pipette, whereas the plastic film tends to wrap around the pipette tip with minimal gap between the pipette and the plastic film. The diameter of the hole in the plastic film is similar to the maximum diameter of the pipette that had crossed through the laminate. This wrapping of the pipette causes difficulty in dispensing and pipetting operations unless there is a vent hole allowing pressures to equilibrate between outside of the tube and the air inside of the tube.

A strategy for successful pipetting of fluid is as follows:
1. Pierce through the laminate structure and have the pipette go close to the bottom of the reagent tube so that the hole created in the laminate is almost as big as the maximum diameter of the pipette (e.g., ~6 mm for a p1000 pipette)
2. Withdraw the pipette up a short distance so that a small annular vent hole is left between the pipette and the laminate. The p1000 pipette has a smallest outer diameter of 1 mm and maximum outer diameter of 6 mm and the conical section of the pipette is about 28 mm long. A vent hole thickness of a hundred microns is enough to create a reliable vent hole. This corresponds to the pipette inserted to a diameter of 5.8 mm, leaving an annulus of 0.1 mm around it.
3. Withdraw fluid from the tube. Note that the tube is designed to hold more fluid than is necessary to withdraw from it for a sample preparation procedure.

Example 5

Foil Piercing and Dissolution of Lyophilized Reagents

The containers of lyophilized reagents provided in conjunction with a holder as described herein are typically sealed by a non-plasticized aluminum foil (i.e., not a laminate as is used to seal the reagent tubes). Aluminum foil bursts into an irregular polygonal pattern when pierced through a pipette and leaves an air vent even though the pipette is moved to the bottom of the tube. In order to save on reagents, it is desirable to dissolve the reagents and maximize the amount withdrawn from the tube. To accomplish this, a star-ridged (stellated)

pattern is placed at the bottom of the container to maximize liquid volume withdrawn, and flow velocity in between the ridges.

Exemplary steps for dissolving and withdrawing fluid are as follows:
1. Pierce through the pipette and dispense the fluid away from the lyophilized material. If the pipette goes below the level of the lyophilized material, it will go into the pipette and may cause jamming of the liquid flow out of the pipette.
2. Let the lyophilized material dissolve for a few seconds.
3. Move pipette down touching the ridged-bottom of the tube
4. Perform an adequate number of suck and spit operations (4-10) to thoroughly mix the reagents with the liquid buffer.
5. Withdraw all the reagents and move pipette to dispense it into the next processing tube.

Example 6

Material and Surface Property of the Lysis Tube

The material, surface properties, surface finish has a profound impact on the sensitivity of the assay performed. In clinical applications, DNA/RNA as low as 50 copies/sample (~1 ml volume) need to be positively detected in a background of billions of other molecules, some of which strongly inhibit PCR. In order to achieve these high level of sensitivities, the surface of the reaction tube as well as the material of the surface has to be chosen to have minimal binding of polynucleotides. During the creation of the injection molding tool to create these plastic tubes, the inherent surfaces created by machining may have large surface area due to cutting marks as large as tens of microns of peaks and valleys. These surfaces have to be polished to SPI A1/A2 finish (mirror finish) to remove the microscopic surface irregularities. Moreover, the presence of these microscopic valleys will trap magnetic beads (0.5-2µ) at unintended places and cause irregular performance. In addition to actual surface roughness, the surface hydrophobicity/surface molecules present may cause polynucleotides to stick at unintended places and reduce sensitivity of the overall test. In addition to the base material uses, such as homogenous polypropylene and other polymers, specific materials used during the molding of these tubes, such as mold release compounds or any additives to aid in the fabrication can have a profound impact on the performance of the reactions.

Example 7

Liquid Dispensing Head

Referring to FIGS. 18, 19A-C, and 63, an exemplary liquid dispenser is attached to a gantry, and receives instructions via electrical cable 1702. Barcode scanner 1701 is mounted on one face of the liquid dispenser. The gantry is mounted on a horizontal rail 1700 to provide movement in the x-direction. Not shown is an orthogonally disposed rail to provide movement in the y-direction. The liquid dispenser comprises a computer controlled motorized pump 1800 connected to fluid distribution manifold 1802 with related computer controlled valving 1801 and a 4-up pipetter with individually sprung heads 1803. The fluid distribution manifold has nine Lee Co. solenoid valves 1801 that control the flow of air through the pipette tips: two valves for each pipette, and an additional valve to vent the pump. Barcode reader 1701 enables positive detection of sample tubes, reagent disposables and microfluidic cartridges. The scanner is mounted to the z-axis so that it can be positioned to read the sample tube, strip, and cartridge barcodes.

Example 8

Integrated Heater/Separator

Figure 64:
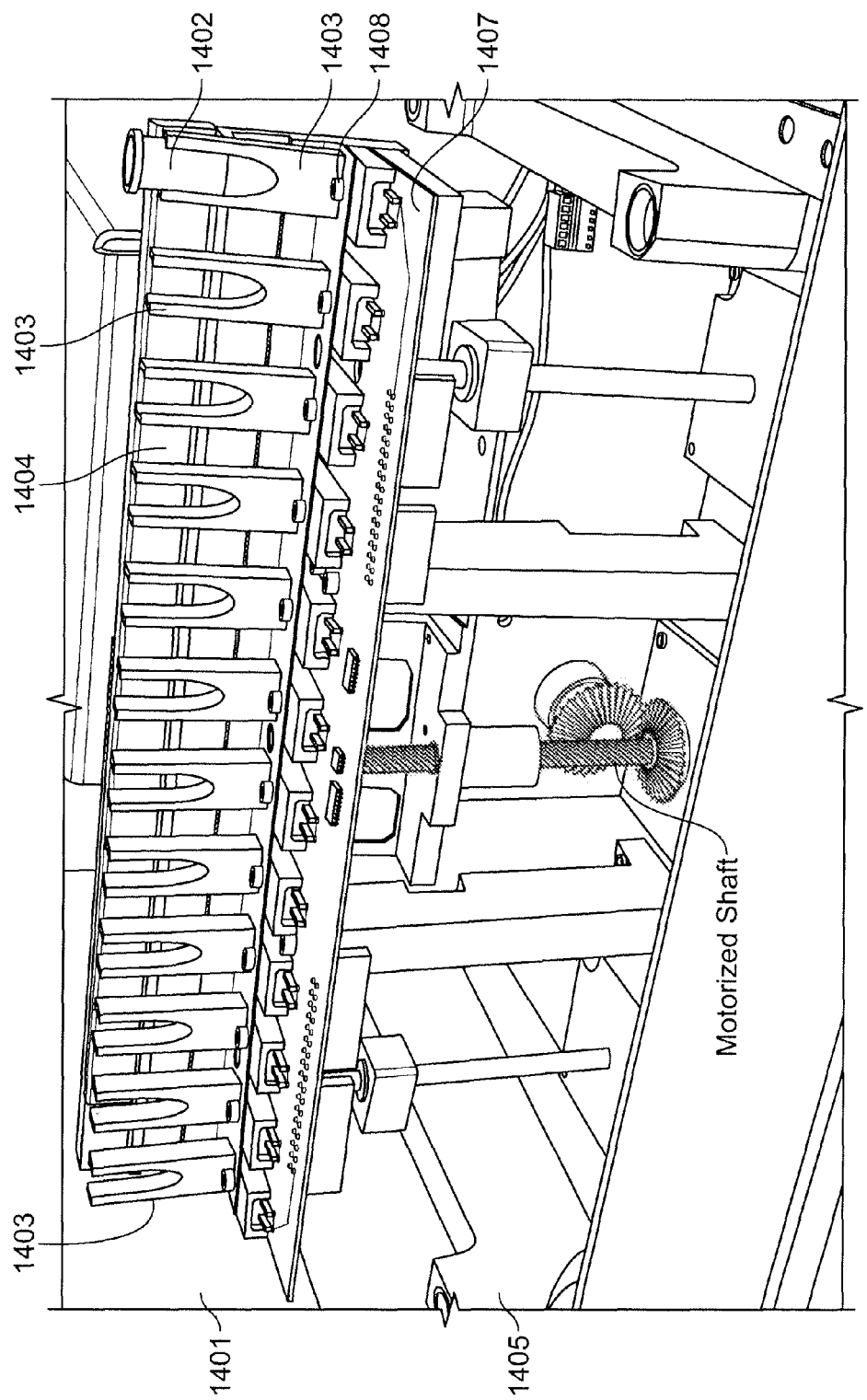
FIG. 64 shows an exemplary heater/separator.

In FIG. 64 an exemplary integrated magnetic separator and heater assembly are shown. Magnetic separator 1400 and heater assembly 1401 were fabricated comprising twelve heat blocks aligned parallel to one another. Each heat block 1403 is made from aluminum, and has an L-shaped configuration having a U-shaped inlet for accepting a process chamber 1402. Each heat block 1403 is secured and connected by a metal strip 1408 and screws 1407. Magnet 1404 is a rectangular block Neodymium (or other permanent rare earth materials, K & J Magnetics, Forcefield Magnetics) disposed behind each heat block 1403 and mounted on a supporting member. Gears 1406 communicate rotational energy from a motor (not shown) to cause the motorized shaft 1405 to raise and lower magnet 1404 relative to each heat block. The motor is computer-controlled to move the magnet at speeds of 1-20 mm/s. The device further comprises a printed circuit board (PCB) 1409 configured to cause the heater assembly to apply heat independently to each process chamber 1402 upon receipt of appropriate instructions. In the exemplary embodiment, the device also comprises a temperature sensor and a power resistor in conjunction with each heater block.

Example 9

Exemplary Software

Exemplary software accompanying use of the apparatus herein can include two broad parts—user interface and device firmware. The user interface software can allow for aspects of interaction with the user such as—entering patient/sample information, monitoring test progress, error warnings, printing test results, uploading of results to databases and updating software. The device firmware can be the low level software that actually runs the test. The firmware can have a generic portion that can be test independent and a portion specific to the test being performed. The test specific portion ("protocol") can specify the microfluidic operations and their order to accomplish the test.

Figure 65A:
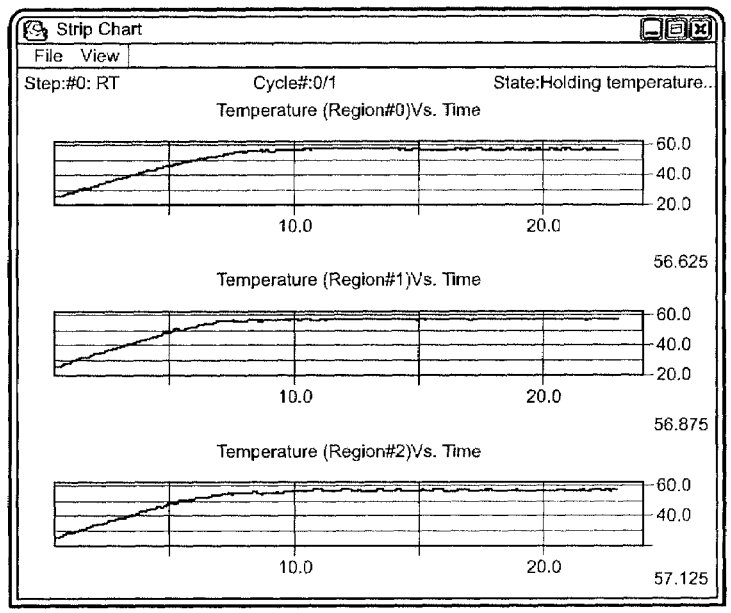
FIGS. 65A and 65B show exemplary aspects of a computer-based user interface.
Figure 65B:
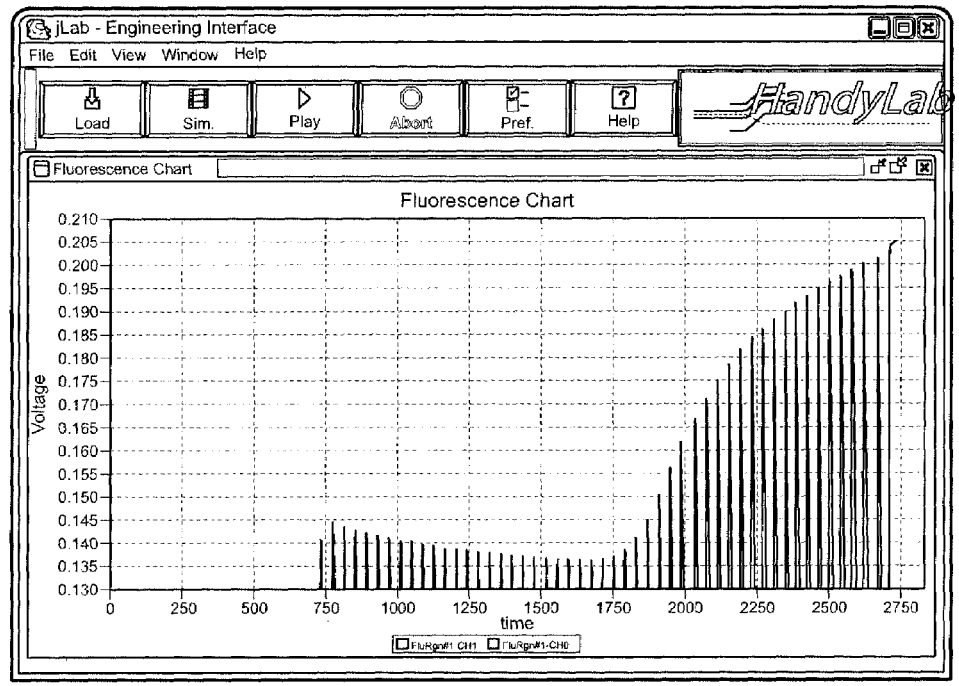

FIGS. 65A and 65B shows screen captures from the programming interface and real time heat sensor and optical detector monitoring. This real time device performance monitoring is for testing purposes; not visible to the user in the final configuration.

User Interface:

A medical grade LCD and touch screen assembly can serve as the user interface via a graphical user interface providing easy operating and minor troubleshooting instructions. The LCD and touch screen have been specified to ensure compatibility of all surfaces with common cleaning agents. A barcode scanner integrated with the analyzer can be configured to scan the barcode off the cartridge (specifying cartridge type, lot#, expiry date) and if available the patient and user ID from one or more sample tubes.

Example 10

Exemplary Preparatory Apparatus

Figure 66:
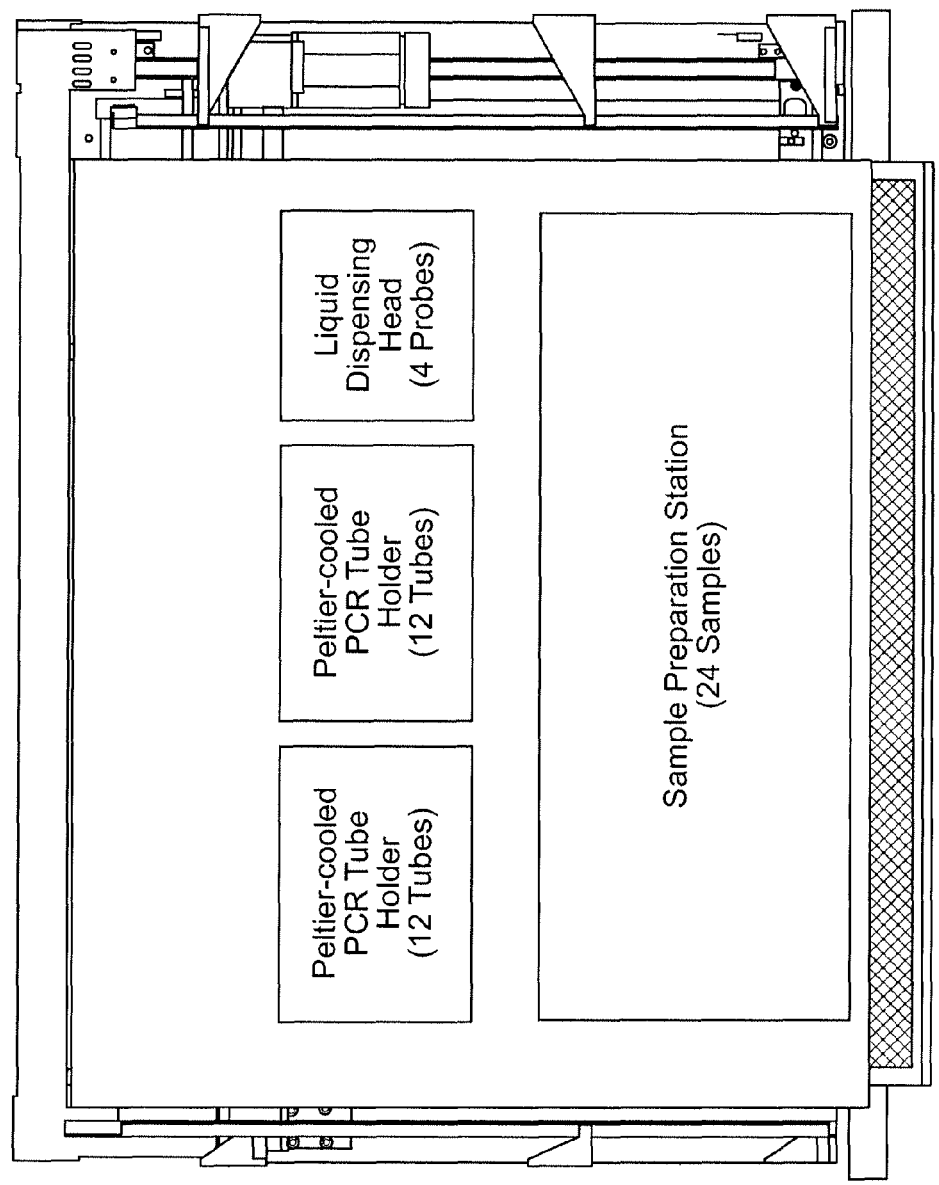
FIG. 66 shows schematically layout of components of a preparatory apparatus.
Figure 67:
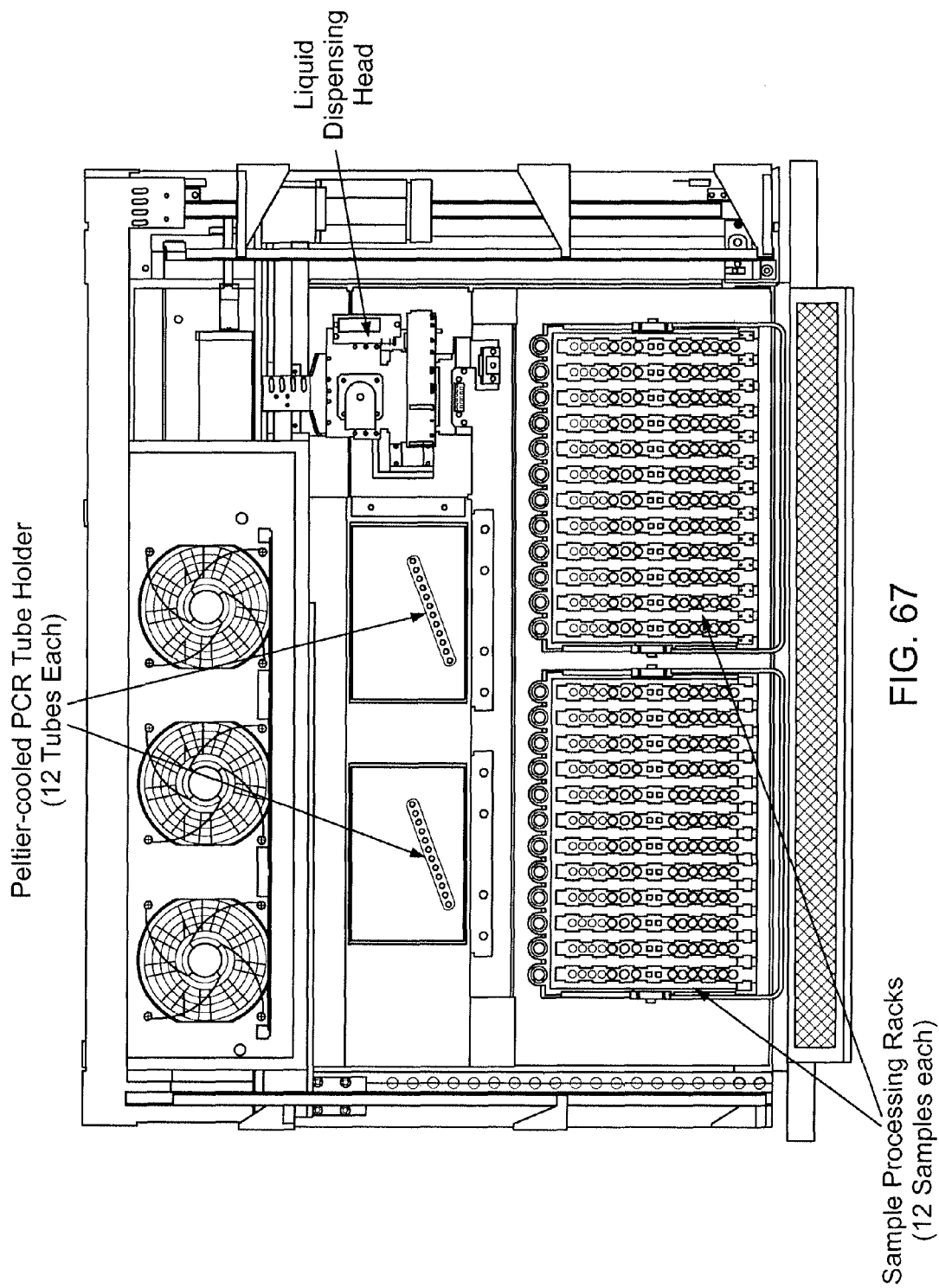
FIG. 67 shows layout of components of an exemplary preparatory apparatus.

This product is an instrument that enables 24 clinical samples to be automatically processed to produce purified nucleic acid (DNA or RNA) in about half an hour (FIG. 66). Purified nucleic acid may be processed in a separate amplification-detection machine to detect the presence of certain target nucleic acids. Samples are processed in a unitized disposable strip, preloaded with sample preparation chemistries and final purified nucleic acids are dispensed into PCR tubes. Fluid handling is enabled by a pipetting head moved by a xyz gantry. (FIG. 67)

The System has the following sub-systems:
Two sample processing racks, each rack processes up to 12 clinical samples in unitized disposable strips
Magnetic separator-cum-tube heater assembly (24 heating stations)
A four-probe liquid dispensing head
3-axis gantry to move the pipette head
Peltier-cooled pcr-tube holding station to receive the purified DNA/RNA
Control electronics
Barcode reader Operation: The user will get a work list for each sample, whether they want to extract DNA or RNA for each clinical sample. The sample tubes are placed on the rack and for each sample type (DNA or RNA), the user slides in a unitized reagent disposable (DNA or RNA processing) into corresponding lane of the rack. The unitized disposable (holder) will have all the sample prep reagents, process tubes as well as disposable pipettes already prepackaged in it. Once all disposables are loaded into the rack, the rack is placed in its location on the instrument. Open pcr tubes are placed in the peltier cooled tube holder where the final purified nucleic acid will be dispensed. The user then closes the door of the instrument and then starts the sample processing using the GUI (Graphical User Interface).

The instrument checks functionality of all subsystems and then reads the barcode of the sample tubes and the unitized reagent disposable. Any mismatch with a pre-existing work list is determined and errors are flagged, if necessary. The instrument then goes through a series of liquid processing, heating, magnetic separations to complete the sample preparation steps for the each of the clinical sample and outputs the purified nucleic acid into the PCR tube. The basic steps involved in each sample processing are sample lysis, nucleic acid capture into magnetic affinity beads, washing of the magnetic beads to remove impurities, releasing the nucleic acid from the magnetic beads, neutralizing the released DNA and the dispensing into the final PCR tube. These tubes are maintained at 4° C. until all samples are processed and user takes away the tube for downstream processing of the nucleic acids.

Example 11

Exemplary Diagnostic Apparatus

The apparatus, in combination with the associated consumables, automatically performs all aspects of nucleic acid testing, including sample preparation, amplification, and detection for up to 48 samples per hour with the first 24 results available in less than an hour. The system is easy to use. An operator simply aliquots a portion of the patient sample into a dedicated tube that contains pre-packaged buffer. The operator places the dedicated tubes into positions on a sample rack. The operator then loads a disposable plastic reagent strip for the appropriate test in the rack. The only other consumable used in the apparatus are microfluidic PCR cartridges for conducting amplification and detection; each cartridge is capable of performing up to twelve PCR tests and two cartridges can be loaded into the analyzer at once. Should the apparatus require a new PCR cartridge, the analyzer will prompt the operator to load the cartridge. The analyzer will then prompt the operator to close the lid to initiate testing. All consumables and sample tubes are barcoded for positive sample identification.

Sample lysis and DNA preparation, which will require approximately half an hour for a full run of 24 samples, is automatically performed by the analyzer's robotic and liquid handling components using protocols and reagents located in unitized, disposable plastic strips. The apparatus then automatically mixes the sample and PCR reagents, and injects the mixture into a cartridge that will be automatically processed by an integrated PCR machine. Rapid, real time PCR and detection requires less than 20 minutes. Results, which will be automatically available upon completion of PCR, are displayed on the instruments touch screen, printed or sent to the hospital information system, as specified by the user (or the user's supervisor).

Each instrument can process up to 24 samples at a time with a total throughput of 48 samples per hour after the first run. The analyzer is slightly less than 1 m wide and fits easily on a standard lab bench. All operations of the unit can be directed using the included barcode wand and touch screen. The analyzer can be interfaced with lab information systems, hospital networks, PCs, printers or keyboards through four USB interfaces and an Ethernet port.

The apparatus has the following characteristics.

Sensitivity: the apparatus will have a limit of detection of ~50 copies of DNA or RNA. (and may have a limit of detection as low as 25-30 copies of DNA/RNA).

Cost per Test: Due to the miniaturized, simplified nature of HandyLab reagents, cartridge and other consumables, the cost of goods per test will be relatively low and very competitive.

Automation: By contrast with current "automated" NAT systems, which all require some degree of reasonably extensive technologist interaction with the system, through the use of unitized tests and full integration of sample extraction, preparation, amplification and detection, the apparatus herein will offer a higher level of automation, and corresponding reduction in technologist time and required skill level, thereby favorably impacting overall labor costs.

Throughput: Throughput is defined as how many tests a system can conduct in a given amount of time. The apparatus will be capable of running 45 tests per hour, on average.

Time to First Result: In a hospital environment, time to first result is an especially important consideration. The apparatus will produce the first 24 results in less than an hour and an additional 24 results every half hour thereafter.

Random Access and STAT: Random access is the ability to run a variety of tests together in a single run and place samples in unassigned locations on the analyzer. Also, with chemistry and immunoassay systems, it is desirable to be able to add tests after a run has started. This is often referred to as "true random access" since the user is provided complete flexibility with regard to what tests can be run where on an analyzer and when a new sample can be added to a run. A STAT is a sample that requires as rapid a result as possible, and therefore is given priority in the testing cue on the analyzer. Today, essentially all chemistry and immunoassay analyzers are true random access and offer STAT capabilities. For NAT, however, very few systems offer any random access or STAT capabilities. The instrument herein will provide random access and STAT capabilities.

Menu: The number and type of tests available for the analyzer is a very important factor in choosing systems. The apparatus herein deploys a launch menu strategy that involves a mix of high volume, "standard" nucleic acid tests combined with novel, high value tests.

Figure 68:
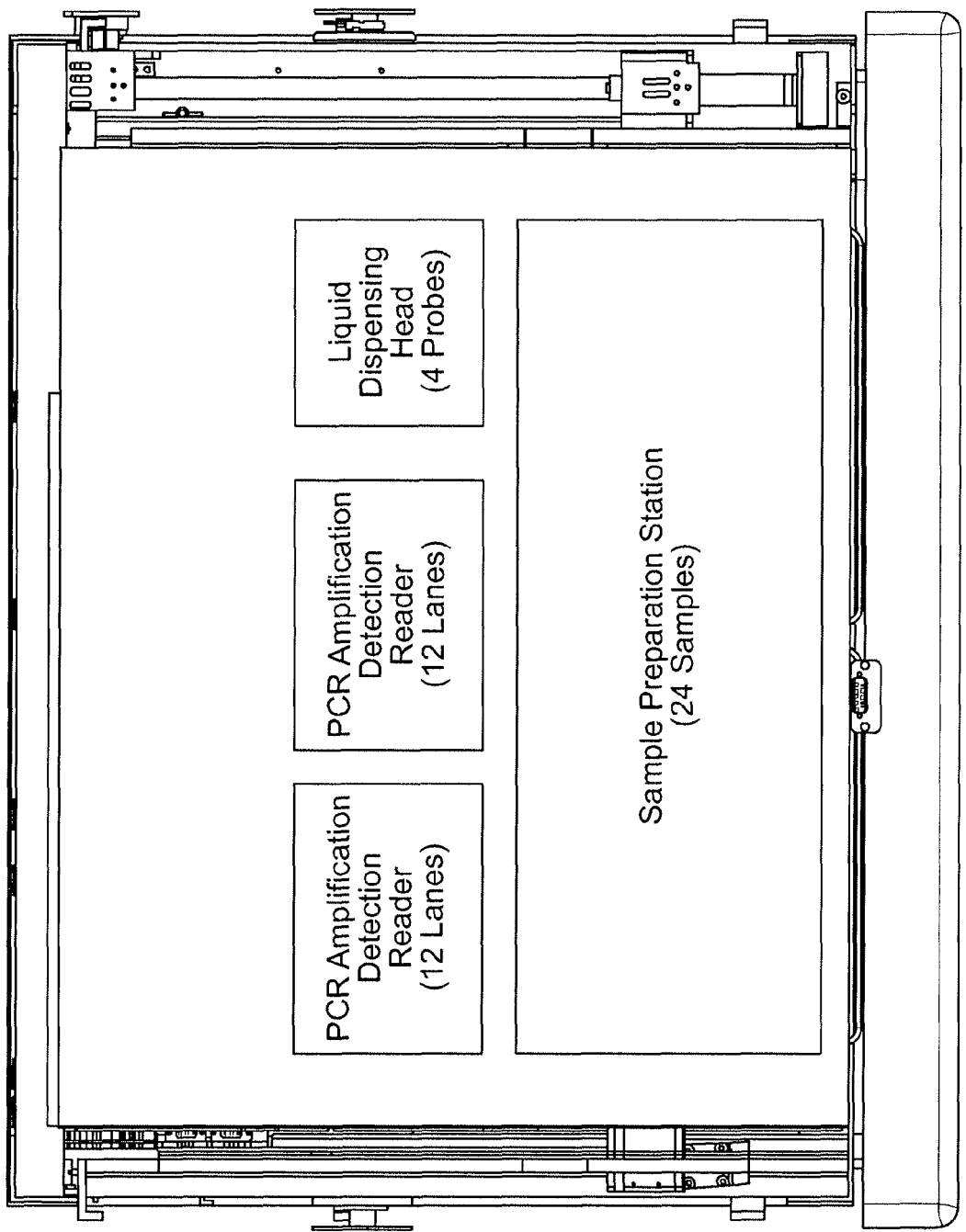
FIG. 68 shows schematically layout of components of a diagnostic apparatus.
Figure 69:
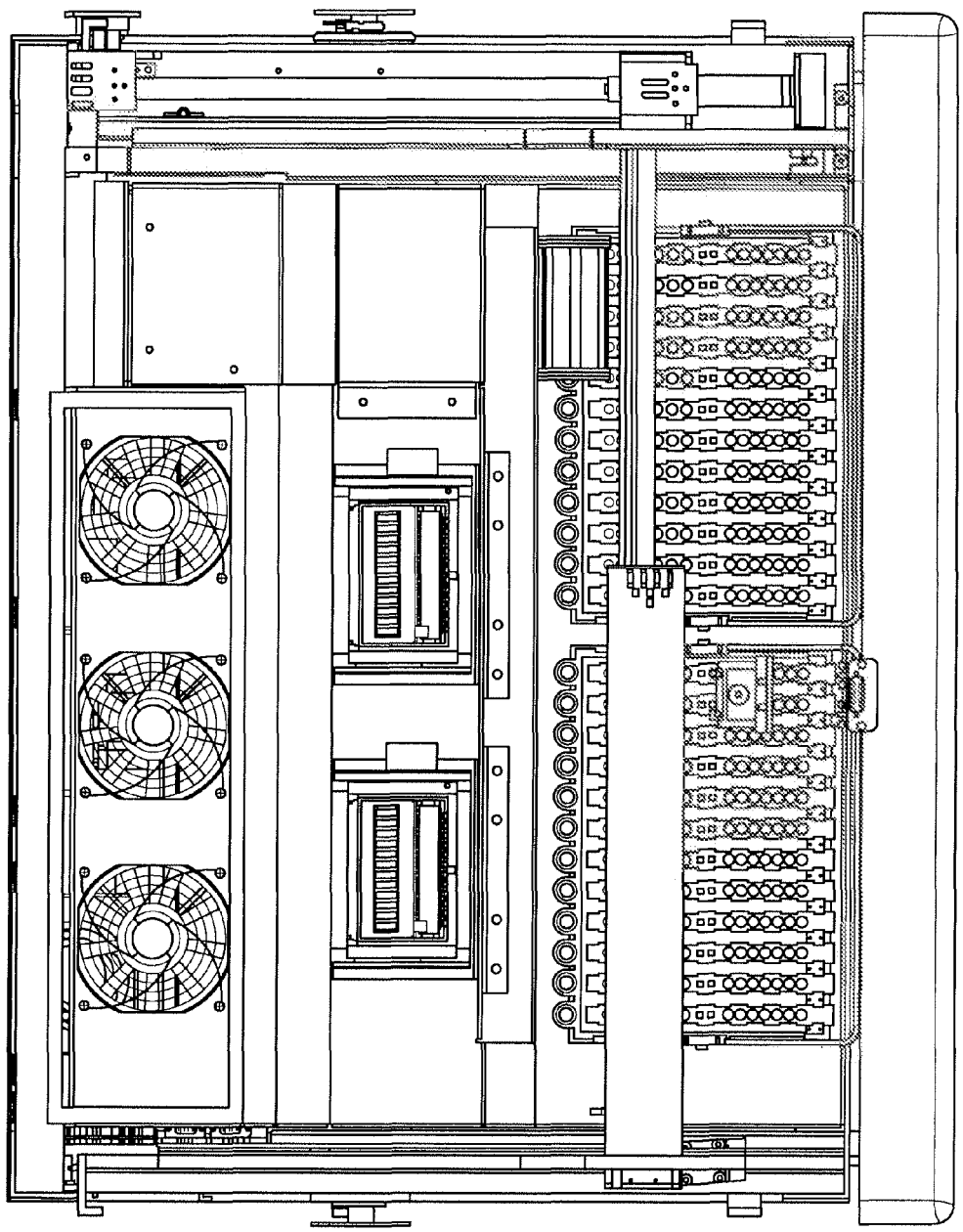
FIG. 69 shows layout of components of an exemplary diagnostic apparatus.

The apparatus enables 24 clinical samples to be automatically processed to purify nucleic acid, mix the purified DNA/RNA with PCR reagents and perform real-time PCR in microfluidic cartridge to provide sample to results in an hour. The exemplary apparatus has two PCR readers, each capable of running a 12 lane microfluidic cartridge using an optical system that has dedicated two-color optical detection system. FIG. 68, FIG. 69.

Figure 70:
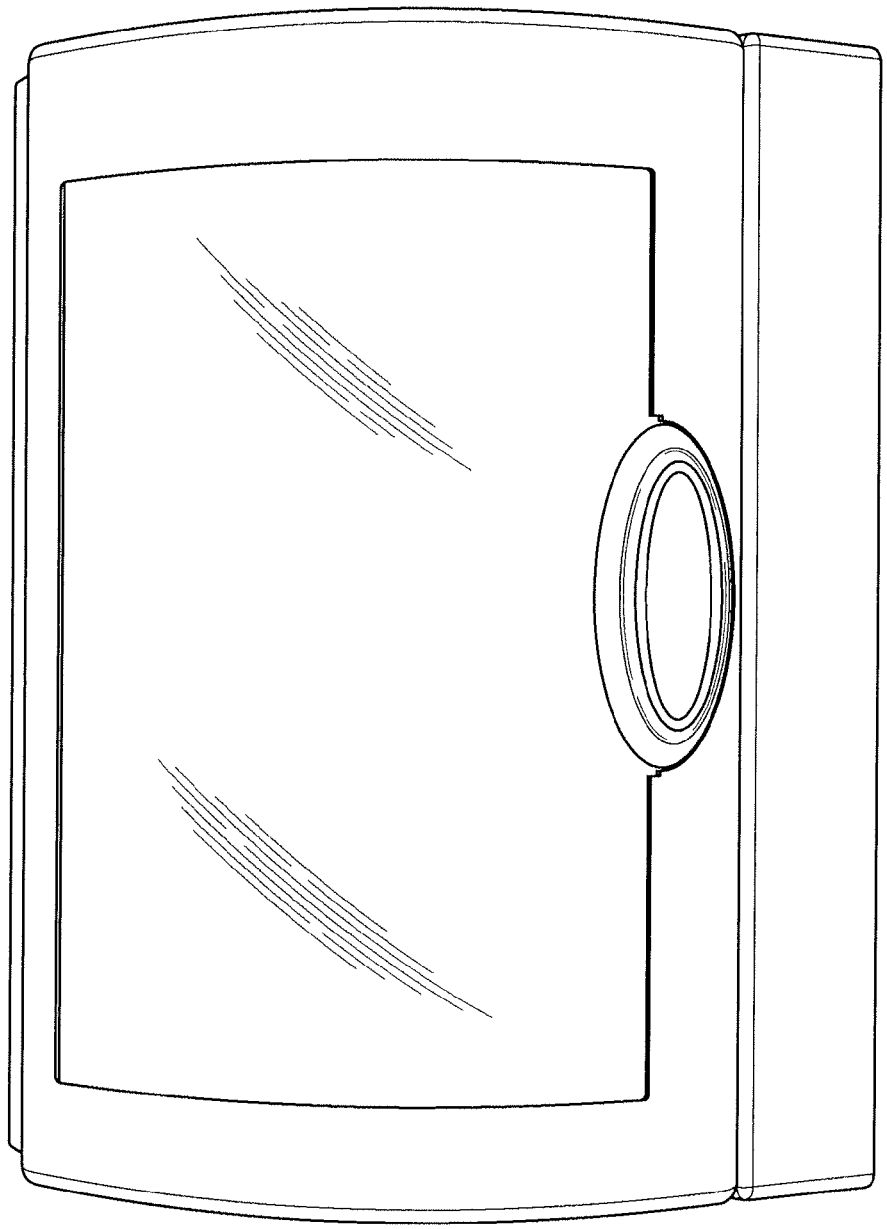
FIGS. 70 and 71 show exterior and interior of an exemplary diagnostic apparatus.
Figure 71:
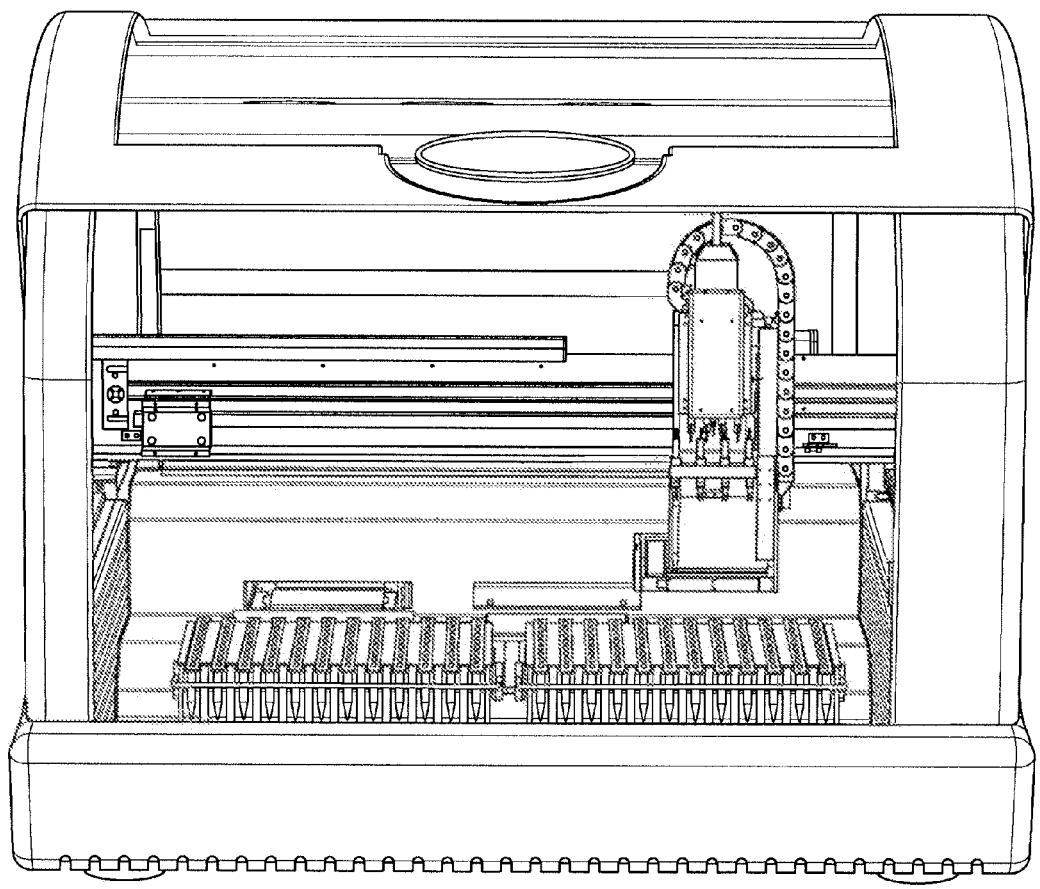

The apparatus has the following sub-systems:
Two sample processing racks, each rack processes up to 12 clinical samples in unitized disposable strips
Magnetic separator-cum-tube heater assembly (24 heating stations)
A four-probe liquid dispensing head
3-axis gantry to move the pipette head
Two PCR amplification-detection station, each capable of running a 12-lane microfluidic cartridge and dedicated 2-color optical detection system for each PCR lane.
Control electronics
Barcode reader
Pictures of exterior (face on) and interior are at FIGS. 70, 71, respectively.

Operation: The user will get a work list for each sample, whether they want to detect certain target analyte (such as GBS, *Chlamydia, Gonnorrhoea*, HSV) for each clinical sample. The sample tubes are placed on the rack and for each sample, the user slides in a unitized reagent disposable (analyte specific) into corresponding lane of the rack. The unitized disposable will have all the sample prep reagents, PCR reagents, process tubes as well as disposable pipettes already prepackaged in it. Once all disposables are loaded into the rack, the rack is placed in its location on the instrument. The user then places two 12-lane microfluidic PCR cartridges in the two trays of the PCR reader. The user then closes the door of the instrument and then starts the sample processing using the GUI (Graphical User Interface).

The instrument checks functionality of all subsystems and then reads the barcode of the sample tubes, the unitized reagent disposables and the microfluidic cartridges. Any mismatch with a pre-existing work list is determined and errors are flagged, if necessary. The instrument than goes through a series of liquid processing, heating, magnetic separation to complete the sample preparation steps for the each of the clinical sample, mixes the purified nucleic acid with PCR reagents and dispenses the final mix into a lane of the microfluidic cartridges. After a microfluidic cartridge is loaded with the final PCR mix, the cartridge tray moves and aligns the cartridge in the reader and the optical detection system presses the cartridge against a microfluidic PCR heater surface. On-chip valves are actuated to close the reaction mix and then thermocycling is started to initiate the PCR reaction. At each cycle of PCR (up to 45 cycles), fluorescence from each PCR lane is detected by the optical detection system (2-colors per PCR lane) and final result is determined based on the threshold cycle (Ct).

The sample preparation steps for 24 samples are performed in about 40 minutes and the PCR reaction in about 20 minutes.

Figure 72A:
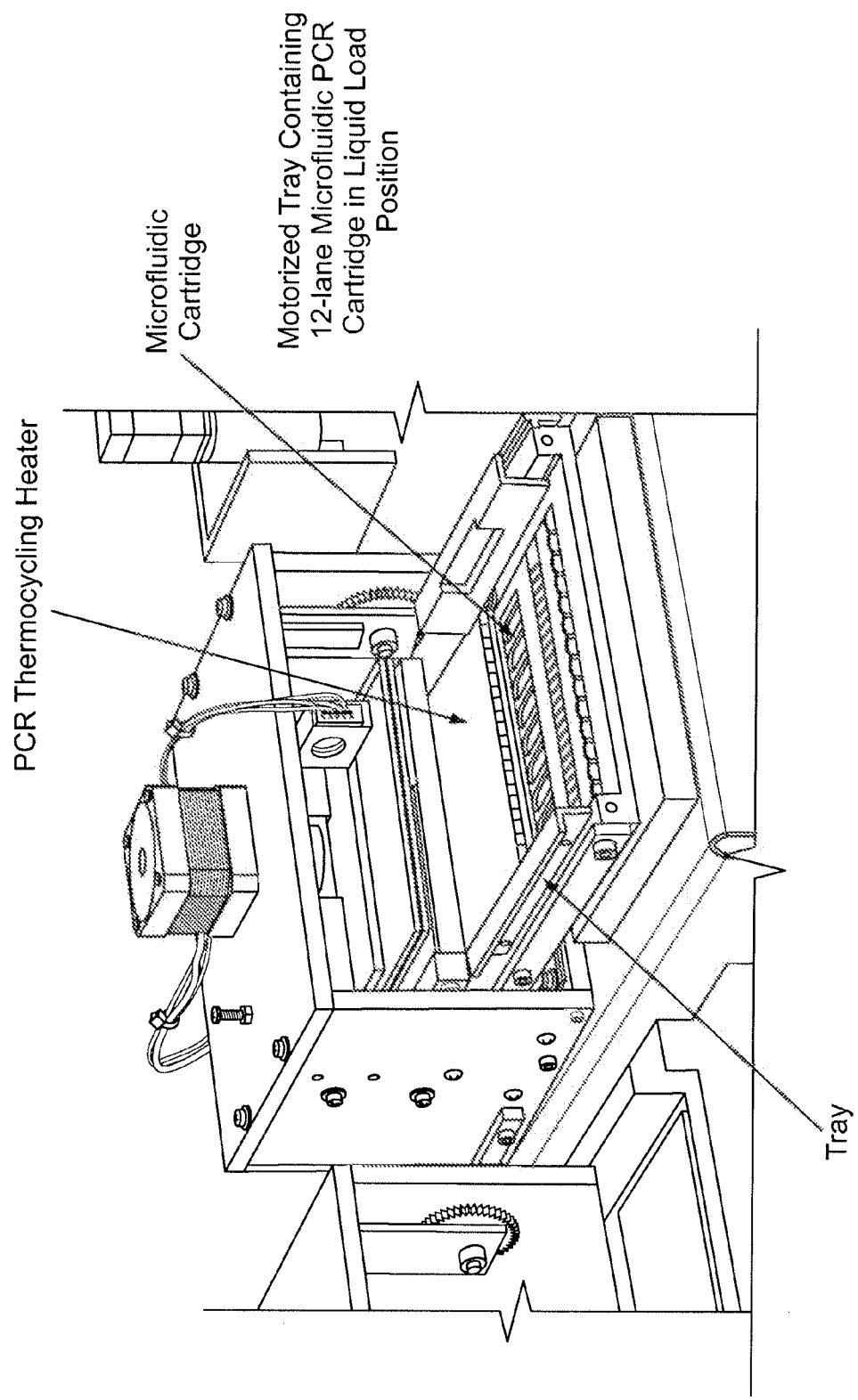
FIGS. 72A and 72B show a thermocycling unit configured to accept a microfluidic cartridge.
Figure 72B:
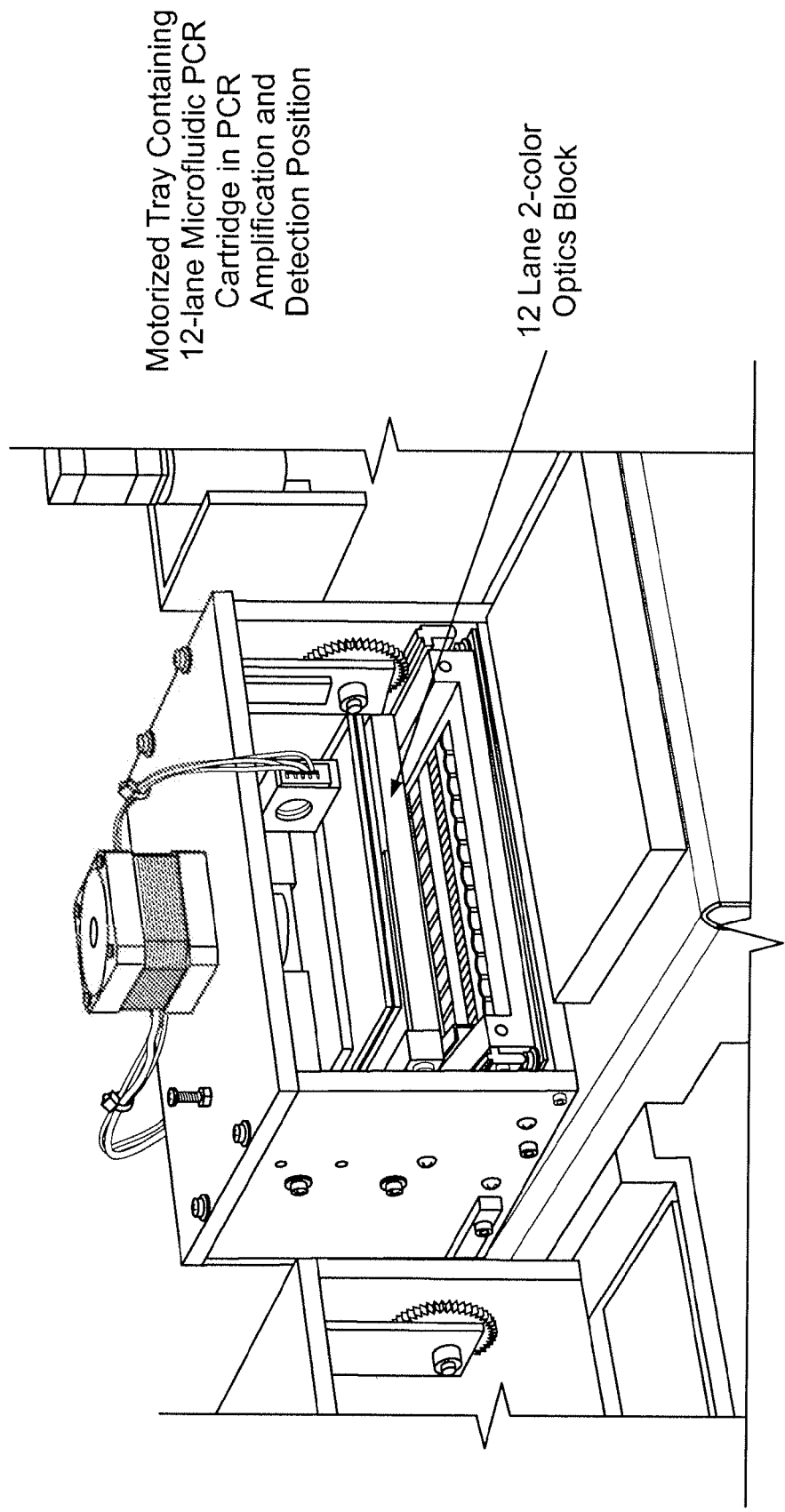

Sample Reader:
The Reader performs function testing of up to twelve properly prepared patient samples by PCR process (real-time PCR) when used in conjunction with HandyLab microfluidic (test) cartridges. Each unit will employ two Reader Modules for a total of up to twenty four tests. (FIGS. 72A and 72B)

Operation of the Reader is designed for minimal customer interaction, requiring the loading and unloading of test cartridges only. During the "Load Disposables" sequence, the Reader will present a motor actuated tray for installation of the disposable cartridge. Sliding a small knob located in the front of the tray, a spring loaded protective cover will raise allowing the test cartridge to be nested properly in place. The cover is then lowered until the knob self-locks into the tray frame, securing the cartridge and preventing movement during the sample loading sequence.

Once the prepared samples have been dispensed via pipettes into the test cartridge, the tray will retract into the Reader, accurately positioning the test cartridge beneath the chassis of the optical assembly. The optical assembly will then be lowered by a captured screw driven stepper motor until contact is made with the test cartridge. At this point the test cartridge is located $\frac{1}{8}$" above the target location on the heater assembly. As downward motion continues the test cartridge and its holder within the tray compress springs on the tray frame (these are used later to return the cartridge to it's normal position and able to clear the encapsulated wire bonds located on the heater assembly during tray operation). Movement of the test cartridge and optical assembly is complete once contact with the heater assembly is made and a minimum of 2 psi is obtained across the two-thirds of the cartridge area about the PCR channels and their controlling gates. At this point the testing of the cartridge is performed using the heater assembly, measured with onboard optics, and controlled via software and electronics much in the same manner as currently operated on similar HandyLab instruments.

Once the functional testing is complete the main motor raises the optic assembly, releasing pressure on the test cartridge to return to it's normal position. When commanded, the tray motor operating in a rack-and-pinion manner, presents the tray to the customer for cartridge removal and disposal. When the tray is in the extended position it is suspended above a support block located on the apparatus chassis. This block prevents the cartridge from sliding trough the holder in the tray during loading and acts as a support while samples are pipetted into the disposable cartridge. Also provided in this support block is an assist lever to lift and grasp the disposable cartridge during removal. All components of the tray as well as support block and cartridge lift assist are removable by the customer, without tools, for cleaning and reinstalled easily.

Microfluidic PCR Heater Module:
The microfluidic PCR heater module comprises a glass wafer with photolithographically defined microheaters and sensors to accurately provide heat for actuation of valves and performing thermocycling required to perform a real-time PCR reaction. The wafer surface has dedicated individually controlled heating zones for each of the PCR lanes in the microfluidic cartridge. For a 12-up cartridge, there are 12 PCR zones and the 24-up cartridge, there are 24 PCR heating zones. The individual heaters and sensors are electrically connected to a Printed circuit board using gold or aluminum wire bonds. A thermally compliant encapsulant provides physical protection the wirebonds. While the present device is made on glass wafer, heaters can be fabricated on Si-on-Glass wafers and other polymeric substrates. Each substrate can have provide specific advantages related to its thermal and mechanical properties. Besides using photolithography process, such heating substrates can also be assembled using off-the-shelf electronic components such as power resistors, peltiers, transistors, maintaining the upper heating surface of each of the component to be at the same level to provide heating to a microfluidic cartridge. Temperature calibration values for each temperature sensor may be stored in a EEPROM or other memory devices co-located in the heater PCBoard.

12-Lane Cartridge:

This 12 channel cartridge is the same basic design that is described in U.S. provisional patent application Ser. No. 60/859,284, filed Nov. 14, 2006, with the following modifications: increase the PCR volume from 2 µl to 4.5 µl, leading to an increase in the input volume from 4 µl to 6 µl. The inlet holes are moved a few millimeters away from the edge of the cartridge to allow room for a 2 mm alignment ledge in the cartridge. A similar alignment ledge is also included on the other edge of the cartridge. (FIGS. 31A, 31B)

Enclosure:

The design of the apparatus enclosure must satisfy requirements: for customer safety during operation; provide access to power and communication interfaces; provide air entry, exit, and filtering; provide one-handed operation to open for installation and removal of materials; incorporate marketable aesthetics.

Cooling:

The cooling for the apparatus will be designed in conjunction with the enclosure and overall system to ensure all assemblies requiring air are within the flow path or receive diverted air.

The current concept is for the air inlet to be located on the bottom of the lower front panel. The air will then pass through a cleanable filter before entering the apparatus. Sheet metal components will direct the air to both the disposable racks and the main power supply. The air will then be directed through the card cages, around the readers and will exit through slots provided in the top of the enclosure.

Base Plate

The XYZ stage and frame are mounted to the base plate in a way where there will be no misalignment between the stage, cartridge and the disposable. The enclosure is mounted to the base plate. Final design of the enclosure determines the bolt hole pattern for mounting. The backplane board mounts to the base plate with standoffs. All other boards mount to the backplane board. The disposable mounts on a rack which will be removable from the brackets mounted to the base plate. The reader brackets bolt to the base plate. Final design of the reader brackets determines the bolt hole pattern. The power supply mounts to the base plate. The base plate extends width and lengthwise under the entire instrument.

Example 12

Exemplary High-Efficiency Diagnostic Apparatus

Figure 73:
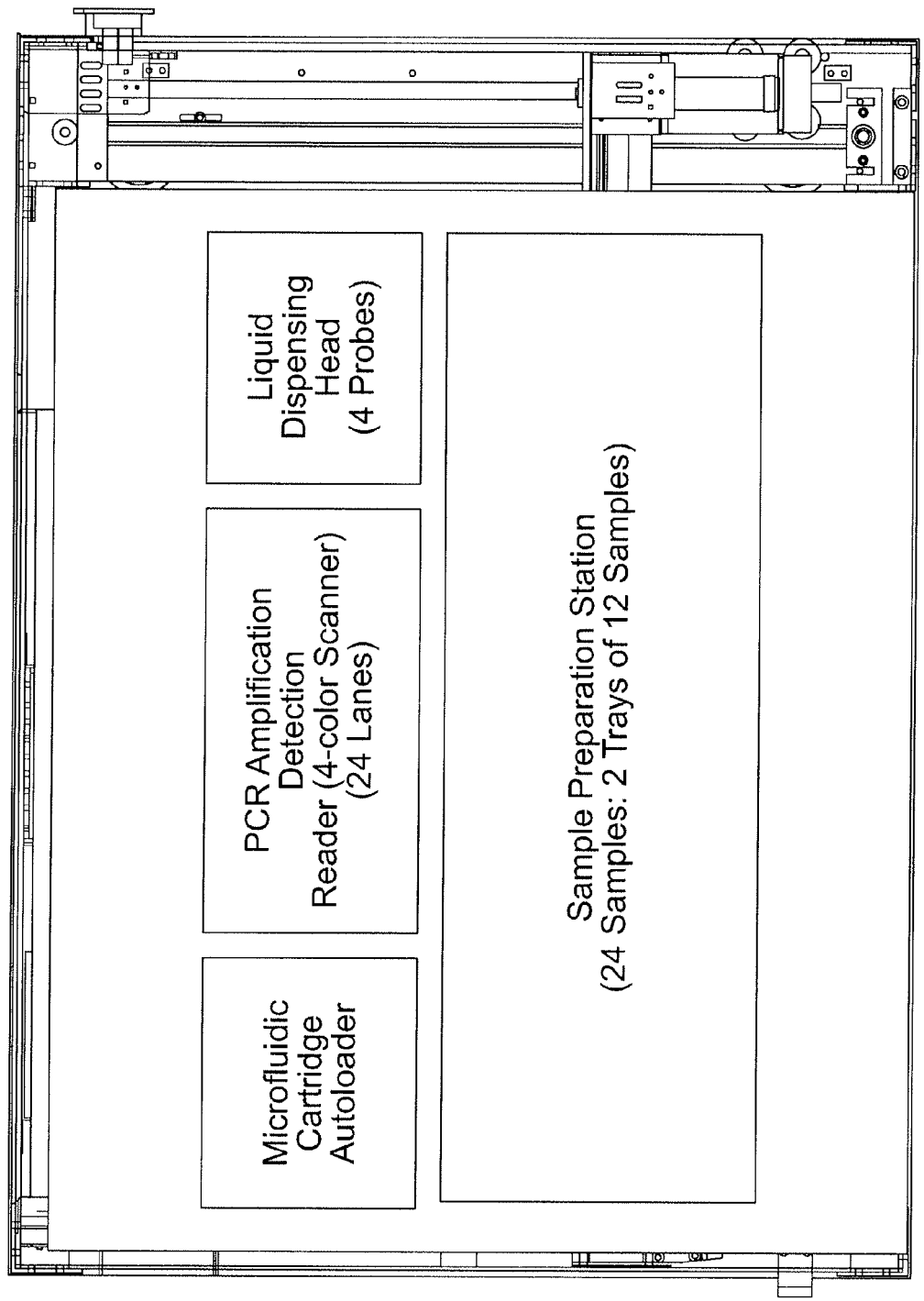
FIG. 73 shows schematically a layout of components of a high-efficiency diagnostic apparatus.
Figure 74:
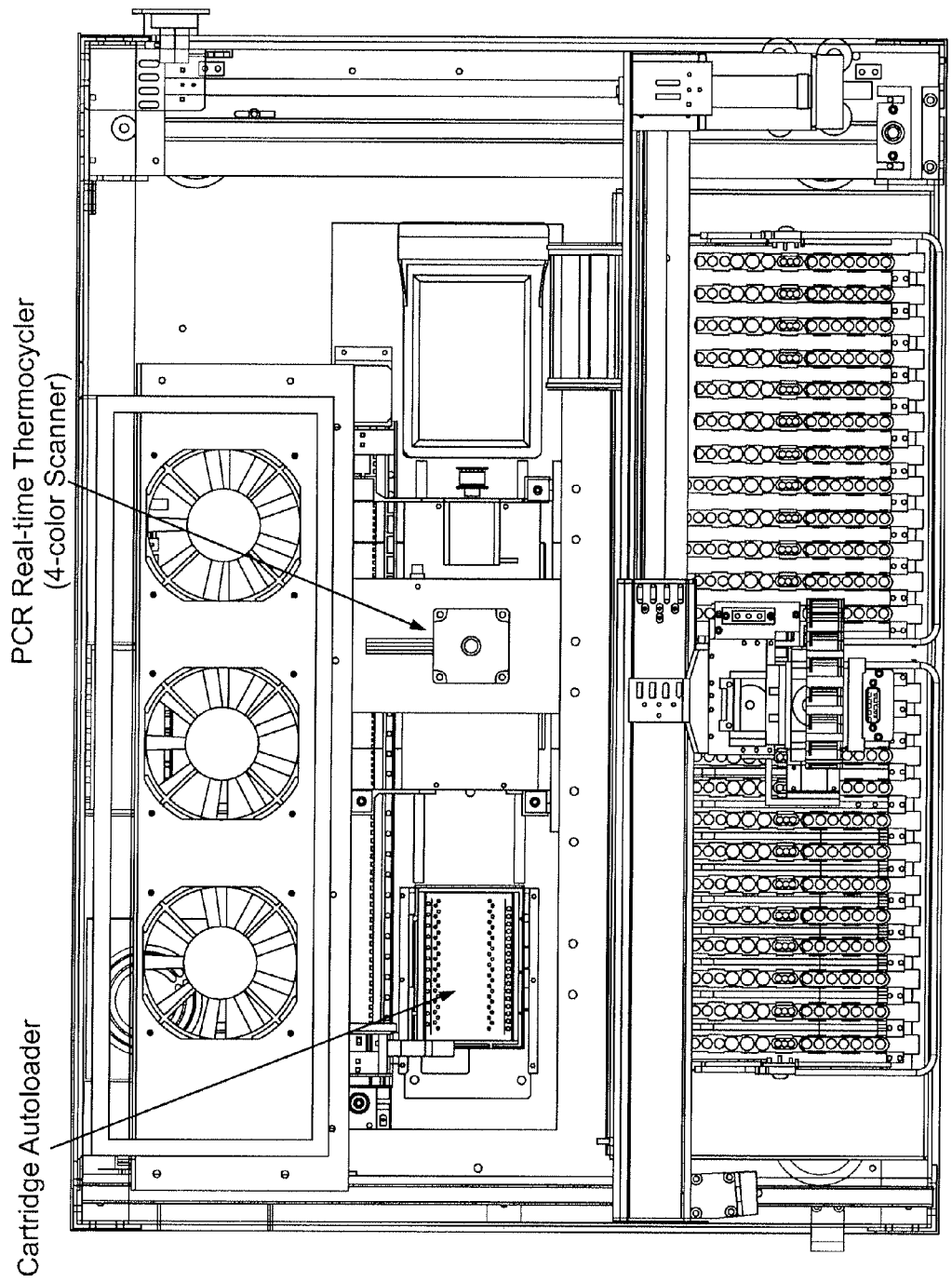
FIG. 74 shows layout of components of an exemplary high-efficiency diagnostic apparatus.

A more highly multiplexed embodiment, also enables 24 clinical samples to be automatically processed to purify nucleic acids, mix the purified DNA/RNA with PCR reagents and perform real-time PCR in a microfluidic cartridge. This product has a single PCR reader, with a scanning read-head, capable of reading up to 4 different colors from each of the PCR lane. The cartridge has 24 PCR channels enabling a single cartridge to run all 24 clinical samples. In addition, this product has a cartridge autoloader, whereby the instrument automatically feeds the PCR reader from a pack of cartridges into the instrument and discard used cartridge into a waste tray. Diagrams are shown in FIGS. 73, and 74.

The apparatus has the following sub-systems:

Two sample processing racks, each rack processes up to 12 clinical samples in unitized disposable strips Magnetic separator-cum-tube heater assembly (24 heating stations)

A four-probe liquid dispensing head 3-axis gantry to move the pipette head

A single PCR amplification-detection station capable of running a 24-lane microfluidic cartridge and a scanner unit to detect up to 4 colors from each PCR lane.

An autoloader unit to feed 24-lane microfluidic cartridge from a box into the PCR detection unit.

Control electronics

Barcode reader

Operation: The user will get a work list for each sample, whether they want to detect certain target analyte (such as GBS, *Chlamydia, Gonnorrhoea*, HSV) for each clinical sample. The sample tubes are placed on the rack and for each sample, the user slides in a unitized reagent disposable (analyte specific) into corresponding lane of the rack. The unitized disposable will have all the sample prep reagents, PCR reagents, process tubes as well as disposable pipettes already prepackaged in it. Once all disposables are loaded into the rack, the rack is placed in its location on the instrument. The user then closes the door of the instrument and then starts the sample processing using the GUI (Graphical User Interface).

The instrument checks functionality of all subsystems and then reads the barcode of the sample tubes, the unitized reagent disposables and presence of a 24-lane microfluidic cartridge. Any mismatch with a pre-existing work list is determined and errors are flagged, if necessary. The instrument than goes through a series of liquid processing, heating, magnetic separation to complete the sample preparation steps for the each of the clinical sample, mixes the purified nucleic acid with PCR reagents and dispenses the final mix into a lane of a 24-lane microfluidic cartridge. After the microfluidic cartridge is loaded with the final PCR mix, the cartridge is moved and aligned by an automated motorized pusher in the PCR reader. The optical detection system, then presses the cartridge against a microfluidic PCR heater surface. On-chip valves are actuated to close the reaction mix and then thermocycling is started to initiate the PCR reaction. At each cycle of PCR (up to 45 cycles), fluorescence from each PCR lane is detected by the optical detection system (2-colors per PCR lane) and final result is determined based on the threshold cycle (Ct). The used cartridge is then pushed out automatically into a waste cartridge bin.

Microfluidic cartridges are stored in a cartridge pack (maximum 24 cartridges) and the instrument alerts the user to replace the cartridge pack and empty out the waste cartridge bin once all cartridges from the pack are used up.

24-Lane Cartridge

Figure 75:
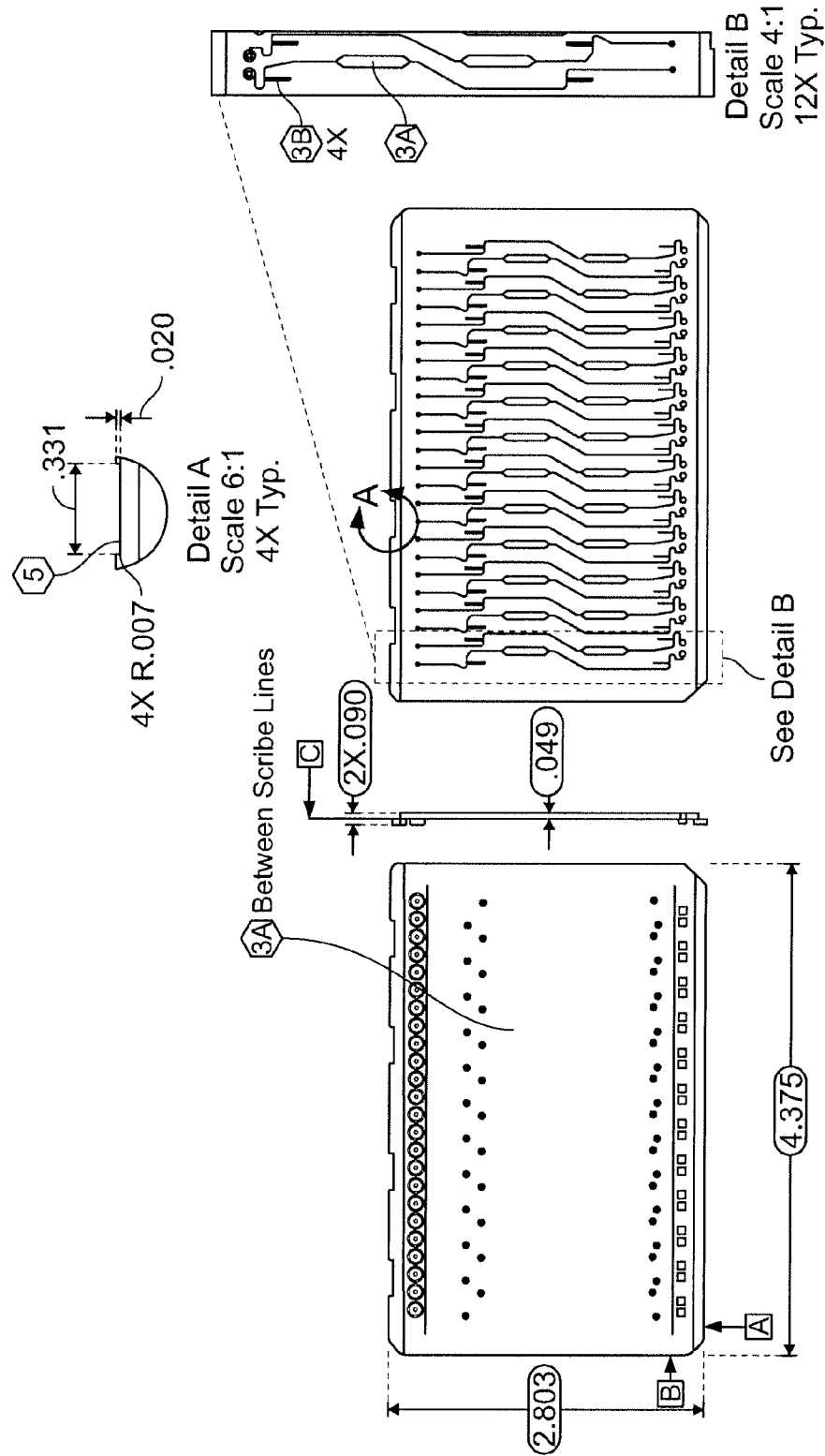
FIG. 75 shows a plan view of a 24-lane microfluidic cartridge.
Figure 76:
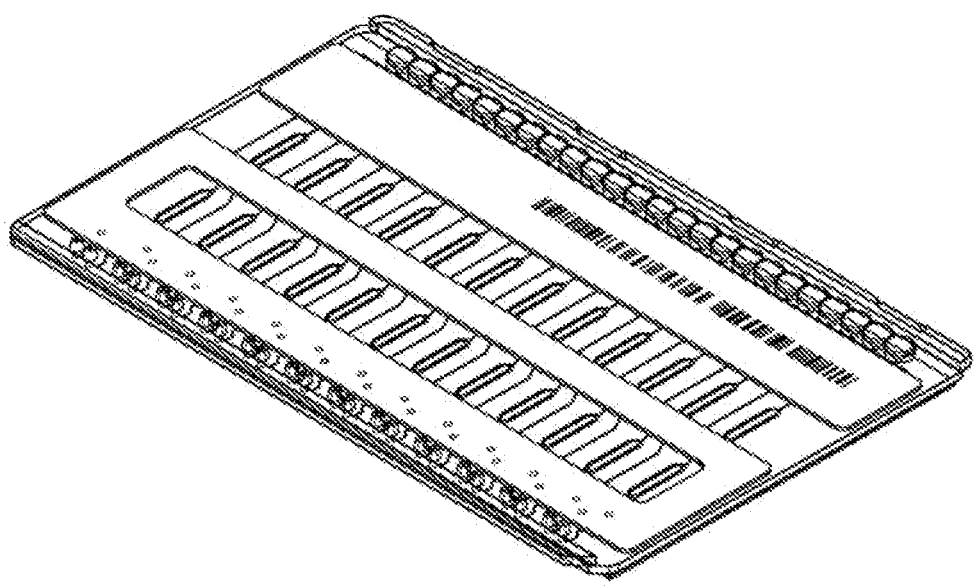
FIG. 76 shows a perspective view of the cartridge of FIG. 75.
Figure 77:
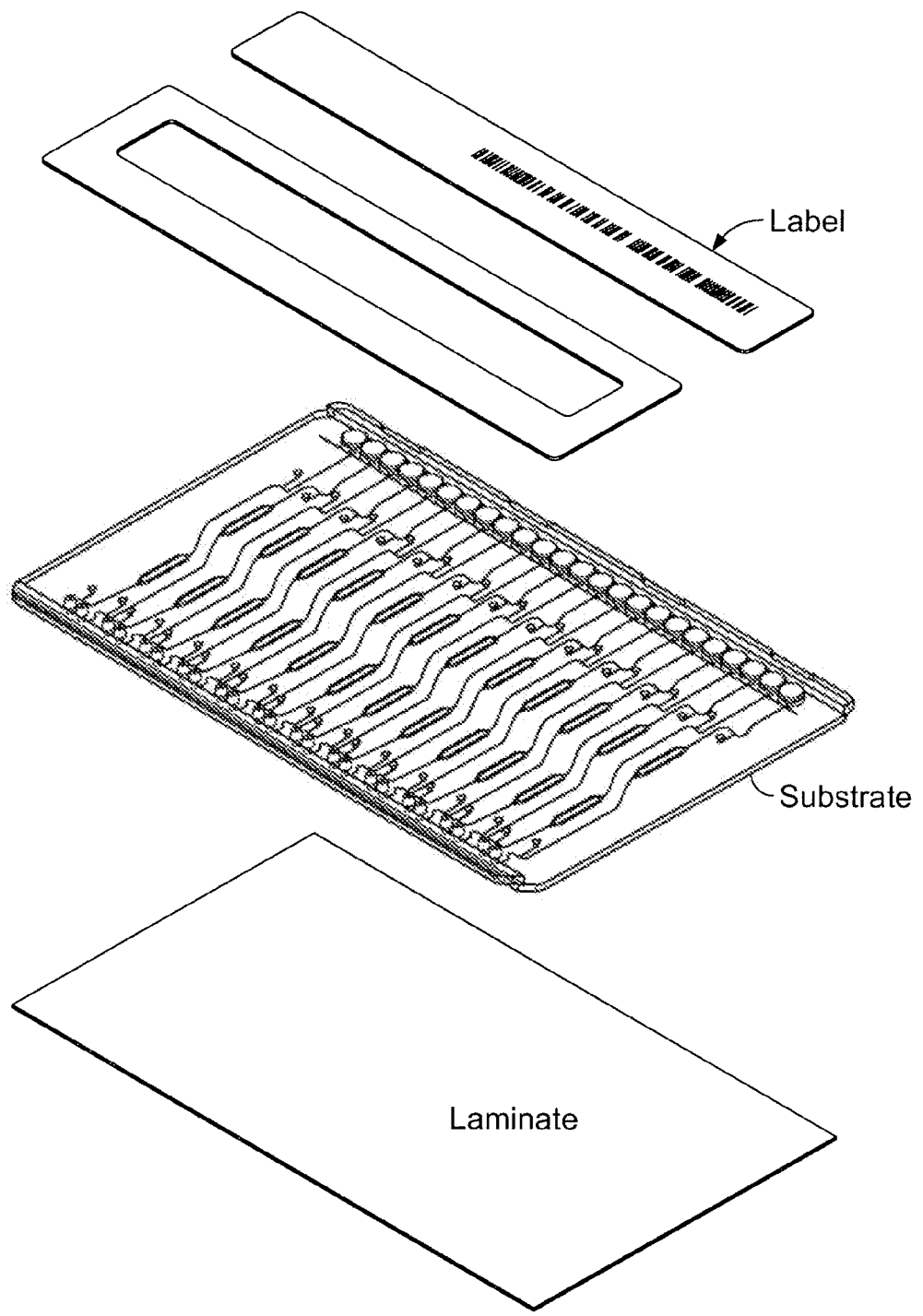
FIG. 77 shows an exploded view of the cartridge of FIG. 75.

The 24-lane cartridge has two rows of 12 PCR lanes. Various views are shown in FIGS. 75-77. The cartridge has 3 layers, a laminate, a substrate, and a label. The label is shown in two pieces. Each Lane has a liquid inlet port, that interfaces with a disposable pipette; a 4 microliter PCR reaction chamber (1.5 mm wide, 300 microns deep and approximately 10 mm long), two microvalves on either side of the PCR reactor and outlet vent. Microvalves are normally open and close the channel on actuation. The outlet holes enables extra liquid (~1 µl) to be contained in the fluidic channel incase more than 6 µl of fluid is dispensed into the cartridge.

The inlet holes of the cartridge are made conical in shape and have a diameter of 3-6 mm at the top to ensure pipettes can be easily landed by the fluid dispensing head within the conical hole. Once the pipette lands within the cone, the concial shape guides the pipette and mechanically seals to provide error free dispensing or withdrawal of fluid into the cartridge. The bigger the holes, the better it is to align with the pipette, however, we need to maximize the number of inlet ports within the width of the cartridge as well as maintain the pitch between holes compatible with the inter-pipette distance. In this particular design, the inter-pipette distance is 18 mm and the distance between the loading holes in the cartridge is 8 mm. So lanes 1, 4, 7, 11 are pipetted into during one dispensing operation; lanes 2, 5, 8 and 12 in the next, and so on and so forth.

The height of the conical holes is kept lower than the height of the ledges in the cartridge to ensure the cartridges can be stacked on the ledges. The ledges on the two long edges of the cartridge enable stacking of the cartridges with minimal surface contact between two stacked cartridges and also help guide the cartridge into the reader from cartridge pack (cf. FIGS. 28-33).

Cartridge Autoloader

The Cartridge autoloader consists of a place for positively locking a pack of 24 microfluidic cartridges, pre-stacked in a spring-loaded box (e.g., FIG. 33). The box has structural elements on the sides to enable unidirectional positioning and locking of the box in the autoloader (FIG. 33). To load a new box, the user moves a sliding element to the left of the autoloader, places and pushes the box in the slot and releases the sliding lock to retain the box in its right location. Springs loaded at the bottom of the box helps push the box up when it needs to be replaced. The spiral spring present at the bottom of the cartridge pack pushed against the cartridges and is able to continually push the cartridge with a force of from 4 to 20 pounds.

The presence or absence of cartridges is detected by reading the barcode on top of the cartridge, if present.

To start a PCR run, the pipette head dispenses PCR reaction mix into the required number of lanes in the top cartridge in the autoloader (e.g., FIG. 28). The pusher pushes the top cartridge from the autoloader box into the two rails that guide the cartridge into the PCR reader. The cartridge is pushed to the calibrated location under the reader and then the optics block is moved down using a stepper motor to push the cartridge against the microheater surface. The bottom of the optics block (aperture plate) has projections on the sides to enable the cartridge to be accurately aligned against the apertures. The stepper motor pushes the cartridge to a pre-calibrated position (e.g., FIG. 30) which provides a minimum contact pressure of 1 psi on the heating surface of the microfluidic cartridge.

After the PCR reaction is complete, the stepper motor moves up 5-10 mm away from the cartridge, relieves the contact pressure and enables to cartridge to travel in its guide rails. The pusher is activated and it pushes the cartridge out to the cartridge waste bin (e.g., FIG. 32). After this step, the pusher travels back to its home position. During its back travel, the pusher is able to rise above the top of the cartridge in the cartridge pack because it has a angular degree of freedom (see figure). A torsion spring ensures the pusher comes back to a horizontal position to enable it to push against the next cartridge in queue. The pusher is mechanically attached to a timing belt. The timing belt can be moved in either direction by turning a geared motor. The pusher is mounted to a slider arrangement to constrain it to move in only one axis (see, e.g., FIG. 31).

The cartridge pushing mechanism can also be made to not only push the cartridge from the autoloader box to the detection position, but also be used to move it back to the autoloading position. This will enable unused lanes in the microfluidic cartridge to be used in the next PCR run.

The cartridge autoloading box is also designed so that once all the cartridges are used, the box can be easily recycled or new cartridges added to it. This reduces the cost to the customer and the manufacturer.

Reader

Figure 78:
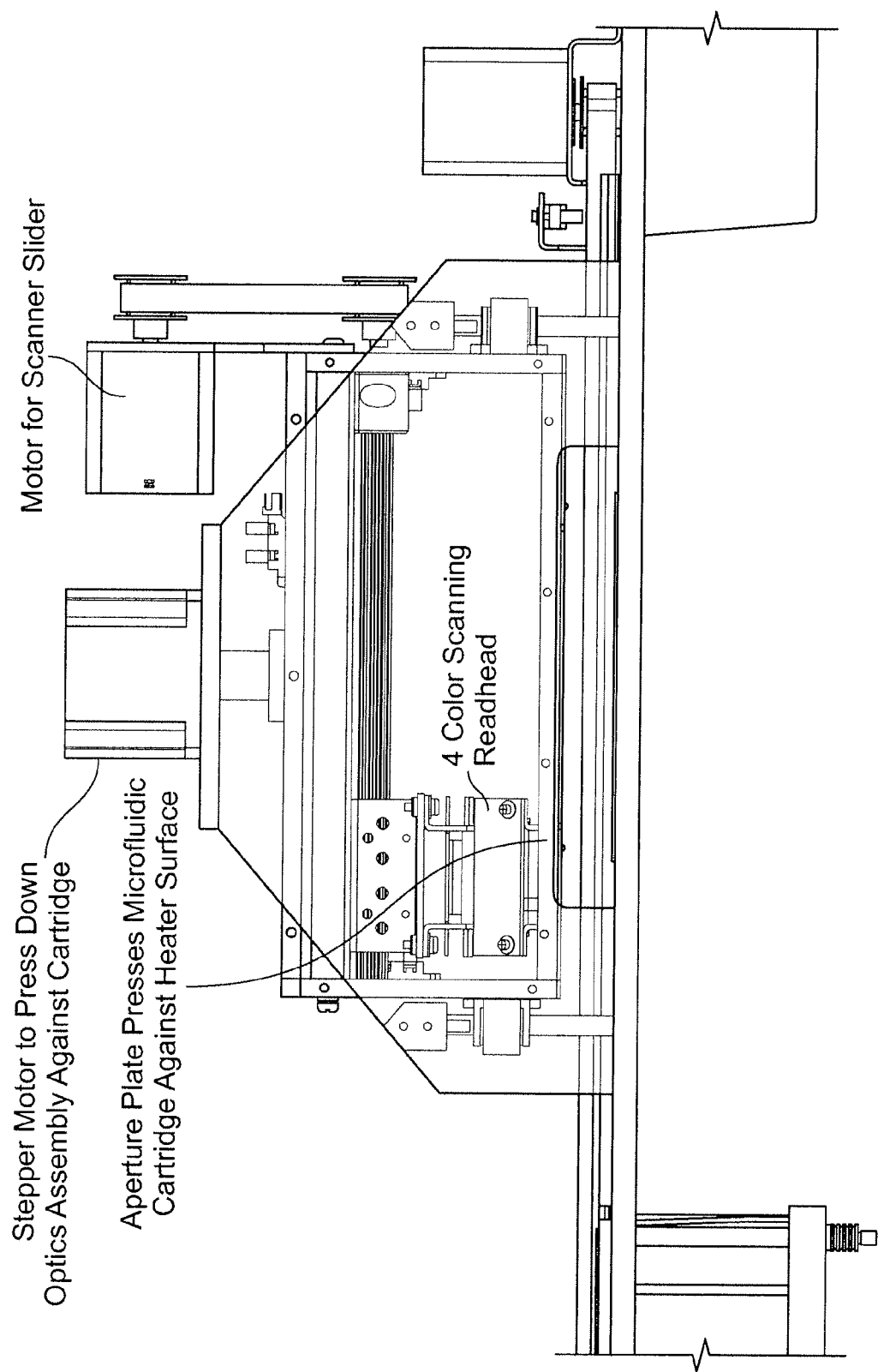
FIG. 78 shows an exemplary detection unit.
Figure 79B:
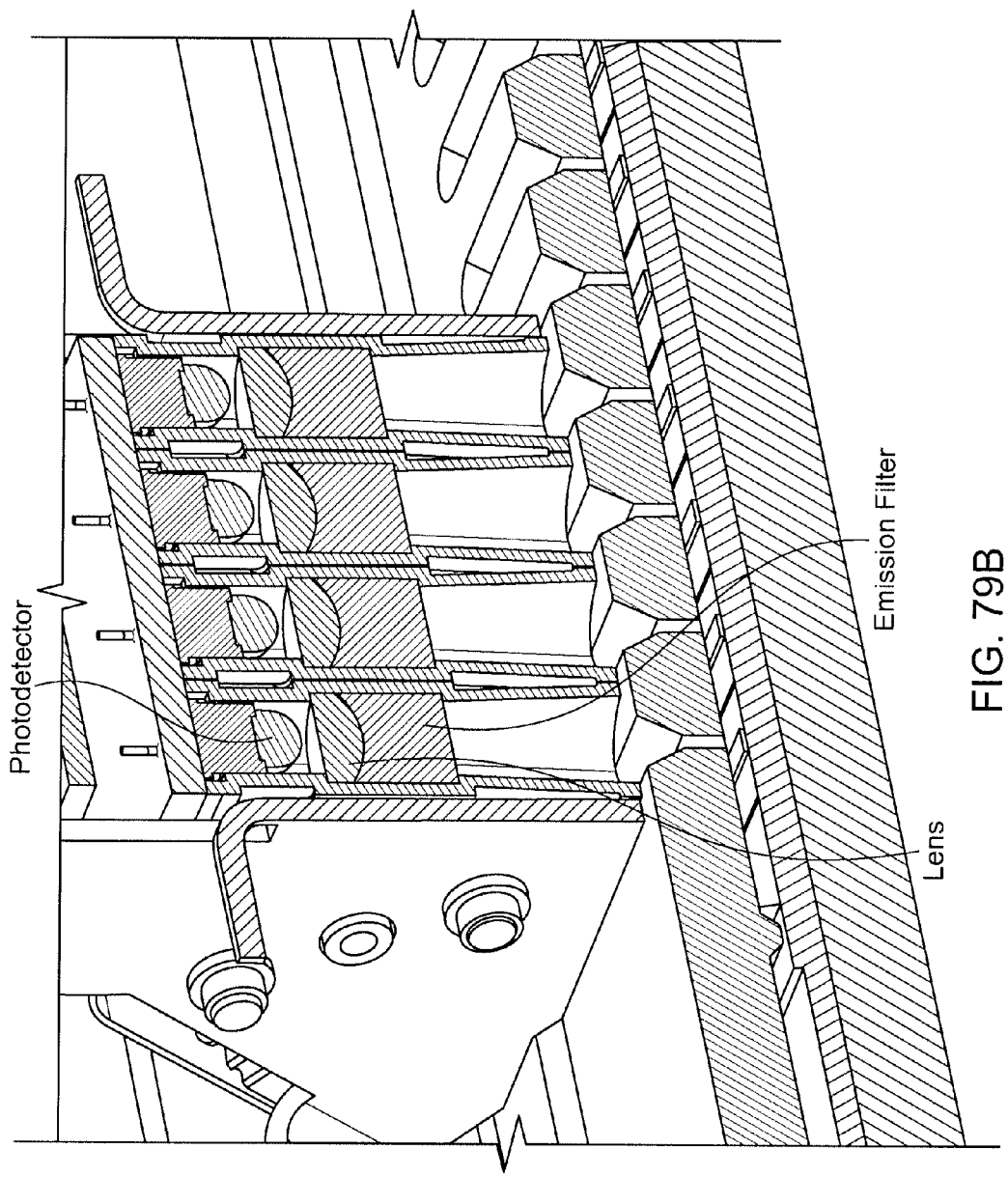

The reader consists of an optical detection unit that can be pressed against a 24-lane microfluidic cartridge to optically interface with the PCR lanes as well as press the cartridge against a microfluidic heater substrate (FIG. 78). The bottom of the optics block has 24 apertures (two rows of 12 apertures) that is similar in dimension of the PCR reactors closest to the cartridge. The aperture plate is made of low fluorescent material, such as anodized black aluminum and during operation, minimized the total background fluorescence while maximizing the collection of fluorescent only from the PCR reactor (FIGS. 79A and 79B). The bottom of the aperture plate has two beveled edges that help align two edges of the cartridges appropriately such that the apertures line up with the PCR reactors. (FIGS. 80, 81)

The optical detection units (total of 8 detection units) are assembled and mounted onto a sliding rail inside the optical box so that the optical units can be scanned over the apertures (FIG. 82). Each unit is able to excite and focus a certain wavelength of light onto the PCR reactor and collect emitted fluorescence of particular wavelength into a photodetector. By using 4 different colors on the top 4 channels and repeating the 4 colors in the bottom channels, the entire scanner can scan up to 4 colors from each of the PCR lanes.

The optics block can be machined out of aluminum and anodized or injection molded using low fluorescence black plastic (FIG. 83). Injection molding can dramatically reduce the cost per unit and also make the assembly of optics easier. The designed units can be stacked back-to-back.

Example 13

Exemplary Electronics for Use with Preparatory and Diagnostic Apparatuses as Described Herein There are multiple independent software modules running on dedicated hardware: Described herein are exemplary specifications for the electronics used in the diagnostic (PCR) system. Additional information related to the PCR System is described elsewhere herein. In some embodiments, the PCR system includes eighteen printed circuit boards (PCBs) of nine different types. Referring to FIG. 86, the system can contain three multiplex (MUX) boards 100a-c, two of which (micro-heater MUX boards 100a-b), can each be used to run a micro-heater board 110a-b and the third (lysis heater MUX board 100c) can run one or more lysis heater boards 116 and 117. Each of the three MUX boards 100a-c can be controlled by a PC processor board via an Ethernet port. The two micro-heater boards 110a-b, each controlled by one of the MUX boards 100a-b, heat micro-zones on the microfluidic cartridge. In some embodiments, the system includes the two lysis heater boards 116 and 117, controlled by the lysis heater MUX board 100c, that heat lysis tubes in each of the two 12 sample racks.

Still referring to the PCBs included in the PCR system, the system can include two 12-channel optical detection boards 130a-b that can each detect optical fluorescence emitted by microfluidic cartridge chemistry. The optical detection boards can be controlled by one or more of the MUX boards 100a-c, using SPI, over a RS-422 interface. The system can include three motor control boards 140a-c, where one board (e.g., motor control board 140c) can control two magnetic separation motors (not shown), and the remaining two motor control boards (e.g., motor control boards 140a-b) can each run one reader tray motor (not shown) and one reader pressure motor (not shown). The motor control board running the magnetic separation motors (e.g., motor control board 140c)

can be controlled via RS-485 interface from the lysis heater MUX board 100*c* and the two motor control boards 140*a-b*, each running one reader tray motor and one reader pressure motor, can be controlled via RS-485 interface by the micro-heater MUX boards 100*a-b*. The system can also include one PC processor board 150, which directs the overall sequencing of the system and can be controlled via external Ethernet and USB interfaces, and one PC processor base board 160, which provides internal interfaces for the PC processor board 150 to the remainder of the system and external interfaces. The system can include one main backplane 180 that interconnects all system boards, one motor control backplane 190 that interconnects the motor control boards 140*a-c* to the main backplane 180 and gantry (not shown), and two door sensor boards (not shown). One door sensor board provides an interconnect between the front door solenoid locks and the PC processor base board 160 and the other door sensor board provides an interconnect between the position sensors and the PC processor base board 160.

In some embodiments, the PCR system can include the off-the-shelf PC processor board 150. The PC processor board 150 can be an ETX form factor board that includes one 10/100 BASE-T Ethernet port, four USB ports, one analog VGA display port, two UART ports, one real-time clock, one parallel port, one PS2 keyboard port, one PS2 mouse port, stereo audio output, one IDE interface, and one 12C interface.

Referring to FIG. 87, the system can also include the PC processor base board 160 that includes a five port 10/100 BASE-T Ethernet bridge 161 for internal communication, one of which can be connected to the 10/100 BASE-T Ethernet port of the PC Processor board 150, another of which can be for diagnostic use (with a connector inside system cover), and three of which can communicate with the three MUX boards 100*a-c* (one port for each MUX board 100*a-c*) through the backplane 180. The PC processor base board 160 can also include one USB to 10/100 BASE-T Ethernet port 162 for external Ethernet connections, one four port USB hub 163 for external connections, one external VGA connector 164, one internal PS2 Mouse connector 165 (with a connector inside the system cover), and one internal PS2 Keyboard connector 166 (with a connector inside the system cover. The PC processor base board 160 can also include one internal stereo audio output 167 to on board speakers 168, one internal CompactFlash connector 169 from an IDE port (with a connector inside the system cover), and one internal RS-232 interface 170 from a UART port (with a connector inside the system cover). Additional components included in the PC processor base board can include one internal RS-485 interface 171 from a UART port (with a connector inside the system cover), one internal temperature sensor 172 connected to the 12C interface, a battery for the real-time clock, and one parallel port 173. The parallel port 173, with connectors inside the system cover, can be internally connected as follows: one bit can be used to drive a high current low side switch for the two door solenoids, one bit can be used to generate a processor interrupt when either door sensor indicates that a door is opened, three bits can be used to program the EEPROM for configuring the Ethernet bridge 161, and two bits can be connected to the Ethernet bridge management interface (not shown). The remaining bits can remain unassigned, with optional pull-up and pull-down resistors, and be brought out to a 10 pin Phoenix contact header.

Referring to FIG. 88, in some embodiments, the system can include the three MUX boards 100*a-c*. While FIG. 88 depicts exemplary MUX board 100*a*, each of the three MUX boards 100*a-c* can include one or more of the features described below. The MUX board 100*a* can include 96 pulse width modulated (PWM) controlled heating channels with heaters (about 33 ohm to about 150 ohm) heaters, that can support 20 or 24 volt (voltage externally provided) drives with a maximum current of about 800 mA. Each PWMs can be 12-bit with programmable start and stop points, can have 1 microsecond resolution, and can have a maximum duty cycle of about 75%. Each PWM period is programmable and is preferably set to 4 ms. The MUX boards can include a 4-wire RTD/heater connection with precision 1 mA sense current that can accommodate about 50 ohm to about 2500 ohm resistive temperature devices and have a measurement accuracy of +/−0.5 ohms. The thermal measurement sample period of the MUX boards is 32 ms including 8×PWM periods where 12 16-bit ADCs 101*a* sample 8 successive channels each. The MUX address can be tagged to the ADC data.

Still referring to the MUX board 100*a* depicted in FIG. 88, an RS-422 optics board interface 102*a* that interconnects over the backplane 180 and transfers data over a 4 wire SPI interface using local handshake signals and interrupts can be included on the MUX board 100*a*. The MUX board 100*a* can also include a 10/100 BASE-T Ethernet interface 103*a* that interconnects to the system over the backplane 180 and an RS-485 interface 104*a* that interconnects to the motor controller 140*a* over the backplane 180.

Referring now to FIG. 89, in some embodiments, the system can include the optical detection boards 130*a-b*. While FIG. 89 depicts exemplary optical detection board 130*a*, each of the optical detection boards 130*a-b* can include one or more of the features described below. The optical detection board 130*a* can include a 12-channel optics board design modified to use an RS-422 interface 131*a*. The optical detection board 130*a* can include 12-3 Watt, blue LEDs 132*a* driven with about 6 V at about a 625 mA maximum. An exemplary LED used in the detection board 130*a* is the Luxeon K2 emitter producing blue light at a wavelength of about 470 nm using about 27 mW @ 700 mA. The optical detection board 130*a* can also include 12-3 Watt, amber LEDs 133*a* driven with about 6 V at about a 625 mA maximum. An exemplary LED used in the detection board 130*a* is the Luxeon K2 emitter producing amber light at a wavelength of about 590 nm using about 60 mW @ 700 mA. The detection board 130*a* can include 24 lensed silicon photodiode detectors 134*a*, an example of which is the Hamamatsu S2386-18L. These photodiode detectors 134*a* are designed in a common TO-18 package. The detection board 130*a* can also include an MSP430 processor 135*a* with two PWM channels, one for the blue channel and one for the amber channel. The board 130*a* can include individual LED enables 136*a* and 137*a* for each of the 12 color pairs set over the local SPI bus.

The PCR system can include a lysis heater board that provides and monitors heating to the lysis tubes. The heater board can include 12-70 Watt TO-247 power resistors (provide heat to the lysis tubes) designed to be fed 24V from one or more of the MUX boards 100*a-c* (e.g., MUX board 100*c*) and 12-2000 ohm Resistive Temperature Devices (RTD) to monitor the temperature of the lysis tubes. Optional resistors can be included to modify the full scale-range of the RTDs. Included on the lysis heater board is a serial EEPROM that may hold a board serial number and can be used to identify the board type and revision level to software.

Referring now to FIG. 90, in some embodiments, the system can include the micro-heater boards 110*a-b*. While FIG. 90 depicts exemplary micro-heater board 110*a*, each of the micro-heater boards 110*a-b* can include one or more of the features described below. In some embodiments, the system can include the micro-heater board 110*a* that includes a serial EEPROM and two optical interrupters. The serial EEPROM may hold a board serial number, can hold RTD calibration data, and can be used to identify the board type and revision level to software. The optical interrupters can be used to sense the reader tray position for the motor control board 140*a* and sends the information to the Blue Cobra (motor controllers), which processes the information on the positions of the reader trays and accordingly controls the power to the emitters supplied by the motor control board 140*a*. The micro-heater board 110*a* can provide connections to the 96 channel micro-heater plate and control the 96 multiplexed heater/RTD devices to control cartridge feature temperature. The heater/RTD devices can be between about 50 ohms to about 500 ohms. The micro-heater board 110*a* can bridge the RS-422 interface from, for example, the MUX board 100*a* to the optical detection board 130*a*. The connection from the micro-heater board 110*a* to the MUX board 100*a* is over the backplane 180, while the connection to the optics board 130*a* is over a 40 pin FFC cable.

Referring now to FIG. 91, in some embodiments, the system can include the motor control boards 140*a-c*. While FIG. 91 depicts exemplary motor control board 140*a*, each of the motor control boards 140*a-c* can include one or more of the features described below. In some embodiments, the system can include the motor control board 140*a* that can control two micro-stepping motors 141*a* and can be connected to the backplane 180 via a RS-485 interface. The output to the motors can be up to 24 V supplied externally through the backplane 180. The output current can be jumper selectable. Exemplary output currents that can be selected via jumper settings can include about 700 mA, about 1.0 A, or 2.3 A. The motor control board 140*a* includes open collector TTL interrupt output to the MUX board 100*a* and flag inputs. The flag inputs can provide 1.5 V power output to the sensors and can be switched on and off by software.

Limit switches are placed on the extreme locations of each axis, e.g., x-minimum and x-maximum, that turns off the power to the motor driving that axis incase of a malfunction happens and the pipette head moves out of the designed working distance. Optional pull-up and pull-down are used with the output of the optical interrupters.)

In some embodiments, the system can include one or more interconnection boards, such as the main backplane 180. The main backplane 180 can interconnect other PCBs, such as the MUX boards 100*a-c*, PC processor base board 160, and heater Interconnect boards. The main backplane 180 can cable to the motor control backplane 190 and to two lysis heater boards. The main backplane 180 can distribute power and signaling, implement 10/100 BASE-T Ethernet and RS-485 over the backplane 180, and supplies voltages from an external connector. Exemplary voltages supplied include +3.3 V, +5.0 V, +12.0 V, −12.0 V, +20.0 V, and +24.0 V.

The system can include the motor control backplane 190 that can distribute power and signaling for all of the motor control boards 140*a-c*. The motor control backplane 190 can supply +5.0 V and 24.0 V from an external connector. The motor control backplane 190 can include 1 slot for the RS-485 signaling from each of the two MUX boards 100*a-b* (total of 2 slots), 6 slots for the RS-485 signaling from the lysis heater controlling MUX board 100*c*, and one connector that provides RS-485 signaling and power to the gantry. The motor control backplane 190 can provide pull-up and pull-down resistors to handle floating buses.

In some embodiments, the system can include a heater interconnect board and a door sensor board. The heater interconnect board can connect the micro-heater boards 110*a-b* to the main backplane 180 using a physical interconnect only (e.g., no active circuits). The door sensor board can provide a cable interface and mixing logic from the optical interrupters, which sense the door is open, and provide a mounting and cabling interface to the door lock solenoid.

Example 14

Exemplary Software for Use with Preparatory and Diagnostic Apparatuses as Described Herein There are multiple independent software modules running on dedicated hardware:
 Reader (2);
 Sample-Prep (1);
 User Interface (1);
 Detector (2)
 Motor control (8)

Inter-module communication among is via an internal Ethernet bus, communication with the user interface is via a high speed SPI bus and communication with motor control via a RS485 serial bus.

The Reader and Sample-Prep software run on identical hardware and are as such identical incorporating the following functions:
 Script Engine (a parameterized form of a protocol)
 Protocol Engine
 Temperature Control (Microfluidics, lysis, release)
 Motor control (via external motor control modules). Salient features of the motor control software are:
 Command/reply in ASCII and addressing capability to allow daisy chaining of communication link.
 Detection (via external detector modules) Detector module controls the LED illumination and photo detector digitization.

The user interface is implemented as a program running under Linux operating system on an embedded x86 compatible PC. The following functions are addressed:
 Graphical User Interface
 Test control and monitor
 Test result storage and retrieval Network connectivity via Ethernet (to lab information systems)
 USB interface
 Printer
 Scanner (Internal and external)
 Keyboard
 Mouse
 Door lock and sense

Example 15

Exemplary Chemistry and Processes of Use

Chemistry Overview:

The chemistry process centers around the detection and identification of organisms in a clinical specimen, by virtue of detecting nucleic acids from the organism in question. This involves isolation of nucleic acids from target organisms that are contained in a clinical specimen, followed by a process that will detect the presence of specific nucleic acid sequences. In addition to target detection, an internal positive control nucleic acid will be added to the collection buffer, and will be taken through the entire extraction and detection process along with target nucleic acids. This control will monitor the effectiveness of the entire process and will minimize the risk of having false negative results.

Nucleic Acid Extraction and Purification:
 Nucleic acid extraction procedures begin with the addition of a clinical specimen to a prepared specimen collection solution. This can be done either at a specimen collection site, or at the testing site. Two collection solution formats will be available: one for body fluids, and one for swab specimens. Collection solutions used at collection sites will serve as specimen transport solutions, and therefore, this solution must maintain specimen and analyte integrity.

The extraction and purification procedure, which is entirely automated, proceeds as follows:

Target organisms are lysed by heating the detergent-containing collection solution.

Magnetic beads, added to the specimen/collection solution mix, non-specifically bind all DNA that is released into the solution.

Magnetic beads are isolated and are washed to eliminate contaminants

DNA is released from the beads using high pH and heat.

DNA containing solution is removed and neutralized with a buffer

Nucleic Acid Amplification:

Nucleic acids that have been captured by magnetic beads, washed, released in high pH, and neutralized with buffer, are added to a mixture of buffers, salts, and enzymes that have been lyophilized in a tube. The mixture is rapidly rehydrated, and then a portion of the solution is loaded onto a microfluidic cartridge. The cartridge is then loaded into the amplification instrument module, which consists of a heating unit capable of thermal cycling, and an optical detection system. Detection of target nucleic acids proceeds as follows:

The liquid in sealed in a reaction chamber.

Rapid thermal cycling is used to potentiate the Polymerase Chain Reaction (PCR), which is used to amplify specific target DNA.

Amplified DNA fluoresces, and can be detected by optical sensors.

A fluorescent probe "tail" is incorporated into each amplified piece of DNA

At a specific temperature, the probe adopts a conformation that produces fluorescence (this is termed a "scorpion" reaction, see FIG. 84).

Fluorescence is detected and monitored throughout the reaction.

Extraction and Amplification/Detection Process:

Extensive bench-scale testing has been performed to optimize the nucleic acid extraction chemistry, including the collection buffer, the wash buffer formulation, the release solution formulation, and the PCR reagent mixes. The fully automated method of extraction, followed by 12-up PCR, was able to provide very high sensitivity consistently at 150 copies/sample.

Examples: *Chlamydia* in Urine (50/50); *Gonorrhoea* in Urine; GBS in Plasma.

Various detection chemistries such as Taqman, Scorpion, SYBRg Green work reliably in the microfluidic cartridge.

Reagent Manufacturing

Feasibility studies were conducted in order to determine whether PCR reagents could be lyophilized in PCR tubes besides the use of 2 μl lyophilized pellets. The studies have indicated that sensitivity of reactions performed using tube-lyophilized reagents is equivalent to that of wet reagents or 2 μl pellet reagents, so feasibility has been proven. Stability studies for this format indicate similar stability data. We have seen 2 microliter lyophilized PCR pellets to be stable to up to 2 years at room temperature, once sealed in nitrogen atmosphere.

Manufacturing Overview Manufacturing the components of the system can be accomplished at HandyLab, Inc., Ann Arbor, Mich. The manufacturing task has been split into five areas that consist of: chemistry manufacture, disposable strip, collection kit, cartridge and analyzer.

Chemistry Manufacturing There are currently seven individual, blended chemistry components identified for potential use with the system described herein. Mixing, blending and processing reagents/chemicals can be performed at HandyLab, Inc., with existing equipment already in place. Additional tooling and fixtures will be necessary as the product matures and we ramp to high volume production, but initial costs will be minimal.

Collection buffer, wash, release & neutralization liquids are simple recipes with very low risk, and can be made in large batches to keep labor costs of mixing/blending at or below targeted projections. They will be mixed and placed into intermediate containers for stock, and then issued to Disposable Strip Manufacturing for dispensing. Mature SOP's are in place from prior project activity.

Affinity Beads (AB) have good potential to be stored and used as a liquid in the strip, but design contingencies for using a lyophilized pellet are in place as a back up. It is critical to keep the beads suspended in solution during dispense. Dispense equipment (e.g., manufactured by Innovadyne) that provides agitation for continuous suspension during dispense has been identified for purchase once stability has been proven for liquid AB storage in the strip. The process to manufacture and magnetize the Affinity Beads spans a 9 hour cycle time to produce a batch of 2,000 aliquots, but that same time period can be used for scaled up recipe batches once we ramp into high volume production. This item has the highest labor content of all chemistry manufacture that is currently required for the apparatus.

PCR reagents/enzymes will be freeze-dried in our existing lyophilizing chamber (Virtis Genesis) but will not require spherical pellet formation. Instead, the mixture is being dispensed into, and then lyophilized, inside the end-use tube. First the chemistries are mixed per established SOPs, and then the following steps are performed to accomplish lyophilization: Individual tubes are placed into a rack/fixture, and the solution is dispensed into each, using existing equipment (EFD Ultra Dispense Station.). The filled rack will be placed inside a stainless steel airtight box (modified to accept stoppers in the lid,) and then placed into the lyophilization chamber and the drying cycle commences unattended. During lyophilization, the stoppers are in a raised position allowing air/nitrogen to circulate into, and moisture to exit the stainless box holding racks of vials. At the end of the cycle, the shelves of our lyophilization chamber lower to seat the stoppers into the lid, forming a seal while still inside the closed chamber, in a moisture free nitrogen atmosphere. The steel boxes are then removed from the chamber, and each rack inside shall be processed in a single operation to seal all vials in that rack. Immediately after sealing, the vials will be die cut from the foil in one operation, allowing individual vials to be forwarded to the Disposable Manufacturing area for placement into a strip. Internal Control will either be added to an existing solution, or will be dispensed into its own cavity in the manner of the collection buffer, wash, neutralization, and release solutions. If lyophilization is required, it will be accomplished in the same manner as the PCR chemistry, and later snapped into the strip. Shelf life stability studies are underway.

Collection Kit Manufacturing

The collection kit will be processed manually in house for initial quantities. Initial quantities will not require capital expenditures as we have all equipment necessary to enable us to meet projections through 2008. We will be using our existing equipment (EFD 754-SS Aseptic Valve & Valvemate 7000 Digital Controller,) to fill the collection vial. The vials have a twist-on top that will be torqued, and the vial will have a proprietary ID barcode on each vial. 24 vials will be placed into a reclosable plastic bag and placed into a carton for shipping.
- Place vials into rack.
- Dispense solution into vials.
- Install and torque caps.
- Label vials.
- Bag vials and label bag.
- Place vial bag and instructions/insert into carton, close and label.

Cartridge Manufacturing:

Existing semi-automatic equipment for laminating & waxing (Think & Tinker DF-4200, & Asymtek Axiom Heated Jet Platform, respectively,) will be utilized to meet all cartridge manufacture requirements. The footprint of the 12-up disposable is the same as the RTa10 cartridge, so additional fixtures are not necessary.
- Laminate micro substrate & trim excess.
- Fill valves with hot wax & inspect.
- Apply label & barcode.
- Band 24 pieces together.
- Bag & seal banded cartridges, label bag.
- Place bag & insert(s) into carton, seal and label.

This portion of the product is relatively simple, although there is a difference between the automated (as used herein) and the stand-alone 12-up cartridge. Venting will not be required on the cartridge, which eliminates the most time consuming process for cartridge manufacture, along with the highest risk and highest cost for fully integrated automation. Over 1,000 pieces of the 12-up with venting have been successfully produced.

Example 16

Exemplary Chemistry Processes

Sample Pre-Processing

For Urine Sample: Take 0.5 ml of urine and mix it with 0.5 ml of HandyLab collection buffer. Filter the sample through HandyLab Inc.'s pre-filter (contains two membranes of 10 micron and 3 micron pore size). Place the sample tube in the position specified for the external sample tube in the 12-up rack.

For Plasma Sample: Take 0.5 ml of plasma and mix it with 0.5 ml of HandyLab collection buffer. Place the sample tube in the position specified for the external sample tube in the 12-up rack.

For GBS swab samples: Take the swab sample and dip it in 1 ml of HandyLab collection buffer. Place the sample tube in the position specified for the external sample tube in the 12-up rack.

The HandyLab sample collection buffer contains 50 mM Tris pH 7, 1% Triton X-100, 20 mM Citrate, 20 mM Borate, 100 mM EDTA, plus 1000 copies of positive control DNA.

Loading the Instrument and Starting Sample Processing
1. Load PCR tube containing PCR master mix in one of the specified snap-in location of the unitized disposable.
2. Load PCR tube containing PCR probes and primers for the target analyte under consideration in the specified location of the unitized disposable.
3. In case of two analyte test, load PCR tube containing probes and primers for second analyte in the specified location of the unitized disposable.
4. Load the unitized disposable in the 12-up rack in the same lane as the sample tube under consideration.
5. Prepare and load unitized reagent strips for other samples in consideration.
6. Load the 12-up rack in one of the locations in the instrument.
7. Load 12-up cartridge in the cartridge tray loading position.
8. Start operation.

Liquid Processing Steps
1. Using Pipette tip #1, the robot transfers the clinical sample from the external sample tube to the lysis tube of the unitized disposable strip.
2. Using the same pipette tip, the robot takes about 100 µl of sample, mixes the lyophilized enzyme and affinity beads, transfers the reagents to the lysis tube. Mixing is performed in the lysis tube by 5 suck and dispense operations.
3. The robot places pipette tip #1 at its designated location in the unitized disposable strip.
4. Heat the lysis tube to 60 C and maintain it for 10 minutes.
5. After 5 minute of lysis, the robot picks up pipette tip #1 and mixes the contents by 3 suck and dispense operations.
6. The robot places pipette tip #1 at its designated location in the unitized disposable strip.
7. After 10 minutes of lysis, a magnet is moved up the side of the lysis tube to a middle height of the sample and held at that position for a minute to capture all the magnetic beads against the wall the tube.
8. The magnet is brought down slowly to slide the captured beads close to the bottom (but not the bottom) of the tube.
9. Using pipette tip #2, aspirate all the liquid and dump it into the waste tube.
10. Aspirate a second time to remove as much liquid as possible from the lysis tube.
11. Using the same pipette tip #2, withdraw 100 µl of wash buffer and dispense it in the lysis tube. During this dispense, the magnet is moved downwards, away from the lysis tube.
12. Perform 15 mix steps to thoroughly mix the magnetic beads with the wash buffer.
13. Wait for 30 seconds.
14. Move magnet up to capture the beads to the side and hold for 15 seconds.
15. Using pipette tip #2, aspirate wash buffer twice to remove as much liquid as possible and dump it back in the wash tube.
16. Move magnet down away from the lysis tube.
17. Place pipette tip # 2 in its specified location of the unitized disposable strip.
18. Pick up a new pipette tip (tip #3) and withdraw 8-10 µl of release buffer and dispense it over the beads in the lysis tube.
19. Wait for 1 minute and then perform 45 mixes.
20. Heat the release solution to 85° C. and maintain temperature for 5 minutes.
21. Place pipette tip # 3 in its specified location of the unitized disposable strip.
22. Bring magnet up the tube, capture all the beads against the tube wall and move it up and away from the bottom of the tube.
23. Pick up a new pipette tip (tip #4) and withdraw all the release buffer from the lysis tube and then withdraw 3-10 µl of neutralization buffer, mix it in the pipette tip and dispense it in the PCR tube. (In case of two analyte detections, dispense half of the neutralized DNA solution into first PCR tube and the rest of the solution in the second PCR tube.

24. Using pipette tip #4, mix the neutralized DNA with the lyophilized reagents by 4-5 suck and dispense operations and withdraw the entire solution in the pipette tip.

25. Using pipette tip #4, load 6 μl of the final PCR solution in a lane of the 12-up cartridge.

The usage of pipette heads during various processes is shown schematically in FIGS. 85A-C.

Real-Time PCR

After all the appropriate PCR lanes of the PCR cartridge is loaded with final PCR solution, the tray containing the cartridge moves it in the PCR Analyzer. The Cartridge is pressed by the Optical detection read-head against the PCR heater. Heaters activate valves to close either ends of the PCR reactor and real-time thermocycling process starts. After completing appropriate PCR cycles (~45 cycles), the analyzer make a call whether the sample has the target DNA based on the output fluorescence data.

Pipette Detection

The pipette head has 4 infrared sensors for detecting the presence of pipettes. This is essential to ensure the computer positively knows that a pipette is present or missing. Since pipettes are picked up using mechanical forcing against the pipette and also dispensed using mechanical motion of a stripper plate, pipette sensing helps preventing errors that otherwise may happen.

Force Sensing of the Pipette Head

The multi-pipette head is assembled in such a way and a force sensor interfaced with it so that any time the pipette head seats against the disposable pipette(s) or the picked pipettes are forced through the laminate in the reagent disposable or the pipette is forced against the bottom of the tubes in the reagent disposable, an upward force acts on the pipette head through the pipette holding nozzle or the pipettes itself. The entire head is pivoted, as shown in Figure and any force acting on the head causes a set-screw on the upper part of the head to press against a force sensor. This force sensor is calibrated for vertical displacement of the head against a non-moving surface. Using this calibration, it can be determined when to stop moving the head in the z-direction to detect whether pipettes are properly seated or if pipettes hit tube bottoms.

Alignment of Pipette Tips while Loading PCR Reagents into the Microfluidic Cartridge The pipettes used in the apparatus can have volumes as small as 10 μl to as large as 1 ml. Larger volume pipettes can be as long as 95 mm (p1000 pipette). When 4 long pipette tips are sprung from the head, even a 10 misalignment during seating can cause the tip to be off-center by 1.7 mm. As it is impossible to have perfect alignment of the tip both at the top where it is interfaced with the tip holder and the bottom, it becomes necessary to mechanically constrain all the tips at another location closer to the bottom. We have used the stripper plate, having a defined hole structure to use it to align all the tips. The stripper plate hole clears all the 4 pipette tips when they are picked up. After the tips are properly seated, the stripper plate is moved in the x-axis using a motor to move all the pipettes against the notch provided in the stripper plate (see FIG. 46b). Now all the pipettes land on the cartridge inlet holes with ease.

Sample Preparation Extensions

The current technology describes details of processing clinical samples to extract polynucleotides (DNA/RNA). The same product platform can be extended to process samples to extract proteins and other macromolecules by changing the affinity molecules present in the magnetic beads. The amplification-detection platform can also be used to perform other enzymatic reactions, such as immunoPCR, Reverse-transcriptase PCR, TMA, SDA, NASBA, LAMP, LCR, sequencing reactions etc. The sample preparation can also be used to prepare samples for highly multiplexed microarray detections as well.

Example 16

Exemplary Material for RNA-Affinity Matrix

An exemplary polynucleotide capture material preferentially retains polynucleotides such as RNA on its surface when placed in contact with a liquid medium that contains polynucleotides mixed with other species such as proteins and peptides that might inhibit subsequent detection or amplification of the polynucleotides.

The exemplary polynucleotide capture material is: Polyamidoamine (PAMAM) Generation 0, available from the Sigma-Aldrich Chemical Company ("Sigma-Aldrich"), product number 412368. PAMAM is a dendrimer whose molecules contain a mixture of primary and tertiary amine groups. PAMAM (Generation 0) has the structure shown herein.

The PAMAM, during use, is immobilized on a solid support such as carboxylated beads, or magnetic beads. The polynucleotide capture material comprises polycationic molecules during an operation of polynucleotide capture. Affinity between the material and polynucleotides is high because polynucleotides such as DNA and RNA typically comprise polyanions in solution.

After polynucleotide molecules are captured on a surface of the material, and remaining inhibitors and other compounds in solution have been flushed away with an alkaline buffer solution, such as aqueous 0.1 mM Tris (pH 8.0), the polynucleotides may themselves be released from the surface of the material by, for example, washing the material with a second, more alkaline, buffer, such as Tris having a pH of 9.0.

Exemplary protocols for using PAMAM in nucleic acid testing are found in U.S. patent application Ser. No. 12/172,214 filed Jul. 11, 2008, incorporated herein by reference.

Example 17

Exemplary Material for DNA-Affinity Matrix

The exemplary polynucleotide capture material is: Polyethyleneimine (PEI), available from the Sigma-Aldrich Chemical Company ("Sigma-Aldrich"), product number 408719.

Exemplary protocols for using PEI in nucleic acid testing are found in U.S. patent application Ser. No. 12/172,208 filed Jul. 11, 2008, incorporated herein by reference.

Example 18

Exemplary Apparatus

Described herein are exemplary specifications for the mechanical design of the PCR system. In some embodiments, the system can be about 28.5 inches deep, or less, and about 43 inches wide, or less, and weight about 250 pounds or less. The system can be designed with a useful life of about 5 years (e.g., assuming 16,000 tests per year) and can be designed such that the sound level for this instrument (during operation) does not exceed 50 dB as measured 12 inches from the instrument in all ordinate directions. In some embodiments, the exterior of the system can be white with texture.

Referring to the overall system, in some embodiments, critical components of the system can remain orthogonal or parallel (as appropriate) to within 0.04 degrees. Exemplary critical components can include motion rails, pipettes, nozzles (e.g., axially as individual nozzles, linearly as an array of four nozzle centroids, or the like), lysis heaters, major edges of the installed cartridge holder in the reader drawer, the front face of the separation magnets, and the like. In the following descriptions, the X-axis (or X direction) refers to the axis extending from left to right when facing the front of the system, the Y-axis (or Y direction) refers to the axis extending from back to front when facing the front of the system, and the Z-axis (or Z direction) refers to the axis extending up from the bottom when facing the front of the system. As viewed from the top of the instrument, the centroid of the leftmost pipette nozzle on the Z-payload (as viewed from the front of the instrument) can be capable of unobstructed travel in the X direction from a point 80 mm from the outermost left baseplate edge to a point 608 mm from the outermost left baseplate edge and can be capable of unobstructed travel in the Y direction from a point 60 mm from the outermost front baseplate edge to a point 410 mm from the outermost front baseplate edge.

Still referring to the system, as viewed from the front of the instrument, the bottom-most face of the pipette nozzles on the Z-payload can be capable of unobstructed travel in the Y direction from a point 156 mm above the top surface of the baseplate to a point 256 mm above the top surface of the baseplate. The 1 ml pipette tips can be capable of penetrating the foil covers included on disposable reagent strips. This penetration may not create contamination, affect the associated chemistries, or damage the pipette tips. Motions can be executed in such a manner as to eliminate mechanical hysteresis, as needed. Gantry motions can be optimized to prevent cross lane contamination and carryover. The rack can align the reagent strips to a tolerance of +/−0.010 inches in the X and Y directions.

Referring now to the gantry, in some embodiments, the gantry can consist of a stepper-motor actuated, belt/screw-driven cartesian robotic system. The gantry can be free to move, with or without attachments, above the modules that are forward of the rear facade and below the bottom-most horizontal face on the Z head, so long as the Z-payload is fully retracted. The gantry can be capable of travel speeds up to about 500 mm/sec in the X and Y directions and up to about 100 mm/sec in the Z direction. The accuracy and precision of the axis motions (e.g., with respect to the X, Y, and Z home sensors) can be 25 mm or better for each axis, and can be retained throughout the maintenance period. The axis drive belts may not leave residue in areas where PCR and samples are processed. The gantry can contain provisions for routing its own and all Z-payload wire harnesses back to the instrument. Belt tension; on the X and Y axes can be set at 41.5+/−3.5 pounds.

Referring now to the Z-payload, the fluid head can have 4 pipette attachment nozzles located on 24 mm centers. Exemplary pipette tips that the pipette nozzles can capture without leakage include Biorobotix tips PN23500048 (50 µL), PN23500049 (1.75 µL), and PN23500046 (1 ml). The Z payload can incorporate a stepper actuated stripper plate capable of removing pipette tips (e.g., the pipette tips described above). The system can include a pump and manifold system that includes software controlled aspiration, dispensing, and venting of individual fluid volumes within each of the four individual tips and simultaneous dispensing and venting on all tips. The pump and manifold system can have an accuracy and precision of about +/−2 µL per tip for volumes that are less than 20 µL and about +/−10% for volumes greater than or equal to 20 µL (e.g., when aspirating or dispensing in individual tips). The total pump stroke volume can be greater than about 8 µL and less than about 1250 µL. The minimum aspirate and dispense speed can be about 10 µL/sec to about 300 µL/sec. The centroid of the bottom-most face of each pipette tip can be axially aligned with the nozzle centroid of the pipette nozzles within 0.2 mm. The bottom-most pipette tip faces can be co-planar within 0.2 mm. The Z-payload can incorporate a Z axis force sensor capable of feedback to software for applied forces of between about 0 and 4 lbs. The Z-payload can incorporate a downward facing barcode reader capable of reading the system barcodes as described elsewhere herein.

Referring now to racks included in the system, disposable reagent strips (e.g., oriented orthogonally to the front of the instrument) can be contained in 2, 12-lane racks. The 12 reagent strips in a given rack can register and lock into the rack upon insertion by a user. The rack can contain an area for 12 sample lysis tubes (e.g., PN 23500043) and hold the tube bottoms co-planar, allowing the user to orient the bar code to face the rear of the instrument. Certain features, including those listed above, can allow the racks to be inserted and oriented in the instrument by a minimally trained user. Proper rack placement can be confirmed by feedback to the software. In some embodiments, the racks can be black and color fast (e.g, the color may not appreciably degrade with use or washing with a 10% bleach solution) and the rack material can be dimensionally stable within 0.1 mm over the operating temperature range of the system. The rack can be designed with provisions to allow the rack can be carried to and from the instrument and to minimize or eliminate the likelihood that the tubes held by the rack will spill when placed on a flat surface.

Referring now to the reader and PCR heater included in the system, the reader can allow for cartridge insertion and removal by, for example, a minimally trained user. The cartridge can remain seated in the reader during system operation. In some embodiments, the cartridge barcode may not be read properly by the barcode scanner if the cartridge is inserted incorrectly (e.g., upside down or backwards), thus the system can instruct a user to correctly reinsert the cartridge into the reader tray when the cartridge is inserted incorrectly. The reader drawer can repeatably locate the cartridge, for loading by the pipette tips, within 0.5 mm. The reader can deliver the cartridge from the loading position into a react and detect position by means of an automated drawer mechanism under software control. The PCR lanes of the cartridge can be aligned, with both the optical system and heater, by the reader tray and drawer mechanism. The cartridge can contact the heaters evenly with about a 1 psi, or greater, average pressure in the areas of the PCR channels and the wax valves. Heater wire bonds can be protected from damage so as not to interfere with system motion. Registration from heater to cartridge and from cartridge to optical path centers can be within +/−0.010 inches. The reader can mechanically cycle a minimum of about 80,000 motions without failure.

Referring now to the one or more lysis heaters included in the system, the heaters for each of the 24 lysis stations can be individually software controlled. The lysis ramp times (e.g., the time that it takes for the water in a lysis tube to rise from a temperature of approximately 2.5° C. to a given temperature) can be less than 120 seconds for a rise to 50° C. and less than 300 seconds for a rise to 75° C. The lysis temperature (e.g., as measured in the water contained in a lysis tube) can be maintained, by the lysis heaters, within +/−3° C. of the desired temperature. The accessible lysis temperature range can be from about 40° C. to about 82° C. Each of the lysis heaters may draw about 16 Watts or more of power when in operation. The lysis heater can designed to maximize the thermal transfer to the lysis tube and also accommodate the tolerances of the parts. The lysis heaters can permit the lysis tubes to be in direct contact with the magnets (described in more detail herein). The lysis heaters may be adjustable in the horizontal plane during assembly and may not interfere with the installed covers of the system.

Referring now to magnets included in the system, the lysis and magnet related mechanisms can fit beneath the rack and may not interfere with rack insertion or registration. The magnets may be high-flux magnets (e.g., have about a 1,000 gauss, or greater, flux as measured within a given lysis tube) and be able to move a distance sufficient to achieve magnetic bead separation in one or more of the lysis tubes filled to a volume of 900 µL. The magnets can be software-controllable at movement rates from about 1 mm/sec to about 25 mm/sec. The wiring, included as part of the heater and controller assemblies, can be contained and protected from potential spills (e.g., spills of the lysis tubes). The magnets can be located about 1.25 inches or greater from the bottom of the lysis tube when not in use and can be retained in such a manner as to maximize contact with the lysis tube while also preventing jamming.

In some embodiments, the system enclosure includes a semi-transparent lid (e.g., with opaque fixtures and/or hardware) in the front of the instrument to allow users to view instrument functions. The lid can include a company and/or product logo and a graspable handle (e.g., enabling the user to raise the lid). When closed, the lid can have an opening force no greater than 15 pounds (e.g., when measured tangential to door rotation at the center of the bottom edge of the handle) and can lock in the open (e.g., "up") position such that no more than about 5 lbs. of force (e.g., applied at the handle and tangential to door rotation) is required to overcome the handle lock and return the lid to the closed position. The lid can include two safety lid locks that are normally locked when power is not applied and can allow the system to monitor the state (e.g., open or closed) of the lid. The lid can be designed such the lid does not fall when between the open and closed positions. The enclosure can include a power switch located on the right side of the instrument. A power cord can protrude from the enclosure in such a way that positioning the instrument does not damage the cords or cause accidental disconnection. The enclosure can prevent the user from coming in contact with, for example, moving parts, high magnetic fields, live electrical connections, and the like. The enclosure can include four supporting feet, located on the underside of the enclosure, to provide a clearance of about 0.75 inches or more between the underside of the enclosure and the table top. The enclose can include a recessed area with access to external accessory connections such as the display port, the Ethernet port, the 4 USB ports, and the like.

Referring now to the cooling sub-system included in the PCR system, an air intake can be provided in the front of the unit and an air exhaust can be provided in the rear portion of the top of the unit. Intake air can pass through the air intake and through a filter element (e.g., a removable and washable filter element). The cooling sub-system can maintain an interior air temperature (e.g., the temperature as is measured at the surface of the reagent strips, such as the reagent strips numbered 1, 12, and 24, at the surface of the PCR cartridges, and the like) about 10° C. higher, or less, than the ambient air temperature. The cooling subsystem can maintain the internal air temperature at or below about 32° C. One or more cooling fans included as part of the cooling subsystem may require about 5.7 Watts, or less, of power per fan.

In some embodiments, the system can include covers on internal subassemblies (with the exception of the gantry). The covers can be cleanable with a 10% bleach solution applied with a soft cloth without significant degradation. The covers can supply a safety barrier between a user and the electronic and moving mechanical assemblies included in the system. The covers on the internal subassemblies can be designed to maximize cooling of the internal subassemblies by maximizing airflow under the covers and minimizing airflow above the covers. The covers can be removable by a service technician and can match the color and texture of the enclosures.

In some embodiments, the system can be designed to operate within a temperature range of about 15° C. to about 30° C. and in a non-condensing relative humidity range (e.g., about 15% to about 80% relative humidity). The analyzer can be designed to perform without damage after exposure to storage at no less than −20° C. for 24 hours or less, storage at no greater than 60° C. for 24 hours or less, and/or storage at about 50,000 feet or less (e.g., 3.4 inches of Hg) for 24 hours or less. The system can be designed with provisions to prevent motions that could damage the instrument during shipping. It can conform to the shipping standards set forth in ASTM D 4169-05, DC 12 and can be designed to allow the baseplate to be securely mounted to a shipping pallet. The racks and the enclosure of the instrument are designed not to degrade or be damaged by daily cleaning with a 10% bleach solution. The power to subassemblies of the system can be supplied by internal power supplies. Exemplary power supplies can receive, as input, about 1590 watts at about 90 to about 264 Vac at between about 47 and about 63 Hz and supply about 1250 watts of output to the subassemblies.

In some embodiments, the system can include a power switch (e.g., a rocker-type switch), located on the right side of the instrument, one or more interface components, and/or one or more interface ports. For example, the system can include an LCD display monitor that is 15 inches, has 1280×1024 pixel resolution and 16-bit color. The system can also include other display monitors such as ones with increased size, resolution, and/or color depth. The LCD display can be connected to the system via a VGA connection. The system can include a white, 2 button USB mouse, a white USB keyboard, a black SJT power cable, and an un-interruptible power supply, with feedback through USB. The system can also include a USB color printer, 2 USB cables (e.g., one for the printer and one for the UPS). The system can include exemplary interface ports, such as, 4 USB ports (e.g., to connect to a pointing device, printer, keyboard, UPS, LIS), 1 VGA port (e.g., for connection to the LCD display), and 1 Ethernet port (e.g., for PC connectivity) located on the left side of the enclosure. An IEC/EN 60320-11C14 power port can be included n the right side of the enclosure.

In some embodiments, the system can include features directed at increasing the safety of a user. For example, door interlocks can be included to prevent user access while the gantry is in motion and/or while other non-interruptible processes are underway. The system can be designed to minimize or eliminate the presence of user-accessible dangerous corners and/or edges on the instrument and designed such that metal parts are properly electrically grounded. Sheet metal or plastic covers can be included over mechanical and electrical components as necessary to protect a user from moving parts and/or live electrical parts and to protect the electronics and motors included in the system from, for example, spills.

Example 19

Exemplary Optics

Described herein are exemplary specifications related to the design of optics used in a PCR Analyzer and/or System. Additional information related to the PCR System is described elsewhere herein. The optical detection system included in the PCR System can be a 12-lane two-color detection system for monitoring real-time PCR fluorescence from a 12-lane microfluidic PCR cartridge. The system can include excitation lights (e.g., blue and amber LED light sources), one or more band pass filters, and one or more focusing lenses. The emitted fluorescence light from the PCR reactor (e.g., included in the microfluidic cartridge) is captured through a pathway into a focusing lens, through a filter, and onto a photodiode. Included in the system, for each PCR lane, are dedicated, fixed individual optical elements for each of the two colors interrogated.

In some embodiments, the limit of detection is 20 DNA copies per reaction of input PCR reaction mix with a minimum signal to base value of 1.15. The 2 color fluorescence system can be used with, for example, FAM (or equivalent) and Cal Red (or equivalent). The system can have the ability to collect fluorescence data in about 100 ms to about 600 ms at the maximum rate of one data point every about two seconds. When collecting data from a PCR lane, LEDs in adjacent lanes increase the signal in the lane being sampled by less than about 1% (e.g., 0.5%). The noise of the detection can be less than about 1% of the maximum signal. The lane-to-lane fluorescence variability with a fluorescence standard (e.g., part # 14000009) can be within Cv of 30% for both FAM and Cal Red, when measured using the dark-current-corrected-fluorescence-slope. The average dark current-corrected-fluorescence-slope for the optical block with 12 lanes can be between about 30 mV to about 90 mV/(% blue LED power) for FAM using the fluorescence standard (Part # 14000009). The average dark current-corrected-fluorescence-slope for the optical block with 12 lanes should be between about 0.75 mV to about 300 mV/(% amber LED power) for Cal Red using the standard fluorescence cartridge (Part # 14000009). The average excitation power for each channel can be independently varied by software from about 5% to about 100%. There may be no source of light activated inside the reader to affect the fluorescence reading. In some embodiments, turning room lights on or off does not affect the optical readings.

In some embodiments, the system can include an optical block with 12 repeats of 2-color fluorescence detection units at a pitch of about 8 mm. The optical detection block can be positioned on top of the microfluidic cartridge, with excitation and emission travelling through the PCR windows of the microfluidic cartridge. The apertures of the optical block can align with the PCR reactor within about +/−200 microns. An optical electronics board containing the LEDs and Photodetectors can be mated flush with the top of the optics block with each of the photodetectors recessed into the bores of its corresponding optical lane. When the microfluidic cartridge is installed in the system, the optical block can be used to deliver a force of about 20 to about 30 lbs. over the active area of the microfluidic cartridge with an average pressure of at least about 1 psi.

The optical block can be made of aluminum and surfaces present in the optical path lengths can be anodized black, for example, to minimize auto-fluorescence as well as light scattering. An aperture plate having 12 slits, each slit about 10 mm in length and 1 mm wide, can be used, for example, to limit the size of the excitation light spots as well as reduce background fluorescence. The thickness of the optics block can be about 1.135+/−0.005 inches. The bottom surface of the optics block can be planar within +/−1 mil to provide uniform pressure over the micro fluidic cartridge. The apertures should be kept clean and free of debris during manufacturing of the optics block and assembly of the optics block into the system.

In some embodiments, the system can include excitation optics with an angle of excitation path equal to 55+/−0.5 inches with respect to normal of the PCR cartridge surface. One exemplary arrangement of optical elements in the excitation path, in order, is LED, lens, filter, aperture, and PCR sample. The system can use a Plano-convex excitation lens (e.g., PCX, 6×9, MgF2TS) oriented with the flat side toward the PCR sample. Included in the optics are one or more excitation paths with tapers that can be designed such that the lens and filter can be placed inside the bore to provide a light spot bigger than the aperture plate. The location of the LED and the sample can be fixed as the design can include a fixed available optical block thickness. The location of the lens and the filter can be determined to provide a excitation spot size of about 6 mm along the length of a PCR lane. The excitation optics can include an LED such as Luxeon Part # LXK2-PB 14-NO0 (e.g., for FAM excitation) that includes a center wavelength of about 470 nm (blue) with a half band width of about 75 nanometers, or less (e.g., for FAM excitation). The excitation optics can also include an LED such as Luxeon Part # LXK2-PL12-Q00 (e.g., for Cal Red excitation) that includes a center wavelength of 575 nm (amber) with a half band width of about 75 nanometers, or less (e.g., for Cal Red excitation). The LEDs used in the excitation optics can remain stable for about 5 years or more or about 10,000 cycles.

The system can include emission optics with an angle of emission path equal to about 15+/−0.5 inches with respect to normal of the PCR cartridge surface. One exemplary arrangement of optical elements in the emission path, in order, is PCR sample, aperture, filter, lens, and photodetector. The emission lens can be plano-convex (e.g., PCX, 6×6 MgF2TS) with the flat side toward the photodetectors. The emission optics can include one or more bores, for the emission path, with tapers that can be designed so as to maximize detected light while enabling snug placement of the filters and lenses. The location of the photodetectors with respect to the sample can be fixed as the design can include a fixed available optical block thickness. The location of the lens and the filter can be determined so as to provide an emission spot size of 6 mm along the length of a PCR lane. An exemplary photodetector that can be used in the emission optics is the Hamamatsu Silicon Photodetector with Lens, S2386-18L.

In some embodiments, the system can include one or more filters with diameters of about 6.0+/−0.1 mm, thicknesses of about 6.0+/−0.1 mm, clear apertures with diameters of less than or equal to about 4 mm. The filters can include a blackened edge treatment performed prior to placement in a mounting ring. If present, the mounting ring can be metal and anodized black. The filters can be manufactured from optical glass with a surface quality that complies with F/F per Mil-C-48497A, an AOI of about 0 deg, a ½ cone AOI of about +8 deg, and can be humidity and temperature stable within the recommend operating range of the system. An exemplary filter can be obtained from Omega Optical Brattleboro, Vt. 05301.

The system can include one or more FITC Exciter Filters (e.g., PN 14000001) with an Omega part number 481AF30-RED-EXC (e.g., drawing # 2006662) used, for example, in FAM excitation. These filters can have a cut-on wavelength of about 466+/−4 nm and a cut-off wavelength of about 496+0/−4 nm. The transmission of filters of this type can be greater than or equal to about 65% of peak. These filters can have a blocking efficiency of greater than or equal to OD4 for wavelengths of ultraviolet to about 439 nm, of greater than or equal to OD4 for wavelengths of about 651 nm to about 1000 nm, of greater than or equal to OD5 for wavelengths of about 501 nm to about 650 nm, and of greater than or equal to OD8, in theory, for wavelengths of about 503 nm to about 580 nm.

The system can include one or more Amber Exciter Filters (e.g., PN 14000002) with a part number 582AF25-RED-EXC (e.g., drawing # 2006664) used, for example, in Cal Red excitation. These filters can have a cut-on wavelength of about 569+/−5 nm and a cut-off wavelength of about 594+0/−5 nm. The transmission of filters of this type can be greater than or equal to about 70% of peak. These filters can have a blocking efficiency of greater than or equal to OD8, in theory, for wavelengths of about 600 nm to about 700 nm.

The system can include one or more FITC Emitter Filters (e.g., PN 14000005) with a part number 534AF40-RED-EM (e.g., drawing # 2006663) used, for example, in FAM emission. These filters can have a cut-on wavelength of 514+/−2 nm and a cut-off wavelength of 554+/−5 nm. The transmission of filters of this type can be greater than or equal to about 70% of peak. These filters can have a blocking efficiency of greater than or equal to OD5 for wavelengths from ultraviolet to about 507 nm, of greater than or equal to OD8, in theory, from about 400 nm to about 504 nm, and of greater than or equal to OD4 avg. from about 593 nm to about 765 nm.

The system can include one or more Amber Emitter Filters (e.g., PN 14000006) with a part number 627AF30-RED-EM (e.g., drawing # 2006665) used, for example, in Cal Red emission. These filters can have a cut-on wavelength of 612+5/−0 nm and a cut-off wavelength of 642+/−5 nm. The transmission of filters of this type can be greater than or equal to about 70% of peak. These filters can have a blocking efficiency of greater than or equal to OD5 for wavelengths from ultraviolet to about 605 nm, of greater than or equal to OD8, in theory, from about 550 nm to about 600 nm, and of greater than or equal to OD5 avg. from about 667 nm to about 900 nm.

Example 20

Exemplary 3-Layer Cartridge

Described herein are exemplary specifications used to design and assemble the microfluidic cartridge as well as exemplary instructions on the use of the cartridge in, for example, the system described herein. In some embodiments, the cartridge can have a maximum limit of detection equal to 20 copies per reaction volume (e.g., 20 copies/4μ), with a target detection of 10 copies per reaction volume. The cartridge can perform 45 reaction cycles in 40 minutes or less (e.g., 45 cycles in 40 minutes, 45 cycles in 20 minutes, 45 cycles in 15 minutes, or the like). The cartridge can utilize two color detection using, for example, the FAM (or equivalent) and CAL RED (or equivalent) fluorescent dyes. Results obtained using the cartridge have been compared with the results obtained using standard real-time PCR instruments.

In some embodiments, the Cartridge can be a one-time use, disposable cartridge that can be disposed of according to typical laboratory procedures. The cartridge can be 4.375 inches long and 2.800 inches wide, with a thickness of 0.094+/−0.005 inches. The cartridge can include features that allow the cartridge to interface with, for example, the system described herein. Exemplary interfacing features include PCR channel walls and the top of the micro-substrate over the PCR channel that are well polished (SPI A1/A2/A3), enabling easy transfer of excitation and emission light between the PCR reactor (e.g., contained in the cartridge) and the detection system (e.g., the analyzer). The cartridge can include a thermal interface, located on the bottom of the cartridge, for interfacing with the analyzer. The thermal interface can have a thin laminate (e.g., less than 150 microns thick, 100 microns thick, or the like) to encourage heat transfer from the heater wafer to, for example, the PCR channels of the cartridge.

The cartridge can include one or more mechanical interfaces with, for example, the analyzer. For example, the cartridge can have a notch in one or more of the corners that can mate with a corresponding shape on the heater module of the analyzer. The notch and corresponding shape can enable the cartridge to be placed only one way in the tray of, for example, the system described herein. In some embodiments, the cartridge has a single notch in one of the corners, with the remaining three corners having a minimum radius of 1 mm to facilitate placement of the cartridge in the analyzer. During use (e.g., when placed in a system described herein and performing a function such as PCR), the cartridge can be pressed, on one side, by the optics block, against the heater wafer (positioned against the opposite side), with a pressure of about 1 psi or greater (e.g., 0.99 psi, 1.2 psi, or the like). When located in the tray of the analyzer, the cartridge can have an alignment slop of +/−200 microns to enable a user to easily place and remove the cartridge from the analyzer tray. The cartridge can have two ledges, that are each 1 mm wide and located along the two long edges of the cartridge, to enable the heating surface to extend below the datum of the tray.

In some embodiments, the cartridge can have the following functional specifications. The cartridge can include an inlet hole that is, for example, cone-shaped with a height of 1 mm from the top surface of the cartridge. The cone can have an inner diameter of 3 mm at the top of the cone and can taper down to a diameter that matches the width of a microchannel (e.g., an inlet channel) that the inlet cone is fluidly connected to. The inlet channel can fluidly connect the inlet hole to a PCR reactor that has an interior volume of, for example, about 4.25 μl to 4.75 μl (e.g., 4.22 μl, 4.5 μl, 4.75 μl, or the like). An outlet microfluidic channel can fluidly connect the PCR reactor to an overflow chamber. The cartridge can also include an outlet vent hole.

The input PCR sample (e.g., a reaction mixture) can be between about 6.0 and 7.0 μl per PCR lane (e.g., 5.9 μl per lane, 6.4 μl per lane, 7.1 μl per lane, or the like) and can be introduced into the cartridge through the inlet hole by, for example, a pipette. The reaction mixture can be transported, via the inlet channel, to the PCR reactor where the reaction mixture can be isolated (e.g., sealed off by valves) to prevent evaporation or movement of the reaction mixture during thermocycling. Once the mixture is sealed inside the chamber, the analyzer can initiate multiplexed real-time PCR on some or all of the reaction mixture (e.g., 4.5 μl, an amount of fluid equal to the inner volume of the reaction chamber, or the like).

The microfluidic substrate of the cartridge can include one or more of the following specifications. The material of the microsubstrate can be optically clear (e.g., have about 90% or greater optical transmission, be 3 mm thick, comply with ASTM D1003, and the like), have auto-fluorescence that is less than that emitted by 2 mm thick ZEONOR 1420R, and have a refractive index of about 1.53 (ASTM D542). The material of the microsubstrate can be amenable to the injection molding of features required for the microfluidic network of the cartridge. The material is preferably compatible with all PCR agents and can withstand temperatures of up to about 130° C. for about 5 minutes or more without yielding or melting. The cartridge can include fiducials, recognizable by HandyLab manufacturing equipment, located in one or more (preferably two) of the corners of the substrate. The cartridge can include fluidic components (e.g., microchannels, valves, end vents, reagent inlet holes, reaction chambers, and the like) necessary to perform the functions of the cartridge (e.g., PCR).

Additional features of the substrate material can include one or more of the following. Minimum clearances of about 1 mm can be designed between functional features to ensure sealing success (e.g., to the analyzer), and to allow simplified fixturing during assembly. The cartridge can include dog-bones under small fluid path ends to, for example, increase mold life. The bottom of the micro tool surface can be roughened (e.g., by vapor hone, EDM, or the like). The substrate material can be capable of adhesion by a label.

In some embodiments, the sealing tape used in the cartridge can include one or more of the following specifications. Laminate can be easily applied to the bottom of the microfluidic substrate. Material of the laminate is preferably pinhole free. The material and adhesive is preferably compatible with the PCR reaction chemistries. The laminate material and glue used should not auto-fluoresce. The material can withstand up to 130° C. for 5 minutes without losing adhesion, yielding, melting, or causing undue stresses on the cartridge. Bubbles should not form in the adhesive layer upon heating (e.g., to 130° C. for 5 minutes) after application to the microsubstrate. The laminate should be less than 5 mills thick to, for example, enable rapid heat transfer.

The high temperature wax included in the cartridge can have the following characteristics. The wax should have a melt point of about 90+/−3° C. (e.g., 87° C., 90° C., 93.1° C., or the like), be biocompatible with PCR reactions, have wettability with microsubstrate material, and have a melt viscosity range, for example, of about Viscosity at 100° C.=20 mm$^2$/s and Hardness at 25° C.=8 dmm. The main label of the cartridge can have the following characteristics. It can have a thickness of 2-4 mils, have suitable bondability to micro features and seal around the valves, include cuts for one or more PCR windows, and a tab (free from adhesive) for aiding in removal of the cartridge from the analyzer. The main label can also have abrasion resistance on the top surface, and be printable. The main label can have an upper and lower alignment pattern for the label to completely cover the valve holes for proper operation of the valves.

The cartridge can include a barcode label applied to the top of the cartridge that is readable by a barcode reader (e.g., the barcode reader included in the analyzer) while the cartridge is installed in the analyzer. The barcode label can include the product name, lot #, expiration date, bar code (2D) and may be printed on. In addition, or in the alternative, a barcode may be applied directly to the main cartridge label using a laser or inkjet type printer.

The packaging that the cartridge is included in can include one or more of the following: package label, carton, carton label, and/or operating instructions. The packaging can be printed on or label attachable, placed inside of a plastic bag, shrink/stretch wrap bag, or the like, and can be stacked in groups of 24. The cartridge bagging without a critical seal should be kept free from dust contamination.

The cartridge can include one or more valves (e.g., temperature controlled, wax-containing valves) for starting, stopping, and/or controlling the flow of material inside the cartridge. The wax contained in the valves can be free of trapped air bubbles that have a diameter greater than half the width of the valve channel. The valve channel can have an air pocket. The wax may not intrude into the fluid path prior to activation. The wax can be filled to the start of the flare to the fluid path.

The cartridge can include micro channels and holes such that the holes are of a size and shape to enable easy, leak-free interfacing with a 175 μl pipette tip. In some examples, the holes size is between about 200 μm and about 4000 μm in diameter. The microchannels can be between about 50 μm and about 1500 μm wide and between about 50 μm and 1000 μm high.

The cartridge can include valves for controlling the flow of fluid within the cartridge (e.g., through the microchannels, reactor chambers, and the like). The valve edges, steps, and general geometry can be designed to encourage exact flow and/or stoppage required during wax load. The valve geometry can be designed to accommodate limitations of wax dispensing equipment (e.g., =/−25% of 75 nL volume). In some embodiments, step down air chambers on the valves are funnel shaped to aid wax loading and the remaining geometry diminishes from the bottom of the funnel to the end point where the wax stops. The path where the valves are to flow into and block, during use, can be narrow enough (e.g., 150-200 microns wide and deep) and have enough length to effectively seal when the valves are activated during use. The valve wax temperature can be about 90° C. When in use to block a portion of a microchannel, the valves can seal to prevent evaporation of fluid and/or physical migration of fluid from the PCR reactor during thermocycling.

The cartridge can include one or more PCR regions for performing PCR on a sample. The channel in the PCR region (e.g., PCR reactor) can be designed such that the temperature of the contents of the channel remain uniformly within about 1° C. of the anneal temperature. The channel walls can have a polish of SPI A1/A2/A3.

In some embodiments, the cartridge is designed to be able to perform diagnostic tests within a temperature range of about 59° F. to about 86° F. (about 15° C. to about 30° C.) and a humidity range of about 15% relative humidity to about 80% relative humidity. The cartridge is designed to be safe and functional when used indoors, used at an altitude of 2000 m or less, and used under non-condensing humidity conditions (e.g., maximum relative humidity of 80% for temperatures up to 31° C. decreasing linearly to 50% relative humidity at 40° C.).

In use, PCR product produced in the cartridge can remain in the used cartridge to, for example, minimize the likelihood of cross contamination. The cartridge can be designed such that a 4 foot drop of the cartridge, while in its packaging, will not damage the cartridge. The cartridge is designed to perform without damage after exposure to the following conditions. The cartridge should be stored at 4° C. to 40° C. for the rated shelf life. Exposure to temperatures between −20° C. and 4° C. or 40° C. and 60° C. should occur for no longer than 24 hours. The cartridge can withstand air pressure changes typical of air transport.

The cartridge can be labeled with the following information (e.g., to identify the cartridge, comply with regulations, and the like). The label can contain a "Research Use Only" label, if applicable, and a CE mark, if applicable. The label can contain the company name and logo (e.g., Handylab®), a part number (e.g., 55000009), a part name (12× Cartridge-nonvented), a lot number (e.g., LOT 123456), an expiration date (e.g., 06/2015), space for writing, a barcode according to barcode specifications (described elsewhere), and/or "Handylab, Inc., Ann Arbor, Mich. 48108 USA".

The cartridge can be include in a carton that can contain information such as, a part number (e.g., 55000009), a part name (12× Cartridge-nonvented), a quantity (e.g., 24), a lot number (e.g., LOT 123456), an expiration date (e.g., 06/2015), an optional UPC code, "Manufactured by Handylab, Inc., Ann Arbor, Mich. 48108 USA", a carton label to state storage limits, a CE mark (if applicable), and/or an AR name and address.

The cartridge packaging can include paper wrap to secure multiple cartridges together and clean package fill to prevent damage, for example, from vibration. The cartridge shipping carton can include features such as, compliance to ASTM 6159, carton may be stored in any direction, refrigeration or fragile labeling of the carton may not be required, and additional cold packs may not be required. The shelf life of the cartridge is 12 months or more.

The cartridge can comply with IEC 61010 (NRTL tested) and an FDA listing may be required for clinical distribution. Cartridges used in a clinical lab device may meet all quality system requirements. Cartridges used for research only in a commercial device may meet all HandyLab quality system requirements. Cartridges for research use only (Alpha or Beta testing) may be design/manufacturing traceable to a DHR (manufacturing record).

The foregoing description is intended to illustrate various aspects of the present inventions. It is not intended that the examples presented herein limit the scope of the present inventions. The technology now being fully described, it will be apparent to one of ordinary skill in the art that many changes and modifications can be made thereto without departing from the spirit or scope of the appended claims.

What is claimed is:

1. A preparatory apparatus configured to extract nucleic acid simultaneously from a number of nucleic-acid containing samples comprising:
    one or more racks, each rack comprising a plurality of lanes, wherein each lane comprises a first location adjacent to and spatially separate from a second location, the first location comprising a slot shaped and sized to receive a holder, the second location comprising an aperture shaped and sized to receive a sample tube;
    a plurality of sample tubes and a corresponding number of holders removably mounted in one of the one or more racks, wherein each holder is removably mounted in the rack adjacent to and spatially separate from its corresponding sample tube, wherein each sample tube is removably mounted in the rack, and wherein each sample tube is configured to accept one of the number of nucleic-acid containing samples, and wherein each holder comprises a process chamber, a waste chamber, one or more pipette tips, and one or more receptacles, wherein the one or more receptacles contain sufficient quantities of one or more reagents for carrying out extraction of nucleic acid from one of the number of nucleic-acid containing sample;
    a magnetic separator positioned to apply a magnetic force to the process chamber of each holder when each holder is mounted in the rack;
    a heater assembly configured to independently heat each of the process chamber of each holder when each holder is mounted in the rack; and
    a liquid dispenser configured to carry out fluid transfer operations between the plurality of sample tubes and the corresponding number of holders.

2. The apparatus of claim 1, further comprising:
    a sample identification verifier configured to check an identity of each of the number of nucleic-acid containing samples.

3. The apparatus of claim 2, wherein the sample identification verifier is selected from the group consisting of: an optical character reader, a bar code reader, and a radio frequency tag reader.

4. The apparatus of claim 1, wherein the liquid dispenser has 4 heads, wherein each head is configured to accept a pipette tip from the one or more pipette tips in a holder.

5. The apparatus of claim 4, wherein no two heads accept pipette tips from the same holder.

6. The apparatus of claim 1, wherein the liquid dispenser is attached to a gantry having 3 degrees of translational freedom.

7. The apparatus of claim 1, further comprising:
    electronic circuitry configured to control operation of: the liquid dispenser; the heater assembly; and the magnetic separator.

8. The apparatus of claim 7, wherein the electronic circuitry controls the motion of the liquid dispenser.

9. The apparatus of claim 7, wherein the electronic circuitry is configured to cause the heater assembly to apply heat independently to the process chambers.

10. The apparatus of claim 7, wherein the electronic circuitry is configured to cause the magnetic separator to move repetitively relative to the process chamber of each holder.

11. The apparatus of claim 1, wherein the holders are suitable for a single use and are disposable.

12. The apparatus of claim 1, wherein the magnetic separator is configured to move repetitively relative to the process chamber of each holder.

13. The apparatus of claim 1, having two racks.

14. The apparatus of claim 1, wherein the number of nucleic-acid containing samples is 12.

15. The apparatus of claim 1, further comprising a second module configured to receive and to store nucleic acid extracted from the number of nucleic-acid containing samples, wherein the second module has separate locations for nucleic acid extracted from each of the nucleic-acid containing samples.

16. The apparatus of claim 1, further comprising a second module configured to receive and to store nucleic acid extracted from the number of nucleic-acid containing samples, wherein the second module comprises a separate microfluidic PCR cartridge for nucleic acid extracted from each of the number of nucleic-acid containing samples.

17. The apparatus of claim 16, wherein the microfluidic PCR cartridge contains lyophilized PCR reagents.

18. The apparatus of claim 16, wherein the microfluidic PCR cartridge contains a first lyophilized PCR reagents suitable for detecting a first analyte, and a second lyophilized PCR reagents suitable for detecting a second analyte.

19. The apparatus of claim 1, further comprising a second module configured to receive and to store nucleic acid extracted from the number of nucleic-acid containing samples, wherein the second module comprises a Peltier cooler.

20. The apparatus of claim 1, further comprising a second module configured to receive and to store nucleic acid extracted from the number of nucleic-acid containing samples, wherein the second module has a plurality of areas for receiving nucleic acid extracted from the number of nucleic-acid containing samples.

21. The apparatus of claim 20, wherein the plurality of areas are configured to be cooled independently of one another.

22. The apparatus of claim 20, wherein the apparatus comprises more than one rack.

23. The apparatus of claim 1, wherein each of the holders comprises a pipette tip sheath configured to surround the one or more pipette tips.

24. The apparatus of claim 23, wherein the pipette sheath is configured to hold 4 pipette tips.

25. The apparatus of claim 1, wherein each of the holders comprises an identifier.

26. The apparatus of claim 25, wherein the identifier is a bar-code.

27. The apparatus of claim 1, wherein each of the holders contains lyophilized sample preparation reagents.

28. The apparatus of claim 1, wherein one of the one or more reagents comprises: a wash buffer, a release buffer, or a neutralization buffer.

29. The apparatus of claim 1, wherein the process chamber of each holder has a stellated ridge-pattern on its interior bottom surface.

30. The apparatus of claim 1, wherein the apparatus is configured to carry out extraction of nucleic acid from the number of nucleic-acid containing samples in less than about 30 minutes.

31. The apparatus of claim 1, wherein the one or more racks are removable.

32. The apparatus of claim 1, wherein each rack is configured to accept the number of nucleic-acid containing samples and the corresponding number of holders when disposed outside of the apparatus.

33. The preparatory apparatus of claim 1, wherein the apparatus is portable or can be situated on a laboratory benchtop.

34. The preparatory apparatus of claim 1, wherein the number of nucleic-acid containing samples are each independently selected from the group consisting of: saliva, urine, blood, semen, mucus, and spinal fluid.

35. The preparatory apparatus of claim 1, wherein the liquid dispenser is configured to carry out fluid transfer operation on two or more lanes simultaneously, said fluid transfer operations requiring only two-dimensional movement of the liquid dispenser in each lane.

* * * * *